United States Patent
Nair et al.

(10) Patent No.: US 12,391,695 B2
(45) Date of Patent: *Aug. 19, 2025

(54) PRMT5 INHIBITORS

(71) Applicant: Lupin Limited, Mumbai (IN)

(72) Inventors: Prathap Sreedharan Nair, Pune (IN); Ganesh Bhausaheb Gudade, Pune (IN); Mahadeo Bhaskar Tryambake, Pune (IN); Chetan Sanjay Pawar, Pune (IN); Dipak Raychand Lagad, Pune (IN); Chaitanya Prabhakar Kulkarni, Pune (IN); Milind Dattatraya Sindkhedkar, Pune (IN); Venkata P. Palle, Pune (IN); Rajender Kumar Kamboj, Pune (IN)

(73) Assignee: Lupin Limited, Mumbai (IN)

( * ) Notice: Subject to any disclaimer, the term of this patent is extended or adjusted under 35 U.S.C. 154(b) by 867 days.

This patent is subject to a terminal disclaimer.

(21) Appl. No.: 17/618,042

(22) PCT Filed: Jun. 9, 2020

(86) PCT No.: PCT/IB2020/055401
§ 371 (c)(1),
(2) Date: Dec. 10, 2021

(87) PCT Pub. No.: WO2020/250123
PCT Pub. Date: Dec. 17, 2020

(65) Prior Publication Data
US 2022/0315589 A1   Oct. 6, 2022

(30) Foreign Application Priority Data

Jun. 10, 2019 (IN) .............. 201921022971
Jun. 10, 2019 (IN) .............. 201921022972

(51) Int. Cl.
C07D 487/04 (2006.01)
A61P 35/00 (2006.01)
C07D 401/12 (2006.01)
C07D 487/14 (2006.01)
C07D 519/00 (2006.01)

(52) U.S. Cl.
CPC ........... C07D 487/04 (2013.01); A61P 35/00 (2018.01); C07D 401/12 (2013.01); C07D 487/14 (2013.01); C07D 519/00 (2013.01)

(58) Field of Classification Search
CPC .. C07D 487/04; C07D 401/12; C07D 519/00; A61P 35/00
See application file for complete search history.

(56) References Cited

U.S. PATENT DOCUMENTS 11,459,330 B2 * 10/2022 Nair .............. A61P 35/00
11,952,380 B2 *  4/2024 Nair .............. C07D 471/04

| | | |
|---|---|---|
| 2009/0149466 A1 | 6/2009 | Gillespie et al. |
| 2010/0125089 A1 | 5/2010 | Soll et al. |
| 2013/0116430 A1 | 5/2013 | Hideyasu et al. |
| 2014/0221345 A1 | 8/2014 | Duncan et al. |
| 2014/0228360 A1 | 8/2014 | Duncan et al. |
| 2014/0329794 A1 | 11/2014 | Duncan et al. |
| 2015/0225407 A1 | 8/2015 | Ren et al. |
| 2016/0222005 A1 | 8/2016 | Stupple et al. |
| 2016/0326208 A1 | 11/2016 | Cortez et al. |
| 2018/0237441 A1 | 8/2018 | Axten et al. |
| 2019/0111060 A1 | 4/2019 | Tatlock et al. |
| 2020/0087281 A1 | 3/2020 | Shaikh et al. |
| 2021/0163486 A1 | 6/2021 | Nair et al. |
| 2023/0066014 A1 * | 3/2023 | Nair .............. A61K 31/473 |

FOREIGN PATENT DOCUMENTS

| | | |
|---|---|---|
| WO | 2006091905 A1 | 8/2006 |
| WO | 2007079162 A1 | 7/2007 |
| WO | 2008/075110 A1 | 6/2008 |
| WO | 2011/079236 A1 | 6/2011 |
| WO | 2011077133 A2 | 6/2011 |
| WO | 2012/002577 A1 | 1/2012 |
| WO | 2012/037108 A1 | 3/2012 |
| WO | 2012/040279 A1 | 3/2012 |
| WO | 2014100695 A1 | 6/2014 |
| WO | 2014100716 A1 | 6/2014 |
| WO | 2014100719 A2 | 6/2014 |
| WO | 2014100730 A1 | 6/2014 |
| WO | 2014100734 A1 | 6/2014 |
| WO | 2014128465 A1 | 8/2014 |
| WO | 2014145214 A2 | 9/2014 |
| WO | 2015/054572 A1 | 4/2015 |
| WO | 2015198229 A1 | 12/2015 |
| WO | 2015200677 A2 | 12/2015 |

(Continued)

OTHER PUBLICATIONS

Nature Reviews Cancer 2013, 13, p. 37.

(Continued)

*Primary Examiner* — Andrew D Kosar
*Assistant Examiner* — Phillip Matthew Rzeczycki
(74) *Attorney, Agent, or Firm* — The Dobrusin Law Firm, P.C.

(57) ABSTRACT

The invention relates to substituted nucleoside analogues of formula (I), pharmaceutically acceptable salts thereof and pharmaceutical compositions for treating diseases, disorders or conditions associated with the overexpression of PRMT5 enzyme. The invention also relates to methods of treating diseases, disorders or conditions associated with the overexpression of PRMT5 enzyme.

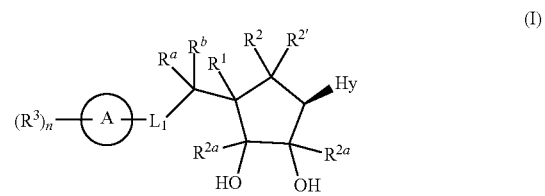

11 Claims, No Drawings

(56) References Cited

FOREIGN PATENT DOCUMENTS

| WO | 2015200680 A2 | 12/2015 |
|---|---|---|
| WO | 2016022605 A1 | 2/2016 |
| WO | 2016034671 A1 | 3/2016 |
| WO | 2016034673 A1 | 3/2016 |
| WO | 2016034675 A1 | 3/2016 |
| WO | 2016038550 A1 | 3/2016 |
| WO | 2016135582 A1 | 9/2016 |
| WO | 2016145150 A2 | 9/2016 |
| WO | 2016178870 A1 | 11/2016 |
| WO | 2017/046737 A1 | 3/2017 |
| WO | 2017/100716 A1 | 6/2017 |
| WO | 2017032840 A1 | 7/2017 |
| WO | 2018065365 A1 | 4/2018 |
| WO | 2018085818 A1 | 5/2018 |
| WO | 2018152501 A1 | 8/2018 |
| WO | 2018/167800 A1 | 9/2018 |
| WO | 2018160824 A1 | 9/2018 |
| WO | 2019/116302 A1 | 6/2019 |

OTHER PUBLICATIONS

Trends in Biochemical Sciences 2011, 36, p. 633.
Cell Mol Life Sci., 2015, 72, p. 2041.
Mol Cell Biol, 2008, 28, p. 6262.
Oncogene, 2017, 36, p. 263.
Oncogene, 2017, 36, p. 1223.
Science, 2016, 351, p. 1214.
Nature Chemical Biology, 2015, 11, p. 432.
Journal of Biological Chemistry, 2013, 288, p. 35534.
Leukemia, 2018, 32, p. 499.
AACR; Cancer Research 2017;77(13 Suppl):Abstract nr 1128.
Leukemia, 2018, 32, p. 996.
The Biochemical Journal, 2012, 446, p. 235.
AACR; Cancer Research 2017;77(13 Suppl):Abstract nr DDT02-04).
Cell Reports, 2017, 21, p. 3498.
AACR; Cancer Res 2015;75(15 Suppl):Abstract nr 4786.
International Journal of Oncology, 2016, 49, p. 1195.
Oncotarget, 2015, 6, p. 22799.
J Histochem Cytochem 2013, 61, p. 206.
Clinical Cancer Research, 2018, CCR-18-1270.
Oncology Reports, 2018, 40, p. 536.
PLOS One, 2013, 8, e74710.
J Clin Invest. 2018, 128, p. 517.
Oncology Letters, 2018, 16, p. 2161.
Oncotarget, 2017, 8, p. 14847.
J Clin Invest, 2016, 126, p. 3961.
Carcinogenesis, 2017, 38, p. 827.
Oncology Reports, 2016, 35, p. 1703.
Molecular Oncology, 2015, 9, p. 617.
Gynecol Oncol., 2016, 140, p. 145.
Pharmazie, 2018, 73, p. 269.
Molecular and Cellular Biology 2008, 28, p. 6262.
The Journal of Biological Chemistry 2013, 288, p. 35534.
Journal of Biological Chemistry—vol. 279 (23), p. 23892.
ACS Medicinal Chemistry Letters 2015, 6, p. 408.
ACS Med. Chem. Lett. 2015, 6, 1150-1155.
JACS, 1949, 71, 6-7.
Journal of Medicinal Chemistry, 2014, vol. 57, # 3, p. 1097-1110.
Organic Letters, 2018, vol. 20, # 2, p. 441-444.
Heterocycles, 2017, vol. 95, #1, p. 445-461.
Journal of Medicinal Chemistry, 1992, vol. 35, # 2, p. 324-331.
Organic Letters, 2012, vol. 14, # 8, p. 2134-2137.
PCT Search Report & Written Opinion dated Sep. 7, 2020, Application No. PCT/IB2020/055401.

* cited by examiner

PRMT5 INHIBITORS

FIELD OF THE INVENTION

The invention relates to substituted nucleoside analogues of formula (I), pharmaceutically acceptable salts thereof and pharmaceutical compositions for treating diseases, disorders or conditions associated with the overexpression of PRMT5 enzyme. The invention also relates to methods of treating diseases, disorders or conditions associated with the overexpression of PRMT5 enzyme.

CROSS-REFERENCE TO RELATED APPLICATIONS

The present application claims the benefit of Indian Provisional Patent Applications Nos. IN201921022971 filed on Jun. 10, 2019, and IN201921022972 filed on Jun. 10, 2019, the disclosures of which are incorporated herein by reference in their entirety for all purposes.

BACKGROUND TO THE INVENTION

Methylation of proteins is a common post-translational modification that affects the protein's activity and its interaction with other biological molecules. N-methylation typically occurs on the nitrogen atoms of arginine, lysine and histidine residues and there are different families of enzymes that catalyze the methylation reaction, each being specific to the amino acid residue that will be methylated.

A family of 9 enzymes, called Protein Arginine N-Methyl Transferases (PRMTs), are responsible for the methylation of the guanidinium group of arginine. The guanidinium group of arginine bears 2 terminal nitrogen atoms that undergo monomethylation or dimethylation. Depending on the type of dimethylation, the enzymes are further classified as type I or type II. Type I PRMTs catalyse the monomethylation or the asymmetric dimethylation whereas type II enzymes catalyse the symmetric dimethylation. Some of the substrates that undergo methylation are histones, Sm ribonucleoproteins, MRE11 and p53 binding protein 1.

The methylation of arginine sidechains has an important role to play in various cell functions that include transcription activation as well as transcription repression, mRNA translation, pre-mRNA splicing, protein trafficking and signal transduction. It also occurs on myriad substrates. The enzymatic activity of the PRMTs hence affects cellular processes like cell proliferation, repair of damaged DNA as well as cell cycle and cell death. It has been shown that PRMT enzyme-mediated hypermethylation leads to certain disease conditions like cancer (Nature Reviews Cancer 2013, 13, p37; Cellular and Molecular Life Sciences 2015, 72, p2041; Trends in Biochemical Sciences 2011, 36, p633).

At present, the most studied type II enzyme is PRMT5, which is conserved across the eukaryotic organisms. Overexpression of PRMT5 is linked with carcinogenesis and decreased patient survival in several human malignancies (Cell Mol Life Sci., 2015, 72, p2041). PRMT5 directly interacts with proteins often dysregulated or mutated in cancers, hence a putative oncogene (Mol Cell Biol, 2008, 28, p6262). PRMT5 mediated transcriptional repression of tumor suppressor genes like p53, RB-1, ST7, or upregulation of Cyclin D1, CDK4, CDK6, eLF4E, MITF, FGFR3 associate with the oncogenesis in both solid tumors and hematological malignancies. PRMT5 is located in the nucleus as well as the cytoplasm and its overexpression has been linked to a wide range of cancers including, but not limited to, glioblastoma multiforme (Oncogene, 2017, 36, p263), prostate cancer (Oncogene, 2017, 36, p1223), and pancreatic cancer (Science, 2016, 351, p1214), mantle cell lymphoma (Nature Chemical Biology, 2015, 11, p432), non-Hodgkin's lymphomas and diffuse large B-cell lymphoma (Journal of Biological Chemistry, 2013, 288, p35534), acute myeloid leukemia (Leukemia, 2018, 32, p499), acute lymphoblastic leukemia (AACR; Cancer Research 2017; 77 (13 Suppl):Abstract nr 1128), multiple myeloma (Leukemia, 2018, 32, p996), non-small cell lung cancer (The Biochemical Journal, 2012, 446, p235), small cell lung cancer (AACR; Cancer Research 2017; 77 (13 Suppl):Abstract nr DDT02-04), breast cancer (Cell Reports, 2017, 21, p3498), triple negative breast cancer (AACR; Cancer Res 2015; 75 (15 Suppl):Abstract nr 4786), gastric cancer (International Journal of Oncology, 2016, 49, p1195), colorectal cancer (Oncotarget, 2015, 6, p22799), ovarian cancer (J Histochem Cytochem 2013, 61, p206), bladder cancer (Clinical Cancer Research, 2018, CCR-18-1270), hepatocellular cancer (Oncology Reports, 2018, 40, p536), melanoma (PLoS One, 2013, 8, e74710; J Clin Invest. 2018, 128, p517), sarcoma (Oncology Letters, 2018, 16, p2161), oropharyngeal squamous cell carcinoma (Oncotarget, 2017, 8, p14847), chronic myelogenous leukemia (J Clin Invest, 2016, 126, p3961), epidermal squamous cell carcinoma (Carcinogenesis, 2017, 38, p827), nasopharyngeal carcinoma (Oncology Reports, 2016, 35, p1703), neuroblastoma (Molecular Oncology, 2015, 9, p617), endometrial carcinoma (Gynecol Oncol., 2016, 140, p145), cervical cancer (Pharmazie, 2018, 73, p269). These findings have led to further research which show that inhibiting PRMT5 reduces cell proliferation (Molecular and Cellular Biology 2008, 28, p6262, The Journal of Biological Chemistry 2013, 288, p35534).

Inhibitors of arginine methyl transferases were first disclosed in 2004 by Cheng et al in the Journal of Biological Chemistry—Vol. 279 (23), p. 23892. Since then, various other compounds and substances having greater selectivity towards either type I or type II arginine methyl transferases have been disclosed. Other publications that disclose small molecules as inhibitors in relation to PRMT5 are: WO2011077133, WO2011079236, WO2014100695, WO2014100716, WO2014100719, WO2014100730, WO2014100734, WO2014128465, WO2014145214, WO2015200677, WO2015200680, WO2015198229, WO2016022605, WO2016034671, WO2016034673, WO2016034675, WO2016038550, WO2016135582, WO2016145150, WO2016178870, WO2017032840, WO2018160824, WO2018152501, WO2018085818, WO2018065365 and ACS Medicinal Chemistry Letters 2015, 6, p408.

SUMMARY OF THE INVENTION

In accordance with one aspect, the invention provides compound of general formula (I), its stereoisomer, or its pharmaceutically acceptable salt,

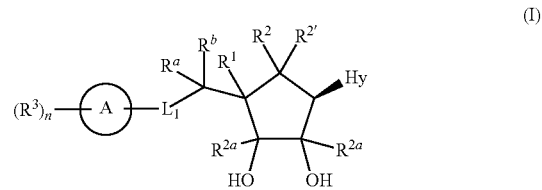

wherein, $L_1$ is selected from bond, —$CR^aR^b$—, —$NR^a$—, S, and O;

$R^a$ and $R^b$ are independently selected at each occurrence from hydrogen, substituted or unsubstituted alkyl, and substituted or unsubstituted cycloalkyl;

ring A is selected from formula (i), (ii), (iii) and (iv), wherein the substituent $R^3$ on ring A may be substituted on any of the ring carbon atoms,

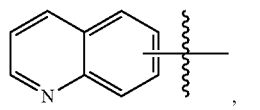

(i)

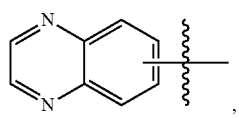

(ii)

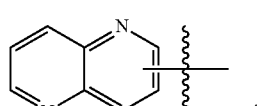

(iii) and

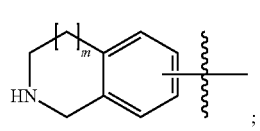

(iv)
;

Hy is selected from formula (a-1) to (h-1), provided that when Hy is (h-1) then ring A cannot be formula (i),

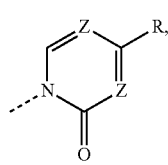

(a-1)

$Z = CR^{10}, N$

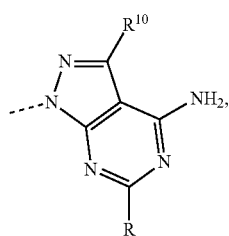

(b-1)

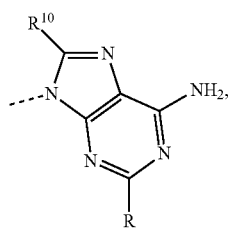

(c-1)

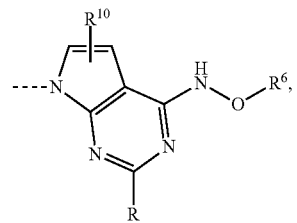

(d-1)

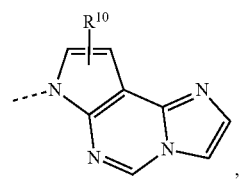

(e-1)

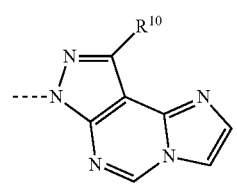

(f-1)

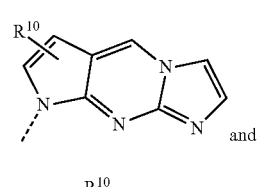

(g-1) and

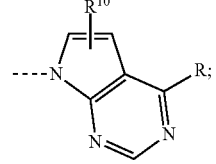

(h-1)

R is selected from —$NR^4R^5$, hydrogen, substituted or unsubstituted alkyl and cycloalkyl;

Z is selected from $CR^{10}$ and N;

$R^1$ and $R^2$ together with the carbon atoms to which they are attached form a bond in order to form a —C=C—; or $R^1$ and $R^2$ together with the carbon atoms to which they are attached form a cyclopropane ring;

$R^{2'}$ and $R^{2a}$ which may be same or different and are independently selected from hydrogen and substituted or unsubstituted alkyl;

$R^3$ is independently selected at each occurrence from halogen, cyano, nitro, substituted or unsubstituted alkyl, —$OR^6$, —$NR^7R^8$, substituted or unsubstituted cycloalkyl, —C(O)OH, —C(O)O-alkyl, —C(O)$R^9$, —C(O)$NR^7R^8$, —$NR^7$C(O)$R^9$, substituted or unsubstituted aryl, substituted or unsubstituted heteroaryl, and substituted or unsubstituted heterocyclyl;

$R^4$ and $R^5$ are independently selected from hydrogen, substituted or unsubstituted alkyl, and substituted or unsubstituted cycloalkyl;

$R^6$ is selected from hydrogen, substituted or unsubstituted alkyl, and substituted or unsubstituted cycloalkyl;

$R^7$ and $R^8$ are independently selected from hydrogen, substituted or unsubstituted alkyl, and substituted or unsubstituted cycloalkyl;

$R^9$ is selected from substituted or unsubstituted alkyl and substituted or unsubstituted cycloalkyl;

$R^{10}$ is selected from hydrogen, halogen, and substituted or unsubstituted alkyl;

'n' is an integer ranging from 0 to 4, both inclusive;

'm' is an integer ranging from 0 to 1, both inclusive;

when an alkyl group is substituted, it is substituted with 1 to 4 substituents independently selected from oxo (=O), halogen, cyano, cycloalkyl, aryl, heteroaryl, heterocyclyl, —OR$^{7a}$, —C(=O)OH, —C(=O)O(alkyl), —NR$^{8a}$R$^{8b}$, —NR$^{8a}$C(=O)R$^{9a}$, and —C(=O)NR$^{8a}$R$^{8b}$;

when the heteroaryl group is substituted, it is substituted with 1 to 4 substituents independently selected from halogen, cyano, alkyl, haloalkyl, cycloalkyl, heterocyclyl, —OR$^{7a}$, —NR$^{8a}$R$^{8b}$, —NR$^{7a}$C(=O)R$^{9a}$, and —C(=O)NR$^{8a}$R$^{8b}$;

when the heterocylyl group is substituted, it is substituted with 1 to 4 substituents independently selected from halogen, cyano, alkyl, haloalkyl, cycloalkyl, heterocyclyl, —OR$^{7a}$, —NR$^{8a}$R$^{8b}$, —NR$^{7a}$C(=O)R$^{9a}$, and —C(=O)NR$^{8a}$R$^{8b}$;

when the aryl group is substituted, it is substituted with 1 to 4 substituents independently selected from halogen, cyano, alkyl, haloalkyl, cycloalkyl, heterocyclyl, —OR$^{7a}$, —NR$^{8a}$R$^{8b}$, —NR$^{7a}$C(=O)R$^{9a}$, and —C(=O)NR$^{8a}$R$^{8b}$;

when the cycloalkyl group is substituted, it is substituted with 1 to 4 substituents independently selected from halogen, cyano, alkyl, haloalkyl, —OR$^{7a}$, —NR$^{8a}$R$^{8b}$, —NR$^{7a}$C(=O)R$^{9a}$, and —C(=O)NR$^{8a}$R$^{8b}$;

R$^{7a}$ is selected from hydrogen, alkyl, haloalkyl, and cycloalkyl;

R$^{8a}$ and R$^{8b}$ are each independently selected from hydrogen, alkyl, and cycloalkyl; and R$^{9a}$ is selected from alkyl and cycloalkyl.

The details of one or more embodiments of the invention set forth in below are only illustrative in nature and not intended to limit to the scope of the invention. Other features, objects and advantages of the inventions will be apparent from the description and claims.

According to one embodiment, the invention provides compound having the structure of formula (II), its stereoisomer, or its pharmaceutically acceptable salt,

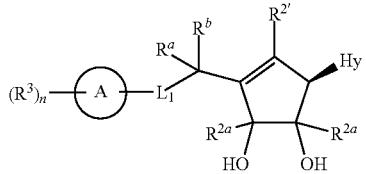
(II)

wherein,

Ring A, Hy, L$_1$, R$^{2a}$, R$^{2'}$, R$^a$, R$^b$, R$^3$ and n are as defined herein above.

According to one embodiment, the invention provides compound having the structure of formula (IIa), its stereoisomer, or its pharmaceutically acceptable salt,

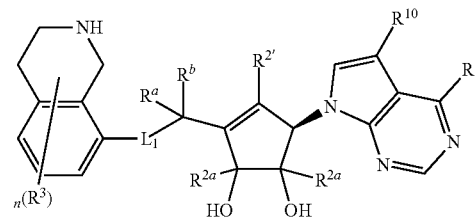
(IIa)

wherein,

L$_1$, R$^{2a}$, R$^{2'}$, R$^a$, R$^b$, R$^3$, R, R$^{10}$ and n are as defined herein above.

According to another embodiment, the invention provides compound having the structure of formula (III), its stereoisomer, or its pharmaceutically acceptable salt,

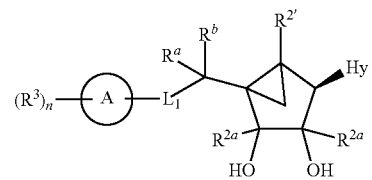
(III)

wherein,

Ring A, Hy, L$_1$, R$^{2a}$, R$^{2'}$, R$^a$, R$^b$, R$^3$ and n are as defined herein above.

In any of the above embodiment of the invention, R$^3$ is independently selected at each occurrence from halogen, substituted or unsubstituted alkyl, and —NR$^7$R$^8$;

In certain embodiment, R$^3$ is independently selected from F, Cl, Br, —NH$_2$, —CH$_3$, and —CH(F)$_2$.

In any of the above embodiment of the invention, L$_1$ is selected from —CH$_2$—, or —NH—.

In any of the above embodiment of the invention, R$^a$, R$^b$, R$^{2'}$ and R$^{2a}$ are independently hydrogen or methyl.

In certain embodiment, R$^a$, R$^b$, R$^{2'}$ and R$^{2a}$ are hydrogen.

In accordance with an embodiment of the invention, ring A is selected from formula (i), (ii), (iii) and (iv), wherein the substituent R$^3$ on ring A may be substituted on any of the ring carbon atoms,

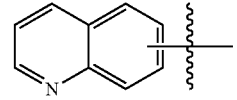
(i)

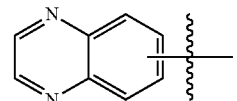
(ii)

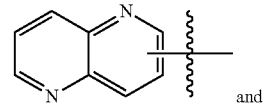
(iii)

and

-continued

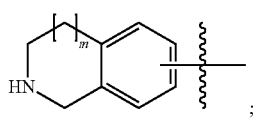
(iv)

In accordance with an embodiment of the invention, Hy is selected from formula (a-1) to (h-1), provided that when Hy is (h-1) then ring A cannot be formula (i),

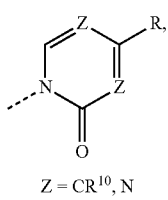
(a-1)

$Z = CR^{10}, N$

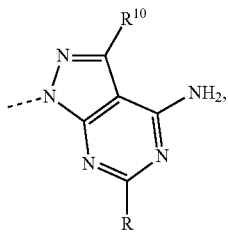
(b-1)

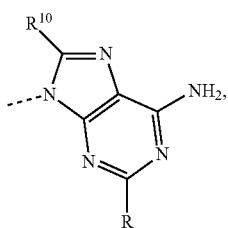
(c-1)

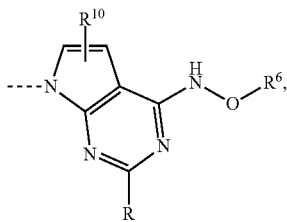
(d-1)

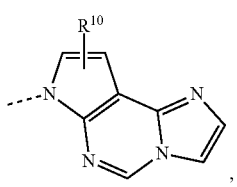
(e-1)

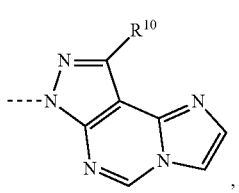
(f-1)

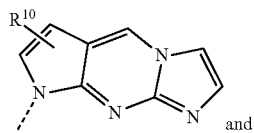
(g-1)

and

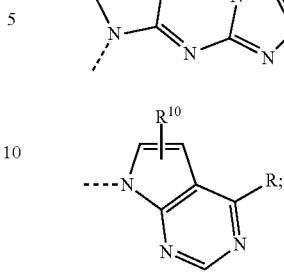
(h-1)

In accordance with an embodiment of the invention, $R^{10}$ is selected from hydrogen, —F, and methyl.

In certain embodiment of the invention, Hy is selected from,

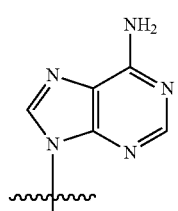 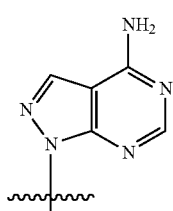

,

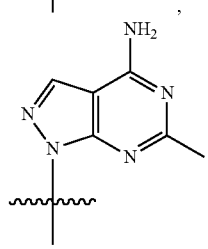

,

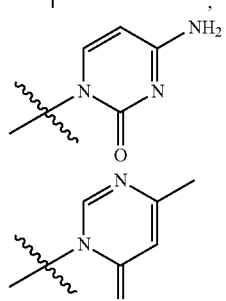 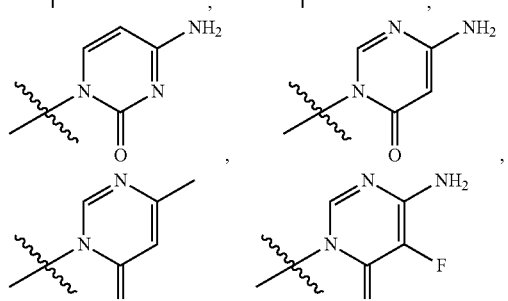

,

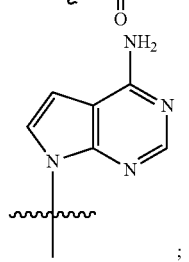

;

In any of the above embodiment of the invention, $R^a$, $R^b$, $R^{2'}$ and $R^{2a}$ are independently hydrogen or methyl; $L_1$ is selected from —CH$_2$—, or —NH—; ring A is selected from formula (i), (ii), (iii) and (iv), wherein the substituent $R^3$ on ring A may be substituted on any of the ring carbon atoms,

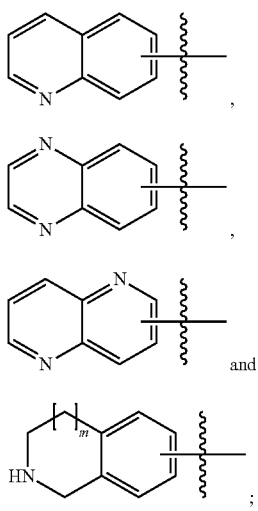

R³ is independently selected at each occurrence from halogen, substituted or unsubstituted alkyl, and —NR⁷R⁸; Hy is selected from formula (a-1) to (h-1), provided that when Hy is selected from formula (a-1) to (h-1), provided that when Hy is (h-1) then ring A cannot be formula (i),

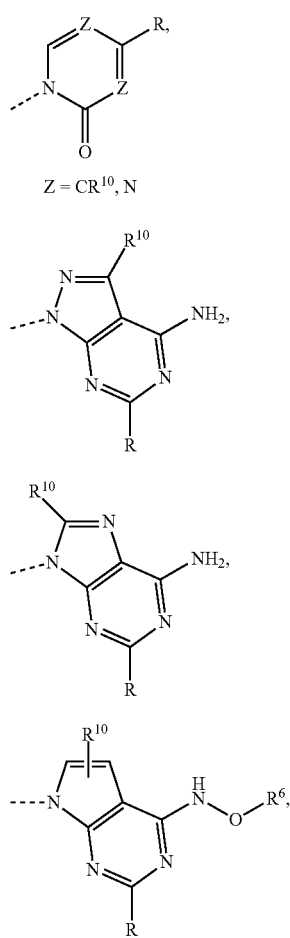

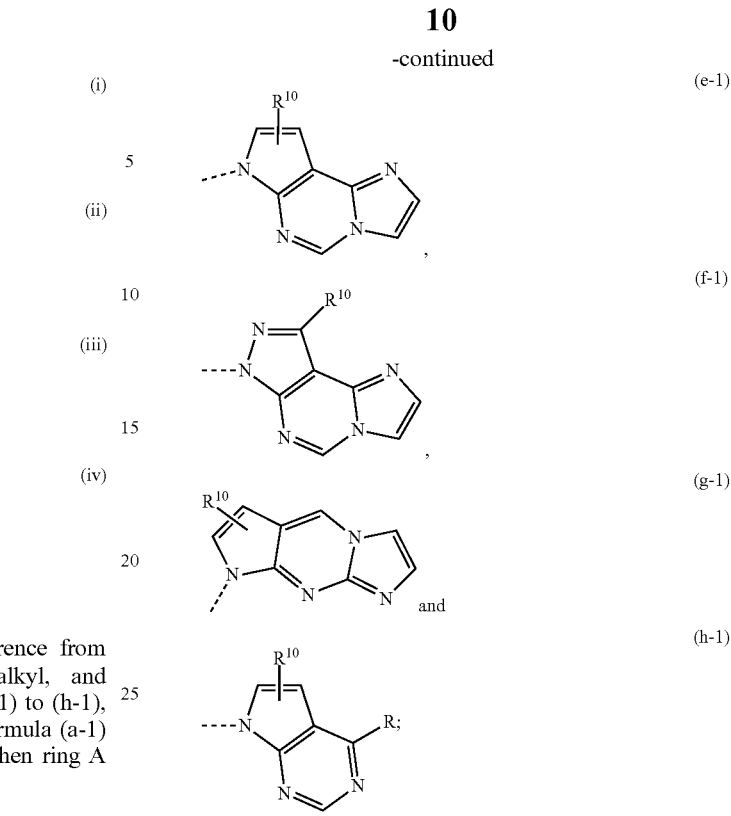

wherein R is selected from —NR⁴R⁵, hydrogen, and substituted or unsubstituted alkyl; Z is selected from CR¹⁰ and N; R¹⁰ is selected from hydrogen, halogen, and substituted or unsubstituted alkyl; R⁴ and R⁵ are independently selected from hydrogen and substituted or unsubstituted alkyl; R⁶ is selected from hydrogen and substituted or unsubstituted alkyl; 'n' is an integer ranging from 0 to 4, both inclusive; 'm' is an integer ranging from 0 to 1, both inclusive.

The examples 1 to 30 given herein are representative compounds, which are only illustrative in nature and are not intended to limit to the scope of the invention.

It should be understood that formula (I), (II), (IIa) and (III) structurally encompasses all stereoisomers and isotopes wherever applicable and pharmaceutically acceptable salts that may be contemplated from the chemical structures generally described herein.

According to one embodiment, there are provided compound of formula (I), (II), (IIa) and (III), its stereoisomer, wherein the compound is in the form of the free base or is a pharmaceutically acceptable salt thereof.

In another aspect of the invention, there are provided compound of formula (I), (II), (IIa) and (III), its stereoisomer, or its pharmaceutically acceptable salt for treating the diseases, disorders, syndromes or conditions associated with PRMT5 enzyme.

In one embodiment of the present invention, there are provided compound of formula (I), (II), (IIa) and (III), its stereoisomer, or its pharmaceutically acceptable salt for treating disease, disorder, syndrome or condition by inhibition of PRMT5 enzyme.

In another aspect of the invention, there are provided compound of formula (I), (II), (IIa) and (III), its stereoisomer, or its pharmaceutically acceptable salt for use as a medicament.

In another aspect of the invention, there are provided compound of formula (I), (II), (IIa) and (III), its stereoisomer, or its pharmaceutically acceptable salt for use in treating the disease, disorder, syndrome or condition associated with PRMT5.

In one embodiment of the present invention, there are provided compound of formula (I), (II), (IIa) and (III), its stereoisomer, or its pharmaceutically acceptable salt for use in treating disease, disorder, syndrome or condition by the inhibition of PRMT5.

In another aspect of the invention, there is provided a method of inhibiting PRMT5 by using a compound selected from formula (I), (II), (IIa) and (III), its stereoisomer, or its pharmaceutically acceptable salt.

In another aspect of the invention, there is provided a method of treating disease, disorder or condition associated with PRMT5 by using a compound selected from formula (I), (II), (IIa) and (III).

In another aspect of the present invention, a method of treating disease, disorder or condition associated with PRMT5 is selected from glioblastoma multiforme, prostate cancer, and pancreatic cancer, mantle cell lymphoma, non-Hodgkin's lymphomas and diffuse large B-cell lymphoma, acute myeloid leukemia, acute lymphoblastic leukemia, multiple myeloma, non-small cell lung cancer, small cell lung cancer, breast cancer, triple negative breast cancer, gastric cancer, colorectal cancer, ovarian cancer, bladder cancer, hepatocellular cancer, melanoma, sarcoma, oropharyngeal squamous cell carcinoma, chronic myelogenous leukemia, epidermal squamous cell carcinoma, nasopharyngeal carcinoma, neuroblastoma, endometrial carcinoma, and cervical cancer.

In another aspect of the invention, there is provided a use of a compound selected from formula (I), (II), (IIa) and (III), its stereoisomer or its pharmaceutically acceptable salt, for the manufacture of a medicament for treating, the disease, disorder, syndrome or condition associated with PRMT5.

In another aspect, the invention provides a pharmaceutical composition comprising at least one compound of formula (I), (II), (IIa) and (III), its stereoisomer, or its pharmaceutically acceptable salt and at least one pharmaceutically acceptable excipient.

In another aspect, the invention provides a pharmaceutical composition comprising a therapeutically effective amount of compound of formula (I), (II), (IIa) and (III), its stereoisomer, or its pharmaceutically acceptable salt, for use in treating, the disease, disorder, syndrome or condition associated with PRMT5 by administering to the subject in need thereof.

In another aspect of the present invention, the disease, disorder, syndrome or condition associated with PRMT5 are selected from the group consisting of glioblastoma multiforme, prostate cancer, and pancreatic cancer, mantle cell lymphoma, non-Hodgkin's lymphomas and diffuse large B-cell lymphoma, acute myeloid leukemia, acute lymphoblastic leukemia, multiple myeloma, non-small cell lung cancer, small cell lung cancer, breast cancer, triple negative breast cancer, gastric cancer, colorectal cancer, ovarian cancer, bladder cancer, hepatocellular cancer, melanoma, sarcoma, oropharyngeal squamous cell carcinoma, chronic myelogenous leukemia, epidermal squamous cell carcinoma, nasopharyngeal carcinoma, neuroblastoma, endometrial carcinoma, and cervical cancer.

In another embodiment of the invention the compound, its stereoisomer, or its pharmaceutically acceptable salt are:

(1S,2R,5R)-3-(2-(2-Amino-3-chloro-5-fluoroquinolin-7-yl)ethyl)-5-(6-amino-9H-purin-9-yl)cyclopent-3-ene-1,2-diol (Compound 1);

(1S,2R,5R)-3-(2-(6-Amino-7-chloro-1,5-naphthyridin-3-yl)ethyl)-5-(4-amino-7H-pyrrolo [2,3-d]pyrimidin-7-yl)cyclopent-3-ene-1,2-diol (Compound 2);

(1S,2R,5R)-5-(4-Amino-7H-pyrrolo[2,3-d]pyrimidin-7-yl)-3-(2-(3-aminoquinoxalin-6-yl)ethyl)cyclopent-3-ene-1,2-diol (Compound 3);

(1R,2R,3S,4R,5S)-4-(4-Amino-7H-pyrrolo[2,3-d]pyrimidin-7-yl)-1-(2-(3-aminoquinoxalin-6-yl)ethyl)bicyclo [3.1.0]hexane-2,3-diol (Compound 4);

(1S,2R,5R)-5-(4-Amino-1H-pyrazolo[3,4-d]pyrimidin-1-yl)-3-(2-(2-amino-3-chloro-5-fluoroquinolin-7-yl)ethyl)cyclopent-3-ene-1,2-diol (Compound 5);

(1S,2R,5R)-3-(2-(2-amino-3-chloro-5-fluoroquinolin-7-yl)ethyl)-5-(4-amino-6-methyl-1H-pyrazolo[3,4-d]pyrimidin-1-yl)cyclopent-3-ene-1,2-diol (Compound 6);

(1S,2R,5R)-5-(4-amino-7H-pyrrolo[2,3-d]pyrimidin-7-yl)-3-(((6-(difluoromethyl)-1,2,3,4-tetrahydroisoquinolin-8-yl)oxy)methyl)cyclopent-3-ene-1,2-diol (Compound 7);

(1S,2R,5R)-5-(4-amino-7H-pyrrolo[2,3-d]pyrimidin-7-yl)-3-(2-(6-methyl-1,2,3,4-tetrahydroisoquinolin-8-yl)ethyl)cyclopent-3-ene-1,2-diol (Compound 8);

(1S,2R,5R)-5-(4-amino-7H-pyrrolo[2,3-d]pyrimidin-7-yl)-3-(2-(5-fluoro-1,2,3,4-tetrahydroisoquinolin-8-yl)ethyl)cyclopent-3-ene-1,2-diol (Compound 9);

(1S,2R,5R)-5-(4-amino-7H-pyrrolo[2,3-d]pyrimidin-7-yl)-3-(2-(6-(difluoromethyl)-1,2,3,4-tetrahydroisoquinolin-8-yl)ethyl)cyclopent-3-ene-1,2-diol (Compound 10);

(1S,2R,5R)-5-(4-amino-7H-pyrrolo[2,3-d]pyrimidin-7-yl)-3-(2-(5-(difluoromethyl)-1,2,3,4-tetrahydroisoquinolin-8-yl)ethyl)cyclopent-3-ene-1,2-diol (Compound 11);

(1S,2R,5R)-5-(4-amino-7H-pyrrolo[2,3-d]pyrimidin-7-yl)-3-(((6-(difluoromethyl)-5-fluoro-1,2,3,4-tetrahydroisoquinolin-8-yl)oxy)methyl)cyclopent-3-ene-1,2-diol (Compound 12);

(1S,2R,5R)-5-(4-amino-7H-pyrrolo[2,3-d]pyrimidin-7-yl)-3-(2-(6-(difluoromethyl)-5-fluoro-1,2,3,4-tetrahydroisoquinolin-8-yl)ethyl)cyclopent-3-ene-1,2-diol (Compound 13);

(1S,2R,5R)-3-(2-(6-(difluoromethyl)-1,2,3,4-tetrahydroisoquinolin-8-yl)ethyl)-5-(4-methyl-7H-pyrrolo[2,3-d]pyrimidin-7-yl)cyclopent-3-ene-1,2-diol (Compound 14);

(1S,2R,5R)-3-(2-(6-(difluoromethyl)-5-fluoro-1,2,3,4-tetrahydroisoquinolin-8-yl)ethyl)-5-(4-methyl-7H-pyrrolo[2,3-d]pyrimidin-7-yl)cyclopent-3-ene-1,2-diol (Compound 15);

4-Amino-1-((1R,4R,5S)-3-(((2-amino-3-chloro-5-fluoroquinolin-7-yl)oxy) methyl)-4,5-dihydroxycyclopent-2-en-1-yl)pyrimidin-2 (1H)-one (Compound 16);

6-amino-3-((1R,4R,5S)-3-(((2-amino-3-chloro-5-fluoroquinolin-7-yl)oxy)methyl)-4,5-dihydroxycyclopent-2-en-1-yl)pyrimidin-4 (3H)-one (Compound 17);

3-((1R,4R,5S)-3-(((2-amino-3-chloro-5-fluoroquinolin-7-yl)oxy)methyl)-4,5-dihydroxycyclopent-2-en-1-yl)-6-methylpyrimidin-4 (3H)-one (Compound 18);

6-amino-3-((1R,4R,5S)-3-(((2-amino-3-chloro-5-fluoroquinolin-7-yl)oxy)methyl)-4,5-dihydroxycyclopent-2-en-1-yl)-5-fluoropyrimidin-4 (3H)-one (Compound 19);

(1S,2R,5R)-5-(4-amino-7H-pyrrolo[2,3-d]pyrimidin-7-yl)-3-(2-(6-chloro-5-fluoro-1,2,3,4-tetrahydroisoquinolin-8-yl)ethyl)cyclopent-3-ene-1,2-diol (Compound 20);

(1S,2R,5R)-5-(4-amino-7H-pyrrolo[2,3-d]pyrimidin-7-yl)-3-(2-(5,6-difluoro-1,2,3,4-tetrahydroisoquinolin-8-yl)ethyl)cyclopent-3-ene-1,2-diol (Compound 21);

(1S,2R,5R)-5-(4-amino-7H-pyrrolo[2,3-d]pyrimidin-7-yl)-3-(2-(6-(difluoromethyl)-5-fluoro-4-methyl-1,2,3,4-tetrahydroisoquinolin-8-yl)ethyl)cyclopent-3-ene-1,2-diol (Compound 22A and B);

(1S,2R,5R)-5-(4-amino-7H-pyrrolo[2,3-d]pyrimidin-7-yl)-3-(2-(6-(difluoromethyl)-5-fluoro-3-methyl-1,2,3,4-tetrahydroisoquinolin-8-yl)ethyl)cyclopent-3-ene-1,2-diol (Compound 23A and B);

(1R,2R,3S,4R,5S)-1-(2-(6-Amino-7-chloro-1,5-naphthyridin-3-yl)ethyl)-4-(4-amino-7H-pyrrolo[2,3-d]pyrimidin-7-yl)bicyclo[3.1.0]hexane-2,3-diol (Compound 24);

(1S,2R,5R)-5-(4-amino-5-methyl-7H-pyrrolo[2,3-d]pyrimidin-7-yl)-3-(2-(6-(difluoromethyl)-5-fluoro-1,2,3,4-tetrahydroisoquinolin-8-yl)ethyl)cyclopent-3-ene-1,2-diol (Compound 25);

(1S,2R,5R)-3-(2-(2-Amino-3-bromoquinolin-7-yl)ethyl)-5-(7H-imidazo[1,2-c]pyrrolo[3,2-e]pyrimidin-7-yl)cyclopent-3-ene-1,2-diol (Compound 26);

(1S,2R,5R)-3-(2-(2-Amino-3-chloro-5-fluoroquinolin-7-yl)ethyl)-5-(7H-imidazo[1,2-c]pyrrolo[3,2-e]pyrimidin-7-yl)cyclopent-3-ene-1,2-diol (Compound 27);

(1S,2R,5R)-3-(2-(2-Amino-3-chloroquinolin-7-yl)ethyl)-5-(8H-imidazo[1,2-a]pyrrolo[2,3-d]pyrimidin-8-yl)cyclopent-3-ene-1,2-diol (Compound 28);

(1S,2R,5R)-3-(2-(2-Amino-3-chloro-5-fluoroquinolin-7-yl)ethyl)-5-(7H-imidazo[1,2-c]pyrazolo[4,3-e]pyrimidin-7-yl)cyclopent-3-ene-1,2-diol (Compound 29); and (1S,2R,5R)-3-(2-(2-Amino-3-chloro-5-fluoroquinolin-7-yl)ethyl)-5-(4-(methoxyamino)-7H-pyrrolo[2,3-d]pyrimidin-7-yl)cyclopent-3-ene-1,2-diol (Compound 30).

In another embodiment of the invention the compound, its stereoisomer, or its pharmaceutically acceptable salt are:

(1S,2R,5R)-3-(2-(2-Amino-3-chloro-5-fluoroquinolin-7-yl)ethyl)-5-(6-amino-9H-purin-9-yl)cyclopent-3-ene-1,2-diol (Compound 1);

(1S,2R,5R)-5-(4-Amino-1H-pyrazolo[3,4-d]pyrimidin-1-yl)-3-(2-(2-amino-3-chloro-5-fluoroquinolin-7-yl)ethyl)cyclopent-3-ene-1,2-diol (Compound 5);

(1S,2R,5R)-3-(2-(2-amino-3-chloro-5-fluoroquinolin-7-yl)ethyl)-5-(4-amino-6-methyl-1H-pyrazolo[3,4-d]pyrimidin-1-yl)cyclopent-3-ene-1,2-diol (Compound 6);

(1S,2R,5R)-5-(4-amino-7H-pyrrolo[2,3-d]pyrimidin-7-yl)-3-(2-(6-(difluoromethyl)-1,2,3,4-tetrahydroisoquinolin-8-yl)ethyl)cyclopent-3-ene-1,2-diol (Compound 10);

(1S,2R,5R)-5-(4-amino-7H-pyrrolo[2,3-d]pyrimidin-7-yl)-3-(2-(6-(difluoromethyl)-5-fluoro-1,2,3,4-tetrahydroisoquinolin-8-yl)ethyl)cyclopent-3-ene-1,2-diol (Compound 13);

(1S,2R,5R)-3-(2-(6-(difluoromethyl)-1,2,3,4-tetrahydroisoquinolin-8-yl)ethyl)-5-(4-methyl-7H-pyrrolo[2,3-d]pyrimidin-7-yl)cyclopent-3-ene-1,2-diol (Compound 14);

(1S,2R,5R)-3-(2-(6-(difluoromethyl)-5-fluoro-1,2,3,4-tetrahydroisoquinolin-8-yl)ethyl)-5-(4-methyl-7H-pyrrolo[2,3-d]pyrimidin-7-yl)cyclopent-3-ene-1,2-diol (Compound 15);

(1S,2R,5R)-5-(4-amino-7H-pyrrolo[2,3-d]pyrimidin-7-yl)-3-(2-(6-(difluoromethyl)-5-fluoro-4-methyl-1,2,3,4-tetrahydroisoquinolin-8-yl)ethyl)cyclopent-3-ene-1,2-diol (Compound 22A and B); and (1S,2R,5R)-5-(4-amino-7H-pyrrolo[2,3-d]pyrimidin-7-yl)-3-(2-(6-(difluoromethyl)-5-fluoro-3-methyl-1,2,3,4-tetrahydroisoquinolin-8-yl)ethyl)cyclopent-3-ene-1,2-diol (Compound 23A and B).

DETAILED DESCRIPTION OF THE INVENTION

Unless otherwise stated, the following terms used in the specification and claims have the meanings given below.

For purposes of interpreting the specification, the following definitions will apply and whenever appropriate, terms used in the singular will also include the plural and vice versa.

The terms "halogen" or "halo" means fluorine, chlorine, bromine, or iodine.

The term "alkyl" refers to an alkane derived hydrocarbon radical that includes solely carbon and hydrogen atoms in the backbone, contains no unsaturation, has from one to six carbon atoms, and is attached to the remainder of the molecule by a single bond, for example $(C_1-C_6)$alkyl or $(C_1-C_4)$alkyl, representative groups include e.g., methyl, ethyl, n-propyl, 1-methylethyl (isopropyl), n-butyl, n-pentyl and the like. Unless set forth or recited to the contrary, all alkyl groups described or claimed herein may be straight chain or branched.

The term "haloalkyl" refers to an alkyl group as defined above that is substituted by one or more halogen atoms as defined above. For example $(C_1-C_6)$ haloalkyl or $(C_1-C_4)$ haloalkyl. Suitably, the haloalkyl may be monohaloalkyl, dihaloalkyl or polyhaloalkyl including perhaloalkyl. A monohaloalkyl can have one iodine, bromine, chlorine or fluorine atom. Dihaloalkyl and polyhaloalkyl groups can be substituted with two or more of the same halogen atoms or a combination of different halogen atoms. Suitably, a polyhaloalkyl is substituted with up to 12 halogen atoms. Non-limiting Examples of a haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl and the like. A perhaloalkyl refers to an alkyl having all hydrogen atoms replaced with halogen atoms. Unless set forth or recited to the contrary, all haloalkyl groups described or claimed herein may be straight chain or branched.

The term "cycloalkyl" refers to a non-aromatic mono or multicyclic ring system having 3 to 12 carbon atoms, such as $(C_3-C_{10})$cycloalkyl, $(C_3-C_6)$cycloalkyl, cyclopropyl, cyclobutyl, cyclopentyl, cyclohexyl and the like. Examples of multicyclic cycloalkyl groups include, but are not limited to, perhydronaphththyl, adamantyl and norbornyl groups, bridged cyclic groups or spirobicyclic groups, e.g., spiro(4,4)non-2-yl and the like.

The term "aryl" refers to an aromatic radical having 6- to 14-carbon atoms, including monocyclic, bicyclic and tricyclic aromatic systems, such as phenyl, naphthyl, tetrahydronaphthyl, indanyl, and biphenyl and the like.

The term "heterocyclic ring" or "heterocyclyl ring" or "heterocyclyl", unless otherwise specified, refers to substituted or unsubstituted non-aromatic 3- to 15-membered ring which consists of carbon atoms and with one or more heteroatom(s) independently selected from N, O or S. The heterocyclic ring may be a mono-, bi- or tricyclic ring system, which may include fused, bridged or spiro ring systems and the nitrogen, carbon, oxygen or sulfur atoms in the heterocyclic ring may be optionally oxidized to various oxidation states. In addition, the nitrogen atom may be optionally quaternized, the heterocyclic ring or heterocyclyl may optionally contain one or more olefinic bond(S), and one or two carbon atoms(S) in the heterocyclic ring or heterocyclyl may be interrupted with —CF$_2$—, —C(O)—, —S(O)—, S(O)$_2$ etc. In addition heterocyclic ring may also be fused with aromatic ring. Non-limiting Examples of heterocyclic rings include azetidinyl, benzopyranyl, chromanyl, decahydroisoquinolyl, indolinyl, isoindolinyl, isochromanyl, isothiazolidinyl, isoxazolidinyl, morpholinyl, oxazolinyl, oxazolidinyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisoquinolyl, tetrahydrofuryl, tetrahydropyranyl, thiazolinyl, thiazolidinyl, thiamorpholinyl, thiamorpholinylsulfoxide, thiamorpholinylsulfoneindoline, benzodioxole, tetrahydroquinoline, tetrahydrobenzopyran and the like. The heterocyclic ring may be attached by any atom of the heterocyclic ring that results in the creation of a stable structure.

The term "heteroaryl" unless otherwise specified, refers to a substituted or unsubstituted 5- to 14-membered aromatic heterocyclic ring with one or more heteroatom(S) independently selected from N, O or S. The heteroaryl may be a mono-, bi- or tricyclic ring system. The heteroaryl ring may be attached by any atom of the heteroaryl ring that results in the creation of a stable structure. Non-limiting Examples of a heteroaryl ring include oxazolyl, isoxazolyl, imidazolyl, furyl, indolyl, isoindolyl, pyrrolyl, triazolyl, triazinyl, tetrazolyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl, phthalazinyl and the like.

The compounds of the present invention may have one or more chiral centers. The absolute stereochemistry at each chiral center may be 'R' or 'S'. The compounds of the invention include all diastereomers and enantiomers and mixtures thereof. Unless specifically mentioned otherwise, reference to one stereoisomer applies to any of the possible stereoisomers. Whenever the stereoisomeric composition is unspecified, it is to be understood that all possible stereoisomers are included.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are non-superimposable mirror images of one another. The term "chiral center" refers to a carbon atom to which four different groups are attached. As used herein, the term "diastereomers" refers to stereoisomers which are not enantiomers. The terms "racemate" or "racemic mixture" refer to a mixture of equal parts of enantiomers.

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; c) lessening the disease, disorder or condition or at least one of its clinical or subclinical symptoms or (d) relieving the disease, i.e., causing regression of the state, disorder or condition or at least one of its clinical or subclinical symptoms.

The term "inhibitor" refers to a molecule that binds to an enzyme to inhibit the activity of the said enzyme either partially or completely.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a disease, disorder or condition, is sufficient to cause the effect in the subject, which is the purpose of the administration. The "therapeutically effective amount" will vary depending on the compound, the disease and its severity and the age, weight, physical condition and responsiveness of the subject to be treated.

Pharmaceutically Acceptable Salts

The compounds of the invention may form salts with acid or base. The compounds of invention may be sufficiently basic or acidic to form stable nontoxic acid or base salts, administration of the compound as a pharmaceutically acceptable salt may be appropriate. Non-limiting Examples of pharmaceutically acceptable salts are inorganic, organic acid addition salts formed by addition of acids including hydrochloride salts. Non-limiting Examples of pharmaceutically acceptable salts are inorganic, organic base addition salts formed by addition of bases. The compounds of the invention may also form salts with amino acids. Pharmaceutically acceptable salts may be obtained using standard procedures well known in the art, for example by reacting sufficiently basic compound such as an amine with a suitable acid.

Screening of the compounds of invention for PRMT5 inhibitory activity can be achieved by using various in vitro and in vivo protocols mentioned herein below or methods known in the art.

Pharmaceutical Compositions

The invention relates to pharmaceutical compositions containing the compounds of the formula (I), (II), (IIa) and (III) or pharmaceutically acceptable salts thereof disclosed herein. In a particular, pharmaceutical compositions containing a therapeutically effective amount of at least one compound of formula (I), (II), (IIa) and (III) described herein and at least one pharmaceutically acceptable excipient (such as a carrier or diluent). Preferably, the contemplated pharmaceutical compositions include the compound(s) described herein in an amount sufficient to inhibit PRMT5 to treat the diseases described herein when administered to a subject.

The subjects contemplated include, for example, a living cell and a mammal, including human. The compound of the invention may be associated with a pharmaceutically acceptable excipient (such as a carrier or a diluent) or be diluted by a carrier, or enclosed within a carrier which can be in the form of a capsule, sachet, paper or other container. The pharmaceutically acceptable excipient includes pharmaceutical agent that does not itself induce the production of antibodies harmful to the individual receiving the composition, and which may be administered without undue toxicity.

Examples of suitable carriers or excipients include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, salicylic acid, fatty acids, fatty acid amines, fatty acid monoglycerides and diglycerides, pentaerytritol fatty acid esters, polyoxyethylene, hydroxymethylcellulose and polyvinylpyrrolidone.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for Example, in a sachet.

The pharmaceutical compositions may be in conventional forms, for example, capsules, tablets, caplets, orally disintegrating tablets, aerosols, solutions, suspensions or products for topical application.

The route of administration may be any route which effectively transports the active compound of the invention to the appropriate or desired site of action. Suitable routes of administration include, but are not limited to, oral, oral inhalation, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral formulations include, but are not limited to, tablets, caplets, capsules (soft or hard gelatin), orally disintegrating tablets, dragees (containing the active ingredient in powder or pellet form), troches and lozenges. Tablets, dragees, or capsules having talc and/or a carbohydrate carrier or binder or the like are particularly suitable for oral application. Liquid formulations include, but are not limited to, syrups, emulsions, suspensions, solutions, soft gelatin and sterile injectable liquids, such as aqueous or non-aqueous liquid suspensions or solutions. For parenteral application, particularly suitable are injectable solutions or suspensions, preferably aqueous solutions with the active compound dissolved in polyhydroxylated castor oil.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as pocketed tablets, capsules, and powders in vials or ampoules. Also, the unit dosage form can be a capsule, tablet, caplet, cachet, or lozenge itself, or it can be the appropriate number of any of these in packaged form.

For administration to subject patients, the total daily dose of the compounds of the invention depends, of course, on the mode of administration. For example, oral administration may require a higher total daily dose, than an intravenous (direct into blood). The quantity of active component in a unit dose preparation may be varied or adjusted from 0.1 mg to 1000 mg by oral administration and 1 µg to 5000 µg by inhalation according to the potency of the active component or mode of administration.

Those skilled in the relevant art can determine suitable doses of the compounds for use in treating the diseases and disorders described herein. Therapeutic doses are generally identified through a dose ranging study in subject based on preliminary evidence derived from the animal studies. Doses must be sufficient to result in a desired therapeutic benefit without causing unwanted side effects for the patient. For example, the daily dosage of the PRMT5 inhibitor can range from about 0.1 to about 30.0 mg/kg by oral administration. Mode of administration, dosage forms, suitable pharmaceutical excipients, diluents or carriers can also be well used and adjusted by those skilled in the art. All changes and modifications envisioned are within the scope of the invention.

Methods of Treatment

The invention provides compound of formula (I), (II), (IIa) and (III) and pharmaceutical compositions thereof as protein arginine methyl transferase-5 (PRMT5) inhibitors for treating the diseases, disorders or conditions associated with overexpression of PRMT5. The invention further provides a method of treating diseases, disorders or conditions associated with overexpression of PRMT5 in a subject in need thereof by administering to the subject a therapeutically effective amount of a compound or a pharmaceutical composition of the invention.

In another aspect, the invention relates to a method of treating diseases, disorders or conditions associated with the overexpression of PRMT5. In this method, a subject in need of such treatment is administered a therapeutically effective amount of a compound of formula (I), (II), (IIa) and (III) or a pharmaceutically acceptable salt thereof as described herein.

In one embodiment of the present invention, the diseases, disorders, or conditions associated with the overexpression of PRMT5 are cancer.

In another embodiment, the invention provides a method of treating cancers, particularly, glioblastoma multiforme, prostate cancer, pancreatic cancer, mantle cell lymphoma, non-Hodgkin's lymphomas and diffuse large B-cell lymphoma, acute myeloid leukemia, acute lymphoblastic leukemia, multiple myeloma, non-small cell lung cancer, small cell lung cancer, breast cancer, triple negative breast cancer, gastric cancer, colorectal cancer, ovarian cancer, bladder cancer, hepatocellular cancer, melanoma, sarcoma, oropharyngeal squamous cell carcinoma, chronic myelogenous leukemia, epidermal squamous cell carcinoma, nasopharyngeal carcinoma, neuroblastoma, endometrial carcinoma, and cervical cancer.

It is to be understood that the invention encompasses the compounds of formula (I), (II), (IIa) and (III), or pharmaceutically acceptable salts thereof for use in the treatment of a disease or disorder mentioned herein.

It is to be understood that the invention encompasses the compounds of formula (I), (II), (IIa) and (III) or pharmaceutically acceptable salts thereof in the manufacture of a medicament for treating a disease or disorder mentioned herein.

General Methods of Preparation

The compound of formula described herein may be prepared by techniques known in the art. In addition, the compound of formula described herein may be prepared by following the reaction sequence as depicted in Schemes provided below. Further, in the following schemes, where specific bases, acids, reagents, solvents, coupling agents, etc., are mentioned, it is understood that other bases, acids, reagents, solvents, coupling agents etc., known in the art may also be used and are therefore included within the scope of the present invention. Variations in reaction conditions, for example, temperature and/or duration of the reaction, which may be used as known in the art, are also within the scope of the present invention. All the isomers of the compound of formula in described in these schemes, unless otherwise specified, are also encompassed within the scope of this invention.

Scheme-1
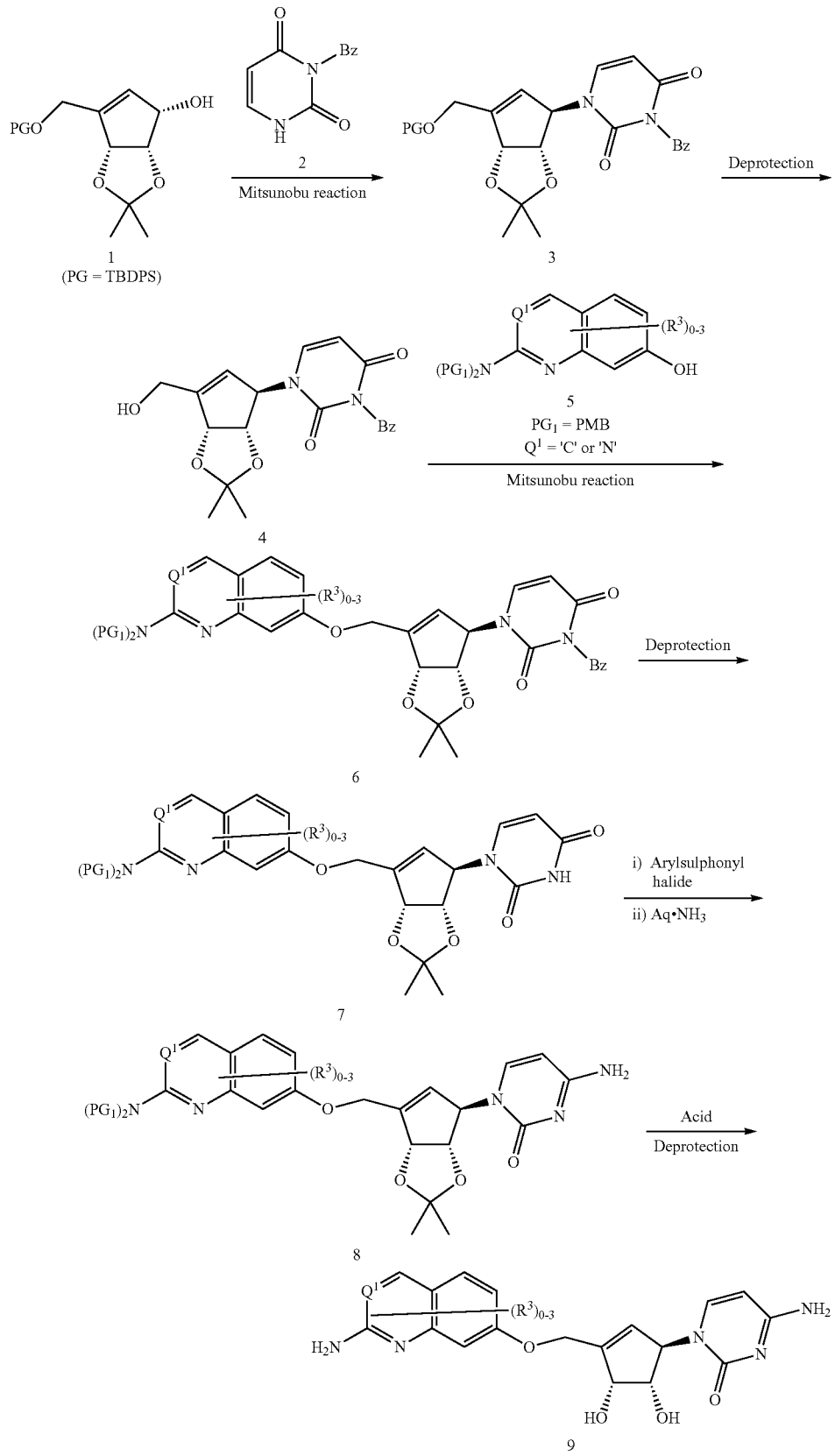

Scheme-1 illustrates the synthesis of compound of formula 9. Mitsunobu reaction of compound of formula 1, which is prepared by following a procedure described in Purinergic Signalling (2015) 11:371-387 with compound of formula 2 using various azo dicarboxylate reagents such as but not limited to DEAD (diethyl azodicarboxylate) or DIAD (diisopropyl azodicarboxylate) in presence of phosphine such as but not limited to PPh$_3$(Triphenylphosphine) gives the compound of formula 3. Typically these reactions are run in etheral solvents such as THF (Tetrahydrofuran), MeTHF (Methyltetrahydrofuran), dioxane, or similar solvents at temperatures ranging from 0° C. to 25° C. Compound of formula 4 is formed upon treatment of compound of formula 3 with fluoride ions such as but not limited to ammonium fluoride, TBAF (Tetra-n-butylammonium fluoride). Typically these reactions are done in etheral solvents such as THF, MeTHF, dioxane, or similar solvents at temperatures ranging from 0° C. to 40° C. Mitsunobu reaction of compound of formula 4 with compound of formula 5 (PG$_1$ is a protecting group such as but not limited to p-methoxybenzyl) using various azo dicarboxylate reagents such as but not limited to DEAD or DIAD in presence of phosphine such as but not limited to PPh$_3$ gives the compound of formula 6. Typically these reactions are run in etheral solvents such as THF, MeTHF, dioxane, or similar solvents at temperatures ranging from 0° C. to 25° C. Deprotection of benzoyl group of compound of formula 6 can be done with reagents like but not limited to NH$_3$ (Ammonia) provides compound of formula 7. Typically these reactions can be run in alcoholic solvents such as MeOH (methanol), EtOH (ethanol) or similar solvents at temperatures ranging from 0° C. to 25° C. Activation of compound of formula 7 with various arylsulphonyl halides such as but not limited 2,4,6-triisopropylbenzenesulfonyl chloride in presence of a base such as but not limited to DMAP (4-Dimethylaminopyridine), DIPEA (N,N-Diisopropylethylamine), NEt$_3$ (triethylamine), followed by displacement with NH$_3$ can furnish the compound of formula 8. Deprotection of compound of formula 8 with acids such as but not limited to HCl or TFA (Trifluoroacetic acid) affords compound of formula 9. Typically, these reactions are run at temperatures ranging from 25° C. to 50° C. Compounds at every step may be purified by standard techniques such as column chromatography, crystallization, reverse phase HPLC (High-performance liquid chromatography) or SFC (Supercritical fluid chromatography).

Scheme 2

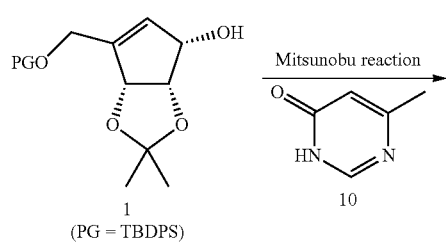

(PG = TBDPS)

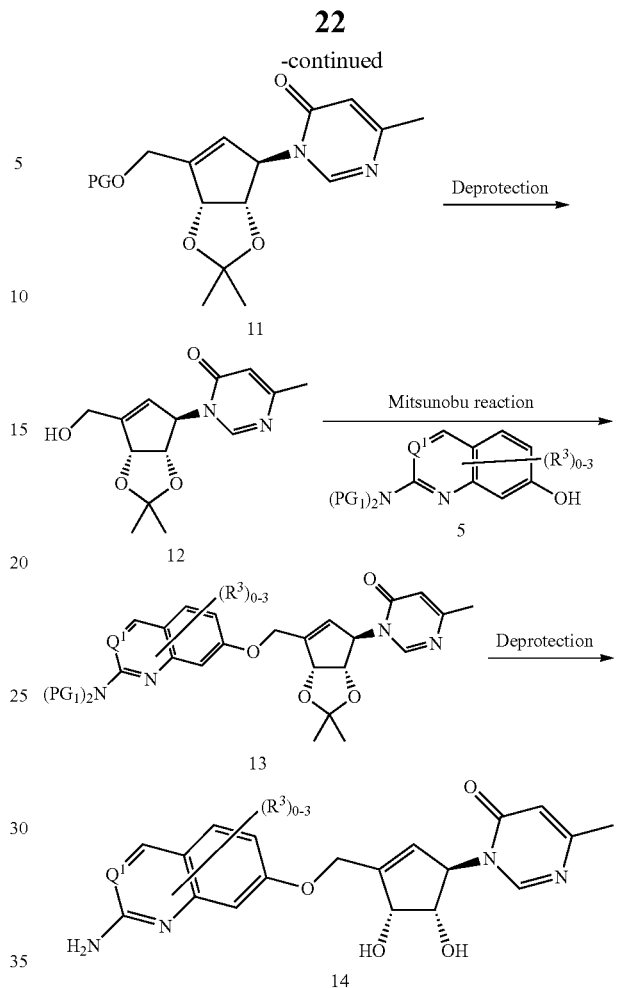

Scheme-2 illustrates the synthesis of compound of formula 14. Mitsunobu reaction of compound of formula 1 with compound of formula 10 using various azo dicarboxylate reagents such as but not limited to DEAD or DIAD in presence of phosphine such as but not limited to PPh$_3$ gives the compound of formula 11. Typically these reactions are run in etheral solvents such as THF, MeTHF, dioxane, or similar solvents at temperatures ranging from 0° C. to 25° C. Compound of formula 12 is formed upon treatment of compound of formula 11 with fluoride ions such as but not limited to ammonium fluoride, TBAF. Typically these reactions are done in etheral solvents such as THF, MeTHF, dioxane, or similar solvents at temperatures ranging from 0° C. to 40° C. Mitsunobu reaction of compound of formula 12 with compound of formula 5 using various azo dicarboxylate reagents such as but not limited to DEAD or DIAD in presence of phosphine such as but not limited to PPh$_3$ gives the compound of formula 13. Typically these reactions are run in etheral solvents such as THF, MeTHF, dioxane, or similar solvents at temperatures ranging from 0° C. to 25° C. Deprotection of compound of formula 13 with acids such as but not limited to HCl or TFA affords compound of formula 14. Typically, these reactions are run at temperatures ranging from 25° C. to 50° C. Compounds at every step may be purified by standard techniques such as column chromatography, crystallization, reverse phase HPLC or SFC.

Scheme 3

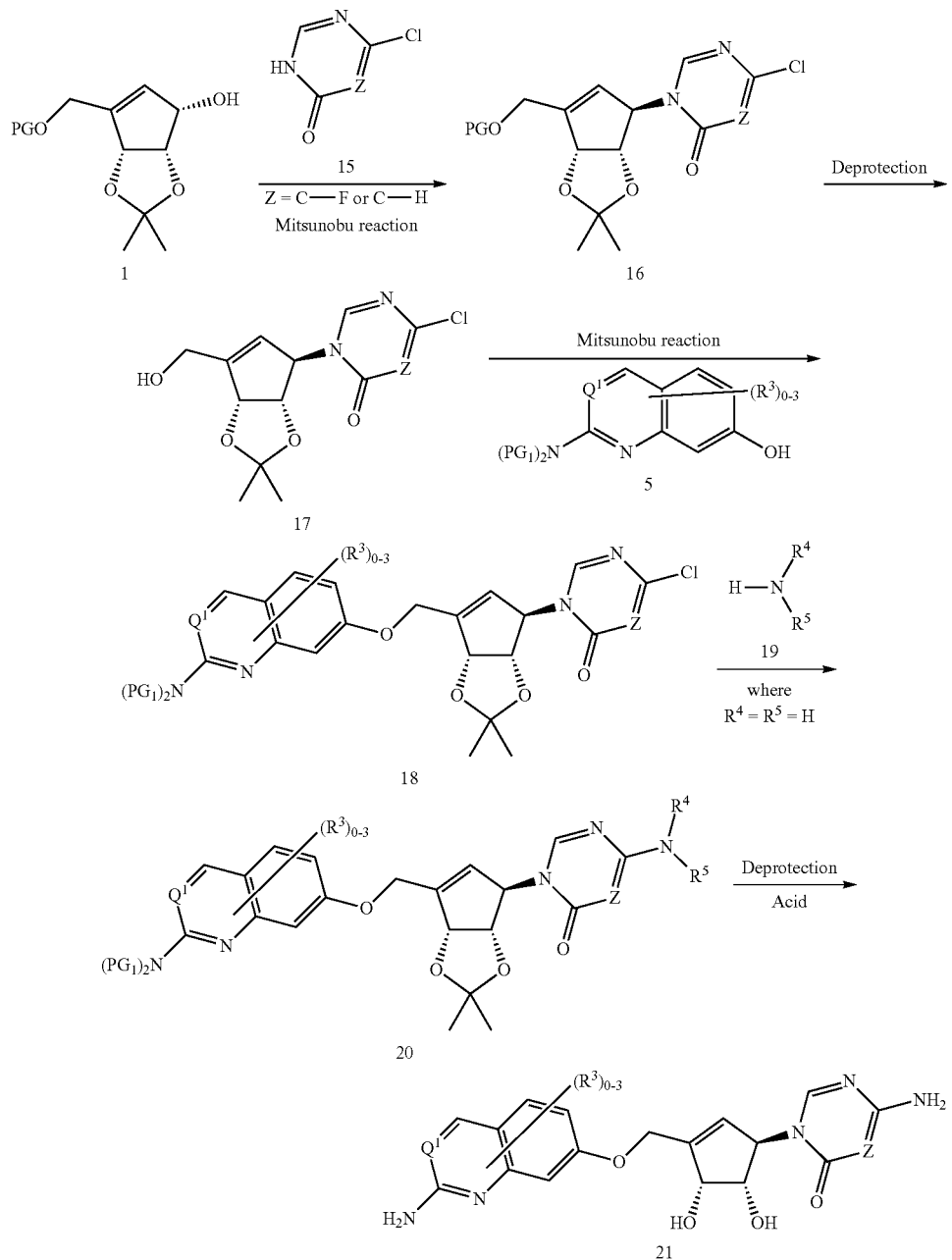

Scheme-3 illustrates the synthesis of compound of formula 21. Mitsunobu reaction of compound of formula 1 with compound of formula 15 using various azo dicarboxylate reagents such as but not limited to DEAD or DIAD in presence of phosphine such as but not limited to PPh$_3$ gives the compound of formula 16. Typically these reactions are run in etheral solvents such as THF, MeTHF, dioxane, or similar solvents at temperatures ranging from 0° C. to 25° C. Compound of formula 17 is formed upon treatment of compound of formula 16 with fluoride ions such as but not limited to ammonium fluoride, TBAF. Typically these reactions are done in etheral solvents such as THF, MeTHF, dioxane, or similar solvents at temperatures ranging from 0° C. to 40° C. Mitsunobu reaction of compound of formula 17 with compound of formula 5 using various azo dicarboxylate reagents such as but not limited to DEAD or DIAD in presence of phosphine such as but not limited to PPh$_3$ gives the compound of formula 18. Typically. these reactions are run in etheral solvents such as THF, MeTHF, dioxane, or similar solvents at temperatures ranging from 0° C. to 25° C. Compound of formula 18 upon treatment with aq.NH$_3$ can give compound of formula 20. Typically. these reactions are done in etheral solvents such as for example dioxane at temperatures ranging from 120° C. to 170° C. in a steel bomb. Deprotection of compound of formula 20 with acids such as but not limited to HCl or TFA affords compound of formula 21. Typically, these reactions are run at temperatures ranging from 25° C. to 50° C. Compounds at every step may be purified by standard techniques such as column chromatography, crystallization, reverse phase HPLC or SFC.
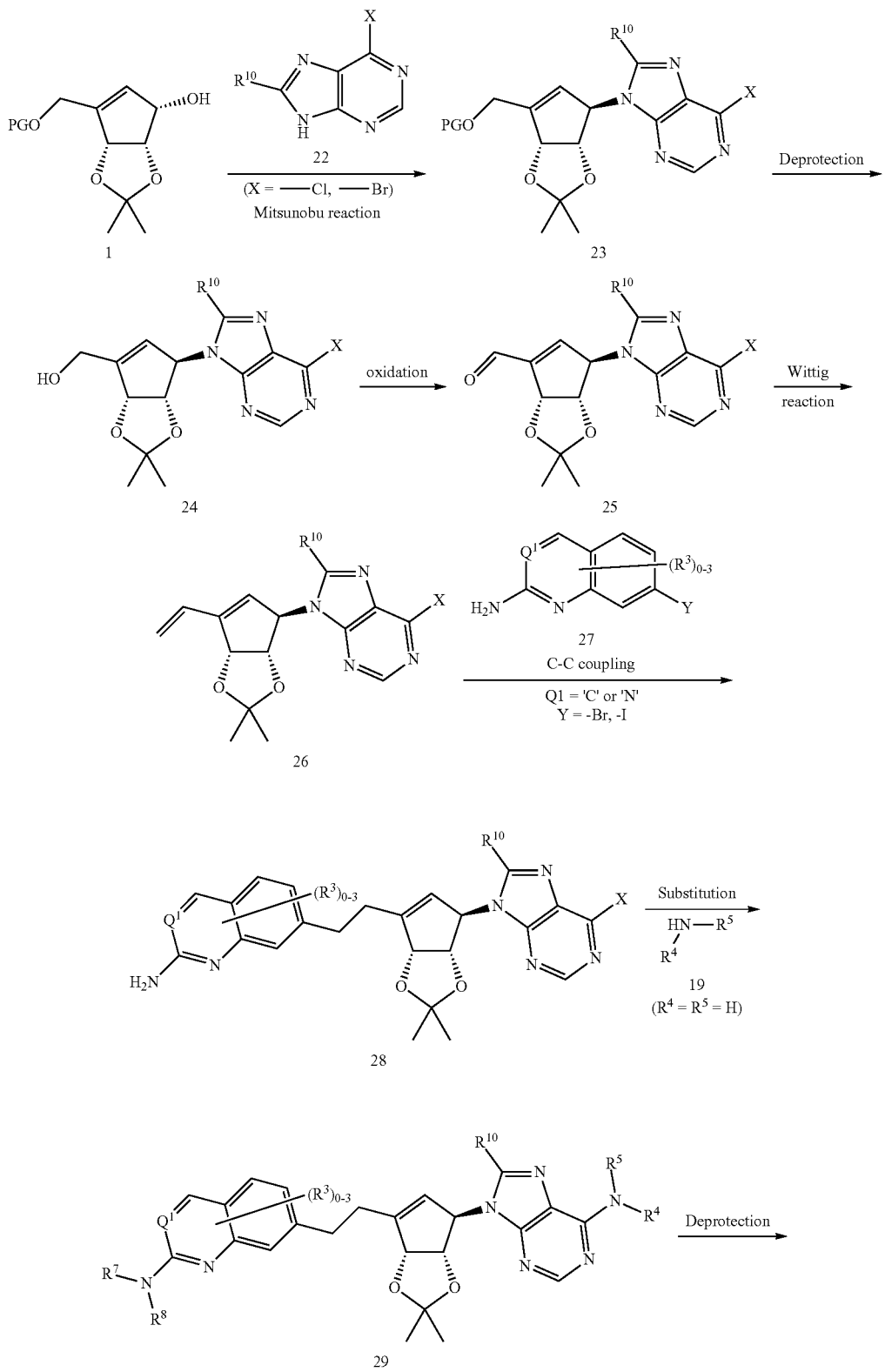
Scheme-4

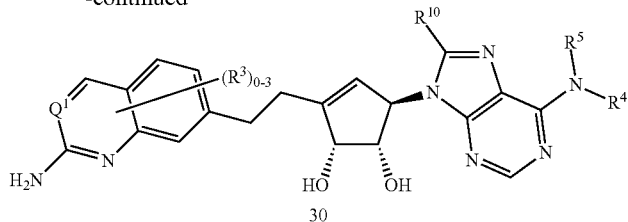

30

Scheme-4 illustrates the synthesis of compound of formula 30. Mitsunobu reaction of compound of formula 1 with compound of formula 22 (X=—Cl, —Br) using various azo dicarboxylate reagents such as but not limited to DEAD or DIAD in presence of phosphine such as but not limited to PPh₃ gives the compound of formula 23. Typically these reactions are run in etheral solvents such as THF, MeTHF, dioxane, or similar solvents at temperatures ranging from 0° C. to 25° C. Compound of formula 24 is formed upon treatment of compound of formula 23 with fluoride ions such as but not limited to TBAF. Typically these reactions are done in etheral solvents such as THF, MeTHF, dioxane, or similar solvents at temperatures ranging from 0° C. to 40° C. Oxidation of compound of formula 24 with various oxidising agents such as but not limited to Dess-Martin periodinane can furnish the compound of formula 25. Typically these reactions can be run in halogenated solvents such as CH₂Cl₂, CHCl₃ or similar solvents at temperatures ranging from 0° C. to 40° C. Reagents such as but not limited to methyltriphenylphosphonium bromide in presence of a base such as but not limited to KO'Bu, NaO'Bu, LiHMDS, NaHMDS, or KHMDS, when treated with compound of formula 25 affords compound of formula 26. Typically these reactions are done in etheral solvents such as THF, MeTHF, dioxane, or similar solvents at temperatures ranging from 0° C. to 25° C. Compound of formula 28 can be synthesized by hydroboration of compound of formula 26 with suitable boranes such as but not limited to 9-BBN followed by addition of inorganic base such as but not limited to tripotassium phosphate or Cs₂CO₃, in presence of Pd catalyst such as but not limited to Pd(dppf)Cl₂ or Pd-118 and compound of formula 27 (Y=—Br, —I), which was synthesized by following a procedure reported in WO2012002577 A1, followed by N-oxide formation, chlorination with phosphoroxychloride, and nucleophilic substitution with PMB-NH₂ or J. Med. Chem, 2017, 60 (9), 3958-3978). Typically these reactions are done in etheral solvents such as THF, MeTHF, dioxane, or similar solvents and run at temperatures ranging from 25° C. to 70° C. Compound of formula 28 (where R⁴ and R⁵ are defined herein above) upon treatment with compound of formula 19 affords compound of formula 29. Typically, these reactions are done in etheral solvents such as for example dioxane at temperatures ranging from 120° C. to 170° C. in a steel bomb. Acetonide deprotection of compound of formula 29 with acids such as but not limited to HCl or TFA affords compound of formula 30. Typically, these reactions are run at temperatures ranging from 25° C. to 50° C. Compounds at every step may be purified by standard techniques such as column chromatography, crystallization, reverse phase HPLC, or SFC.

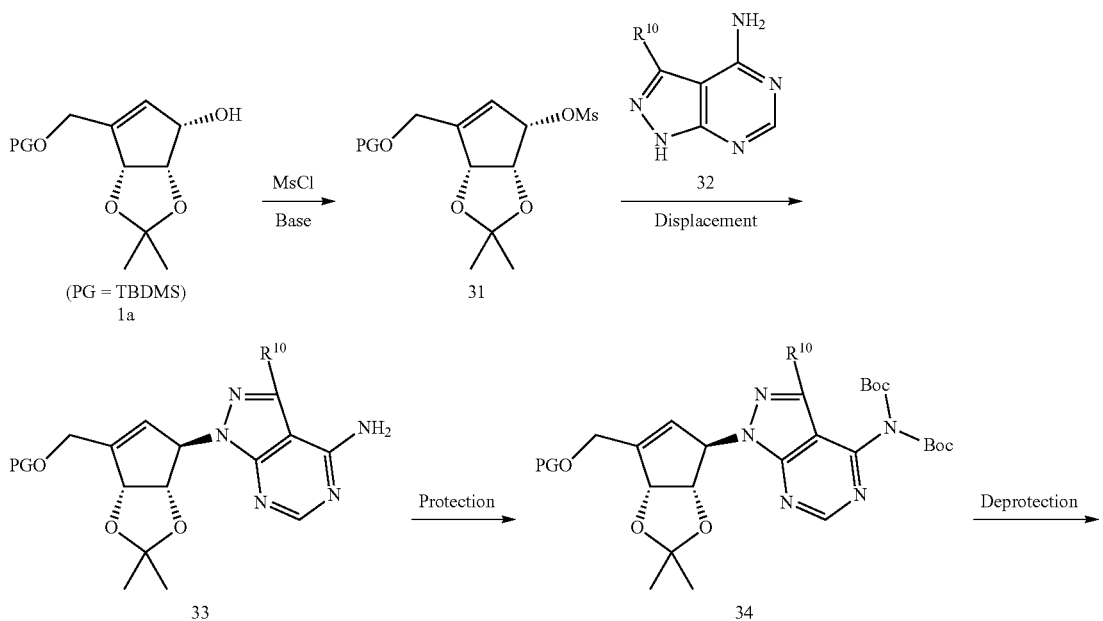

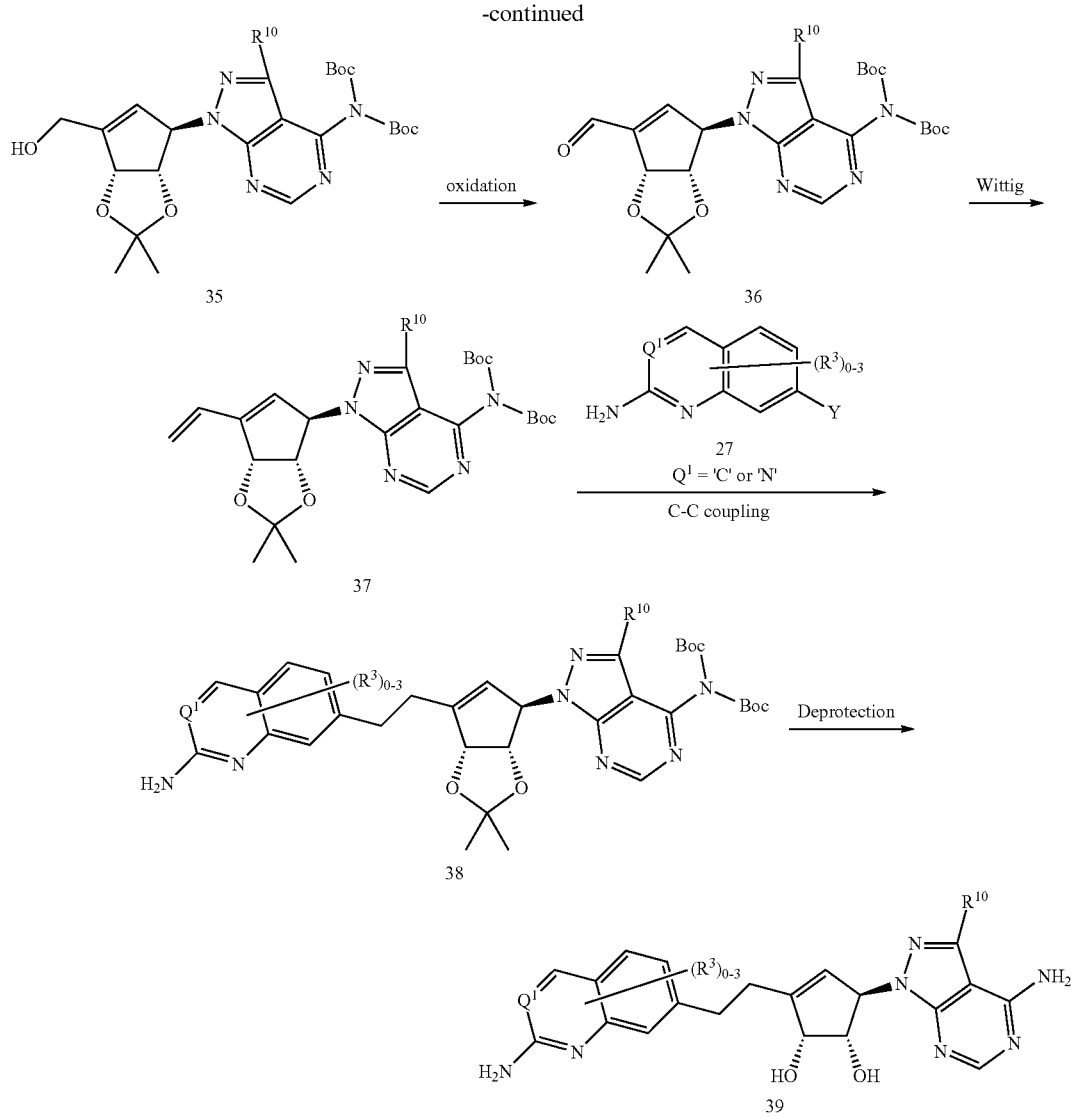

Scheme-5 illustrates the synthesis of compound of formula 39. Compound of formula 1 can be treated with various sulphonyl chloride such as but not limited to MsCl, TsCl etc. in presence of base such as but not limited to $NEt_3$, DIPEA etc. gives the compound of formula 31. Typically these reactions are run in halogenated solvents such as $CH_2Cl_2$, $CHCl_3$ or similar solvents at temperatures ranging from 0° C. to 25° C. Compound of formula 33 can be synthesized by nucleophilic substitution of compound of formula 31 with compound of formula 32 in presence of base such as but not limited to NaH, LiH etc. Typically these reactions are done in solvents such as DMF, DMAc, NMP or similar solvents at temperatures ranging from 0° C. to 25° C. Compound of formula 34 is prepared by treating it with anhydride such as but not limited to $(Boc)_2O$ in presence of base such as but not limited to $NEt_3$, DIPEA, DMAP etc. at temperatures ranging from 0° C. to 25° C. Typically these reactions are run in etheral solvents such as THF, MeTHF, dioxane, or similar solvents. Compound of formula 35 is formed upon treatment of compound of formula 34 with fluoride ions such as but not limited to TBAF. Typically, these reactions are done in etheral solvents such as THF, MeTHF, dioxane, or similar solvents at temperatures ranging from 0° C. to 25° C. Oxidation of compound of formula 35 with various oxidising agents such as but not limited to Dess-Martin periodinane can furnish the compound of formula 36. Typically, these reactions are run in halogenated solvents such as $CH_2Cl_2$, $CHCl_3$ or similar solvents at temperatures ranging from 0° C. to 25° C. Reagents such as but not limited to methyltriphenylphosphonium bromide in presence of a base such as but not limited to $KO^tBu$, $NaO^tBu$, LiHMDS, NaHMDS, or KHMDS when treated with compound of formula 36 affords compound of formula 37. Typically these reactions are run in etheral solvents such as THF, MeTHF, dioxane, or similar solvents at temperatures ranging from 0° C. to 25° C. Compound of formula 38 can be synthesized upon treatment of compound of formula 37 with suitable boranes such as but not limited to 9-BBN followed by addition of inorganic base such as but not limited to tripotassium phosphate or $Cs_2CO_3$, in presence of Pd catalyst such as but not limited to $Pd(dppf)Cl_2$ or Pd-118 and compound of formula 27 (Y=—Br, —I), which was synthesized by following a procedure reported in WO2012002577 A1, followed by N-oxide formation, chlorination with Phosphoroxychloride, and nucleophilic substitution with PMB-NH$_2$ or J. Med. Chem, 2017, 60 (9), 3958-3978). Typically, these reactions are done in etheral solvents such as THF, MeTHF, dioxane, or similar solvents at temperatures ranging from 25° C. to 70° C. Acetonide deprotection of compound of formula 38 with acids such as but not limited to HCV/MeOH or TFA affords compound of formula 39. Typically these reactions are run at temperatures ranging from 25° C. to 50° C. Compounds at every step may be purified by standard techniques such as column chromatography, crystallization, reverse phase HPLC, or chiral HPLC or SFC.

Scheme-6

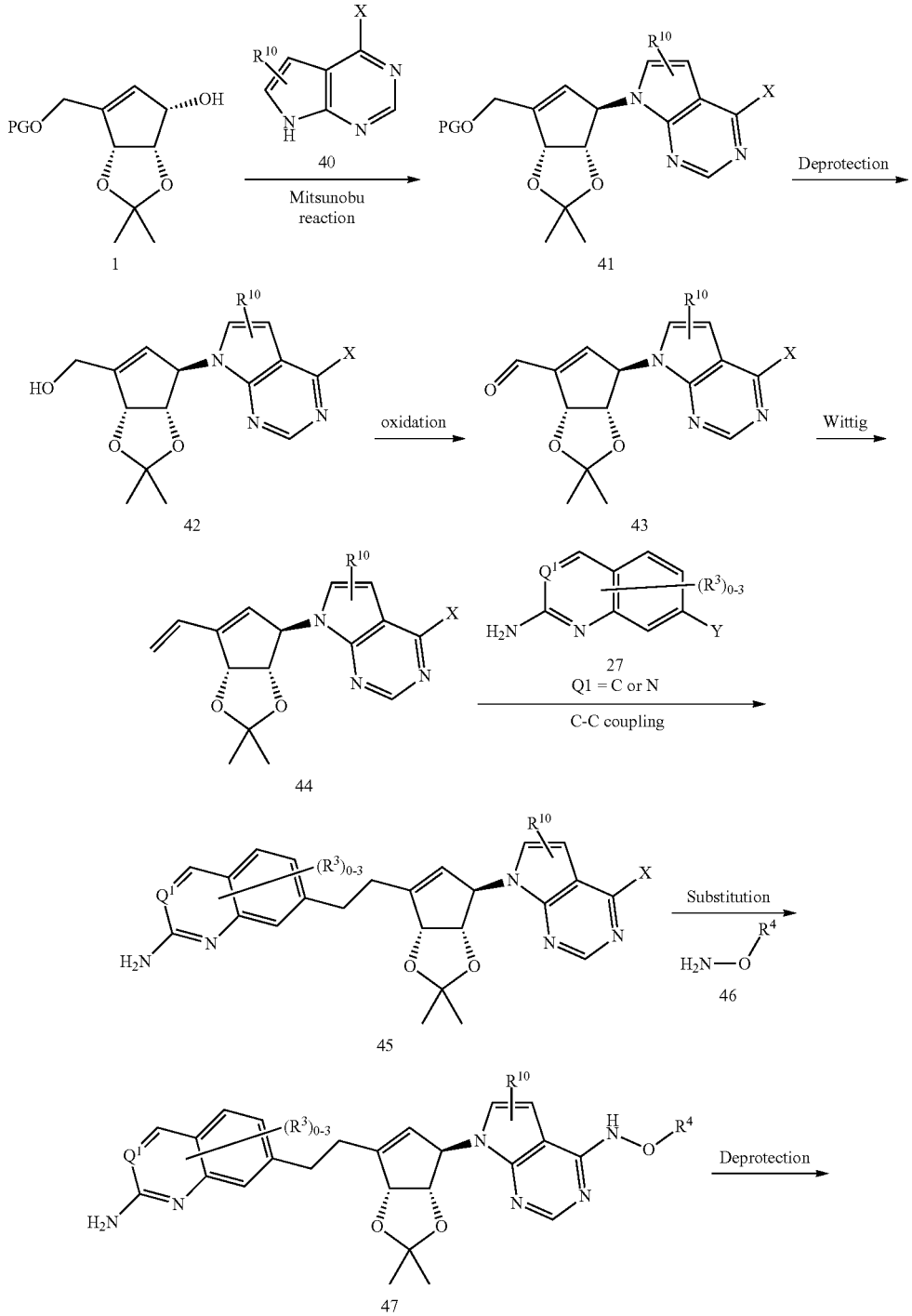

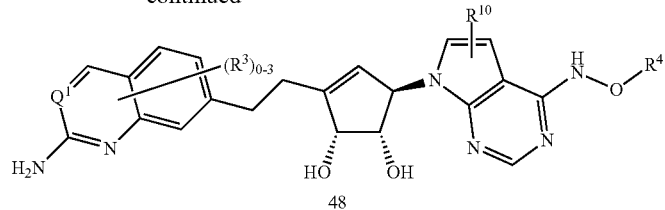

48

Scheme-6 illustrates the synthesis of compound of formula 48. Compound of formula 1 (where PG=protecting group such as TBDPS), is prepared by following a procedure described in Purinergic Signalling (2015) 11:371-387. Mitsunobu reaction of compound of formula 1 with compound of formula 40 (X=—Cl, —Br) using various azo dicarboxylate reagents such as but not limited to DEAD or DIAD in presence of phosphine such as but not limited to $PPh_3$ gives the compound of formula 41. Typically, these reactions are run in etheral solvents such as THF, MeTHF, dioxane, or similar solvents at temperatures ranging from 0° C. to 25° C. Compound of formula 42 is formed upon treatment of compound of formula 41 with fluoride ions such as but not limited to TBAF, ammonium fluoride. Typically these reactions are done in etheral solvents such as THF, MeTHF, dioxane, or similar solvents at temperatures ranging from 0° C. to 40° C. Oxidation of compound of formula 42 with various oxidising agents such as but not limited to Dess-Martin periodinane can furnish the compound of formula 43. Typically these reactions can be run in halogenated solvents such as $CH_2Cl_2$ $CHCl_3$ or similar solvents at temperatures ranging from 0° C. to 40° C. Reagents such as but not limited to methyltriphenylphosphonium bromide in presence of a base such as but not limited to KO$^t$Bu, NaO$^t$Bu, LiHMDS, NaHMDS, or KHMDS, when treated with compound of formula 43 affords compound of formula 44. Typically these reactions are done in etheral solvents such as THF, MeTHF, dioxane, or similar solvents at temperatures ranging from 0° C. to 25° C. Compound of formula 45 can be synthesized by hydroboration of compound of formula 44 with suitable boranes such as but not limited to 9-BBN followed by addition of inorganic base such as but not limited to tripotassium phosphate or $Cs_2CO_3$, in presence of Pd catalyst such as but not limited to or Pd(dppf)$Cl_2$ or Pd-118 and compound of formula 27 (Y=—Br, —I), which was synthesized by following a procedure reported in WO2012002577 A1, followed by N-oxide formation, chlorination with Phosphoroxychloride, and nucleophilic substitution with PMB-NH$_2$ or J. Med. Chem, 2017, 60 (9), 3958-3978). Typically these reactions are done in etheral solvents such as THF, MeTHF, dioxane, or similar solvents at temperatures ranging from 25° C. to 70° C. Compound of formula 45 upon treatment with compound of formula 46 (where $R^4$ is hydrogen) affords compound of formula 47. Typically, these reactions are done in etheral solvents such as for example dioxane at temperatures ranging from 120° C. to 170° C. in a steel bomb. Acetonide deprotection of compound of formula 47 with acids such as but not limited to HCl or TFA affords compound of formula 48. Typically, these reactions are run at temperatures ranging from 25° C. to 50° C. Compounds at every step may be purified by standard techniques such as column chromatography, crystallization, reverse phase HPLC, or SFC.

Scheme-7

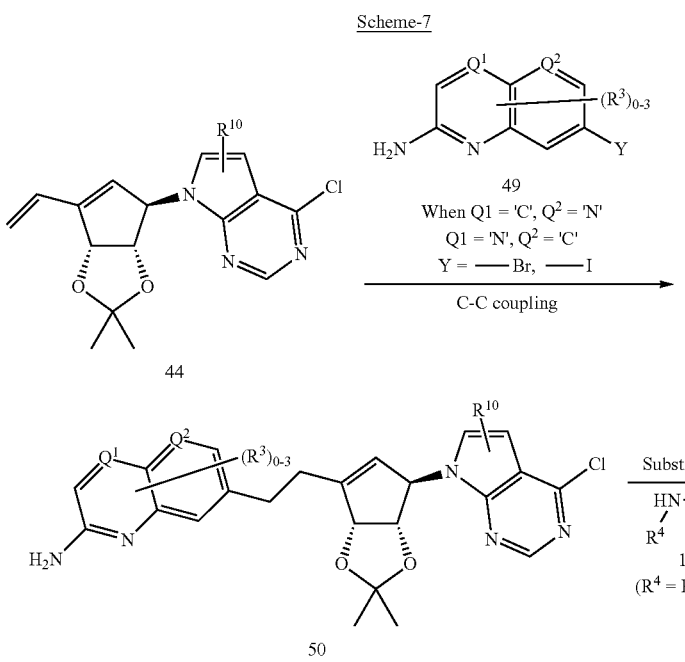

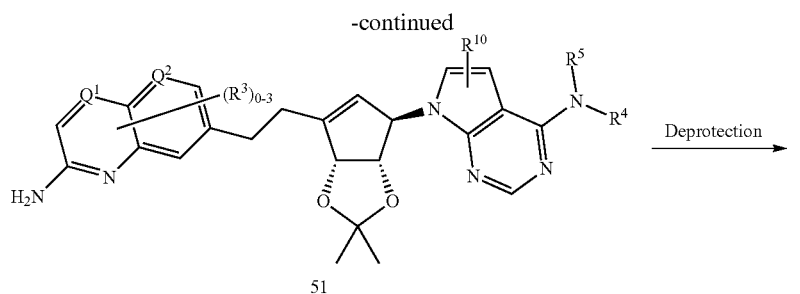

Scheme-7 illustrates the synthesis of compound of formula 52. Compound of formula 50 can be synthesized by hydroboration of compound of formula 44 with suitable boranes such as but not limited to 9-BBN followed by addition of inorganic base such as but not limited to tripotassium phosphate or $Cs_2CO_3$, in presence of Pd catalyst such as but not limited to $Pd(dppf)Cl_2$ or Pd-118 and compound of formula 49 (Y=—Br, —I). Typically, these reactions are done in etheral solvents such as THF, MeTHF, dioxane, or similar solvents at temperatures ranging from 25° C. to 70° C. Compound of formula 50 upon treatment with compound of formula 19 affords compound of formula 51. Typically, these reactions are done in etheral solvents such as for example dioxane at temperatures ranging from 120° C. to 170° C. in a steel bomb. Acetonide deprotection of compound of formula 51 with acids such as but not limited to HCl (hydrochloric acid) or TFA affords compound of formula 52. Typically, these reactions are run at temperatures ranging from 25° C. to 50° C. Compounds at every step may be purified by standard techniques such as column chromatography, crystallization, reverse phase HPLC, or SFC.

Scheme-8

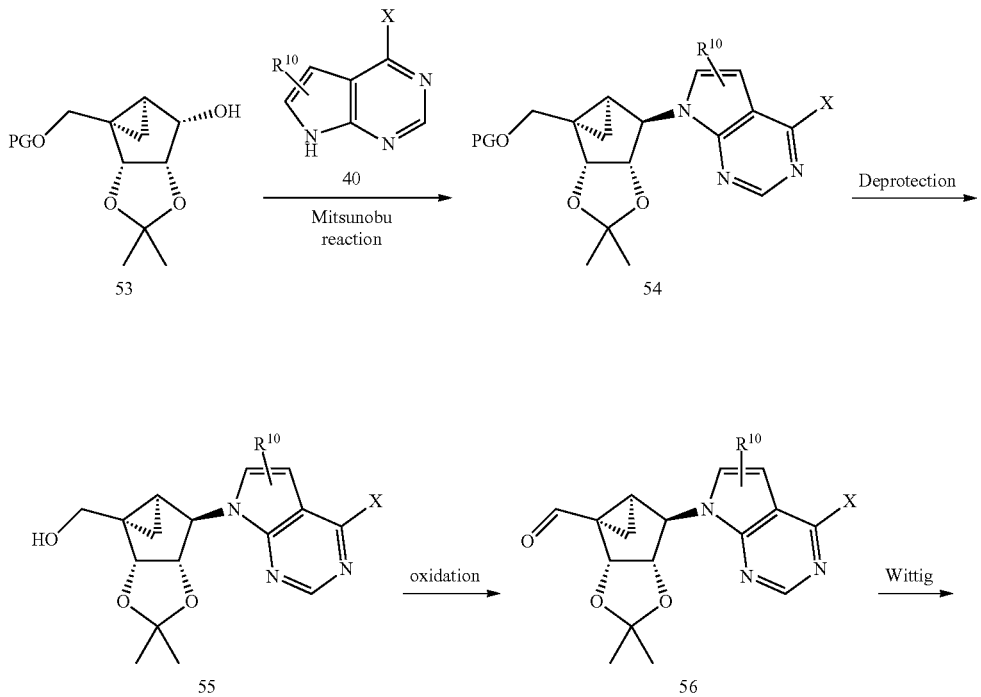

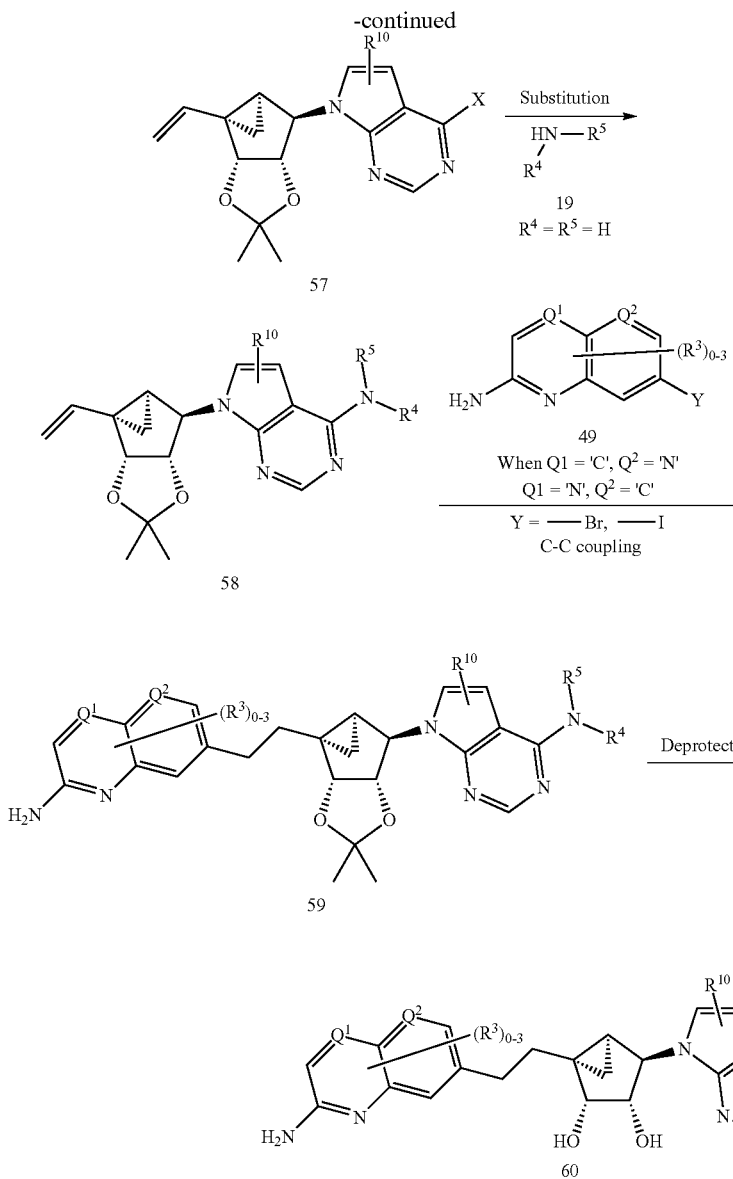

Scheme-8 illustrates the synthesis of compound of formula 60. Compound of formula 53 (where PG=Protecting group such as but not limited to TBDPS), is prepared by following a procedure reported in Purinergic Signalling (2015) 11:371-387. Mitsunobu reaction of compound of formula 53 with compound of formula 40 (X=—Cl, —Br) using various azo dicarboxylate reagents such as but not limited to DEAD or DIAD in presence of phosphine such as but not limited to PPh₃ gives the compound of formula 54. Compound of formula 55 is formed upon treatment of compound of formula 54 with fluoride ions such as but not limited to TBAF. Typically these reactions are done in etheral solvents such as THF, MeTHF, dioxane, or similar solvents at temperatures ranging from 0° C. to 25° C. Oxidation of compound of formula 55 with various oxidising agents such as but not limited to Dess-Martin periodinane can furnish the compound of formula 56. Reagents such as but not limited to methyltriphenylphosphonium bromide in presence of a base such as but not limited to KOᵗBu, NaOᵗBu, LiHMDS, NaHMDS, or KHMDS when treated with compound of formula 56 affords compound of formula 57. Compound of formula 57 upon treatment with compound of formula 19 (where R⁴ and R⁵ are hydrogen) affords compound of formula 58. Typically, these reactions are done in etheral solvents such as for example dioxane at temperatures ranging from 120° C. to 170° C. in a steel bomb. Compound of formula 59 can be synthesized by hydroboration of compound of formula 58 with suitable boranes such as but not limited to 9-BBN followed by addition of inorganic base such as but not limited to tripotassium phosphate or cesium carbonate, in presence of Pd catalyst such as but not limited to Pd(dppf)Cl₂ or Pd-118 and compound of formula 49 (Y=—Br, —I). Acetonide deprotection of compound of formula 59 with acids such as but not limited to HCl or TFA affords compound of formula 60. Typically, these reactions are run at temperatures ranging from 25° C. to 50° C. Compounds at every step may be purified by standard techniques such as column chromatography, crystallization, reverse phase HPLC, or SFC.

Scheme-9

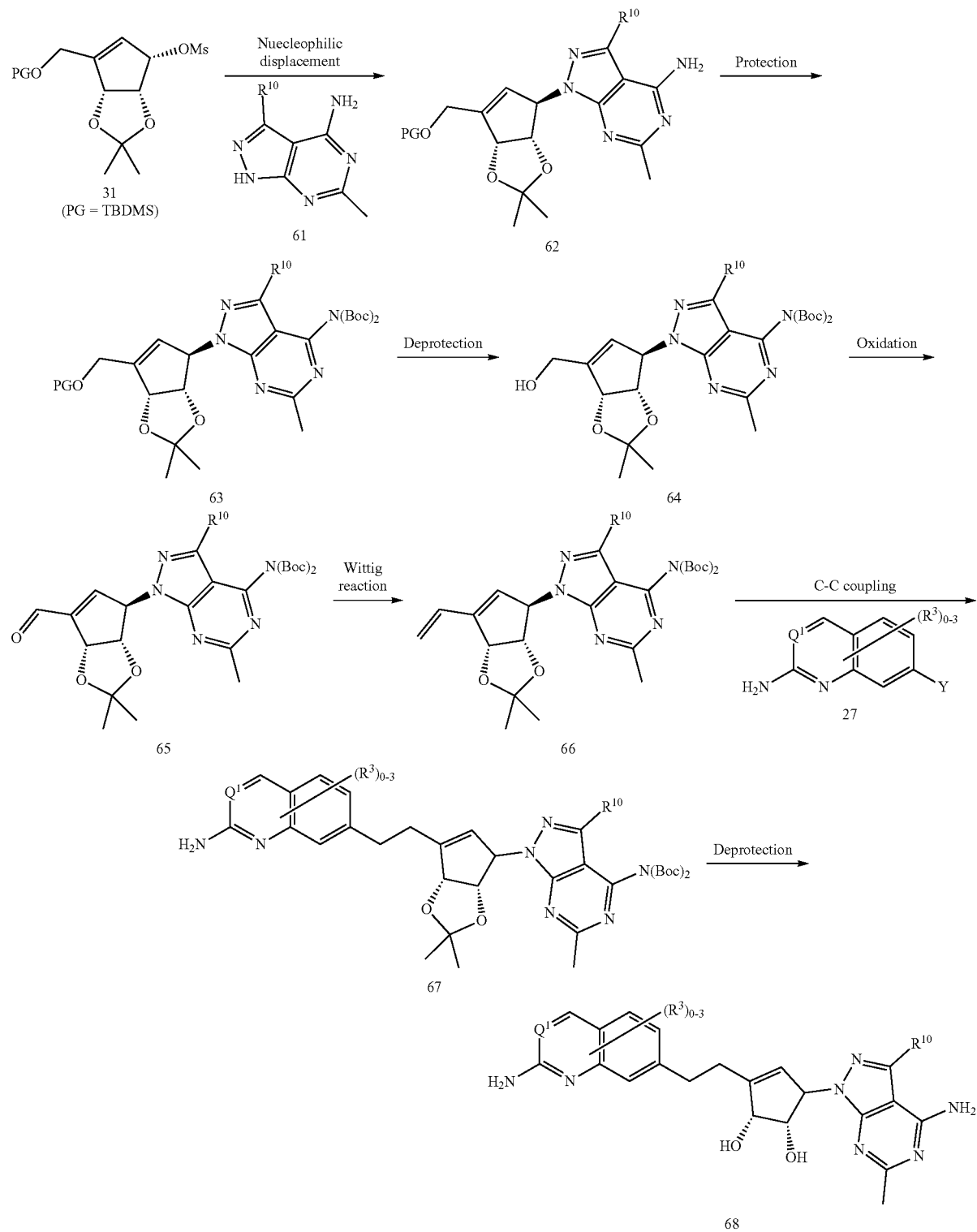

Scheme-9 illustrates the synthesis of compound of formula 68. Compound of formula 62 can be synthesized by nucleophilic substitution of compound of formula 31 with compound of formula 61 in presence of base such as but not limited to NaH, LiH etc. Typically these reactions are done in solvents such as DMF, DMAc, NMP or similar solvents at temperatures ranging form 0° C. to 25° C. Compound of formula 63 is prepared by treating compound of formula 62 with anhydride such as but not limited to (Boc)$_2$O in presence of base such as but not limited to NEt$_3$, DIPEA, DMAP etc. at temperatures ranging from 0° C. to 25° C. Typically these reactions are run in etheral solvents such as for example THF, MeTHF, dioxane, or similar solvents. Compound of formula 64 is formed upon treatment of compound of formula 63 with fluoride ions such as but not limited to TBAF. Typically these reactions are done in etheral solvents such as for example THF, MeTHF, dioxane, or similar solvents at temperatures ranging from 0° C. to 25° C. Oxidation of compound of formula 64 with various oxidising agents such as but not limited to Dess-Martin periodinane can furnish the compound of formula 65. Typically these reactions are run in halogenated solvents such as $CH_2Cl_2$, $CHCl_3$ or similar solvents at temperatures ranging from 0° C. to 25° C. Reagents such as but not limited to methyltriphenylphosphonium bromide in presence of a base such as but not limited to KO$^t$Bu, NaO$^t$Bu, LiHMDS, NaHMDS, or KHMDS when treated with compound of formula 65 affords compound of formula 66. Typically these reactions are run in etheral solvents such as for example THF, MeTHF, dioxane, or similar solvents at temperatures ranging from 0° C. to 25° C. Compound of formula 67 can be synthesized upon treatment of compound of formula 66 with suitable boranes such as but not limited to 9-BBN followed by addition of inorganic base such as but not limited to tripotassium phosphate or $Cs_2CO_3$, in presence of Pd catalyst such as but not limited to Pd(dppf)Cl$_2$ or Pd-118 and compound of formula 27 (Y=—Br, —I) which was synthesized by following the procedure reported in WO2012002577 A1, followed by N-oxide formation, chlorination with Phosphoroxychloride, and nucleophilic substitution with PMB-NH$_2$ or J. Med. Chem, 2017, 60 (9), 3958-3978). Typically these reactions are done in etheral solvents such as for example THF, MeTHF, dioxane, or similar solvents at temperatures ranging from 25° C. to 70° C. Deprotection of compound of formula 67 with acids such as but not limited to HCl/MeOH or TFA affords compound of formula 68. Typically, these reactions are run at temperatures ranging from 25° C. to 50° C. Compounds at every step may be purified by standard techniques such as column chromatography, crystallization, reverse phase HPLC, or SFC.

Scheme-10

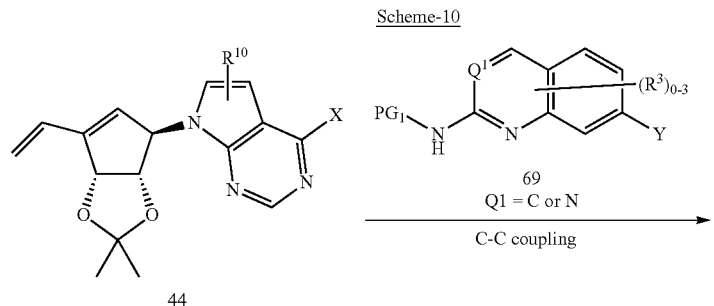

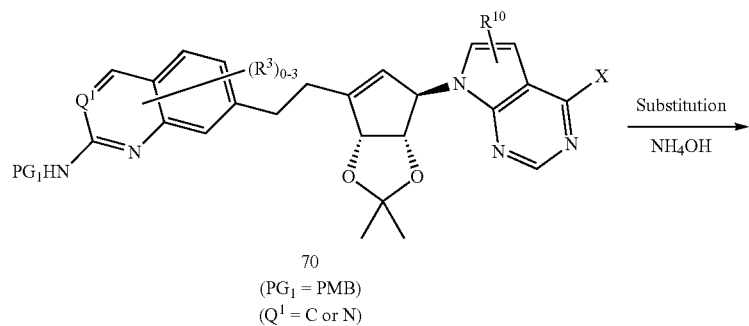

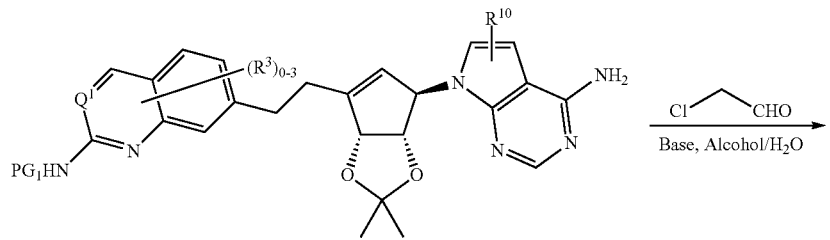

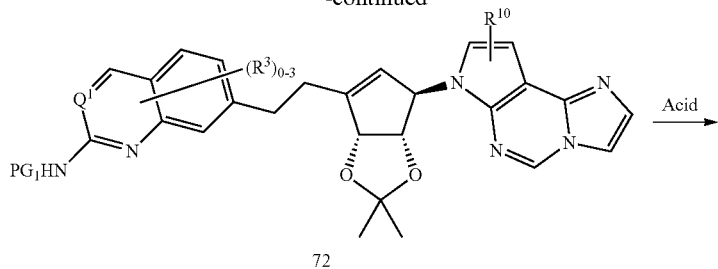

72

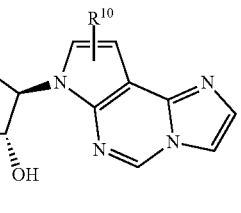

73

Scheme-10 illustrates the synthesis of compound of formula 73. Compound of formula 70 can be synthesized by hydroboration of compound of formula 44 with suitable boranes such as but not limited to 9-BBN followed by addition of inorganic base such as but not limited to tripotassium phosphate or $Cs_2CO_3$, in presence of Pd catalyst such as but not limited to Pd(dppf)$Cl_2$ or Pd-118 and compound of formula 69 (Y=—Br, —I), which was synthesized by following the similar procedure reported in Journal of the American Chemical Society, 1949, vol. 71, p. 6-10. Typically, these reactions are done in etheral solvents such as THF, MeTHF, dioxane, or similar solvents at temperatures ranging from 25° C. to 70° C. Compound of formula 70, upon treatment with aq.NH3 affords compound of formula 71. Typically, these reactions are done in etheral solvents such as for example dioxane and run at temperatures ranging from 120° C. to 170° C. in a steel bomb. Cyclization of compound of formula 71 with 2-halo-acetaldehyde such as but not limited to chloroacetaldehyde in presence of a base such as but not limited to $NaHCO_3$ can give compound of formula 72. Typically these reactions are done in protic solvents such as for example EtOH, MeOH, $H_2O$ and run at temperatures ranging from 50° C. to 80° C. Acetonide deprotection of compound of formula 72 with acids such as but not limited to HCl or TFA affords compound of formula 73. Typically these reactions are run at temperatures ranging from 25° C. to 50° C. Compounds at every step may be purified by standard techniques such as column chromatography, crystallization, reverse phase HPLC or SFC.

Scheme-11

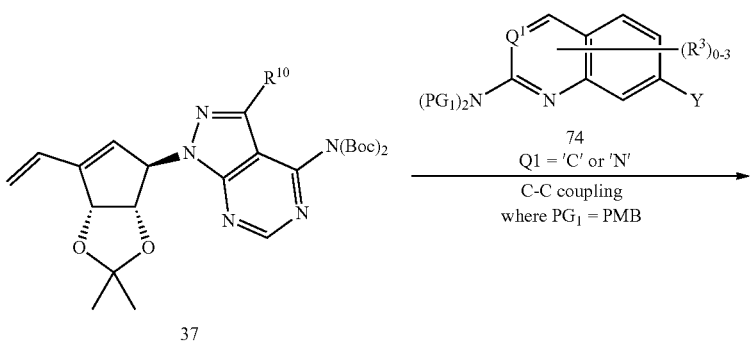

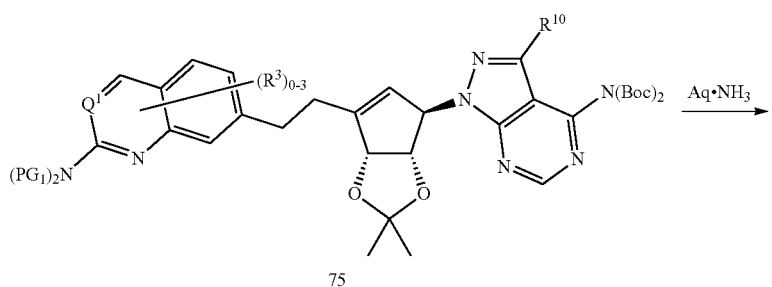

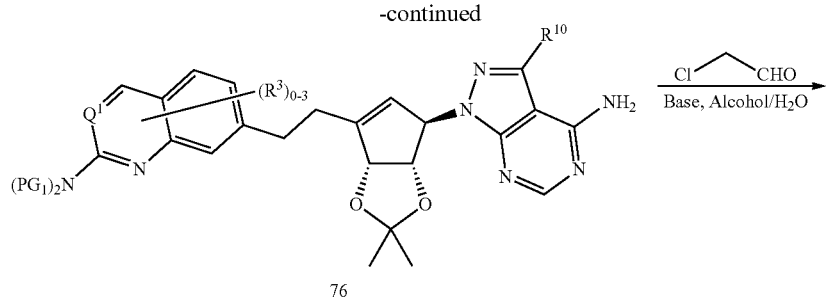

76

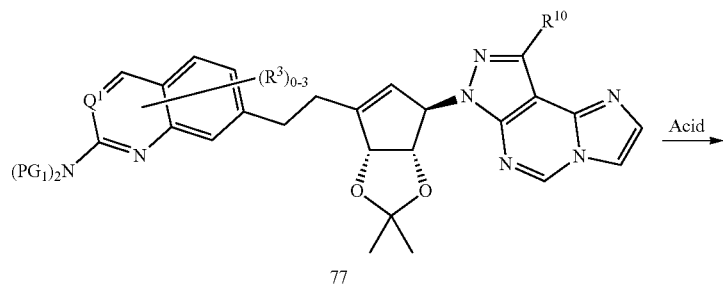

77

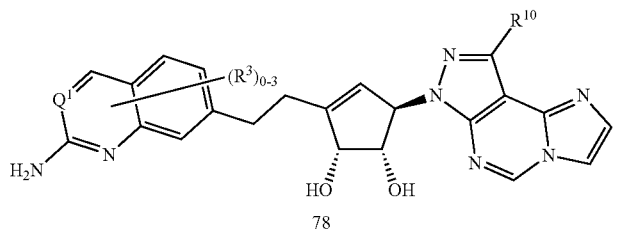

78

Scheme-11 illustrates the synthesis of compound of formula 78. Compound of formula 75 can be synthesized by hydroboration of compound of formula 37 with suitable boranes such as but not limited to 9-BBN followed by addition of inorganic base such as but not limited to tripotassium phosphate or $Cs_2CO_3$, in presence of Pd catalyst such as but not limited to $Pd(dppf)Cl_2$ or Pd-118 and compound of formula 74 (Y=Br, —I; $PG_1$ is protecting group such as p-methoxybenzyl). Typically these reactions are done in etheral solvents such as THF, MeTHF, dioxane, or similar solvents and run at temperatures ranging from 25° C. to 70° C. Compound of formula 75 upon treatment aq.NH3 with can give compound of formula 76. Typically, these reactions are done in etheral solvents such as for example dioxane at temperatures ranging from 120° C. to 170° C. in a steel bomb. Cyclization of compound of formula 76 with 2-halo-acetaldehyde such as but not limited to chloroacetaldehyde can give compound of formula 77. Typically these reactions are done in protic solvents such as for example EtOH, MeOH, $H_2O$ and run at temperatures ranging from 50° C. to 80° C. Acetonide deprotection of compound of formula 77 with acids such as but not limited to HCl or TFA affords compound of formula 78. Typically, these reactions are run at temperatures ranging from 25° C. to 50° C. Compounds at every step may be purified by standard techniques such as column chromatography, crystallization, reverse phase HPLC or SFC.

Scheme-12

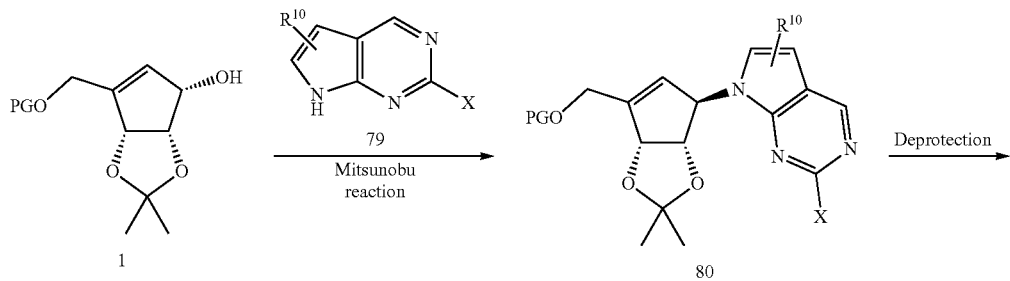

-continued
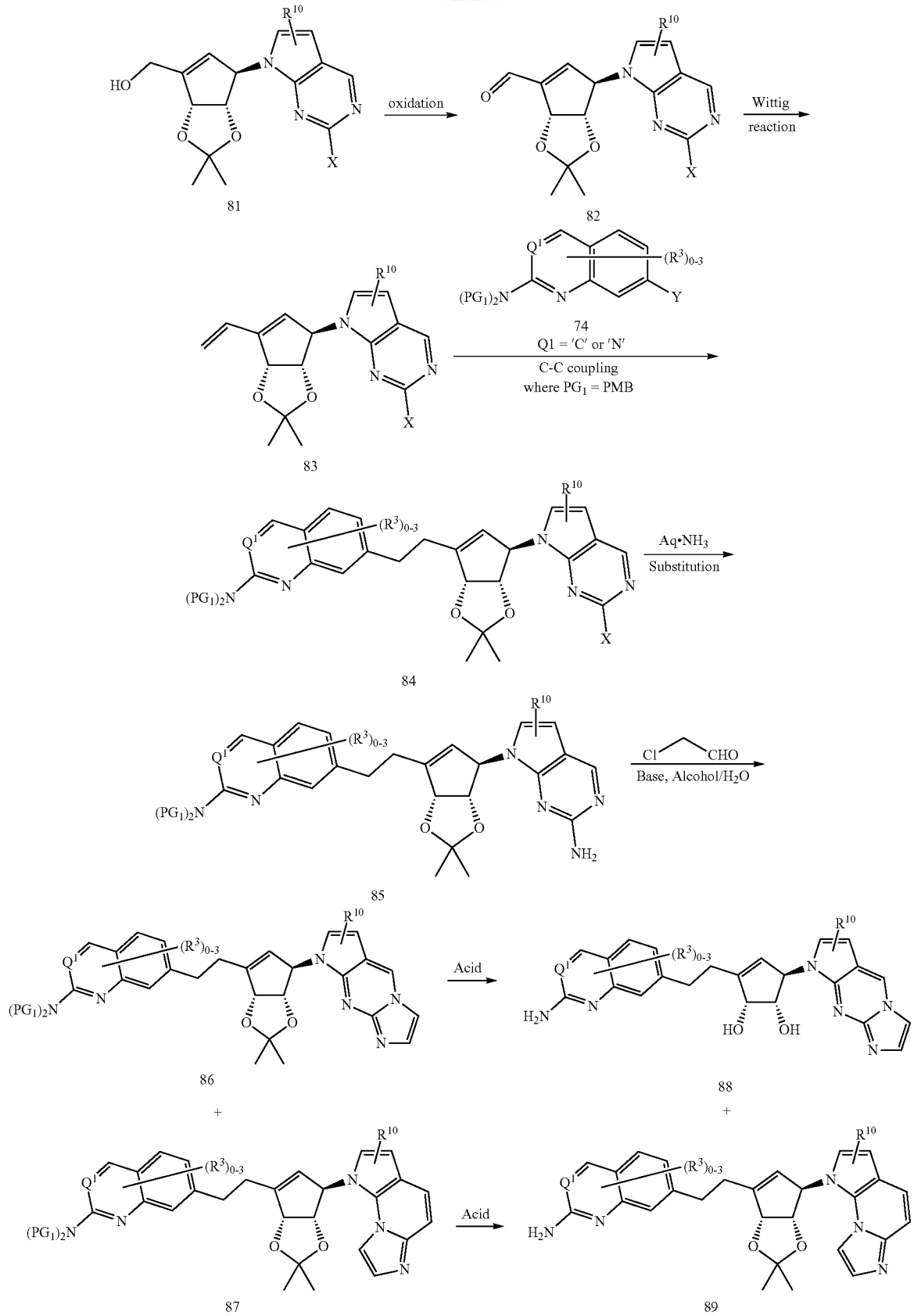

Scheme-12 illustrates the synthesis of compound of formula 88 and 89. Mitsunobu reaction of compound of formula 1 with compound of formula 79 using various azo dicarboxylate reagents such as but not limited to DEAD or DIAD in presence of phosphine such as but not limited to PPh₃ gives the compound of formula 80. Typically these reactions are run in etheral solvents such as THF, MeTHF, dioxane, or similar solvents at temperatures ranging from 0° C. to 25° C. Compound of formula 81 is formed upon treatment of compound of formula 80 with fluoride ions such as but not limited to TBAF. Typically these reactions are done in etheral solvents such as THF, MeTHF, dioxane, or similar solvents at temperatures ranging from 0° C. to 40° C. Oxidation of compound of formula 81 with various oxidising agents such as but not limited to Dess-Martin periodinane can furnish the compound of formula 82. Typically these reactions can be run in halogenated solvents such as $CH_2Cl_2$, $CHCl_3$ or similar solvents at temperatures ranging from 0° C. to 40° C. Reagents such as but not limited to methyltriphenylphosphonium bromide in presence of a base such as but not limited to KO$^t$Bu, NaO$^t$Bu, LiHMDS, NaHMDS, or KHMDS when treated with compound of formula 82 can afford the compound of formula 83. Typically these reactions are done in etheral solvents such as THF, MeTHF, dioxane, or similar solvents at temperatures ranging from 0° C. to 25° C. Compound of formula 84 can be synthesized by hydroboration of compound of formula 83 with suitable boranes such as but not limited to 9-BBN followed by addition of inorganic base such as but not limited to tripotassium phosphate or $Cs_2CO_3$, in presence of Pd catalyst such as but not limited to Pd(dppf)Cl₂ or Pd-118 and compound of formula 74 (Y=Br, —I; PG₁ is protecting group such as p-methoxybenzyl). Typically, these reactions are done in etheral solvents such as for example THF, MeTHF, dioxane, or similar solvents and run at temperatures ranging from 25° C. to 70° C. Compound of formula 84 upon treatment with aq.NH3 can give compound of formula 85. Typically, these reactions are done in etheral solvents such as for example dioxane at temperatures ranging from 120° C. to 170° C. in a steel bomb. Cyclization of compound of formula 85 with 2-halo-acetaldehyde such as but not limited to chloroacetaldehyde can give a mixture of compound of formula 86 and compound of formula 87. Typically these reactions are done in protic solvents such as for example EtOH, MeOH, H₂O and run at temperatures ranging from 50° C. to 80° C. Deprotection of compound of formula 86 with acids such as but not limited to HCl or TFA affords compound of formula 88. Additionally, deprotection of compound of formula 87 with acids such as but not limited to HCl or TFA affords compound of formula 89. Typically these reactions are run at temperatures ranging from 25° C. to 50° C. Compounds at every step may be purified by standard techniques such as column chromatography, crystallization, reverse phase HPLC or SFC.

Scheme-13

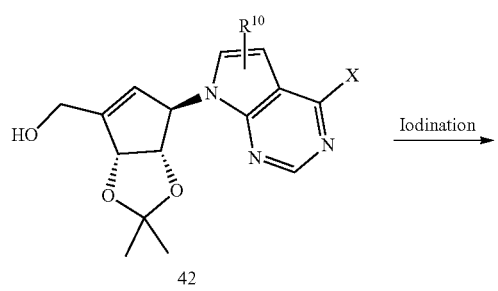

42

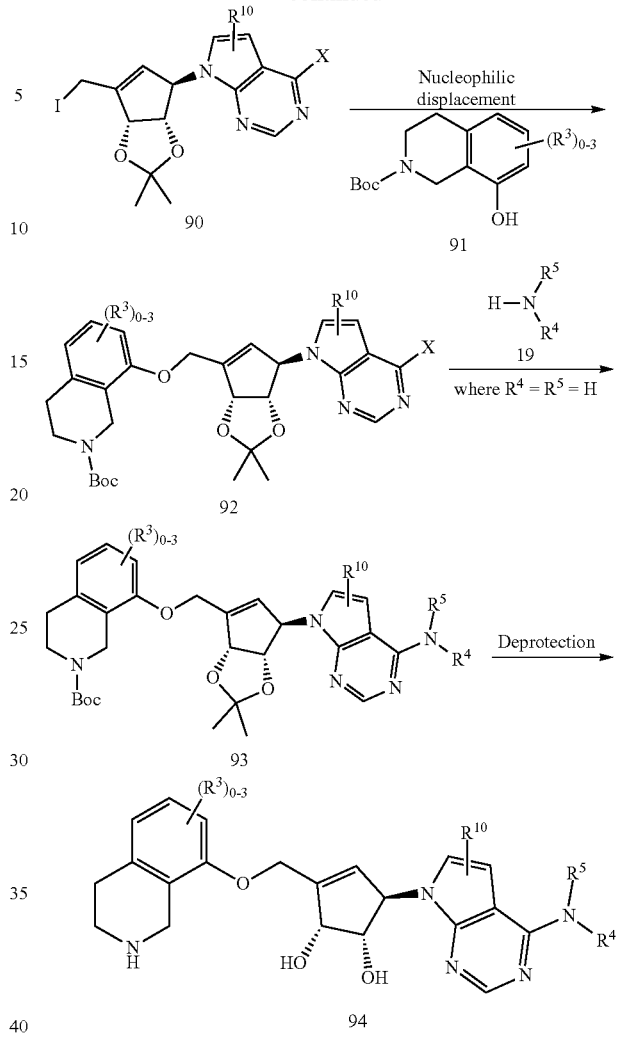

Scheme 13 illustrates the synthesis of compound of formula 94. Iodination of compound of formula 42 with bases such as but not limited to imidazole in presence of phosphine such as but not limited to PPh₃ gives the compound of formula 90. Typically these reactions can be run in halogenated solvents such as $CH_2Cl_2$, $CHCl_3$ or similar solvents at temperatures ranging from 0° C. to 25° C. Nucleophilic displacement of compound of formula 90 with compound of formula 91 in presence of bases such as but not limited to $Cs_2CO_3$ or $K_2CO_3$ gives the compound of formula 92. Typically these reactions can be run in polar aprotic solvents such as DMF, DMAc or similar solvents at temperatures ranging from 0° C. to 25° C. Compound of formula 92 upon treatment with compound of formula 19 can give compound of formula 93. Typically these reactions are done in etheral solvents such as for example dioxane at temperatures ranging from 120° C. to 170° C. in a steel bomb. Additionally, deprotection of compound of formula 93 with acids such as but not limited to HCl or TFA affords compound of formula 94. Typically these reactions are run at temperatures ranging from 25° C. to 50° C. Compounds at every step may be purified by standard techniques such as column chromatography, crystallization, reverse phase HPLC or SFC.

Scheme-14

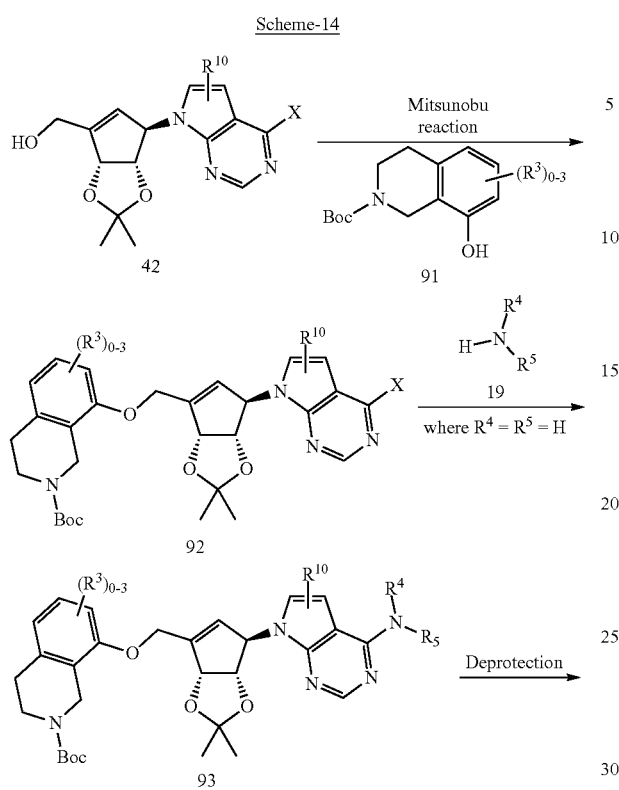
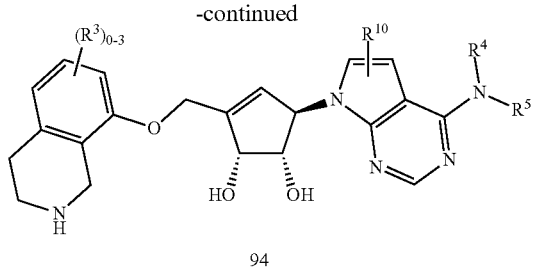

Scheme-14 illustrates the synthesis of compound of formula 94. Mitsunobu reaction of compound of formula 42 with compound of formula 91 using various azo dicarboxylate reagents such as but not limited to DEAD or DIAD in presence of phosphine such as but not limited to $PPh_3$ gives the compound of formula 92. Typically these reactions are run in etheral solvents such as for example THF, MeTHF, dioxane, or similar solvents at temperatures ranging from 0° C. to 25° C. Compound of formula 92 upon treatment with compound of formula 19 can give compound of formula 93. Typically these reactions are done in etheral solvents such as for example dioxane at temperatures ranging from 120° C. to 170° C. in a steel bomb. Additionally, deprotection of compound of formula 93 with acids such as but not limited to HCl or TFA affords compound of formula 94. Typically these reactions are run at temperatures ranging from 25° C. to 50° C. Compounds at every step may be purified by standard techniques such as column chromatography, crystallization, reverse phase HPLC or SFC.

Scheme-15

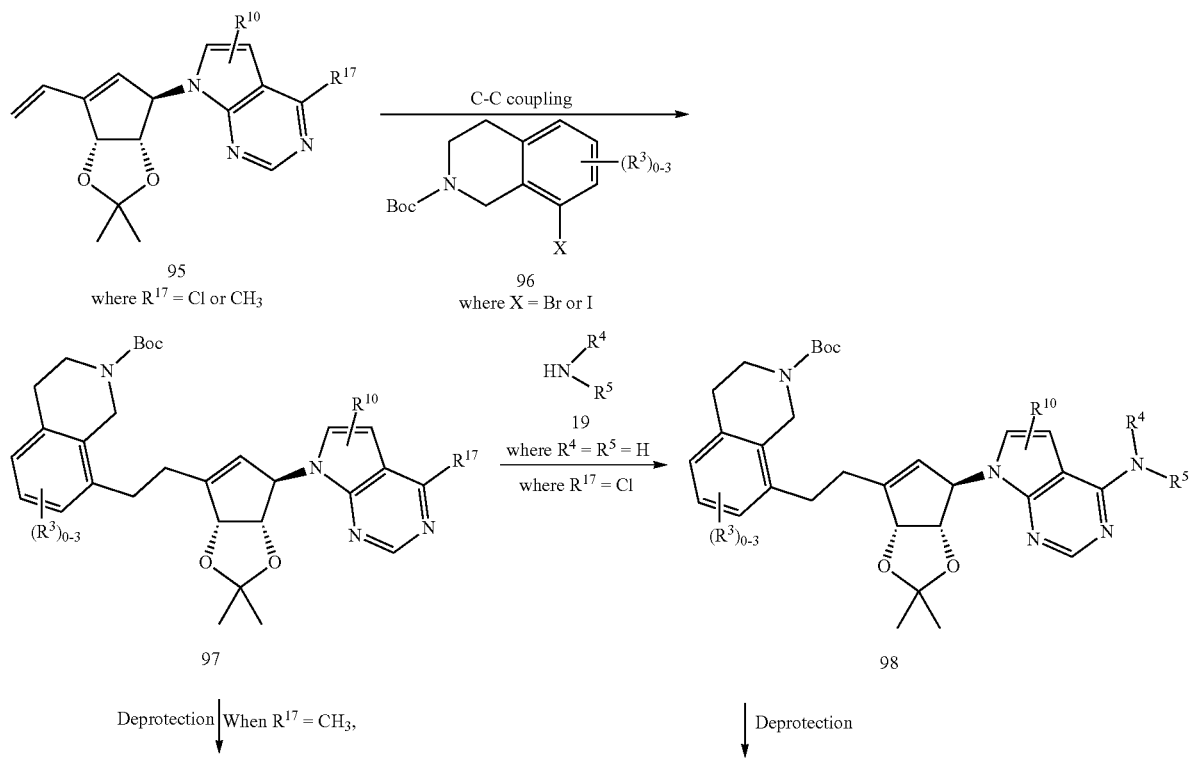

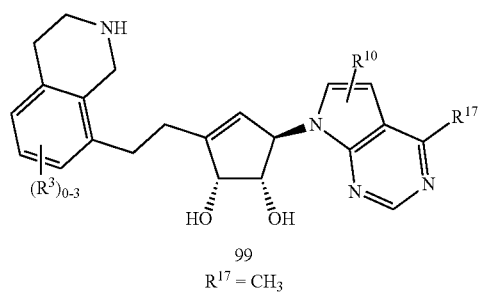

99
R¹⁷ = CH₃

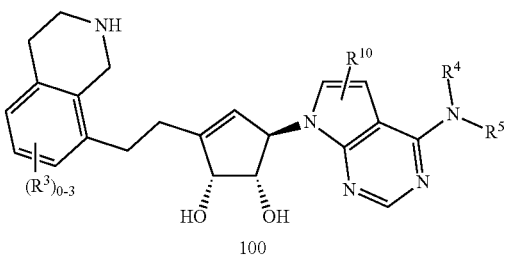

100

Scheme-15 illustrates the synthesis of compound of formula 100. Compound of formula 97 can be synthesized by hydroboration of compound of formula 95 with suitable boranes such as but not limited to 9-BBN followed by addition of inorganic base such as but not limited to tripotassium phosphate or Cs₂CO₃, in presence of Pd catalyst such as but not limited to Pd(dppf)Cl₂ or Pd-118 and compound of formula 96 (Y=Br, —I). Typically, these reactions are done in etheral solvents such as THF, MeTHF, dioxane, or similar solvents and run at temperatures ranging from 25° C. to 70° C. Compound of formula 97 upon treatment with compound of formula 19 can give compound of formula 98. Typically, these reactions are done in etheral solvents such as for example dioxane at temperatures ranging from 120° C. to 170° C. in a steel bomb. Additionally, deprotection of compound of formula 97 with acids such as but not limited to HCl or TFA affords compound of formula 99. Typically, these reactions are run at temperatures ranging from 25° C. to 50° C. Deprotection of compound of formula 98 with acids such as but not limited to HCl or TFA affords compound of formula 100. Typically, these reactions are run at temperatures ranging from 25° C. to 50° C. Compounds at every step may be purified by standard techniques such as column chromatography, crystallization, reverse phase HPLC or SFC.

Scheme-16

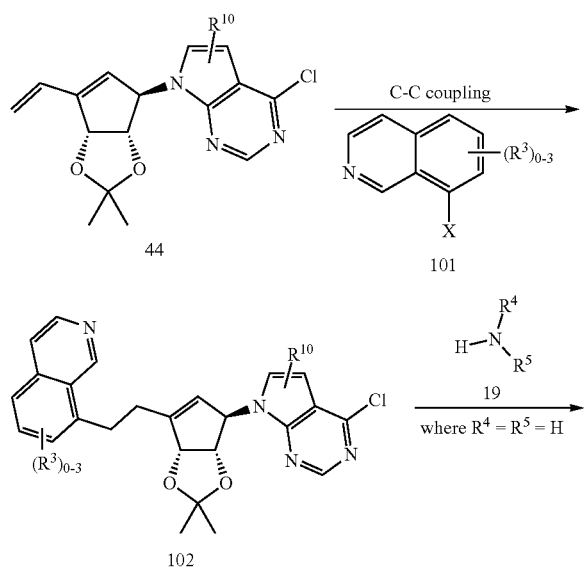

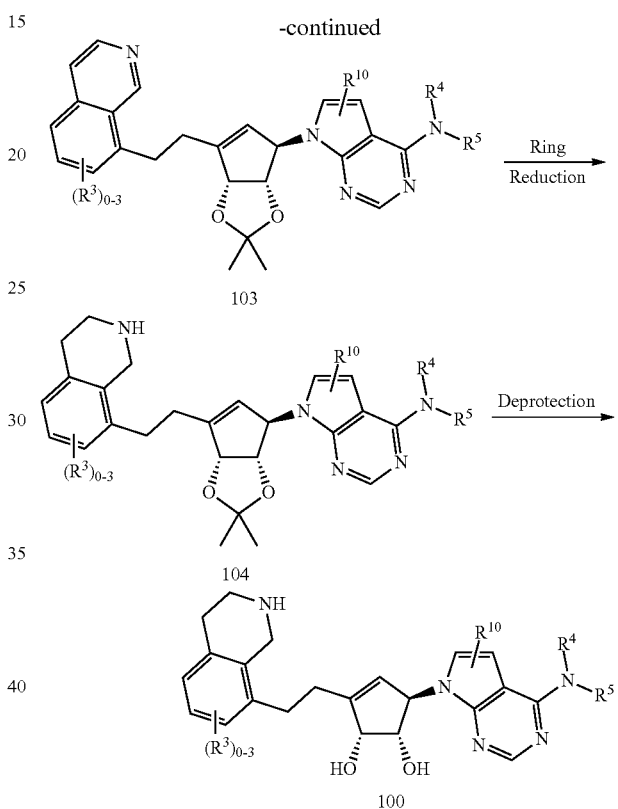

Scheme-16 illustrates the synthesis of compound of formula 100. Compound of formula 102 can be synthesized by hydroboration of compound of formula 44 with suitable boranes such as but not limited to 9-BBN followed by addition of inorganic base such as but not limited to tripotassium phosphate or Cs₂CO₃, in presence of Pd catalyst such as but not limited to Pd(dppf)Cl₂ or Pd-118 and compound of formula 101 (Y=Br, —I). Typically these reactions are done in etheral solvents such as THF, MeTHF, dioxane, or similar solvents and run at temperatures ranging from 25° C. to 70° C. Compound of formula 102 upon treatment with compound of formula 19 can give compound of formula 103. Typically these reactions are done in etheral solvents such as for example dioxane at temperatures ranging from 120° C. to 170° C. in a steel bomb. Compound of formula 103 upon treatment with reducing agents such as but not limited to NaBH₄ affords compound of formula 104. Typically these reactions are done in acidic solvents such as for example acetic acid at temperatures ranging from 0° C. to 25° C. Additionally, deprotection of compound of formula 104 with acids such as but not limited to HCl or TFA affords compound of formula 100. Typically these reactions are run at temperatures ranging from 25° C. to 50° C. Compounds at every step may be purified by standard techniques such as column chromatography, crystallization, reverse phase HPLC or SFC.

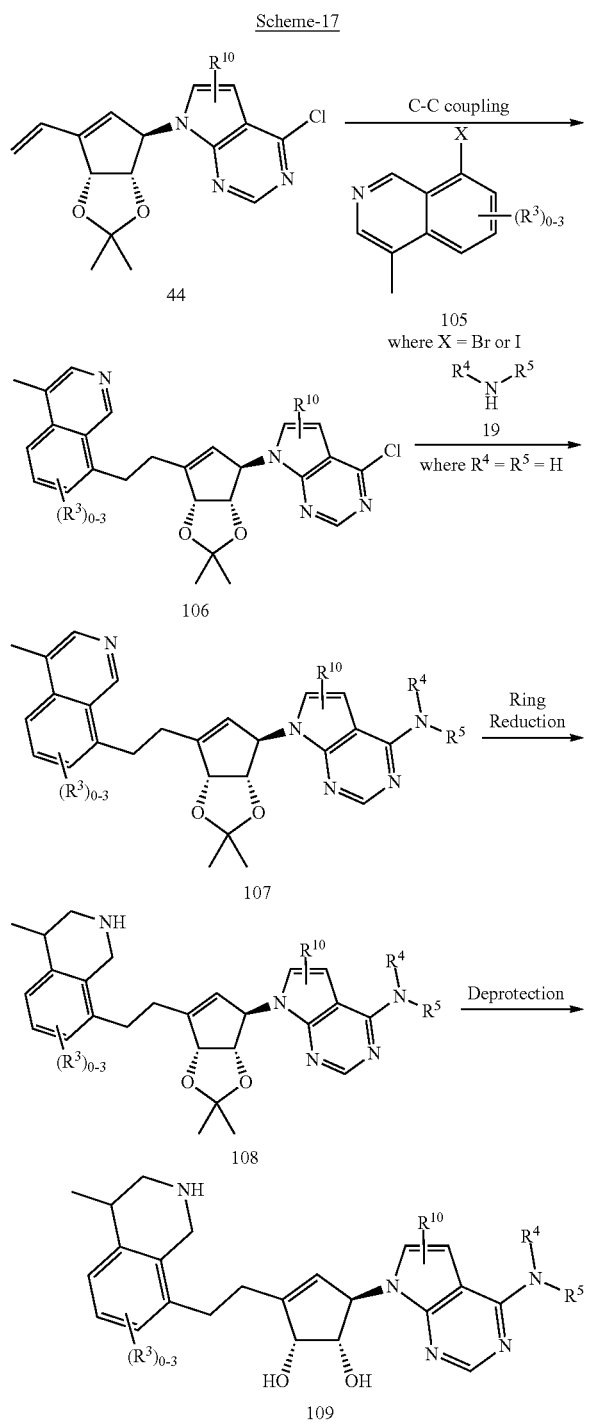

Scheme-17

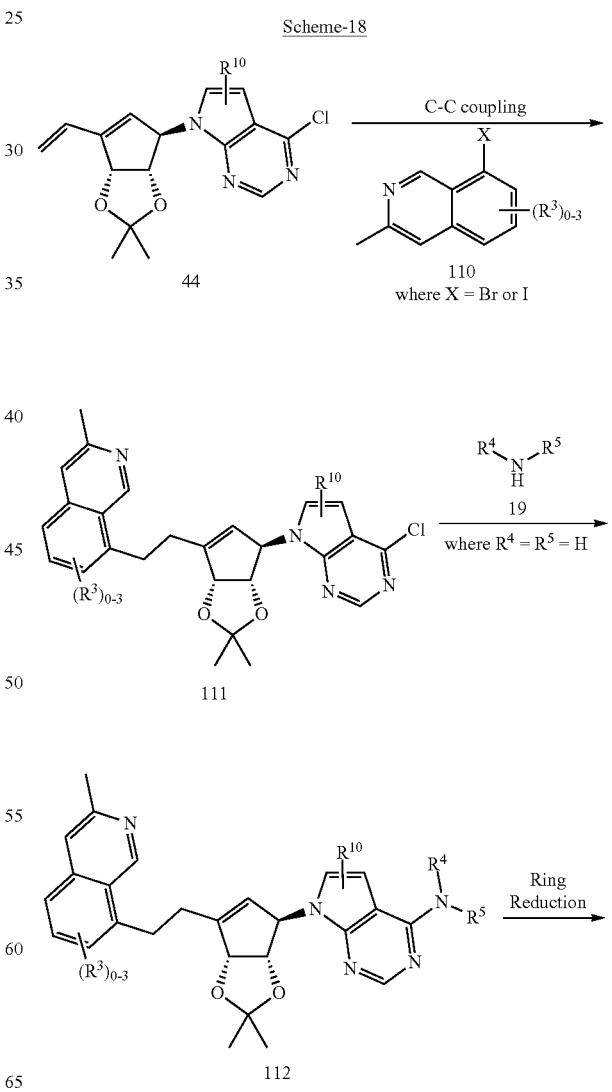

Scheme-18

Scheme-17 illustrates the synthesis of compound of formula 109. Compound of formula 106 can be synthesized by hydroboration of compound of formula 44 with suitable boranes such as but not limited to 9-BBN followed by addition of inorganic base such as but not limited to tripotassium phosphate or $Cs_2CO_3$, in presence of Pd catalyst such as but not limited to $Pd(dppf)Cl_2$ or Pd-118 and compound of formula 105 (Y=Br, —I). Typically, these reactions are done in etheral solvents such as THF, MeTHF, dioxane, or similar solvents and run at temperatures ranging from 25° C. to 70° C. Compound of formula 106 upon treatment with compound of formula 19 can give compound of formula 107. Typically, these reactions are done in etheral solvents such as for example dioxane at temperatures ranging from 120° C. to 170° C. in a steel bomb. Compound of formula 107 upon treatment with reducing agents such as but not limited to $NaBH_4$ affords compound of formula 108. Typically, these reactions are done in acidic solvents such as for example acetic acid at temperatures ranging from 0° C. to 25° C. Additionally, deprotection of compound of formula 108 with acids such as but not limited to HCl or TFA affords compound of formula 109. Typically, these reactions are run at temperatures ranging from 25° C. to 50° C. Compounds at every step may be purified by standard techniques such as column chromatography, crystallization, reverse phase HPLC or SFC.

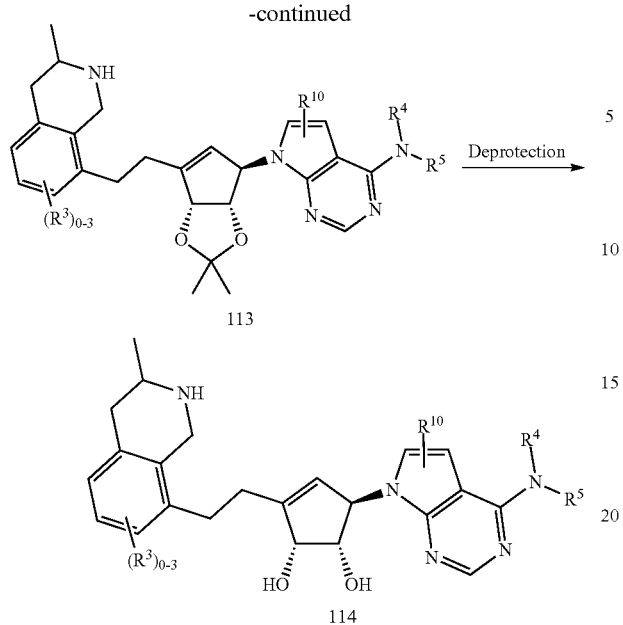

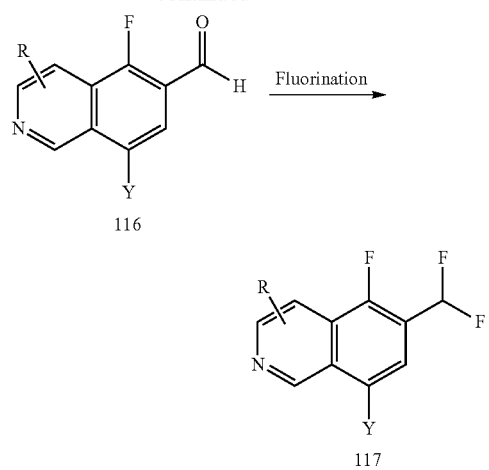

Scheme-18 illustrates the synthesis of compound of formula 114. Compound of formula 111 can be synthesized by hydroboration of compound of formula 44 with suitable boranes such as but not limited to 9-BBN followed by addition of inorganic base such as but not limited to tripotassium phosphate or Cs₂CO₃, in presence of Pd catalyst such as but not limited to Pd(dppf)Cl₂ or Pd-118 and compound of formula 110 (Y=Br, —I). Typically, these reactions are done in etheral solvents such as THF, MeTHF, dioxane, or similar solvents and run at temperatures ranging from 25° C. to 70° C. Compound of formula 111 upon treatment with compound of formula 19 can give compound of formula 112. Typically, these reactions are done in etheral solvents such as for example dioxane at temperatures ranging from 120° C. to 170° C. in a steel bomb. Compound of formula 112 upon treatment with reducing agents such as but not limited to NaBH₄ affords compound of formula 113. Typically, these reactions are done in acidic solvents such as for example acetic acid at temperatures ranging from 0° C. to 25° C. Additionally, deprotection of compound of formula 113 with acids such as but not limited to HCl or TFA affords compound of formula 114. Typically, these reactions are run at temperatures ranging from 25° C. to 50° C. Compounds at every step may be purified by standard techniques such as column chromatography, crystallization, reverse phase HPLC or SFC.

Scheme-19 illustrates the synthesis of compound of formula 117. Formylation reaction of compound of formula 115 with formylating agent such as but not limited to DMF in presence of hindered base such as but not limited to LDA gives the compound of formula 116. Typically these reactions are run in etheral solvents such as THF, MeTHF, dioxane, or similar solvents at temperatures ranging from −78° C. to 0° C. Compound of formula 116 upon treatment with nucleophilic fluorinating agents such as but not limited to DAST can give compound of formula 117. Typically these reactions can be run in halogenated solvents such as CH₂Cl₂, CHCl₃ or similar solvents at temperatures ranging from 0° C. to 25° C.

Scheme-19

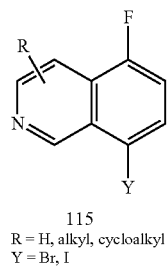

115
R = H, alkyl, cycloalkyl
Y = Br, I

Scheme-20

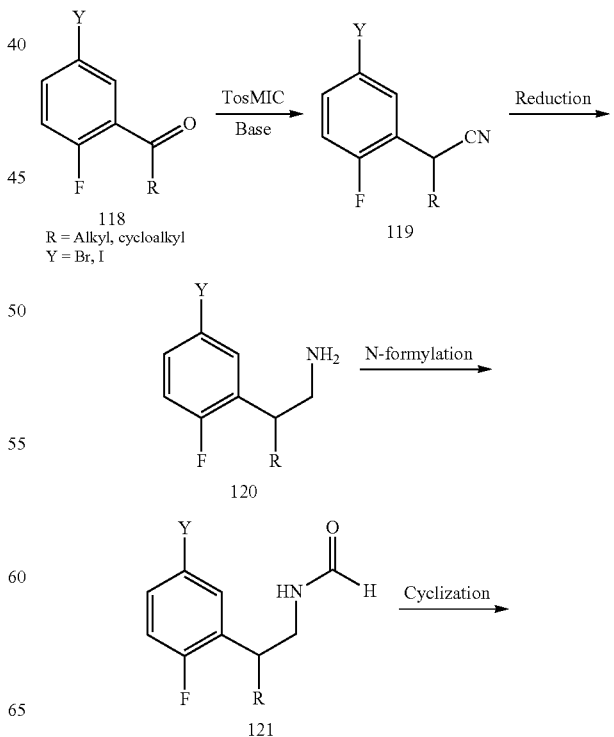

-continued

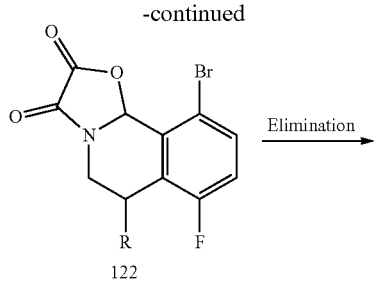

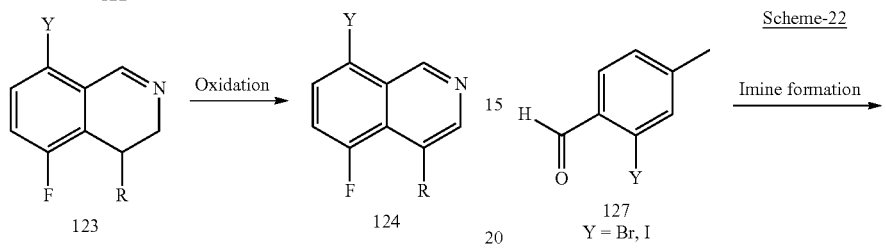

Scheme-20 illustrates the synthesis of compound of formula 124. Compound of formula 118 upon treatment with reagents such as but not limited to TosMIC in presence of base such as but not limited to KO$^t$Bu or NaO$^t$Bu can give compound of formula 119. Typically these reactions can be run in mixture of solvents such as but not limited to $^t$BuOH and DME or similar solvents at temperatures ranging from 0° C. to 25° C. Compound of formula 119 can be converted into compound of formula 120 by using borane reagents such as but not limited to BH$_3$.DMS or BH$_3$.THF. Typically these reactions are run in etheral solvents such as THF, MeTHF, dioxane, or similar solvents at temperatures ranging from 0° C. to 70° C. Reaction of compound of formula 120 with reagents such as but not limited to ethyl formate gives the compound of formula 121. Typically these reactions are run at temperatures ranging from 0° C. to 60° C. Compound of formula 121 upon treatment with reagents such as but not limited to oxalyl chloride in presence of Lewis acid such as but not limited to FeCl$_3$ can give compound of formula 122. Typically these reactions can be run in halogenated solvents such as CH$_2$Cl$_2$, CHCl$_3$ or similar solvents at temperatures ranging from 0° C. to 25° C. Subsequent reaction in acidic condition at temperatures ranging from 0° C. to 65° C. affords compound of formula 123. Typically these reactions can be run in protic solvents such as methanol, ethanol or similar solvents. Compound of formula 123 upon treatment with reagents such as but not limited to MnO$_2$ can give compound of formula 124. Typically these reactions are run in etheral solvents such as THF, MeTHF, dioxane, or similar solvents at temperatures ranging from 25° C. to 100° C.

Scheme-21 illustrates the synthesis of compound of formula 126. Chlorination reaction of compound of formula 125 with chlorinating agents such as but not limited to perchloroethane in presence of hindered base such as but not limited to LDA gives the compound of formula 126. Typically, these reactions are run in etheral solvents such as THF, MeTHF, dioxane, or similar solvents at temperatures ranging from −78° C. to 0° C.

Scheme-22

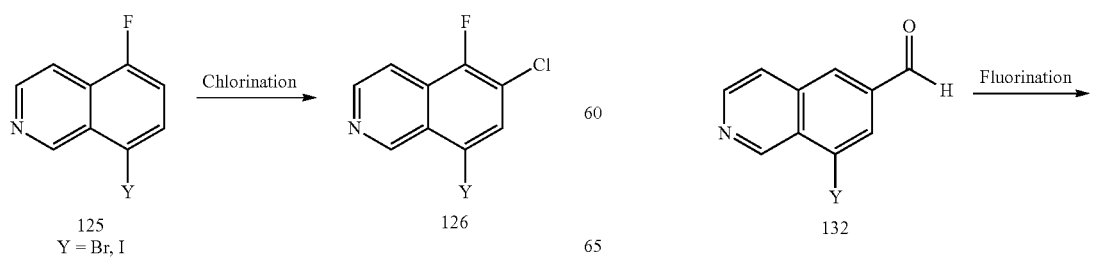

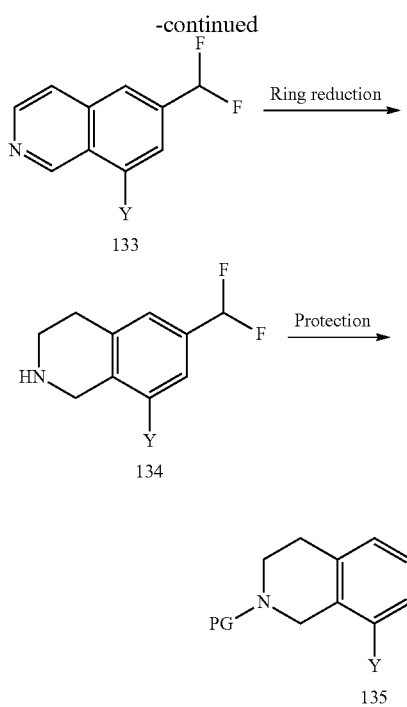

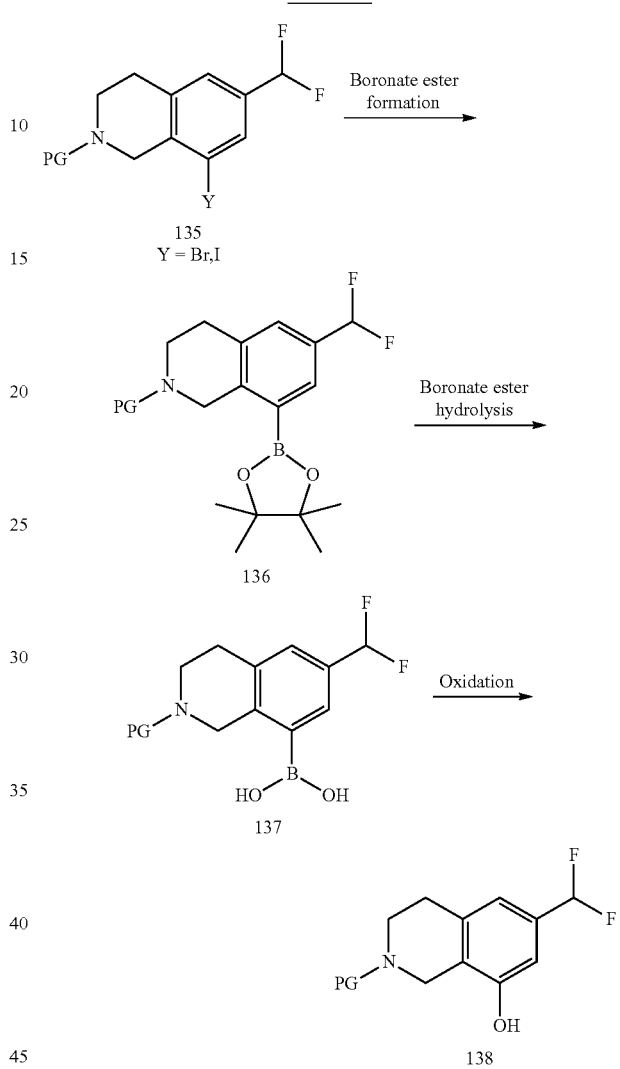

Scheme-22 illustrates the synthesis of compound of formula 135. Treatment of compound of formula 127 with aminoaldehyde dimethylacetal gives compound of formula 128. Typically these reactions can be run in hydrocrbon solvents such as toluene or xylene or similar solvents at temperatures ranging from 25° C. to 130° C. Reduction of imine of formula 128 with reducing agent such as but not limited to NaBH$_4$ provides compound of formula 129. Typically these reactions can be run in protic solvents such as methanol, ethanol or similar solvents at temperatures ranging from 0° C. to 25° C. Tosylation of compound of formula 129 with reagents such as but not limited to tosyl chloride in presence of base such as but not limited to pyridine gives compound of formula 130. Typically these reactions can be run in halogenated solvents such as CH$_2$Cl$_2$, CHCl$_3$ or similar solvents at temperatures ranging from 0° C. to 25° C. Cyclization of compound of formula 130 with Lewis acids such as but not limited to AlCl$_3$ gives compound of formula 131. Typically these reactions can be run in halogenated solvents such as CH$_2$Cl$_2$, CHCl$_3$ or similar solvents at temperatures ranging from 0° C. to 25° C. Oxidation of compound of formula 131 with oxidizing agents such as but not limited to SeO$_2$ gives compound of formula 132. Typically these reactions can be run in hydrocarbon solvents such as o-dichlorobenzene or xylene or similar solvents at temperatures ranging from 150° C. to 180° C. Compound of formula 132 upon treatment with nucleophilic fluorinating agents such as but not limited to DAST can give compound of formula 133. Typically these reactions can be run in halogenated solvents such as CH$_2$Cl$_2$, CHCl$_3$ or similar solvents at temperatures ranging from 0° C. to 25° C. Compound of formula 133 upon treatment with reducing agents such as but not limited to NaBH$_4$ affords compound of formula 134. Typically these reactions are done in acidic solvents such as for example acetic acid at temperatures ranging from 0° C. to 25° C. Compound of formula 135 is prepared by treating compound of formula 134 with anhydride such as but not limited to (Boc)$_2$O in presence of base such as but not limited to NEt$_3$, DIPEA, DMAP etc. at temperatures ranging from 0° C. to 25° C.

Scheme-23 illustrates the synthesis of compound of formula 138. Compound of formula 136 can be synthesized by treating compound of formula 135 with suitable boranes such as but not limited to bispinacoloto diboron followed by addition of inorganic base such as but not limited to potassium acetate, in presence of Pd catalyst such as but not limited to Pd(dppf)Cl$_2$ or Pd(PPh$_3$)$_2$Cl$_2$. Typically these reactions are done in etheral solvents such as THF, MeTHF, dioxane, or similar solvents and run at temperatures ranging from 25° C. to 100° C. Compound of formula 136 can be converted into compound of formula 137 by using oxidizing agents such as but not limited to sodium periodate. Typically these reactions can be run in solvents such as acetone or similar solvents at temperatures ranging from 0° C. to 25° C. Compound of formula 137 can be converted into compound of formula 138 by treating with agents such as but not limited to H$_2$O$_2$/AcOH, H$_2$O$_2$/Citric acid. Typically these reactions can be run at temperatures ranging from 0° C. to 25° C.

Scheme-24

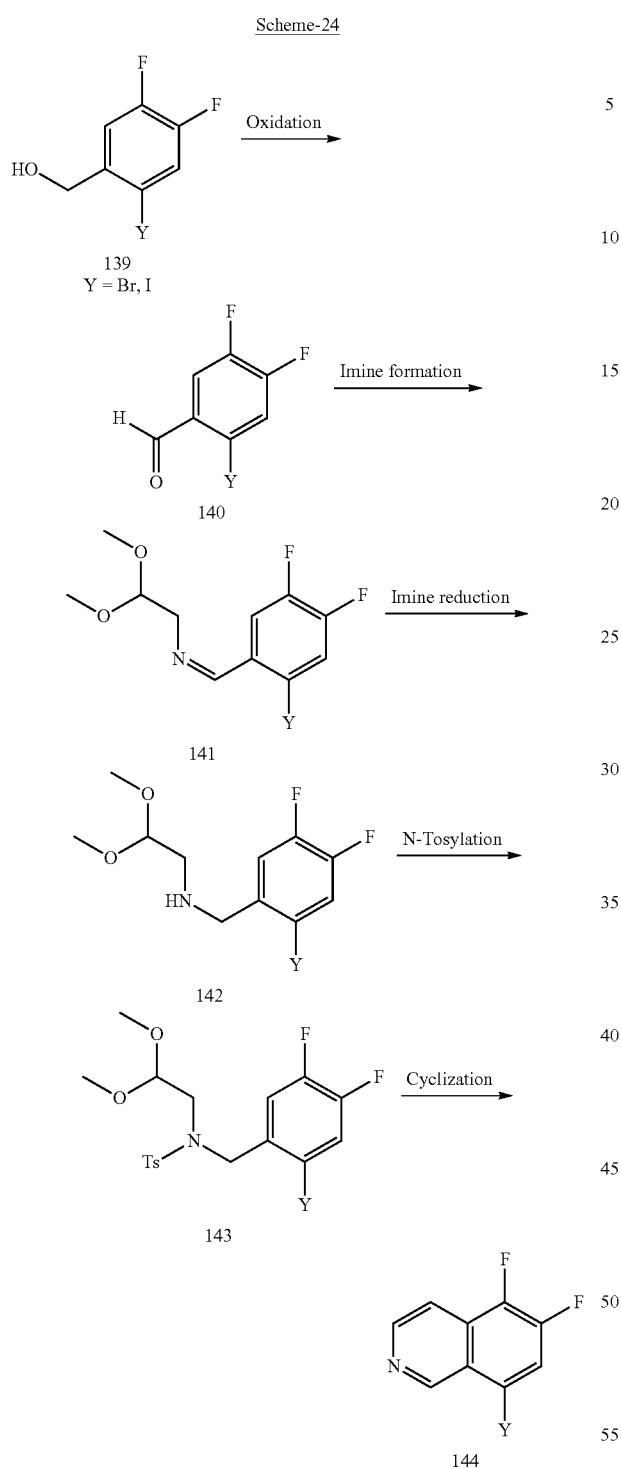

run in hydrocrbon solvents such as toluene or xylene or similar solvents at temperatures ranging from 25° C. to 130° C. Reduction of imine of formula 141 with reducing agent such as but not limited to $NaBH_4$ provides compound of formula 142. Typically these reactions can be run in protic solvents such as for example methanol, ethanol or similar solvents at temperatures ranging from 0° C. to 25° C. Tosylation of compound of formula 142 with reagents such as but not limited to tosyl chloride in presence of base such as but not limited to pyridine gives compound of formula 143. Typically, these reactions can be run in halogenated solvents such as $CH_2Cl_2$, $CHCl_3$ or similar solvents at temperatures ranging from 0° C. to 25° C. Cyclization of compound of formula 143 with Lewis acids such as but not limited to $AlCl_3$ gives compound of formula 144. Typically, these reactions can be run in halogenated solvents such as $CH_2Cl_2$, $CHCl_3$ or similar solvents at temperatures ranging from 0° C. to 25° C.

Scheme 25

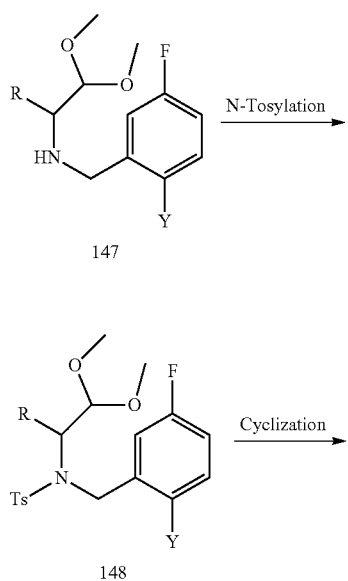

Scheme-24 illustrates the synthesis of compound of formula 144. Compound of formula 139 can be converted into compound of formula 140 by using oxidizing agents such as but not limited to PCC. Typically, these reactions can be run in halogenated solvents such as $CH_2Cl_2$, $CHCl_3$ or similar solvents at temperatures ranging from 0° C. to 25° C. Treatment of compound of formula 140 with reagents such as but not limited to aminoaldehyde dimethylacetal gives compound of formula 141. Typically, these reactions can be

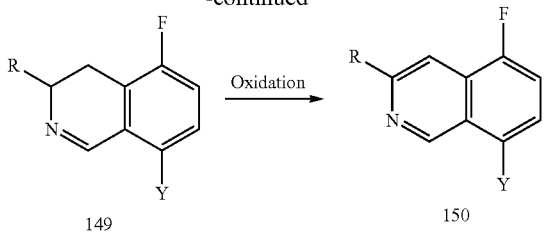

Y = Br, I; R = Alkyl, cycloalkyl

Scheme-25 illustrates the synthesis of compound of formula 150. Treatment of compound of formula 145 with reagent such as but not limited to 1,1-dimethoxypropan-2-one gives compound of formula 146. Typically, these reactions can be run in hydrocrbon solvents such as toluene or xylene or halogenated solvents such as $CH_2Cl_2$, $CHCl_3$ or similar solvents. Reduction of compound of formula 146 with reducing agent such as but not limited to $NaBH_4$ provides compound of formula 147. Typically these reactions can be run in protic solvents such as for example methanol, ethanol or similar solvents at temperatures ranging from 0° C. to 25° C. Tosylation of compound of formula 147 with reagents such as but not limited to tosyl chloride in presence of base such as but not limited to pyridine gives compound of formula 148. Typically, these reactions can be run in halogenated solvents such as $CH_2Cl_2$, $CHCl_3$ or similar solvents at temperatures ranging from 0° C. to 25° C. Cyclization of compound of formula 148 with Lewis acids such as but not limited to $AlCl_3$ gives compound of formula 149. Typically, these reactions can be run in halogenated solvents such as $CH_2Cl_2$, $CHCl_3$ or similar solvents at temperatures ranging from 0° C. to 25° C. Compound of formula 149 upon treatment with reagents such as but not limited to $MnO_2$ can give compound of formula 150. Typically, these reactions are run in etheral solvents such as THF, MeTHF, dioxane, or similar solvents at temperatures ranging from 25° C. to 100° C.

The following examples are provided to further illustrate the present invention and therefore should not be construed in any way to limit the scope of the present invention.

Abbreviations

The following abbreviations may be used herein:
AcOH=Acetic acid
Aq.=aqueous
$AlCl_3$=Aluminum chloride
ca=about or approximately
$NH_4Cl$=Ammonium chloride
$BH_3$.DMS=Borane dimethyl sulfide complex
$BH_3$.THF=Borane tetrahydrofuran complex
9-BBN=9-Borabicyclononane
BINAP=2,2'-Bis(diphenylphosphino)-1,1'-binaphthyl
Boc=tert-Butoxycarbonyl
$(Boc)_2O$=Di-tert-butyl dicarbonate
t-Bu or tBu=tert-Butyl
t-BuOH=tert-Butyl alcohol
$Cs_2CO_3$=Cesium Carbonate
$CHCl_3$=Chloroform
$CDCl_3$=Deuterated chloroform
DAST=Diethylaminosulphur trifluoride
dba=Dibenzylideneacetone
DBU=1,8-Diazabicyclo[5.4.0]undec-7-ene
$CH_2Cl_2$ or DCM=Dichloromethane
DMP=Dess Martin Periodinane
DEAD=Diethyl azodicarboxylate
DIAD=Diisopropyl azodicarboxylate
DIPEA=Diisopropylethylamine
DMAP=4-Dimethylaminopyridine
DMF=N,N-Dimethylformamide
DMAc=N,N-Dimethylacetamide
DME=1,2-Dimethoxyethane
DMS=Dimethylsulfide
DMSO=Dimethylsulphoxide
DMSO-$d_6$=Deuterated dimethylsulphoxide
Et=ethyl
EtOH=Ethanol
EtOAc=Ethyl acetate
$FeCl_3$=Iron(III) chloride
GCMS=Gas chromatography-mass spectrometry
g=gram
HPLC=High Performance Liquid Chromatography
HCl=Hydrochloric acid
$H_2O$=Water
$H_2O_2$=Hydrogen peroxide
$H_2SO_4$=Sulphuric acid
$K_2CO_3$=Potassium carbonate
KOH=Potassium hydroxide
$KO^tBu$=Potassium tert-butoxide
$K_3PO_4$=Potassium phosphate
KHMDS=Potassium bis(trimethylsilyl)amide
LiH=Lithium hydride
LDA=Lithium diisopropylamide
LHMDS=Lithium bis(trimethylsilyl)amide
LCMS=Liquid chromatography mass spectrometry
m-CPBA=meta-chloroperoxybenzoic acid
mg=milligram
Me=Methyl
MeOH=Methanol
MeOD=Deuterated methanol
MeTHF=2-Methyltetrahydrofuran
MS=Molecular sieves
MsCl=Methanesulphonyl chloride
$MgSO_4$=Magnesium sulphate
$MnO_2$=Manganese (IV) oxide
m/z=mass-to-charge ratio
NaH=Sodium hydride
$NaBH_4$=Sodium borohydride
$NaO^tBu$=Sodium tert-butoxide
$NaHCO_3$=Sodium bicarbonate
$Na_2S_2O_3$=Sodium thiosulphate
$Na_2SO_3$=Sodium sulphite
NaHMDS=Sodium bis(trimethylsilyl)amide
NMP=N-Methyl-2-pyrrolidone
NBS=N-Bromosuccinimide
NCS=N-Chlorosuccinimide
NIS=N-Iodosuccinimide
NMO=N-Methylmorpholine-N-oxide
NMR=Nuclear magnetic resonance
$N_2$=Nitrogen
Ph=phenyl
$PPh_3$=Triphenylphosphine
PDC=Pyridinium dichlorochromate
$Pd(OAc)_2$=Palladium acetate
Pd/C=Palladium on carbon
Pd-118=[1,1'-Bis(di-tert-butylphosphino)ferrocene]dichloropalladium(II)
$Pd(PPh_3)_4$=Tetrakis(triphenylphosphine)palladium(0)
$POCl_3$=Phosphorous oxychloride
$PdCl_2(dppf)$=[1,1'-Bis(diphenylphosphino)ferrocene]dichloropalladium(II)

Pd(PPh$_3$)$_2$Cl$_2$=Bis(triphenylphosphine)palladium(II) dichloride
PCC=Pyridinium chlorochromate
PMB=p-Methoxybenzyl
PTSA=p-Toluenesulphonic acid
Rt=Retention time
rt=room temperature
Sat.=saturated
SFC=Supercritical fluid chromatography
SeO$_2$=Selenium dioxide
TLC=Thin layer chromatography
TBAF=Tetrabutylammonium fluoride
TsCl=p-Toluenesulphonyl chloride
TBDMS=tert-Butyldimethylsilyl
TBDPS=tert-Butyldiphenylsilyl
Et$_3$N or NEt$_3$ or TEA=Triethylamine
TFA=Trifluoroacetic acid
p-TsOH=p-Toluenesulphonic acid

EXPERIMENTAL

Intermediates

6-Chloropyrimidin-4 (3H)-one

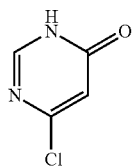

The title compound was prepared by following same reaction protocol as described in US2009/149466 A1.

4,6-Dichloro-5-fluoropyrimidine

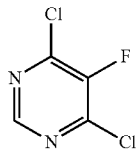

The title compound was prepared by following same reaction protocol as described in WO2012/40279 A1.

6-Chloro-5-fluoropyrimidin-4 (3H)-one

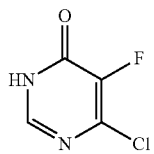

A mixture of 4,6-dichloro-5-fluoropyrimidine (3.20 g, 19.17 mmol), HCl (14.31 ml, 165 mmol), water (15 ml) in dioxane (15 ml) was heated at 70° C. for 6 h. Allowed to cool the reaction mixture to rt and solvent was evaporated under reduced pressure to get 1.5 g of a crude compound. This residue was purified by combiflash (R$_f$200, Teledyne/Isco) instrument onto a redisep® R$_f$ column with gradient elution (0 to 30%) of ethyl acetate in petroleum ether to afford (1.2 g, 42.2%) of the title compound. GCMS m/z=148.11 (M+, 70%).

3-Benzoylpyrimidine-2,4 (1H,3H)-dione

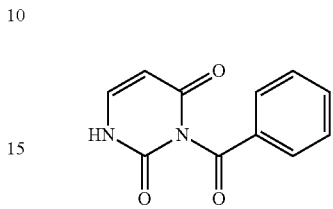

The title compound was prepared by following same reaction protocol as described in ACS Med. Chem. Lett. 2015, 6, 1150-1155.

2-Amino-4-bromo-6-fluorobenzaldehyde

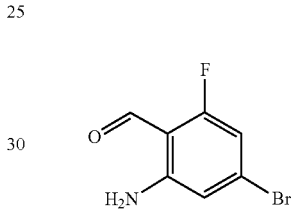

To a stirred solution of 4-bromo-2-fluoro-6-nitrobenzaldehyde (prepared by following same reaction protocol as described in, WO 2015/054572 A1; 4.15 g, 16.73 mmol) in ethanol (20 ml) & acetic acid (20 ml) was added iron powder (2.80 g, 50.2 mmol) at 0° C. and stirred the reaction mixture for 1 h. The reaction mixture was diluted with ethyl acetate (70 ml) and netralized with aq. sat. NaHCO$_3$ (sodium bicarbonate, 100 ml). The resulting emulsion was filtered through celite. Layers were separated, organic layer was washed with brine (100 ml) and dried over anhydrous Na$_2$SO$_4$ (sodium sulphate). The organic layer was filtered and concentrated in vacuo to afford the title compound (3.36 g, 92%) as a light green solid which was used for next step without purification. $^1$H NMR (400 MHz, DMSO-d$_6$) δ 10.10 (s, 1H), 7.78-7.54 (m, 2H), 6.84 (t, J=1.5 Hz, 1H), 6.64 (dd, J=11.1, 1.8 Hz, 1H).

7-Bromo-3-chloro-5-fluoroquinolin-2-amine

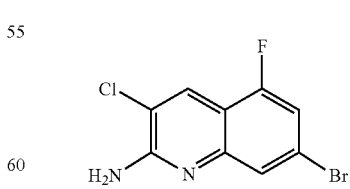

To a stirred solution of 2-amino-4-bromo-6-fluorobenzaldehyde (9.48 g, 43.5 mmol) in dry acetonitrile (150 ml) was added DBU (1,8-Diazabicyclo[5.4. 0]undec-7-ene) (19.66 ml, 130 mmol) and Lithium Chloride (3.69 g, 87 mmol) at 0° C. followed by dropwise addition of diethyl (chloro(cyano)methyl) phosphonate (9.2 g, 43.5 mmol) in 50 ml acetonitrile at same temperature. The reaction mixture was stirred at 25° C. for 16 h. The reaction mixture was diluted with ethyl acetate (150 ml) and washed with water (200 ml). Layers were separated, organic layer was washed with brine (100 ml) and dried over anhydrous Na$_2$SO$_4$ (sodium sulphate). The organic layer was filtered and concentrated in vacuo to give 11.2 g of crude compound. This residue was purified by combiflash (R$_f$200, Teledyne/Isco) instrument onto a redisep® R$_f$ column with gradient elution (0 to 30%) of ethyl acetate in petroleum ether to afford the title compound (9.48 g, %) as a white solid. $^1$H NMR (400 MHz, DMSO-d$_6$) δ 8.23 (s, 1H), 7.51 (d, J=1.9 Hz, 1H), 7.32 (dd, J=9.5, 1.9 Hz, 1H), 7.25 (s, 2H); LCMS m/z=275 (M+1; 100%).

3-Bromo-7-iodo-N-(4-methoxybenzyl)quinolin-2-amine

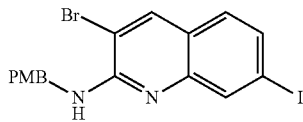

The title compound was prepared by following an analogous reaction protocol as described in WO2012/037108 A1.

7-Bromo-3-chloro-5-fluoro-N-(4-methoxybenzyl)quinolin-2-amine

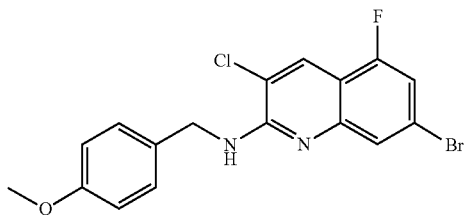 [SMILES: COc1ccc(CNc2nc3cc(Br)cc(F)c3cc2Cl)cc1]

The title compound was prepared by following an analogous reaction protocol as described in WO2012/037108 A1 using appropriate starting materials. $^1$H NMR (400 MHz, DMSO-d6) δ 8.22 (d, J=0.8 Hz, 1H), 7.96 (t, J=6.1 Hz, 1H), 7.58 (dd, J=1.8, 1.0 Hz, 1H), 7.39-7.28 (m, 3H), 6.91-6.82 (m, 2H), 4.62 (d, J=6.1 Hz, 2H), 3.71 (s, 3H); LCMS m/z=397 (M+1; 100%).

7-Bromo-3-chloro-5-fluoro-N, N-bis(4-methoxybenzyl)quinolin-2-amine

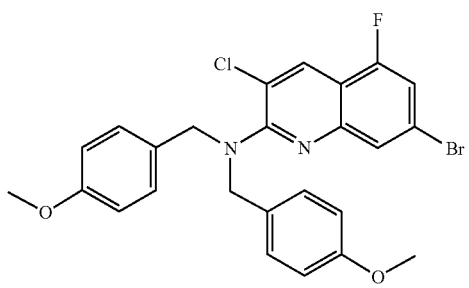 [SMILES: COc1ccc(CN(Cc2ccc(OC)cc2)c2nc3cc(Br)cc(F)c3cc2Cl)cc1]

To a stirred suspension of 7-bromo-3-chloro-5-fluoroquinolin-2-amine (1.5 g, 5.44 mmol) in DMF (Dimethyl formamide, 25 ml), was added NaH (sodium hydride, 0.544 g, 13.61 mmol) at 0° C. The resulting mixture was stirred at 0° C. for 15 min. 4-Methoxybenzyl chloride (1.854 ml, 13.61 mmol) was added dropwise under N$_2$ atmosphere. The reaction mixture was then stirred for 3 h at 25° C. The reaction mixture was poured into ice water (150 mL) and extracted with ethyl acetate (200 ml). Layers were separated, organic layer was washed with brine (100 ml) and dried over anhydrous Na$_2$SO$_4$. The organic layer was filtered and concentrated in vacuo to give 2.7 g of crude compound. This residue was purified by combiflash (R$_f$200, Teledyne/Isco) instrument onto a redisep® R$_f$ column with gradient elution (0 to 20%) of ethyl acetate in petroleum ether to afford the title compound (2.2 g, 78%) as an off-white solid. $^1$H NMR (400 MHz, DMSO-d6) δ 8.39 (d, J=0.9 Hz, 1H), 7.76 (t, J=1.3 Hz, 1H), 7.52 (dd, J=9.4, 1.7 Hz, 1H), 7.29-7.23 (m, 4H), 6.91-6.84 (m, 4H), 4.60 (s, 4H), 3.71 (s, 6H); LCMS m/z=515.68, 517.68 (M+, M+2; 100%).

3-Chloro-5-fluoro-N,N-bis(4-methoxybenzyl)-7-(4,4,5,5-tetramethyl-1,3,2-dioxaborolan-2-yl)quinolin-2-amine

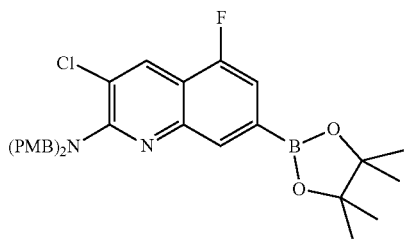

A mixture of 7-bromo-3-chloro-5-fluoro-N,N-bis(4-methoxybenzyl)quinolin-2-amine (2.5 g, 4.85 mmol), bispinacoloto diboron (1.477 g, 5.82 mmol), [1,1'-Bis(diphenylphosphino) ferrocene]dichloropalladium(II) complex with dichloromethane (0.396 g, 0.485 mmol)), potassium acetate (0.809 g, 8.24 mmol) in DMSO (35 ml) was heated at 80° C. for 30 min in preheated oil bath. The reaction mixture was cooled to rt. The reaction mixture was poured into ice water (50 mL) and extracted with ethyl acetate (100 ml). Layers were separated, organic layer was washed with brine (30 ml) and dried over anhydrous Na$_2$SO$_4$. The organic layer was filtered and concentrated in vacuo to give 2.3 g of a crude compound. This residue was purified by combi-flash (R$_f$200, Teledyne/Isco) instrument onto a redisep® R$_f$ column with gradient elution (0 to 10%) of ethyl acetate in petroleum ether to afford the title compound (1.5 g, 55%) as an off-white solid. $^1$H NMR (400 MHz, DMSO-d6) δ 8.44 (d, J=0.8 Hz, 1H), 7.81 (d, J=1.0 Hz, 1H), 7.35-7.17 (m, 5H), 6.95-6.79 (m, 4H), 4.58 (s, 4H), 3.70 (s, 6H), 1.33 (s, 12H); LCMS m/z=563.2 (M+, 100%).

2-(Bis(4-methoxybenzyl)amino)-3-chloro-5-fluoro-quinolin-7-ol

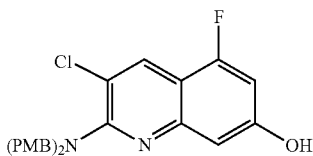

To a stirred solution of 3-chloro-5-fluoro-N,N-bis(4-methoxybenzyl)-7-(4,4,5,5-tetramethyl-1,3,2-dioxaborolan-2-yl)quinolin-2-amine (3 g, 5.33 mmol) in THF (tetrahydrofuran, 40 ml) was added glacial acetic acid (0.610 ml, 10.66 mmol) dropwise at 0° C. and stirred for 1 h. Aq.solution of hydrogen peroxide (3.27 ml, 32.0 mmol) was added slowly at 0° C. The reaction mixture was stirred for 16 h. The mixture was diluted with EtOAc (ethyl acetate, 25 ml) and water (25 ml). Layers were separated and the organic layer was stirred with aq. sodium sulfite (25 ml) at 25° C. for 15 minutes. Layers were separated, the organic layer was washed with brine (30 ml) and dried over anhydrous $Na_2SO_4$. The solvent was evaporated under reduced pressure to give 2.1 g of a crude compound. This residue was purified by combi-flash ($R_f$ 200, Teledyne/Isco) instrument onto a redisep® $R_f$ column with gradient elution (0 to 25%) of ethyl acetate in petroleum ether to afford the title compound (1.6 g, 66.3%) as an off-white solid. $^1H$ NMR (400 MHz, DMSO-d6) δ 10.46 (s, 1H), 8.21 (s, 1H), 7.25 (d, J=8.0 Hz, 4H), 6.86 (d, J=8.1 Hz, 4H), 6.83-6.72 (m, 2H), 4.51 (s, 4H), 3.71 (d, J=3.0 Hz, 6H); LCMS m/z=453.1 (M+, 100%).

3-Amino-5-bromopicolinaldehyde

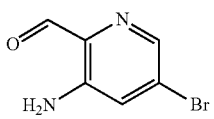

To a stirred solution of 5-bromo-3-nitropicolinaldehyde (prepared by following same reaction protocol as described in US2010/125089; 1 g, 4.33 mmol) in ethanol (5 ml) & acetic acid (5 ml) was added iron powder (0.725 g, 12.99 mmol) at 0° C. and stirred the reaction mixture for 30 mins. The reaction mixture was allowed to stir at 25° C. for 30 mins. The reaction mixture was diluted with ethyl acetate (20 ml) and netralized with aq. sat. $NaHCO_3$ (30 ml). The resulting emulsion was filtered through celite. Layers were separated, organic layer was washed with brine (20 ml) and dried over anhydrous $Na_2SO_4$ The organic layer was filtered and concentrated in vacuo to afford (0.21 g, 24.13%) as a light green solid which was used for next step without purification. $^1H$ NMR (400 MHz, DMSO-d6) δ 9.86 (s, 1H), 8.03 (d, J=2.0 Hz, 1H), 7.50 (d, J=1.9 Hz, 1H), 7.30 (s, 2H); LCMS m/z=201.39, 203.39 (M+, M+2; 100%).

7-Bromo-3-chloro-1,5-naphthyridin-2-amine

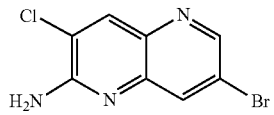

To a stirred solution of 3-amino-5-bromopicolinaldehyde (0.185 g, 0.922 mmol) in acetonitrile (5 ml) was added DBU (0.096 ml, 0.638 mmol) and lithium chloride (0.060 g, 1.418 mmol) at 0° C. followed by dropwise addition of diethyl (chloro(cyano)methyl)phosphonate (0.150 g, 0.709 mmol) in acetonitrile (3 ml). Stirred the reaction mixture at 25° C. for 16 h. The reaction mixture was diluted with ethyl acetate (10 ml) and washed with water (10 ml). Layers were separated, the organic layer was washed with brine (20 ml) and dried over anhydrous $Na_2SO_4$. The organic layer was filtered and concentrated in vacuo to afford 0.2 g of a crude compound. This residue was purified by combiflash ($R_f$ 200, Teledyne/Isco) instrument onto a redisep® $R_f$ column with gradient elution (0-50%) of ethyl acetate in petroleum ether to afford the title compound (0.13 g, 70.9%) as an off white solid. $^1H$ NMR (400 MHz, DMSO-d6) δ 7.96-7.88 (m, 2H), 7.34 (d, J=2.1 Hz, 1H), 6.34 (s, 2H); LCMS m/z=257.02, 259.52, 261.90 (M-1, M+, M+2; 100%).

7-Bromoquinoxalin-2-amine

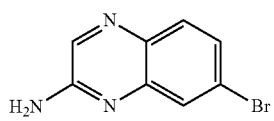

The title compound was prepared by following an analogous reaction protocol as described in Wolf et al, JACS, 1949, 71, 6-10.

4-chloro-5-methyl-7H-pyrrolo[2,3-d]pyrimidine

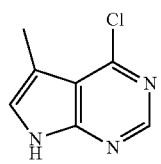

The title compound was prepared by following same reaction protocol as described in WO2008/75110 A1.

6-methyl-1H-pyrazolo[3,4-d]pyrimidin-4-amine

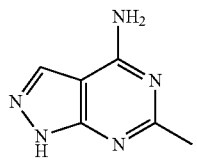

The title compound was prepared by following same reaction protocol as described in WO2017/46737 A1.

1H-pyrazolo[3,4-d]pyrimidin-4-amine

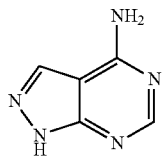

The title compound was prepared by following same reaction protocol as described in US2015/225407 A1.

Tert-butyl 6-(difluoromethyl)-5-fluoro-8-hydroxy-3,4-dihydroisoquinoline-2 (1H)-carboxylate

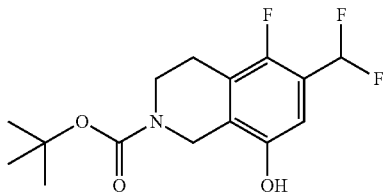 [SMILES: CC(C)(C)OC(=O)N1CCc2c(F)c(C(F)F)cc(O)c2C1]

The title compound was prepared by following same reaction protocol as described in US2019/0111060A1.

tert-butyl 6-(difluoromethyl)-5-fluoro-8-(((trifluoromethyl)sulfonyl)oxy)-3,4-dihydroisoquinoline-2 (1H)-carboxylate

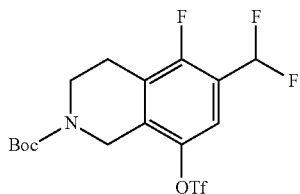 [SMILES: CC(C)(C)OC(=O)N1CCc2c(F)c(C(F)F)cc(OS(=O)(=O)C(F)(F)F)c2C1]

To a stirred solution of tert-butyl 6-(difluoromethyl)-5-fluoro-8-hydroxy-3,4-dihydroisoquinoline-2 (1H)-carboxylate (1 g, 3.15 mmol) in DCM (40 ml) was added Et3N (0.879 ml, 6.30 mmol) and trifluoromethanesulfonic anhydride (0.586 ml, 3.47 mmol) at 0° C. and stirred the reaction mixture for 1 h. The reaction mixture was diluted with dichloromethane (10 ml) and washed with water (20 ml). Layers were separated, organic layer was washed with brine (10 ml) and dried over anhydrous Na₂SO₄. The organic layer was filtered and concentrated in vacuo to give 1.2 g of a crude compound. This residue was purified by combiflash (R$_f$200, Teledyne/Isco) instrument onto a redisep® R$_f$ column with gradient elution (0 to 5%) of ethyl acetate in petroleum ether to afford (1.079 g, 76%) of the title compound. $^1$H NMR (400 MHz, Chloroform-d) δ 7.42 (d, J=5.5 Hz, 1H), 6.89 (t, J=56 Hz, 1H), 4.69 (s, 2H), 3.72 (t, J=6.0 Hz, 2H), 2.94-2.82 (m, 2H), 1.51 (s, 9H).

tert-butyl 6-(difluoromethyl)-5-fluoro-8-(4,4,5,5-tetramethyl-1,3,2-dioxaborolan-2-yl)-3,4-dihydroisoquinoline-2 (1H)-carboxylate

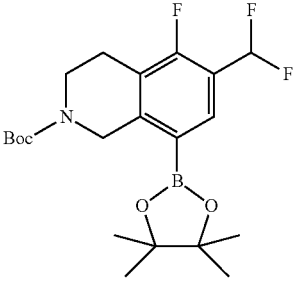 [SMILES: CC(C)(C)OC(=O)N1CCc2c(F)c(C(F)F)cc(B3OC(C)(C)C(C)(C)O3)c2C1]

A mixture of tert-butyl 6-(difluoromethyl)-5-fluoro-8-(((trifluoromethyl)sulfonyl)oxy)-3,4-dihydroisoquinoline-2 (1H)-carboxylate (1 g, 2.225 mmol), bispinacoloto diboron (1.695 g, 6.68 mmol) & Et₃N (1.861 ml, 13.35 mmol) in dioxane (10 ml) was degassed with nitrogen for 5 min in a sealed tube. PdCl₂(dppf) (0.163 g, 0.223 mmol) was added and stirred the reaction mixture at 130° C. for 16 h. The reaction mixture was diluted with ethyl acetate (10 ml) and washed with water (20 ml). Layers were separated, organic layer was washed with brine (10 ml) and dried over anhydrous Na₂SO₄. The organic layer was filtered and concentrated in vacuo to give 1.3 g of a crude compound. This residue was purified by reverse phase preparative HPLC in acidic condition to afford (0.32 g, 33.7%) of the title compound. $^1$H NMR (400 MHz, Chloroform-d) δ 7.92 (d, J=7.8 Hz, 1H), 6.80 (t, J=52 Hz, 1H), 4.90 (s, 2H), 3.67 (t, J=5.9 Hz, 2H), 2.96-2.73 (m, 2H), 1.52 (s, 9H), 1.37 (s, 12H).

tert-butyl 8-bromo-6-(difluoromethyl)-5-fluoro-3,4-dihydroisoquinoline-2 (1H)-carboxylate

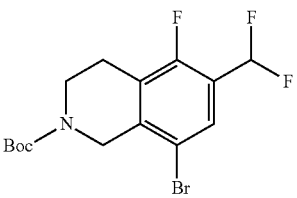 [SMILES: CC(C)(C)OC(=O)N1CCc2c(F)c(C(F)F)cc(Br)c2C1]

To a stirred solution of tert-butyl 6-(difluoromethyl)-5-fluoro-8-(4,4,5,5-tetramethyl-1,3,2-dioxaborolan-2-yl)-3,4-dihydroisoquinoline-2 (1H)-carboxylate (0.32 g, 0.749 mmol) was dissolved in MeOH (1 ml) was added copper(II) bromide (0.502 g, 2.247 mmol) in water (1 ml) at rt. The resulting mixture was stirred at 70° C. for 10 h. The reaction mixture was diluted with ethyl acetate (10 ml) and washed with water (10 ml). Layers were separated, organic layer was washed with brine (10 ml) and dried over anhydrous Na₂SO₄. The organic layer was filtered and concentrated in vacuo to give 0.25 g of a crude compound. This residue was purified by combiflash (R$_f$200, Teledyne/Isco) instrument onto a redisep® R$_f$ column with gradient elution (0 to 5%) of ethyl acetate in petroleum ether to afford (0.18 g, 63.2%) of the title compound. $^1$H NMR (400 MHz, Chloroform-d)

δ 7.66 (d, J=6.4 Hz, 1H), 6.86 (t, J=54.8 Hz, 1H), 4.56 (s, 2H), 3.67 (t, J=5.9 Hz, 2H), 2.85 (t, J=6.0 Hz, 2H), 1.53 (s, 9H).

8-bromo-5-fluoroisoquinoline

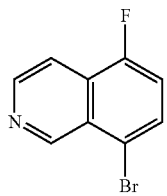 [SMILES: Fc1ccc(Br)c2cnccc12]

The title compound was prepared by following same reaction protocol as described in WO2018/167800 A1.

8-bromo-5-fluoroisoquinoline-6-carbaldehyde

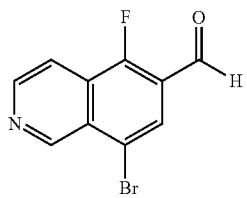 [SMILES: O=Cc1cc(Br)c2cnccc2c1F]

To a stirred solution of 8-bromo-5-fluoroisoquinoline (1.7 g, 7.52 mmol) in THF (15 ml) was added LDA (2 M in THF/Heptane/Ethylbenzene) (5.64 ml, 11.28 mmol) at −78° C. and stirred for 1 h. DMF (1.747 ml, 22.56 mmol) was added at −78° C. and stirred for 30 min. The resulting mixture was quenched with ice water and allowed to warm to rt. The reaction mixture was diluted with ethyl acetate (20 ml) and washed with water (20 ml). Layers were separated, organic layer was washed with brine (20 ml) and dried over anhydrous Na$_2$SO$_4$. The organic layer was filtered and concentrated in vacuo to give 1 g of crude compound. This residue was purified by combiflash (R$_f$200, Teledyne/Isco) instrument onto a redisep® R$_f$ column with gradient elution (0 to 10%) of ethyl acetate in petroleum ether to afford (0.467 g, 24.44%) of the title compound. LCMS m/z=254.14 (M+; 90%).

8-bromo-6-(difluoromethyl)-5-fluoroisoquinoline

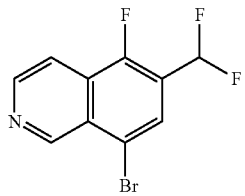 [SMILES: Fc1c(C(F)F)cc(Br)c2cnccc12]

To a stirred solution of 8-bromo-5-fluoroisoquinoline-6-carbaldehyde (233 mg, 0.917 mmol) in DCM (6 ml) was added DAST (0.606 ml, 4.59 mmol) at 0° C. and stirred the reaction mixture for 15 min. The resulting mixture was allowed to warm to rt and stirred for 16 h. The resulting mixture was diluted with dichloromethane (10 ml) and quenched with cold sat.aq.NaHCO$_3$ solution (20 ml). Stirred the reaction mixture at rt for 20 mins. Layers were separated, organic layer was washed with brine (20 ml) and dried over anhydrous Na$_2$SO$_4$. The organic layer was filtered and concentrated in vacuo to give 0.8 g of a crude compound. This residue was purified by combiflash (R$_f$200, Teledyne/Isco) instrument onto a redisep® R$_f$ column with gradient elution (0 to 10%) of ethyl acetate in petroleum ether to afford (0.166 g, 65.6%) of the title compound. LCMS m/z=276.02 (M+; 100%).

8-bromo-6-(difluoromethyl)-5-fluoro-1,2,3,4-tetra-hydroisoquinoline

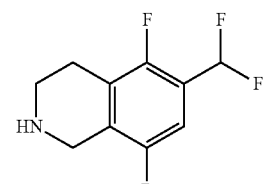

To a stirred solution of 8-bromo-6-(difluoromethyl)-5-fluoroisoquinoline (200 mg, 0.724 mmol) in acetic acid (4.6 ml) was added NaBH$_4$ (96 mg, 2.54 mmol) in portions at rt. The reaction mixture was stirred at rt for 1.5 h. The solvent was removed in vacuo at 40° C. The reaction mixture was diluted with dichloromethane (20 ml) and basified with sat. aq. NaHCO$_3$ solution (20 ml). Layers were separated, organic layer was washed with brine (20 ml) and dried over anhydrous Na$_2$SO$_4$. The organic layer was filtered and concentrated in vacuo to give (0.2 g, 99%) of sufficiently pure compound, which was carried to next step without further purification. LCMS m/z=280.0 (M+; 100%).

tert-butyl 8-bromo-6-(difluoromethyl)-5-fluoro-3,4-dihydroisoquinoline-2 (1H)-carboxylate

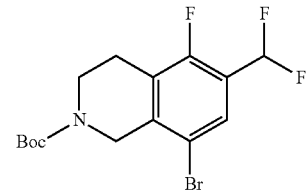 [SMILES: CC(C)(C)OC(=O)N1CCc2c(F)c(C(F)F)cc(Br)c2C1]

To a stirred solution of 8-bromo-6-(difluoromethyl)-5-fluoro-1,2,3,4-tetrahydroisoquinoline (200 mg, 0.714 mmol) in DCM (3 ml), was added Et$_3$N (0.199 ml, 1.428 mmol) and BOC-anhydride (0.199 ml, 0.857 mmol) at 0° C. The resulting mixture was stirred at rt for 2 h. The reaction mixture was diluted with DCM (20 ml) and washed with water (20 ml). Layers were separated, organic layer was washed with brine (20 ml) and dried over anhydrous Na$_2$SO$_4$. The organic layer was filtered and concentrated in vacuo to give 0.32 g of a crude compound. This residue was purified by combiflash (R$_f$200, Teledyne/Isco) instrument onto a redisep® R$_f$ column with gradient elution (0 to 9%) of ethyl acetate in petroleum ether to afford (0.215 g, 79%) of the title compound. $^1$H NMR (400 MHz, Chloroform-d)

δ 7.66 (d, J=6.4 Hz, 1H), 6.86 (t, J=54 Hz, 1H), 4.56 (s, 2H), 3.67 (t, J=5.9 Hz, 2H), 2.85 (t, J=5.8 Hz, 2H), 1.53 (s, 9H).

(E)-1-(2-bromo-4-methylphenyl)-N-(2,2-dimethoxyethyl)methanimine

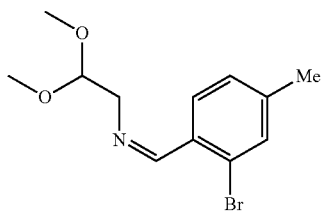 [SMILES: COC(C/N=C\c1ccc(C)cc1Br)OC]

A stirred mixture of 2-bromo-4-methylbenzaldehyde (73 g, 367 mmol) and 2,2-dimethoxyethan-1-amine (47.9 ml, 440 mmol) in toluene (450 ml) was heated with a Dean-Stark trap at 125° C. for 4 h. The mixture was allowed to cool to room temperature and concentrated to give a crude compound (105 g, 100%) as light yellow oil. This crude compound was carried forward for the next step without further purification. $^1$H NMR (400 MHz, Chloroform-d) δ 8.64 (m, 1H), 7.93 (d, J=8.0 Hz, 1H), 7.41 (dd, J=1.7, 0.8 Hz, 1H), 7.20-7.13 (m, 1H), 4.71 (t, J=5.3 Hz, 1H), 3.83 (dd, J=5.3, 1.4 Hz, 2H), 3.45 (s, 6H), 2.37 (s, 3H).

N-(2-bromo-4-methylbenzyl)-2,2-dimethoxyethan-1-amine

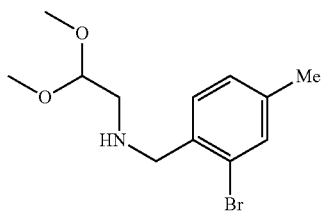 [SMILES: COC(CNCc1ccc(C)cc1Br)OC]

To a solution of (E)-1-(2-bromo-4-methylphenyl)-N-(2,2-dimethoxyethyl)methanimine (105 g, 367 mmol) in ethanol (820 ml), was added sodium borohydride (20.82 g, 550 mmol) portionwise at 10° C. The resulting mixture was stirred at rt for 2 h. The resulting mixture was quenched by slow addition of 100 ml acetone. The volatiles were removed in vacuo to give 102 g of a crude compound. This residue was purified by combiflash (R$_f$200, Teledyne/Isco) instrument onto a redisep® R$_f$ column with gradient elution (0 to 5%) of methanol in dichloromethane to afford (83 g, 78%) of the title compound. LCMS m/z=288.27 (M+).

N-(2-bromo-4-methylbenzyl)-N-(2,2-dimethoxyethyl)-4-methylbenzenesulfonamide

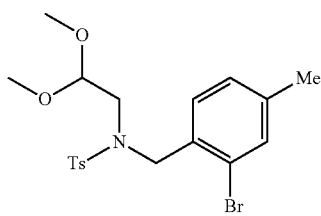 [SMILES: COC(CN(Cc1ccc(C)cc1Br)S(=O)(=O)c1ccc(C)cc1)OC]

To a solution of N-(2-bromo-4-methylbenzyl)-2,2-dimethoxyethan-1-amine (83 g, 288 mmol) in DCM (1000 ml), was added pyridine (116 ml, 1440 mmol) at rt. The solution of p-toluenesulfonyl chloride (93 g, 490 mmol) in DCM (300 ml) was added to above solution in a dropwise manner. The resulting mixture was stirred at rt for 16 h. The reaction mixture was diluted with water (1000 ml) and extracted with dichloromethane (500 ml×2). Layers were separated, organic layer was washed with brine (500 ml) and dried over anhydrous Na$_2$SO$_4$. The organic layer was filtered and concentrated in vacuo to give 135 g of a crude compound. This residue was purified by combiflash (R$_f$200, Teledyne/Isco) instrument onto a redisep® R$_f$ column with gradient elution (0 to 25%) of ethyl acetate in dichloromethane to afford the title compound (120 g, 94%) as a colourless oil. LCMS m/z=444.17 (M+2).

8-bromo-6-methylisoquinoline

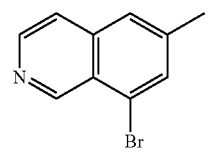

To a stirred suspension of aluminum chloride (217 g, 1628 mmol) in DCM (1400 ml) was added a solution of N-(2-bromo-4-methylbenzyl)-N-(2,2-dimethoxyethyl)-4-methylbenzenesulfonamide (120 g, 271 mmol) in DCM (600 ml) dropwise at 0° C. The resulting mixture was allowed to warm to rt and stirred for 16 h. The reaction mixture was poured into ice cold water (2 lit) and DCM (500 ml) and stirred for 1 h. Layers were separated, organic layer was washed with brine (500 ml) and dried over anhydrous Na$_2$SO$_4$. The organic layer was filtered and concentrated in vacuo to give 150 g of a crude compound. This residue was purified by combiflash (R$_f$200, Teledyne/Isco) instrument onto a redisep® R$_f$ column with gradient elution (0 to 50%) of ethyl acetate in petroleum ether to afford (50 g, 83%) of the title compound. LCMS m/z=224.0 (M+2, 100%).

8-bromoisoquinoline-6-carbaldehyde

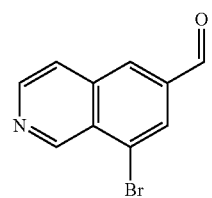 [SMILES: O=Cc1cc(Br)c2cnccc2c1]

A suspension of selenium dioxide (28.0 g, 252 mmol) and 8-bromo-6-methylisoquinoline (20 g, 90 mmol) in 1,2-dichlorobenzene (120 ml) was heated to 180° C. for 7 h. The reaction mixture was diluted with 25% MeOH in DCM (500 ml) and filtered through celite bed, washed with 25% MeOH in DCM (500 ml). The filtrate was concentrated under reduced pressure and this residue was purified by combiflash (R$_f$200, Teledyne/Isco) instrument onto a redisep® R$_f$ column with gradient elution (0 to 70%) of ethyl acetate in petroleum ether to afford (5.1 g, 23.99%) of the title compound. GCMS m/z=235.08 (M+1).

8-bromo-6-(difluoromethyl)isoquinoline

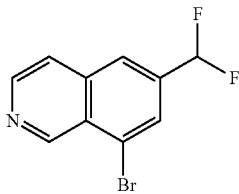 [SMILES: FC(F)c1cc(Br)c2cnccc2c1]

To a stirred solution of 8-bromoisoquinoline-6-carbaldehyde (5 g, 21.18 mmol) in DCM (120 ml) was added DAST (28.0 ml, 212 mmol) at 0° C. in a dropwise manner and stirred for 15 min. The resulting mixture was stirred at rt for 16 h. The reaction mixture was diluted with DCM (50 ml) and quenched with cold aq.sat. NaHCO$_3$ solution and stirred for 20 mins. Layers were separated, organic layer was washed with brine (100 ml) and dried over anhydrous Na$_2$SO$_4$. The organic layer was filtered and concentrated in vacuo to give 4.6 g of a crude compound. This residue was purified by combiflash (R$_f$200, Teledyne/Isco) instrument onto a redisep® R$_f$ column with gradient elution (0 to 30%) of ethyl acetate in petroleum ether to afford (3.3 g, 60.4%) of the title compound. GCMS m/z=257.08-259.08 (M+, 100%)

8-bromo-6-(difluoromethyl)-1,2,3,4-tetrahydroisoquinoline

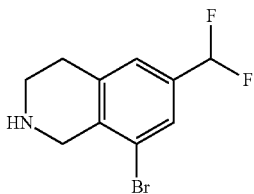 [SMILES: FC(F)c1cc(Br)c2c(c1)CCNC2]

To a stirred solution of 8-bromo-6-(difluoromethyl)isoquinoline (3 g, 11.62 mmol) in acetic acid (65 ml) was added NaBH$_4$ (1.539 g, 40.7 mmol) in portions at rt. The reaction mixture was stirred at rt for 1.5 h. The solvent was removed in vacuo at 40° C. The reaction mixture was diluted with dichloromethane (50 ml) and basified with sat. aq. NaHCO$_3$ solution (50 ml). Layers were separated, organic layer was washed with brine (50 ml) and dried over anhydrous Na$_2$SO$_4$. The organic layer was filtered and concentrated in vacuo to give (3.05 g, 100%) of sufficiently pure compound, which was carried to next step without further purification. GCMS m/z=262.08 (M+, 100%).

Tert-butyl 8-bromo-6-(difluoromethyl)-3,4-dihydroisoquinoline-2 (1H)-carboxylate

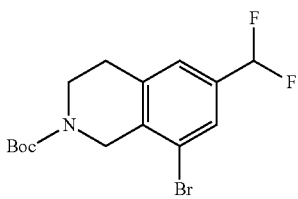 [SMILES: CC(C)(C)OC(=O)N1CCc2cc(C(F)F)cc(Br)c2C1]

To a stirred solution of 8-bromo-6-(difluoromethyl)-1,2,3,4-tetrahydroisoquinoline (3 g, 11.45 mmol) in DCM (70 ml) was added Et$_3$N (3.19 ml, 22.89 mmol) and BOC-anhydride (3.19 ml, 13.74 mmol) at 0° C. The resulting mixture was stirred at rt for 2 h. The reaction mixture was diluted with DCM (20 ml) and washed with water (20 ml). Layers were separated, organic layer was washed with brine (20 ml) and dried over anhydrous Na$_2$SO$_4$. The organic layer was filtered and concentrated in vacuo to give 3.2 g of a crude compound. This residue was purified by combiflash (R$_f$200, Teledyne/Isco) instrument onto a redisep® R$_f$ column with gradient elution (0 to 10%) of ethyl acetate in petroleum ether to afford (2.9 g, 69.9%) of the title compound. $^1$H NMR (400 MHz, Chloroform-d) δ 7.59 (s, 1H), 7.26 (s, 1H), 6.59 (t, J=56.3 Hz, 1H), 4.58 (s, 2H), 3.67 (t, J=5.8 Hz, 2H), 2.90 (t, J=5.9 Hz, 2H), 1.53 (s, 9H).

Tert-butyl 6-(difluoromethyl)-8-(4,4,5,5-tetramethyl-1,3,2-dioxaborolan-2-yl)-3,4-dihydroisoquinoline-2 (1H)-carboxylate

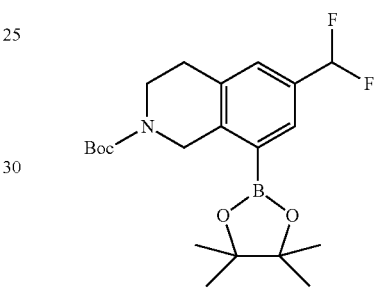

PdCl$_2$(dppf) (0.586 g, 0.801 mmol) was added in one portion to a degassed mixture of tert-butyl 8-bromo-6-(difluoromethyl)-3,4-dihydroisoquinoline-2 (1H)-carboxylate (5.8 g, 16.01 mmol), bispinacoloto diboron (8.13 g, 32.0 mmol) and potassium acetate (6.29 g, 64.1 mmol) in dioxane (60 ml) at rt and stirred at 100° C. for 2 h. The mixture was then cooled to rt and filtered through Celite, washed with ethyl acetate (50 ml). The filtrate was concentrated in vacuo to give 7.2 g of a crude compound. This residue was purified by combiflash (R$_f$200, Teledyne/Isco) instrument onto a redisep® R$_f$ column with gradient elution (0-5%) of ethyl acetate in petroleum ether to afford (6.5 g, 99%) of the title compound. LCMS m/z=410.23 (M+1, 100%).

(2-(tert-butoxycarbonyl)-6-(difluoromethyl)-1,2,3,4-tetrahydroisoquinolin-8-yl)boronic acid

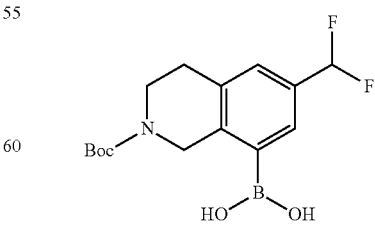

Sodium periodate (10.19 g, 47.6 mmol) was added to a solution of tert-butyl 6-(difluoromethyl)-8-(4,4,5,5-tetramethyl-1,3,2-dioxaborolan-2-yl)-3,4-dihydroisoquinoline-2

(1H)-carboxylate (6.50 g, 15.88 mmol) in a mixture of solvent i.e. water (11.5 ml, Ratio: 1.000) and acetone (57.5 ml, Ratio: 5) at rt. Stirred the resulting mixture for 1 h at rt. 1N aqueous HCl (15.88 ml, 15.88 mmol) was added at rt and stirred the reaction mixture for additional 4 h. The reaction mixture was quenched with water (100 mL) and extracted with ethyl acetate (100 mL×2). Layers were separated, the combined organic layer was washed with brine (50 mL). Dried the organic layer over anhydrous Na$_2$SO$_4$, filtered and concentrated in vacuo to give 4 g of a crude compound. This residue was purified by combiflash (R$_f$200, Teledyne/Isco) instrument onto a redisep® R$_f$ column with gradient elution (0 to 10%) of methanol in dichloromethane to afford (2.3 g, 44.3%) of the title compound. LCMS m/z=328.34(M+).

Tert-butyl 6-(difluoromethyl)-8-hydroxy-3,4-dihydroisoquinoline-2 (1H)-carboxylate

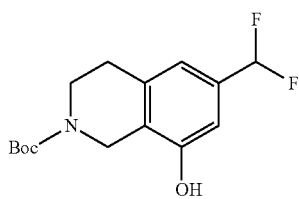 [SMILES: CC(C)(C)OC(=O)N1CCc2cc(C(F)F)cc(O)c2C1]

A mixture of (2-(tert-butoxycarbonyl)-6-(difluoromethyl)-1,2,3,4-tetrahydroisoquinolin-8-yl)boronic acid (0.1 g, 0.306 mmol), hydrogen peroxide (0.031 ml, 0.306 mmol) and 5% solution of citric acid (2.4 ml, 0.031 mmol) was stirred at rt for 2 h. The reaction mixture was diluted with ethyl acetate (20 ml) and washed with water (20 ml). Layers were separated, organic layer was washed with brine (20 ml) and dried over anhydrous Na$_2$SO$_4$. The organic layer was filtered and concentrated in vacuo to give 0.12 g of a crude compound. This residue was purified by combiflash (R$_f$200, Teledyne/Isco) instrument onto a redisep® R$_f$ column with gradient elution (0 to 15%) of ethyl acetate in petroleum ether to afford (0.083 g, 91%) of the title compound. LCMS m/z=300.40 (M+).

8-bromo-5-(difluoromethyl)isoquinoline

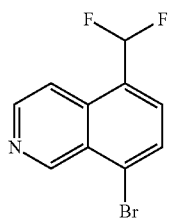

To a stirred mixture of 5-bromoisoquinoline-8-carbaldehyde and 8-bromoisoquinoline-5-carbaldehyde (88:12), which was synthesized by following the same procedure as reported in WO2007/79162, 2007, A1; (985 mg, 2.086 mmol) in DCM (20 ml) was added DAST (2.76 ml, 20.86 mmol) at 0° C. and stirred for 15 min. Warmed the reaction mixture to rt and stirred for 16 h. The reaction mixture was diluted with DCM (50 ml) and basified with aq.sat.NaHCO$_3$ (50 ml). Layers were separated, the organic layer was washed with brine (20 ml) and dried over anhydrous Na$_2$SO$_4$. The organic layer was filtered and concentrated in vacuo to give 1.1 g of a crude compound. This residue was purified by combiflash (R$_f$200, Teledyne/Isco) instrument onto a redisep® R$_f$ column with gradient elution (0 to 11%) of ethyl acetate in petroleum ether to afford 0.717 g of a mixture of 5-bromo-8-(difluoromethyl)isoquinoline and 8-bromo-5-(difluoromethyl)isoquinoline. This mixture was purified by chiral preparative HPLC (Chiralpak IG, Flow Rate: 1.00 ml/min, Mobile Phase A: HEX_0.1% DEA, Mobile Phase B: IPA-MEOH_0.1% DEA, A_B_80_20 @ 276 nm) to afford the minor isomer, 8-bromo-5-(difluoromethyl)isoquinoline (0.101 g, Rt=7.14 min) and the major isomer, 5-bromo-8-(difluoromethyl)isoquinoline (0.502 g, Rt=7.98 min). The structural elucidation was done on the basis of information reported in WO2007/079162. Minor isomer: $^1$H NMR (400 MHz, DMSO-d6) δ 9.61 (d, J=0.9 Hz, 1H), 8.79 (d, J=6.0 Hz, 1H), 8.16 (d, J=7.7 Hz, 1H), 8.10-8.05 (m, 1H), 7.98 (dd, J=7.8, 1.4 Hz, 1H), 7.63 (t, J=54.0 Hz, 1H); LCMS m/z=258.14, 259.96 (M+, M+2, 100%). Major isomer: $^1$H NMR (400 MHz, DMSO-d6) δ 9.62 (q, J=1.4 Hz, 1H), 8.81 (d, J=5.9 Hz, 1H), 8.29 (d, J=7.8 Hz, 1H), 8.10 (dd, J=5.9, 0.9 Hz, 1H), 7.93-7.62 (m, 2H); LCMS m/z=257.06, 259.77 (100%).

2-(5-bromo-2-fluorophenyl)propanenitrile

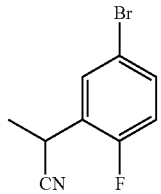

To a stirred suspension of 1-(5-bromo-2-fluorophenyl)ethan-1-one (20 g, 92 mmol) and 1-(isocyanomethylsulfonyl)-4-methylbenzene (21.59 g, 111 mmol) in DME (94 ml) was added KO$^t$Bu (20.68 g, 184 mmol) at 0° C. and stirred for 1 h under N$_2$ atmosphere. The reaction mixture was allowed to warm to rt and stirred for 1 h. The reaction mixture was quenched with water (200 ml) and extracted with ethyl acetate (200 ml×2). Layers were separated, organic layer was washed with brine (200 ml) and dried over anhydrous Na$_2$SO$_4$. The organic layer was filtered and concentrated in vacuo to give 26 g of a crude compound. This residue was purified by column chromatography on silica gel (mesh 100-200) with isocratic elution of 10% ethyl acetate in petroleum ether to afford the title compound (18 g, 86%) as a white solid. $^1$H NMR (400 MHz, DMSO-d$_6$) δ 7.70 (dd, J=6.7, 2.6 Hz, 1H), 7.65-7.61 (m, 1H), 7.31 (dd, J=10.2, 8.8 Hz, 1H), 4.47 (q, J=7.2 Hz, 1H), 1.57 (d, J=7.2 Hz, 3H).

2-(5-bromo-2-fluorophenyl)propan-1-amine

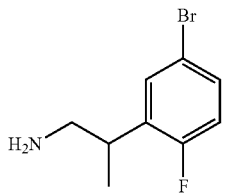

To a stirred solution of 2-(5-bromo-2-fluorophenyl)propanenitrile (18 g, 79 mmol) in tetrahydrofuran (225 ml) was added borane-methyl sulfide complex (22.48 ml, 237 mmol) at rt. The resulting mixture was stirred at 65° C. for 16 h under N₂ atmosphere. The reaction mixture was quenched with 6M HCl (~50 mL) and reflux for 2 h. Cooled the reaction mixture to rt, made the pH basic with 6M NaOH (~70 mL) and extracted with DCM (500 mL×3). The combined extract was dried over sodium sulphate and concentrated in vacuo to get 18.2 g of a crude compound. This residue was purified by column chromatography on silica gel (mesh 100-200) with isocratic elution of 10% (7N methanolic ammonia) in dichloromethane to afford (16.3 g, 89%) of the title compound. LCMS: m/z=232.0 (M+, 100%).

N-(2-(5-bromo-2-fluorophenyl)propyl)formamide

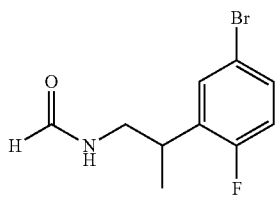

A stirred solution of 2-(5-bromo-2-fluorophenyl)propan-1-amine (14 g, 60.3 mmol) in ethyl formate (24.55 ml, 302 mmol) was stirred to 55° C. for 18 h under N₂ atmosphere. The volatiles were evaporated under reduced pressure to get (15.5 g, 99%) of a crude compound as an oil, which was used for next step without further purification. LCMS: m/z=262.02 (M+2).

10-bromo-7-fluoro-6-methyl-6,10b-dihydro-5H-oxazolo[2,3-a]isoquinoline-2,3-dione

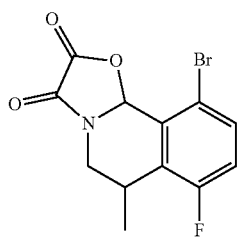 [SMILES: CC1CN2C(=O)C(=O)OC2c2c(Br)ccc(F)c21]

To a stirred solution of N-(2-(5-bromo-2-fluorophenyl)propyl)formamide (13.6 g, 52.3 mmol) in DCM (460 ml) was added oxalyl chloride (5.03 ml, 57.5 mmol) at rt under nitrogen atmosphere and stirred for 30 min. Then reaction mixture was cooled to −10° C. and iron (III) chloride (10.18 g, 62.7 mmol) was added lot-wise. The reaction mixture was allowed to warm to rt and stirred for 16 h. The reaction mixture was diluted with dichloromethane (100 ml) and basified with sat. aq. NaHCO₃ solution (150 ml). Layers were separated, organic layer was washed with brine (100 ml) and dried over anhydrous Na₂SO₄. The organic layer was filtered and concentrated in vacuo to give (13.9 g, 85%) of a crude compound, which was used for next step without further purification. LCMS: m/z=244.27 (M+2, 100%).

8-bromo-5-fluoro-4-methyl-3,4-dihydroisoquinoline

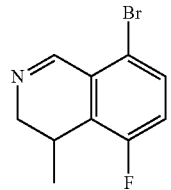

To a stirred solution of 10-bromo-7-fluoro-6-methyl-6,10b-dihydro-5H-oxazolo[2,3-a]isoquinoline-2,3-dione (8.6 g, 27.4 mmol) in methanol (310 ml) was added H₂SO₄ (16 ml, 300 mmol) at rt. The resulting mixture was stirred at 65° C. for 16 h under N2 atmosphere. The solvent was removed in vacuo, the resulting residue was made basic with sat.aq. sodium bicarbonate and extracted with ethyl acetate (100 ml×2). Layers were separated, organic layer was washed with brine (100 ml) and dried over anhydrous Na₂SO₄. The organic layer was filtered and concentrated in vacuo to give (6.63 g, 100%) of a crude compound, which was used for next step without further purification. LCMS: m/z=242.33 (M+, 100%).

8-bromo-5-fluoro-4-methylisoquinoline

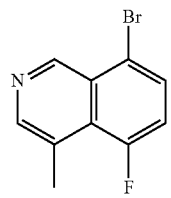

To a stirred solution of 8-bromo-5-fluoro-4-methyl-3,4-dihydroisoquinoline (8 g, 33.0 mmol) in dioxane (240 ml) was added manganese dioxide (43.1 g, 496 mmol) at rt. The resulting mixture was stirred at 101° C. for 48 h under N2 atmosphere. The reaction mixture was filtered through celite and the filtrate was concentrated in vacuo to get 3.7 g of a crude compound. This residue was purified by combiflash (R_f 200, Teledyne/Isco) instrument onto a redisep® R_f column with gradient elution (0 to 25%) of ethyl acetate in petroleum ether to afford the title compound (3 g, 37.8%) as a light yellow solid. LCMS: m/z=242.27 (M+2, 100%).

8-bromo-5-fluoro-4-methylisoquinoline-6-carbaldehyde

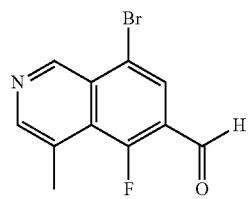

To a stirred solution of 8-bromo-5-fluoro-4-methylisoquinoline (4 g, 16.66 mmol) in THF (70 ml) was added LDA (2 M in THF/Heptane/Ethylbenzene) (2.7 ml, 24.99 mmol) at −78° C. and stirred for 1 h. DMF (3.87 ml, 50.0 mmol) was added and stirred the reaction mixture at −78° C. for 1 h. The reaction mixture was quenched with ice water (50 ml) and extracted with ethyl acetate (50 ml×2). Layers were separated, organic layer was washed with brine (20 ml) and dried over anhydrous Na$_2$SO$_4$. The organic layer was filtered and concentrated in vacuo to give 3.5 g of a crude compound. This residue was triturated with n-pentane to give (3.5 g, 78%) of the title compound.

LCMS: m/z=270.08 (M+2, 100%).

8-bromo-6-(difluoromethyl)-5-fluoro-4-methylisoquinoline

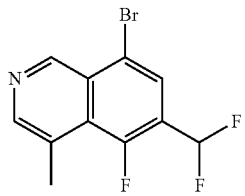 [SMILES: Cc1cncc2c(Br)cc(C(F)F)c(F)c12]

To a stirred solution of 8-bromo-5-fluoro-4-methylisoquinoline-6-carbaldehyde (3.5 g, 13.06 mmol) in DCM (100 ml) was added DAST (8.62 ml, 65.3 mmol) at 0° C. in a dropwise manner and stirred for 15 min. The resulting mixture was stirred at rt for 16 h. The reaction mixture was diluted with DCM (50 ml) and quenched with cold aq.sat. NaHCO$_3$ solution (50 ml) and stirred for 20 mins. Layers were separated, organic layer was washed with brine (50 ml) and dried over anhydrous Na$_2$SO$_4$. The organic layer was filtered and concentrated in vacuo to give 3.6 g of a crude compound. This residue was purified by combiflash (R$_f$200, Teledyne/Isco) instrument onto a redisep® R$_f$ column with gradient elution (0 to 20%) of ethyl acetate in petroleum ether to afford (2.8 g, 73.9%) of the title compound. LCMS: m/z=291.77 (M+1, 100%).

8-bromo-6-chloro-5-fluoroisoquinoline

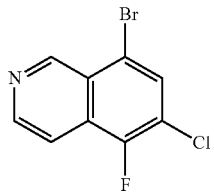 [SMILES: Fc1c(Cl)cc(Br)c2cnccc12]

To a stirred solution of 8-bromo-5-fluoroisoquinoline (2 g, 8.85 mmol) in THF (40 ml) was added LDA (2 M in THF/Heptane/Ethylbenzene) (8.52 ml, 13.27 mmol) at −78° C. and stirred for 1 h. Perchloroethane (2.51 g, 10.62 mmol) was added and stirred the reaction mixture at −78° C. for 30 mins. The reaction mixture was quenched with ice water (50 ml) and extracted with ethyl acetate (50 ml×2). Layers were separated, organic layer was washed with brine (20 ml) and dried over anhydrous Na$_2$SO$_4$. The organic layer was filtered and concentrated in vacuo to give 0.22 g of a crude compound. This residue was purified by combiflash (R$_f$200, Teledyne/Isco) instrument onto a redisep® R$_f$ column with gradient elution (0 to 15%) of ethyl acetate in petroleum ether to afford (0.160 g, 7%) of the title compound. LCMS: m/z=262.0 (M+2, 100%).

2-bromo-4,5-difluorobenzaldehyde

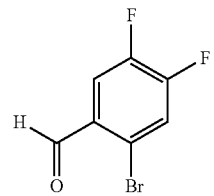 [SMILES: O=Cc1cc(F)c(F)cc1Br]

A mixture of (2-bromo-4,5-difluorophenyl)methanol (15 g, 67.3 mmol), PCC (17.40 g, 81 mmol) in DCM (350 ml) was stirred at rt for 2 h. The solvent was evaporated in vacuo at 35° C., and the resulting residue was purified by column chromatography on silica gel (mesh 100-200) with isocratic elution of 10% ethyl acetate in petroleum ether to afford the title compound (10 g, 67%) as a white solid. $^1$H NMR (400 MHz, Chloroform-d) δ 10.25 (d, J=3.0 Hz, 1H), 7.79 (dd, J=10.0, 8.3 Hz, 1H), 7.54 (dd, J=9.1, 6.7 Hz, 1H).

(E)-1-(2-bromo-4,5-difluorophenyl)-N-(2,2-dimethoxyethyl)methanimine

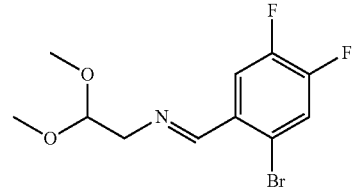 [SMILES: COC(C/N=C/c1cc(F)c(F)cc1Br)OC]

A stirred mixture of 2-bromo-4,5-difluorobenzaldehyde (10 g, 45.2 mmol) and 2,2-dimethoxyethan-1-amine (5.71 g, 54.3 mmol) in toluene (100 ml) was heated with a Dean-Stark trap at 130° C. for 4 h. The resulting mixture was allowed to cool to rt and concentrated in vacuo to give a crude compound (13.94 g, 100%) as light yellow oil. This crude compound was carried forward for the next step without further purification. LCMS: m/z=331.40 (M+23).

N-(2-bromo-4,5-difluorobenzyl)-2,2-dimethoxyethan-1-amine

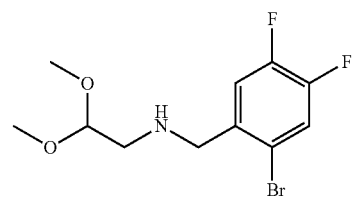 [SMILES: COC(CNCc1cc(F)c(F)cc1Br)OC]

To a stirred solution of (E)-1-(2-bromo-4,5-difluorophenyl)-N-(2,2-dimethoxyethyl)methanimine (13.94 g, 45.2 mmol) in ethanol (150 ml) was added sodium borohydride (2.57 g, 67.9 mmol) at rt portionwise and stirred for 2 h.

Acetone (30 ml) was slowly added to the reaction mixture at 0° C. The volatiles were removed in vacuo and the residue was purified by combiflash (R$_f$200, Teledyne/Isco) instrument onto a redisep® R$_f$ column with gradient elution (0 to 5%) of methanol in dichloromethane to afford (14 g, 99%) of the title compound. LCMS: m/z=310.28 (M+, 10%).

N-(2-bromo-4,5-difluorobenzyl)-N-(2,2-dimethoxyethyl)-4-methylbenzenesulfonamide

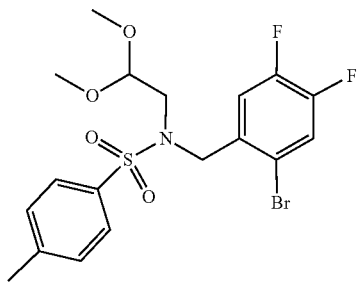 [SMILES: COC(CN(Cc1cc(F)c(F)cc1Br)S(=O)(=O)c1ccc(C)cc1)OC]

To a stirred solution of N-(2-bromo-4,5-difluorobenzyl)-2,2-dimethoxyethan-1-amine (14 g, 45.1 mmol) in DCM (180 ml), was added pyridine (18.26 ml, 226 mmol) at rt. The solution of p-toluenesulfonyl chloride (14.63 g, 77 mmol) in DCM (71 ml) was added to above solution in a dropwise manner. The resulting mixture was stirred at rt for 16 h. The reaction mixture was diluted with water (500 ml) and extracted with dichloromethane (200 ml×2). Layers were separated, organic layer was washed with brine (200 ml) and dried over anhydrous Na$_2$SO$_4$. The organic layer was filtered and concentrated in vacuo to give 20.5 g of a crude compound. This residue was purified by combiflash (R$_f$200, Teledyne/Isco) instrument onto a redisep® R$_f$ column with gradient elution (0 to 30%) of ethyl acetate in petroleum ether to afford (18 g, 86%) of the title compound. LCMS: m/z=488.0 (M+23, 100%).

8-bromo-5,6-difluoroisoquinoline

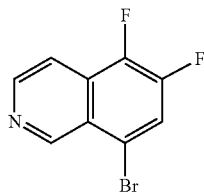 [SMILES: Fc1cc(Br)c2cnccc2c1F]

To a stirred suspension of aluminum chloride (17.23 g, 129 mmol) in DCM (110 ml) was added a solution of N-(2-bromo-4,5-difluorobenzyl)-N-(2,2-dimethoxyethyl)-4-methylbenzenesulfonamide (10 g, 21.54 mmol) in DCM (40 ml) dropwise at 0° C. The resulting mixture was allowed to warm to rt and stirred for 16 h. The reaction mixture was poured into ice cold water (500 ml) and DCM (250 ml) and stirred for 1 h. Layers were separated, organic layer was washed with brine (500 ml) and dried over anhydrous Na$_2$SO$_4$. The organic layer was filtered and concentrated in vacuo to give 4 g of a crude compound. This residue was purified by combiflash (R$_f$200, Teledyne/Isco) instrument onto a redisep® R$_f$ column with gradient elution (0 to 40%) of ethyl acetate in petroleum ether to afford the title compound (1.5 g, 28.5%) as an off white solid. LCMS: m/z=244.14 (M+, 100%).

(2-bromo-5-fluorophenyl)methanamine

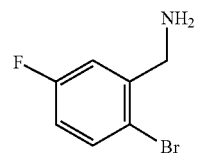

The title compound was prepared by following same reaction protocol as described in Organic Letters, 2018, vol. 20, #2, p. 441-444.

(E)-N-(2-bromo-5-fluorobenzyl)-1,1-dimethoxypropan-2-imine

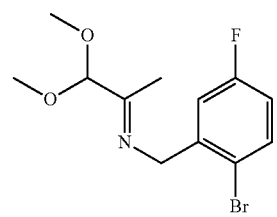 [SMILES: COC(OC)/C(C)=N/Cc1cc(F)ccc1Br]

A mixture of (2-bromo-5-fluorophenyl)methanamine (29 g, 142 mmol), 1,1-dimethoxypropan-2-one (19.78 ml, 163 mmol) and magnesium sulfate (17.11 g, 142 mmol) in DCM (150 ml) was stirred at rt for 15 h. The resulting mixture was filtered through celite and the filtrate was evaporated in vacuo to give (41 g, 95%) of the title compound, which was directly used for next step without further purification.

N-(2-bromo-5-fluorobenzyl)-1,1-dimethoxypropan-2-amine

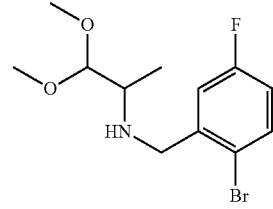 [SMILES: COC(OC)C(C)NCc1cc(F)ccc1Br]

To a stirred solution of (E)-N-(2-bromo-5-fluorobenzyl)-1,1-dimethoxypropan-2-imine (41 g, 135 mmol) in methanol (700 ml) was added NaBH$_4$ (6.12 g, 162 mmol) portionwise at 0° C. and stirred the reaction mixture for 20 min. The resulting mixture was allowed to warm to rt and stirred for 2 h. Acetone (250 mL) was slowly added into the flask to quench the reaction at 0° C. Evaporated the solvent in vacuo to provide 43 g of a crude compound. This residue was purified by combiflash (R$_f$200, Teledyne/Isco) instrument onto a redisep® R$_f$ column with gradient elution (0 to 30%)

of ethyl acetate in petroleum ether to afford the title compound (39 g, 94%) as a light yellow oil. LCMS: m/z=306.28 (M+, 15%).

8-bromo-5-fluoro-3-methyl-3,4-dihydroisoquinoline

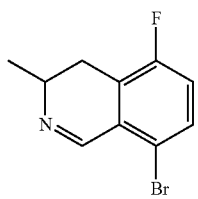

Chlorosulphonic acid (43.5 ml, 653 mmol) was added slowly to N-(2-bromo-5-fluorobenzyl)-1,1-dimethoxypropan-2-amine (20 g, 65.3 mmol) at −10° C. and stirred the reaction mixture for 15 h at rt. The resulting mixture was basified with cold aq. sat. NaHCO₃ solution and extracted with ethyl acetate (200 ml×2). Layers were separated, organic layer was washed with brine (200 ml) and dried over anhydrous Na₂SO₄. The organic layer was filtered and concentrated in vacuo to give 11.3 g of a crude compound. This residue was purified by combiflash (R$_f$200, Teledyne/Isco) instrument onto a redisep® R$_f$ column with gradient elution (0 to 10%) of ethyl acetate in petroleum ether to afford (9 g, 56.9%) of the title compound. LCMS: m/z=242.02 (M+, 100%).

8-bromo-5-fluoro-3-methylisoquinoline

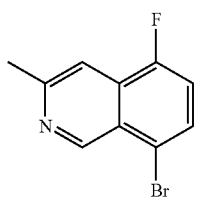

To a stirred solution of 8-bromo-5-fluoro-3-methyl-3,4-dihydroisoquinoline (9 g, 37.2 mmol) in dioxane (350 ml) in a sealed tube, was added manganese dioxide (48.5 g, 558 mmol) at rt. The resulting mixture was stirred at 101° C. for 12 h under N₂ atmosphere. The reaction mixture was filtered through celite and the filtrate was concentrated in vacuo to get 4.1 g of a crude compound. This residue was purified by combiflash (R$_f$200, Teledyne/Isco) instrument onto a redisep® R$_f$ column with gradient elution (0 to 10%) of ethyl acetate in petroleum ether to afford (3.6 g, 40.3%) of the title compound. LCMS: m/z=240.02 (M+, 100%).

8-bromo-5-fluoro-3-methylisoquinoline-6-carbaldehyde

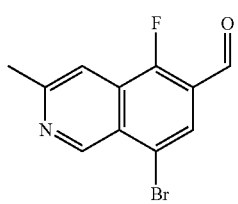

To a stirred solution of 8-bromo-5-fluoro-3-methylisoquinoline (3.60 g, 15 mmol) in THF (80 ml) was added LDA (11.25 ml, 22.49 mmol) at −78° C. and stirred for 1 h. DMF (3.48 ml, 45.0 mmol) was added slowly and stirred the reaction mixture for 1 h. The resulting mixture was quenched with aq. sat. NH₄Cl solution (100 ml) and extracted with ethyl acetate (50 ml×2). Layers were separated, organic layer was washed with brine (50 ml) and dried over anhydrous Na₂SO₄. The organic layer was filtered and concentrated in vacuo to give 1.7 g of a crude compound. This residue was purified by combiflash (R$_f$200, Teledyne/Isco) instrument onto a redisep® R$_f$ column with gradient elution (0 to 15%) of ethyl acetate in petroleum ether to afford (1.3 g, 32.3%) of the title compound. LCMS: m/z=268.08 (M+, 100%).

8-bromo-6-(difluoromethyl)-5-fluoro-3-methylisoquinoline

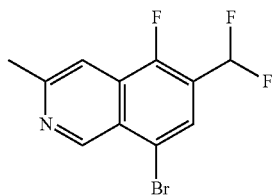 [SMILES: Cc1cc2c(F)c(C(F)F)cc(Br)c2cn1]

To a stirred solution of 8-bromo-5-fluoro-3-methylisoquinoline-6-carbaldehyde (0.800 g, 2.98 mmol) in DCM (50 ml) was added DAST (1.971 ml, 14.92 mmol) at 0° C. and stirred the reaction mixture for 15 min. The resulting mixture was allowed to warm to rt and stirred for 3 h. The resulting mixture was diluted with dichloromethane (20 ml) and quenched with cold sat.aq.NaHCO₃ solution (20 ml). Stirred the reaction mixture at rt for 20 mins. Layers were separated, organic layer was washed with brine (20 ml) and dried over anhydrous Na₂SO₄. The organic layer was filtered and concentrated in vacuo to give 0.82 g of crude compound. This residue was purified by combiflash (R$_f$200, Teledyne/Isco) instrument onto a redisep® R$_f$ column with gradient elution (0 to 10%) of ethyl acetate in petroleum ether to afford (0.65 g, 75%) of the title compound. LCMS: m/z=290.14 (M+, 100%).

((3aR,6R,6aS)-6-(4-Chloro-7H-pyrrolo[2,3-d]pyrimidin-7-yl)-2,2-dimethyl-6,6a-dihydro-3aH-cyclopenta[d][1,3]dioxol-4-yl)methanol

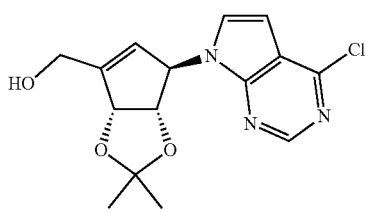 [SMILES: CC1(C)O[C@@H]2[C@H](O1)C(CO)=C[C@H]2n1ccc2c(Cl)ncnc21]

The title compound was prepared by following the same reaction protocol as was described in Kenneth A. Jacobson et. al; Purinergic Signalling (2015) 11:371-387.

4-chloro-7-((3aS,4R,6aR)-6-(iodomethyl)-2,2-dimethyl-3a,6a-dihydro-4H-cyclopenta[d][1,3]dioxol-4-yl)-7H-pyrrolo[2,3-d]pyrimidine

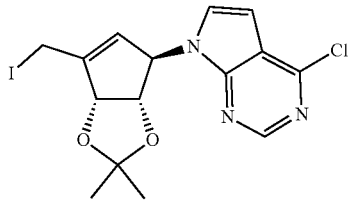 [SMILES: CC1(C)O[C@@H]2[C@H](O1)C(CI)=C[C@H]2n1ccc2c(Cl)ncnc21]

To a stirred solution of imidazole (0.931 g, 13.67 mmol) and triphenylphosphine (2.119 g, 8.08 mmol) in DCM (40 ml) at 0° C. was added iodine (2.051 g, 8.08 mmol) slowly. A solution of ((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)methanol (2 g, 6.22 mmol) in DCM (40 ml) was added and stirred for 10 min. The reaction mixture was warmed to rt and stirred for 3 h. The reaction mixture was quenched with water (20 ml) and extracted with ethyl acetate (20 ml×2). Layers were separated, organic layer was washed with brine (20 ml) and dried over anhydrous Na$_2$SO$_4$. The organic layer was filtered and concentrated in vacuo to give 2.3 g of a crude compound. This residue was purified by combiflash (R$_f$200, Teledyne/Isco) instrument onto a redisep® R$_f$ column with gradient elution (0 to 7%) of ethyl acetate in petroleum ether to afford (1.91 g, 71.2%) of the title compound. LCMS m/z=432.04 (M+)

(3aS,4R,6aR)-4-(4-Chloro-7H-pyrrolo[2,3-d]pyrimidin-7-yl)-2,2-dimethyl-3a,6a-dihydro-4H-cyclopenta[d][1,3]dioxole-6-carbaldehyde

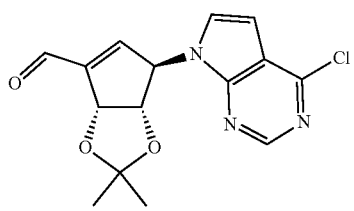 [SMILES: CC1(C)O[C@@H]2[C@H](O1)C(C=O)=C[C@H]2n1ccc2c(Cl)ncnc21]

To a stirred solution of ((3aS,4R,6aR)-4-(4-Chloro-7H-pyrrolo[2,3-d]pyrimidin-7-yl)-2,2-dimethyl-3a,6a-dihydro-4H-cyclopenta[d][1,3]dioxol-6-yl)methanol (2.50 g, 7.77 mmol) in CH$_2$Cl$_2$ (40 ml) at 0° C., was added Dess-Martin Periodinane (3.95 g, 9.32 mmol) portion-wise and stirred for 1 h. The reaction mixture was diluted with dichloromethane (50 ml) and washed with water (50 ml). The organic layer was separated, dried over MgSO$_4$, filtered and concentrated in vacuo to give 2.71 g of crude compound. This residue was purified by combiflash (R$_f$200, Teledyne/Isco) instrument onto a redisep® R$_f$ column with gradient elution (0-30%) of ethyl acetate in petroleum ether to afford the title compound (2.32 g, 93%) as a colorless oil. $^1$H NMR (400 MHz, Chloroform-d) δ 10.00 (s, 1H), 8.67 (s, 1H), 7.12 (d, J=3.6 Hz, 1H), 6.78 (dd, J=2.6, 0.9 Hz, 1H), 6.69 (d, J=3.7 Hz, 1H), 5.97 (dt, J=2.8, 1.4 Hz, 1H), 5.76 (dd, J=5.9, 1.5 Hz, 1H), 4.88 (dt, J=5.9, 1.1 Hz, 1H), 1.54 (s, 3H), 1.40 (s, 3H); LCMS m/z=320.2 (M+1, 100%).

4-Chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine

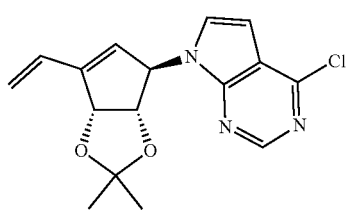 [SMILES: C=CC1=C[C@@H](n2ccc3c(Cl)ncnc32)[C@@H]2OC(C)(C)O[C@H]12]

To a cooled suspension of methyl(triphenyl)phosphonium bromide (5.03 g, 14.07 mmol) in THF (30 mL) at 0° C., was added 1M KHMDS in THF (14.07 mL, 14.07 mmol) slowly and stirred for 5 min. The reaction mixture was allowed to warm to 25° C. and stirred for 10 min. Cooled the reaction mixture to 0° C. and slowly added a solution of (3aS,4R,6aR)-4-(4-Chloro-7H-pyrrolo[2,3-d]pyrimidin-7-yl)-2,2-dimethyl-3a,6a-dihydro-4H-cyclopenta[d][1,3]dioxole-6-carbaldehyde (1.8 g, 5.63 mmol) in THF (1 ml). Stirred the reaction mixture at 25° C. for 10 min. The reaction mixture was quenched with sat.aqueous NH$_4$Cl (50 ml) and extracted with ethyl acetate (50 ml). The organic layer was separated, dried over Na$_2$SO$_4$, filtered and concentrated in vacuo to give 2.1 g of crude compound. This residue was purified by combiflash (R$_f$200, Teledyne/Isco) instrument onto a redisep® R$_f$ column with gradient elution (0-7%) of ethyl acetate in petroleum ether to afford the title compound (0.81 g, 45.3%) as an off-white solid. $^1$H NMR (400 MHz, Chloroform-d) δ 8.72 (s, 1H), 7.11 (d, J=3.6 Hz, 1H), 6.66-6.57 (m, 2H), 5.94 (d, J=2.6 Hz, 1H), 5.81-5.75 (m, 2H), 5.57 (dd, J=6.0, 1.5 Hz, 1H), 5.49 (d, J=10.9 Hz, 1H), 4.66 (dt, J=6.0, 1.0 Hz, 1H), 1.52 (s, 3H), 1.40 (s, 3H); LCMS m/z=318.09 (M+1, 100%).

7-((3aS,4R,6aR)-6-(((tert-Butyldiphenylsilyl)oxy)methyl)-2,2-dimethyl-3a,6a-dihydro-4H-cyclopenta[d][1,3]dioxol-4-yl)-4-methyl-7H-pyrrolo[2,3-d]pyrimidine (A)

7-((3aS,4R,6aR)-6-(((tert-Butyldiphenylsilyl)oxy)methyl)-2,2-dimethyl-3a,6a-dihydro-4H-cyclopenta[d][1,3]dioxol-4-yl)-7H-pyrrolo[2,3-d]pyrimidine (B)

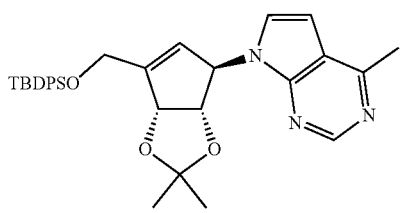

A

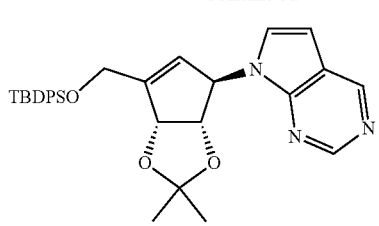

To a degassed solution of 7-((3aS,4R,6aR)-6-(((tert-butyl-diphenylsilyl)oxy)methyl)-2,2-dimethyl-3a,6a-dihydro-4H-cyclopenta[d][1,3]dioxol-4-yl)-4-chloro-7H-pyrrolo[2,3-d]pyrimidine (5 g, 8.93 mmol) in dioxane (80 ml) and water (10 ml), was added potassium phosphate tribasic (4.66 g, 26.8 mmol), dichloro[1,1'-bis(di-t-butylphosphino) ferrocene]palladium(II) (0.582 g, 0.893 mmol) and 2,4,6-trimethyl-1,3,5,2,4,6-trioxatriborinane (12.48 ml, 89 mmol) at 25° C. The reaction mixture was heated at 80° C. for 8 h. The reaction mixture was diluted with ethyl acetate (50 ml) and washed with water (50 ml). Layers were separated and the organic layer was washed with brine (50 ml) and dried over anhydrous sodium sulphate. The organic layer was filtered and concentrated in vacuo to give 4.3 g of crude compound. This crude residue was purified by combiflash ($R_f$200, Teledyne/Isco) instrument onto a redisep® $R_f$ column with gradient elution (0 to 20%) of ethyl acetate in petroleum ether to afford the title compound, A (3.2 g, 66%) and B (0.75 g, 15.98%) as an off-white solids. $^1$H NMR of A (400 MHz, Chloroform-d) δ 8.83 (s, 1H), 7.71 (tt, J=6.6, 1.5 Hz, 4H), 7.48-7.37 (m, 6H), 6.91 (d, J=3.6 Hz, 1H), 6.57 (d, J=3.6 Hz, 1H), 5.88 (s, 2H), 5.25 (d, J=5.7 Hz, 1H), 4.60 (d, J=5.7 Hz, 1H), 4.55-4.45 (m, 2H), 2.77 (s, 3H), 1.45 (s, 3H), 1.32 (s, 3H), 1.11 (s, 9H); LCMS m/z=540.4 (M+1; 100%); $^1$H NMR of B (400 MHz, Chloroform-d) δ 7.71 (tt, J=6.6, 1.5 Hz, 4H), 7.53-7.35 (m, 6H), 6.98 (d, J=3.6 Hz, 1H), 6.57 (d, J=3.6 Hz, 1H), 5.90 (d, J=14.5 Hz, 2H), 5.26 (d, J=5.7 Hz, 1H), 4.61 (d, J=5.7 Hz, 1H), 4.51 (d, J=9.3 Hz, 2H), 1.46 (s, 3H), 1.33 (s, 3H), 1.28 (s, 2H), 1.11 (s, 9H); LCMS m/z=526.44 (M+1; 100%).

((3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxol-6-yl)methanol

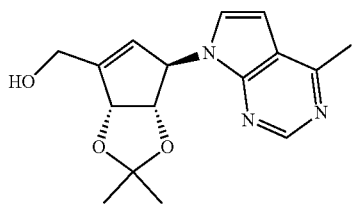 [SMILES: Cc1ncnc2c1ccn2[C@@H]1C=C(CO)[C@H]2OC(C)(C)O[C@H]21]

To a stirred solution of 7-((3aS,4R,6aR)-6-(((tert-butyldiphenylsilyl)oxy)methyl)-2,2-dimethyl-3a,6a-dihydro-4H-cyclopenta[d][1,3]dioxol-4-yl)-4-methyl-7H-pyrrolo[2,3-d]pyrimidine (3.20 g, 5.93 mmol) in THF (20 ml), was slowly added TBAF (8.89 ml, 8.89 mmol) at 25° C. and stirred the reaction mixture at 25° C. for 15 h. Volatiles were removed in vacuo and the crude residue was purified by combiflash ($R_f$200, Teledyne/Isco) instrument onto a redisep® $R_f$ column with gradient elution (0 to 100%) of ethyl acetate in petroleum ether to afford the title compound (1.5 g, 84%) as an off-white solid. $^1$H NMR (400 MHz, Chloroform-d) δ 8.81 (s, 1H), 7.06 (d, J=3.6 Hz, 1H), 6.55 (d, J=3.6 Hz, 1H), 5.90-5.78 (m, 2H), 5.41 (ddd, J=5.8, 1.7, 0.9 Hz, 1H), 4.65 (dt, J=5.8, 0.9 Hz, 1H), 4.56-4.42 (m, 2H), 3.35 (d, J=8.2 Hz, 1H), 2.74 (s, 3H), 1.53 (s, 3H), 1.37 (s, 3H); LCMS m/z=302.21 (M+1; 100%).

(3aS,4R,6aR)-2,2-Dimethyl-4-(4-methyl-7H-pyrrolo[2,3-d]pyrimidin-7-yl)-3a,6a-dihydro-4H-cyclopenta[d][1,3]dioxole-6-carbaldehyde

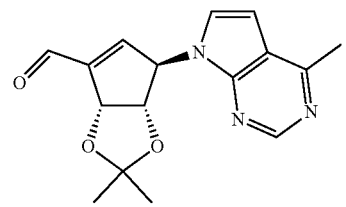 [SMILES: Cc1ncnc2c1ccn2[C@@H]1C=C(C=O)[C@H]2OC(C)(C)O[C@H]21]

To a stirred solution of 7-((3aS,4R,6aR)-6-(((tert-Butyl-diphenylsilyl)oxy)methyl)-2,2-dimethyl-3a,6a-dihydro-4H-cyclopenta[d][1,3]dioxol-4-yl)-7H-pyrrolo[2,3-d]pyrimidine (1.50 g, 4.98 mmol) in dichloromethane (100 ml) at 0° C., was added Dess-Martin Periodinane (2.53 g, 5.97 mmol) portion-wise and stirred for 1 h. The reaction mixture was diluted with methylene chloride (50 ml) and washed with water (50 ml). Layers were separated, the organic layer was washed with brine (50 ml) and dried over anhydrous sodium sulphate. The organic layer was filtered and concentrated in vacuo to give a crude compound and this crude residue was purified by combiflash ($R_f$200, Teledyne/Isco) instrument onto a redisep® $R_f$ column with gradient elution (0 to 30%) of ethyl acetate in petroleum ether to afford the title compound (0.95 g, 63.8%) as an off-white solid. $^1$H NMR (400 MHz, Chloroform-d) δ 10.00 (s, 1H), 8.80 (s, 1H), 7.02 (d, J=3.6 Hz, 1H), 6.82-6.76 (m, 1H), 6.63 (d, J=3.6 Hz, 1H), 6.00 (dt, J=2.7, 1.4 Hz, 1H), 5.76 (dd, J=5.9, 1.5 Hz, 1H), 4.87 (dt, J=5.9, 1.1 Hz, 1H), 2.77 (s, 3H), 1.53 (s, 3H), 1.38 (s, 3H); LCMS m/z=300.15 (M+1; 100%)

7-((3aS,4R,6aR)-2,2-Dimethyl-6-vinyl-3a,6a-dihydro-4H-cyclopenta[d][1,3]dioxol-4-yl)-4-methyl-7H-pyrrolo[2,3-d]pyrimidine

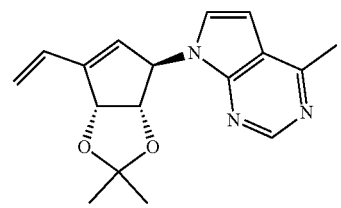 [SMILES: C=CC1=C[C@@H](n2ccc3c(C)ncnc32)[C@@H]2OC(C)(C)O[C@H]12]

The title compound was synthesized by following an analogous reaction protocol as was described in the preparation of 4-chloro-7-((3aS,4R,6aR)-2,2-dimethyl-6-vinyl-3a,6a-dihydro-4H-cyclopenta[d][1,3] dioxol-4-yl)-7H-pyrrolo[2,3-d]pyrimidine. $^1$H NMR (400 MHz, Chloroform-d) δ 8.83 (s, 1H), 7.01 (d, J=3.6 Hz, 1H), 6.68-6.53 (m, 2H), 5.95 (d, J=2.5 Hz, 1H), 5.80-5.71 (m, 2H), 5.56 (dd, J=6.0, 1.4 Hz, 1H), 5.47 (d, J=10.8 Hz, 1H), 4.65 (d, J=5.8 Hz, 1H), 2.75 (s, 3H), 1.52 (s, 3H), 1.40 (s, 3H); LCMS m/z=298.5 (M+1; 100%).

7-((3aS,4R,6aR)-6-(((tert-Butyldiphenylsilyl)oxy) methyl)-2,2-dimethyl-4,6a-dihydro-3aH-cyclopenta [d][1,3]dioxol-4-yl)-2-chloro-7H-pyrrolo[2,3-d]pyrimidine

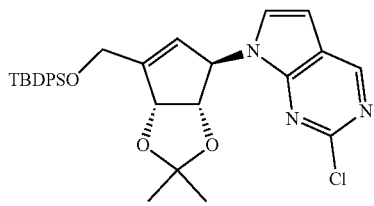

To a stirred solution of (3aS,4S,6aR)-6-(((tert-Butyldiphenylsilyl)oxy)methyl)-2,2-dimethyl-3a,6a-dihydro-4H-cyclopenta[d][1,3]dioxol-4-ol (synthesized as per Tetrahedron, 2007, vol. 63, #39, p. 9836-9841, 1.2 g, 2.83 mmol) in THF (15 ml) was added 2-chloro-7H-pyrrolo[2,3-d]pyrimidine (0.738 g, 4.80 mmol), triphenylphosphine (2.59 g, 9.89 mmol) and DIAD (1.923 ml, 9.89 mmol) slowly at 0° C. and stirred for 5 mins. The reaction mixture was brought to 25° C. and stirred for 1 h. Volatiles were removed in vacuo and the crude residue was purified by combiflash (R$_f$200, Teledyne/Isco) instrument onto a redisep® R$_f$ column with gradient elution (0 to 15%) of ethyl acetate in petroleum ether to afford the title compound (1.1 g, 69.5%) as an off-white solid. $^1$H NMR (400 MHz, Chloroform-d) δ 8.84 (s, 1H), 7.70 (ddt, J=6.6, 5.0, 1.5 Hz, 4H), 7.50-7.34 (m, 6H), 6.94 (d, J=3.6 Hz, 1H), 6.59 (d, J=3.6 Hz, 1H), 5.84 (dt, J=19.8, 2.2 Hz, 2H), 5.30 (d, J=5.7 Hz, 1H), 4.63 (d, J=5.6 Hz, 1H), 4.57-4.42 (m, 2H), 1.43 (s, 3H), 1.33 (s, 3H), 1.10 (s, 9H); LCMS m/z=560.3 (M+; 100%).

(3aR,6R,6aS)-6-(2-Chloro-7H-pyrrolo[2,3-d]pyrimidin-7-yl)-2,2-dimethyl-6,6a-dihydro-3aH-cyclopenta [d][1,3]dioxol-4-yl)methanol

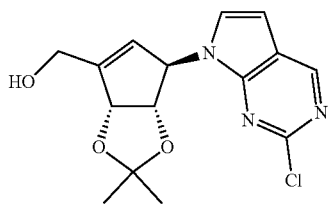 [SMILES: CC1(C)O[C@@H]2[C@H](O1)C(CO)=C[C@H]2n1ccc2cnc(Cl)nc21]

To a stirred solution of 7-((3aS,4R,6aR)-6-(((tert-butyldiphenylsilyl)oxy)methyl)-2,2-dimethyl-3a,6a-dihydro-4H-cyclopenta[d][1,3]dioxol-4-yl)-2-chloro-7H-pyrrolo[2,3-d]pyrimidine (500 mg, 0.893 mmol) in THF (5 ml) at 0° C., was added TBAF (1.250 ml, 1.250 mmol) slowly and stirred the reaction mixture at the same temperature for 10 min. The reaction mixture was brought to 25° C. and stirred for 30 mins. Volatiles were removed in vacuo and the crude residue was purified by combiflash (R$_f$200, Teledyne/Isco) instrument onto a redisep® R$_f$ column with gradient elution (0 to 40%) of ethyl acetate in petroleum ether to afford the title compound (0.27 g, 94%) as a colourless oil. $^1$H NMR (400 MHz, Chloroform-d) δ 8.81 (s, 1H), 7.28 (s, 1H), 7.08 (d, J=3.7 Hz, 1H), 6.57 (d, J=3.7 Hz, 1H), 5.92-5.62 (m, 2H), 5.47 (d, J=5.7 Hz, 1H), 4.69 (dt, J=5.6, 0.9 Hz, 1H), 4.59-4.37 (m, 2H), 1.52 (s, 3H), 1.38 (s, 3H); LCMS m/z=321.09 (M+; 100%).

(3aR,6R,6aS)-6-(2-Chloro-7H-pyrrolo[2,3-d]pyrimidin-7-yl)-2,2-dimethyl-6,6a-dihydro-3aH-cyclopenta [d][1,3]dioxole-4-carbaldehyde

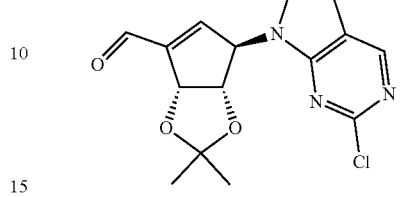

The title compound was synthesized by following an analogous reaction protocol as was described in the preparation of (3aS,4R,6aR)-2,2-Dimethyl-4-(4-methyl-7H-pyrrolo[2,3-d]pyrimidin-7-yl)-3a,6a-dihydro-4H-cyclopenta[d] [1,3]dioxole-6-carbaldehyde. $^1$H NMR (400 MHz, Chloroform-d) δ 9.99 (s, 1H), 8.86 (s, 1H), 7.04 (d, J=3.7 Hz, 1H), 6.75 (dd, J=2.6, 0.9 Hz, 1H), 6.65 (d, J=3.7 Hz, 1H), 6.00 (dt, J=2.7, 1.4 Hz, 1H), 5.77 (dd, J=5.9, 1.5 Hz, 1H), 4.88 (dd, J=5.9, 1.2 Hz, 1H), 1.53 (s, 3H), 1.40 (s, 3H); LCMS m/z=319.90 (M+; 100).

2-Chloro-7-((3aS,4R,6aR)-2,2-dimethyl-6-vinyl-4, 6a-dihydro-3aH-cyclopenta[d][1,3]dioxol-4-yl)-7H-pyrrolo[2,3-d]pyrimidine

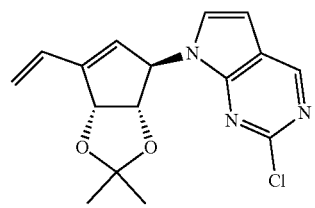 [SMILES: C=CC1=C[C@@H](n2ccc3cnc(Cl)nc32)[C@@H]2OC(C)(C)O[C@H]12]

The title compound was synthesized by following an analogous reaction protocol as was described in the preparation of 4-chloro-7-((3aS,4R,6aR)-2,2-dimethyl-6-vinyl-3a,6a-dihydro-4H-cyclopenta[d][1,3] dioxol-4-yl)-7H-pyrrolo[2,3-d]pyrimidine. $^1$H NMR (400 MHz, Chloroform-d) δ 8.82 (s, 1H), 7.03 (d, J=3.6 Hz, 1H), 6.64-6.53 (m, 2H), 5.93 (d, J=2.6 Hz, 1H), 5.81-5.69 (m, 2H), 5.60 (dd, J=5.8, 1.4 Hz, 1H), 5.53-5.44 (m, 1H), 4.68 (dd, J=5.8, 1.1 Hz, 1H), 1.45 (s, 6H); LCMS m/z=318.15 (M+; 100).

7-((3aS,4R,6aR)-6-(((tert-butyldiphenylsilyl)oxy) methyl)-2,2-dimethyl-3a,6a-dihydro-4H-cyclopenta [d][1,3]dioxol-4-yl)-4-chloro-5-methyl-7H-pyrrolo [2,3-d]pyrimidine

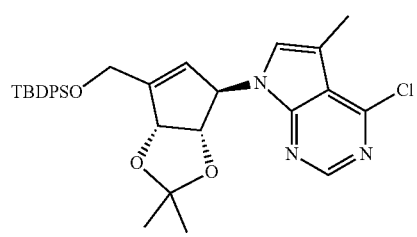

To a stirred solution of (3aS,4S,6aR)-6-(((tert-butyldiphenylsilyl)oxy)methyl)-2,2-dimethyl-3a,6a-dihydro-4H-cyclopenta[d][1,3]dioxol-4-ol (5.0 g, 11.78 mmol) in THF (5 ml) at 0° C. was added triphenylphosphine (9.27 g, 35.3 mmol) followed by the slow addition of DIAD (6.87 ml, 35.3 mmol) and stirred for 30 min. Warmed the reaction to rt and stirred for 16 h. The reaction mixture was diluted with MTBE (300 mL) and filtered. The filtrate was evaporated in vacuo to get 4.6 g of a crude compound. This residue was purified by combi-flash ($R_f$200, Teledyne/Isco) instrument onto a redisep® $R_f$ column with gradient elution (0 to 5%) of ethyl acetate in petroleum ether to afford the title compound (4 g, 59.2%) as a colourless oil. LCMS: m/z=374.17 (M+, 100%).

((3aS,4R,6aR)-4-(4-chloro-5-methyl-7H-pyrrolo[2,3-d]pyrimidin-7-yl)-2,2-dimethyl-3a,6a-dihydro-4H-cyclopenta[d][1,3]dioxol-6-yl)methanol

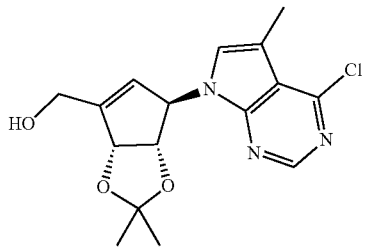 [SMILES: Cc1cn([C@@H]2C=C(CO)[C@H]3OC(C)(C)O[C@H]32)c2ncnc(Cl)c12]

To a stirred solution of 7-((3aS,4R,6aR)-6-(((tert-butyldiphenylsilyl)oxy)methyl)-2,2-dimethyl-3a,6a-dihydro-4H-cyclopenta[d][1,3]dioxol-4-yl)-4-chloro-5-methyl-7H-pyrrolo[2,3-d]pyrimidine (4 g, 6.97 mmol) in THF (50 ml) was added TBAF (8.36 ml, 8.36 mmol) slowly at 0° C. and stirred the reaction mixture for 30 min. Warmed the reaction to rt and stirred for 16 h. The volatiles were evaporated in vacuo to give 2.7 g of a crude compound. This residue was purified by combi-flash ($R_f$200, Teledyne/Isco) instrument onto a redisep® $R_f$ column with gradient elution (0 to 70%) of ethyl acetate in petroleum ether to afford the title compound (2.1 g, 90%) as a colourless oil. LCMS: m/z=336.1 (M+1, 100%).

(3aS,4R,6aR)-4-(4-chloro-5-methyl-7H-pyrrolo[2,3-d]pyrimidin-7-yl)-2,2-dimethyl-3a,6a-dihydro-4H-cyclopenta[d][1,3]dioxole-6-carbaldehyde

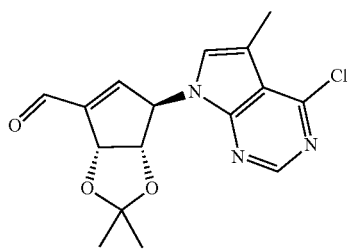 [SMILES: Cc1cn([C@@H]2C=C(C=O)[C@H]3OC(C)(C)O[C@H]32)c2ncnc(Cl)c12]

To the stirred solution of ((3aS,4R,6aR)-4-(4-chloro-5-methyl-7H-pyrrolo[2,3-d]pyrimidin-7-yl)-2,2-dimethyl-3a,6a-dihydro-4H-cyclopenta[d][1,3]dioxol-6-yl)methanol (2.1 g, 6.25 mmol) in DCM (30 ml) was added Dess-Martin Periodinane (3.18 g, 7.50 mmol) portion-wise at rt and stirred for 2 h. The reaction mixture was diluted with DCM (50 mL) and filtered through celite. The filtrate was washed with 1:1 saturated mixture of NaHCO$_3$ and sodium thiosulfate (100 mL×2). Layers were separated, organic layer was washed with brine (50 ml) and dried over anhydrous Na$_2$SO$_4$. The organic layer was filtered and concentrated in vacuo to give 1.8 g of a crude compound. This residue was purified by combi-flash ($R_f$200, Teledyne/Isco) instrument onto a redisep® $R_f$ column with gradient elution (0 to 40%) of ethyl acetate in petroleum ether to afford the title compound (1.5 g, 71.9%) as an off white solid. $^1$H NMR (400 MHz, DMSO-d$_6$) δ 9.91 (s, 1H), 8.61 (s, 1H), 7.45 (d, J=1.3 Hz, 1H), 7.11-7.02 (m, 1H), 5.97-5.96 (m, 1H), 5.59 (dd, J=6.0, 1.4 Hz, 1H), 4.77-4.75 (m, 1H), 2.41 (d, J=1.2 Hz, 3H), 1.40 (s, 3H), 1.29 (s, 3H).

4-chloro-7-((3aS,4R,6aR)-2,2-dimethyl-6-vinyl-3a,6a-dihydro-4H-cyclopenta[d][1,3]dioxol-4-yl)-5-methyl-7H-pyrrolo[2,3-d]pyrimidine

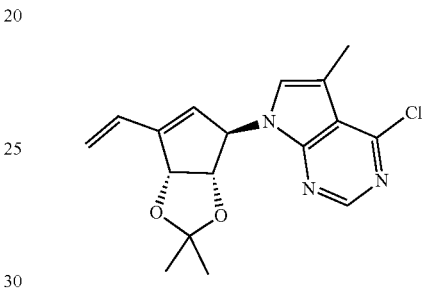

To a stirred suspension of methyltriphenylphosphonium bromide (1.712 g, 4.79 mmol) in THF (50 ml) was added KHMDS (4.79 ml, 4.79 mmol) portion-wise at 0° C. and stirred the reaction mixture for 10 min. A solution of (3aS,4R,6aR)-4-(4-chloro-5-methyl-7H-pyrrolo[2,3-d]pyrimidin-7-yl)-2,2-dimethyl-3a,6a-dihydro-4H-cyclopenta[d][1,3]dioxole-6-carbaldehyde (1.0 g, 3.00 mmol) in THF (10 ml) was added slowly and stirred at 0° C. for 10 min. The reaction mixture was quenched with sat.aq. NH$_4$Cl (50 ml) and extracted with ethyl acetate (20 ml×2). Layers were separated, organic layer was washed with brine (50 ml) and dried over anhydrous Na$_2$SO$_4$. The organic layer was filtered and concentrated in vacuo to give 1.3 g of a crude compound. This residue was purified by combiflash ($R_f$200, Teledyne/Isco) instrument onto a redisep® $R_f$ column with gradient elution (0 to 10%) of ethyl acetate in petroleum ether to afford the title compound (0.7 g, 70.4%) as an off white solid. $^1$H NMR (400 MHz, DMSO-d6) δ 8.59 (s, 1H), 7.31 (d, J=1.3 Hz, 1H), 6.60 (dd, J=17.6, 10.8 Hz, 1H), 5.87 (d, J=2.7 Hz, 1H), 5.77 (d, J=2.7 Hz, 1H), 5.66-5.55 (m, 2H), 5.42 (dd, J=10.8, 1.6 Hz, 1H), 4.65 (d, J=5.9 Hz, 1H), 2.40 (d, J=1.2 Hz, 3H), 1.39 (s, 3H), 1.31 (s, 3H)

(3aR,4S,6aR)-6-(((tert-butyldimethylsilyl)oxy)methyl)-2,2-dimethyl-3a,6a-dihydro-4H-cyclopenta[d][1,3]dioxol-4-yl methanesulfonate

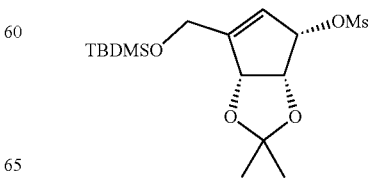

The title compound was prepared by following same reaction protocol as described in Heterocycles, 2017, vol. 95, #1, p. 445-461.

1-((3aS,4R,6aR)-6-(((tert-Butyldimethylsilyl)oxy)methyl)-2,2-dimethyl-3a,6a-dihydro-4H-cyclopenta[d][1,3]dioxol-4-yl)-1H-pyrazolo[3,4-d]pyrimidin-4-amine

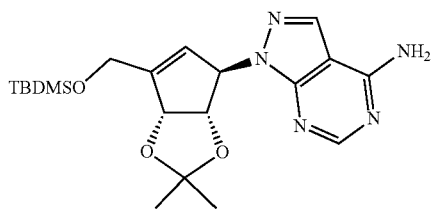 [SMILES: CC1(C)O[C@@H]2[C@H](O1)C(CO[Si](C)(C)C(C)(C)C)=C[C@H]2n1ncc2c(N)ncnc21]

To a stirred suspension of 1H-pyrazolo[3,4-d]pyrimidin-4-amine (1.785 g, 13.21 mmol) in DMF (50 ml) was added NaH (0.581 g, 14.53 mmol) at 0° C. and stirred the reaction mixture for 30 mins. A solution of (3aR,4S,6aR)-6-(((tert-butyldimethylsilyl)oxy)methyl)-2,2-dimethyl-3a,6a-dihydro-4H-cyclopenta[d][1,3]dioxol-4-yl methanesulfonate (5.00 g, 13.21 mmol) in DMF (25 mL) was added slowly at 0° C. and stirred for 5 mins. The reaction mixture was brought to 25° C. and stirred for 16 h. The reaction mixture was quenched with sat.aq. NH$_4$Cl (50 ml) and extracted with ethyl CH$_2$Cl$_2$ (50 ml). The organic layer was separated, dried over Na$_2$SO$_4$, filtered and concentrated in vacuo to give 3.5 g of crude compound. This residue was purified by combiflash (R$_f$200, Teledyne/Isco) instrument onto a redisep® R$_f$ column with gradient elution (0-60%) of ethyl acetate in petroleum ether to afford the title compound (2.1 g, 38.1%) as an off-white solid. $^1$H NMR (400 MHz, Chloroform-d) δ 8.40 (s, 1H), 7.99 (d, J=3.4 Hz, 1H), 5.96 (s, 1H), 5.74 (d, J=2.4 Hz, 1H), 5.38 (d, J=5.8 Hz, 1H), 4.-91-4.89 (m, 1H), 4.43 (d, J=2.3 Hz, 2H), 1.51 (s, 3H), 1.38 (s, 3H), 0.92 (s, 9H), 0.10 (d, J=3.6 Hz, 6H); LCMS m/z=417.23 (M+; 100%).

tert-Butyl(tert-butoxycarbonyl)(1-((3aS,4R,6aR)-6-(((tert-butyldimethylsilyl)oxy)methyl)-2,2-dimethyl-3a,6a-dihydro-4H-cyclopenta[d][1,3]dioxol-4-yl)-1H-pyrazolo[3,4-d]pyrimidin-4-yl)carbamate

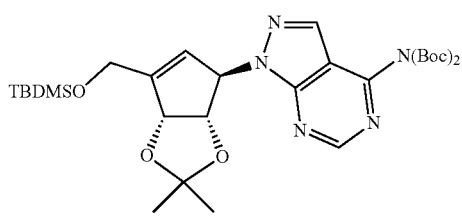

To a stirred solution of 1-((3aS,4R,6aR)-6-(((tert-butyldimethylsilyl)oxy)methyl)-2,2-dimethyl-3a,6a-dihydro-4H-cyclopenta[d][1,3]dioxol-4-yl)-1H-pyrazolo[3,4-d]pyrimidin-4-amine (2.1 g, 5.03 mmol) in THF (30 ml) was added triethylamine (2.103 ml, 15.09 mmol), DMAP (0.061 g, 0.503 mmol) at 25° C. and stirred the reaction mixture for 10 min. BOC-anhydride (2.452 ml, 10.56 mmol) was added and stirred the reaction mixture at 25° C. for 16 h. Volatiles were removed in vacuo and the crude residue was purified by combiflash (R$_f$200, Teledyne/Isco) instrument onto a redisep® R$_f$ column with gradient elution (0 to 15%) of ethyl acetate in petroleum ether to afford the title compound (1.85 g, 59.5%) as a colourless oil. LCMS m/z=618.32 (M+; 100%).

tert-Butyl (tert-butoxycarbonyl)(1-((3aS,4R,6aR)-6-(hydroxymethyl)-2,2-dimethyl-3a,6a-dihydro-4H-cyclopenta[d][1,3]dioxol-4-yl)-1H-pyrazolo[3,4-d]pyrimidin-4-yl)carbamate

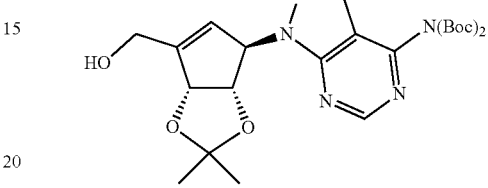

The title compound was synthesized by following an analogous reaction protocol as was described in the preparation ((3aS,4R,6aR)-4-(4-chloro-5-methyl-7H-pyrrolo[2,3-d]pyrimidin-7-yl)-2,2-dimethyl-3a,6a-dihydro-4H-cyclopenta[d][1,3]dioxol-6-yl)methanol. LCMS m/z=504.2 (M+; 100).

tert-Butyl (tert-butoxycarbonyl)(1-((3aS,4R,6aR)-6-formyl-2,2-dimethyl-3a,6a-dihydro-4H-cyclopenta[d][1,3]dioxol-4-yl)-1H-pyrazolo[3,4-d]pyrimidin-4-yl)carbamate

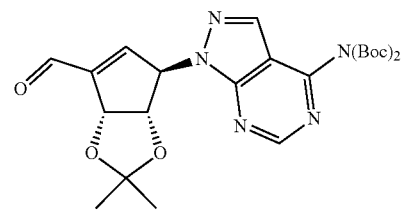

The title compound was synthesized by following an analogous reaction protocol as was described in the preparation (3aS,4R,6aR)-4-(4-chloro-5-methyl-7H-pyrrolo[2,3-d]pyrimidin-7-yl)-2,2-dimethyl-3a,6a-dihydro-4H-cyclopenta[d][1,3]dioxole-6-carbaldehyde. LCMS m/z=502.44 (M+; 20%).

tert-Butyl (tert-butoxycarbonyl)(1-((3aS,4R,6aR)-2,2-dimethyl-6-vinyl-3a,6a-dihydro-4H-cyclopenta[d][1,3]dioxol-4-yl)-1H-pyrazolo[3,4-d]pyrimidin-4-yl)carbamate

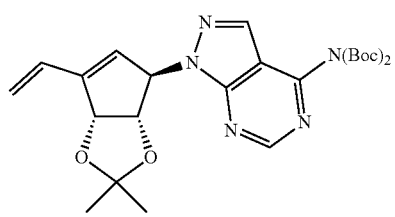

The title compound was synthesized by following an analogous reaction protocol as was described in the preparation 4-chloro-7-((3aS,4R,6aR)-2,2-dimethyl-6-vinyl-3a,6a-dihydro-4H-cyclopenta[d][1,3]dioxol-4-yl)-5-methyl-7H-pyrrolo[2,3-d]pyrimidine. LCMS m/z=500.49 (M+; 20%).

1-((3aS,4R,6aR)-6-(((tert-butyldimethylsilyl)oxy)methyl)-2,2-dimethyl-3a,6a-dihydro-4H-cyclopenta[d][1,3]dioxol-4-yl)-6-methyl-1H-pyrazolo[3,4-d]pyrimidin-4-amine

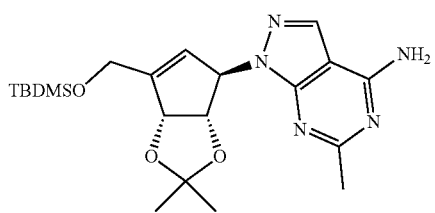 [SMILES: Cc1nc(N)c2cnn([C@@H]3C=C(CO[Si](C)(C)C(C)(C)C)[C@H]4OC(C)(C)O[C@H]43)c2n1]

To a stirred solution of 6-methyl-1H-pyrazolo[3,4-d]pyrimidin-4-amine (0.788 g, 5.28 mmol) in DMF (20 ml) was added NaH (0.317 g, 7.92 mmol) at 0° C. and stirred for 15 min. A solution of (3aR,4S,6aR)-6-(((tert-butyldimethylsilyl)oxy)methyl)-2,2-dimethyl-3a,6a-dihydro-4H-cyclopenta[d][1,3]dioxol-4-yl methanesulfonate (2.00 g, 5.28 mmol) in DMF (5 mL) was added slowly and stirred at rt for 15 h. The reaction mixture was diluted with diethyl ether (50 ml×2) and washed with water (25 ml). Layers were separated, organic layer was washed with brine (50 ml) and dried over anhydrous Na$_2$SO$_4$. The organic layer was filtered and concentrated in vacuo to give (1.6 g, 70.2%) of a crude compound, which was directly used for next step without purification. LCMS m/z=432.30 (M+1).

tert-butyl (tert-butoxycarbonyl)(1-((3aS,4R,6aR)-6-(((tert-butyldimethylsilyl)oxy)methyl)-2,2-dimethyl-3a,6a-dihydro-4H-cyclopenta[d][1,3]dioxol-4-yl)-6-methyl-1H-pyrazolo[3,4-d]pyrimidin-4-yl)carbamate

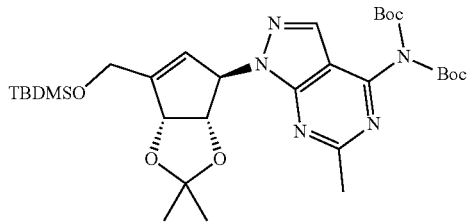 [SMILES: Cc1nc(N(C(=O)OC(C)(C)C)C(=O)OC(C)(C)C)c2cnn([C@@H]3C=C(CO[Si](C)(C)C(C)(C)C)[C@H]4OC(C)(C)O[C@H]43)c2n1]

To a stirred solution of 1-((3aS,4R,6aR)-6-(((tert-butyldimethylsilyl)oxy)methyl)-2,2-dimethyl-3a,6a-dihydro-4H-cyclopenta[d][1,3]dioxol-4-yl)-6-methyl-1H-pyrazolo[3,4-d]pyrimidin-4-amine (1.60 g, 3.71 mmol) in THF (20 ml) was added TEA (2.067 ml, 14.83 mmol), DMAP (0.045 g, 0.371 mmol) at rt and stirred for 10 min. BOC-anhydride (3.44 ml, 14.83 mmol) was added and stirred for 15 h. The volatiles were evaporated in vacuo to give 2 g of a crude compound, which was directly used for next step without any purification. LCMS m/z=632.09 (M+).

tert-butyl (tert-butoxycarbonyl)(1-((3aS,4R,6aR)-6-(hydroxymethyl)-2,2-dimethyl-3a,6a-dihydro-4H-cyclopenta[d][1,3]dioxol-4-yl)-6-methyl-1H-pyrazolo[3,4-d]pyrimidin-4-yl)carbamate

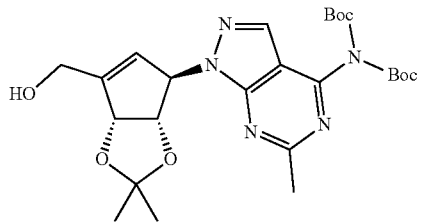 [SMILES: Cc1nc(N(C(=O)OC(C)(C)C)C(=O)OC(C)(C)C)c2cnn([C@@H]3C=C(CO)[C@H]4OC(C)(C)O[C@H]43)c2n1]

To a stirred solution of tert-butyl (tert-Butoxycarbonyl)(1-((3aS,4R,6aR)-6-(((tert-butyldimethylsilyl)oxy)methyl)-2,2-dimethyl-3a,6a-dihydro-4H-cyclopenta[d][1,3]dioxol-4-yl)-6-methyl-1H-pyrazolo[3,4-d]pyrimidin-4-yl)carbamate (2.0 g) in THF (20 ml) was added TBAF (4.43 ml, 4.43 mmol) slowly and stirred at rt for 15 h. The volatiles were evaporated in vacuo to give 1.5 g of a crude compound. This residue was purified by combi-flash (R$_f$200, Teledyne/Isco) instrument onto a redisep® R$_f$ column with gradient elution (0 to 30%) of ethyl acetate in petroleum ether to afford the title compound (1.1 g, 67.1%) as a colourless oil. LCMS m/z=518.07 (M+1).

tert-butyl (tert-butoxycarbonyl)(1-((3aS,4R,6aR)-6-formyl-2,2-dimethyl-3a,6a-dihydro-4H-cyclopenta[d][1,3]dioxol-4-yl)-6-methyl-1H-pyrazolo[3,4-d]pyrimidin-4-yl)carbamate

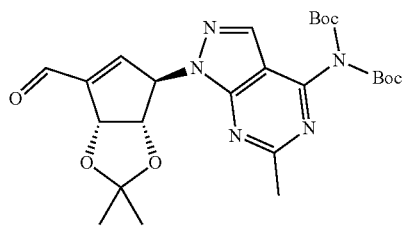 [SMILES: Cc1nc(N(C(=O)OC(C)(C)C)C(=O)OC(C)(C)C)c2cnn([C@@H]3C=C(C=O)[C@H]4OC(C)(C)O[C@H]43)c2n1]

To a stirred solution of tert-butyl (tert-butoxycarbonyl)(1-((3aS,4R,6aR)-6-(hydroxymethyl)-2,2-dimethyl-3a,6a-dihydro-4H-cyclopenta[d][1,3]dioxol-4-yl)-6-methyl-1H-pyrazolo[3,4-d]pyrimidin-4-yl)carbamate (1.10 g) in DCM (25 ml) was added Dess-Martin Periodinane (3.61 g, 8.50 mmol) portion-wise at rt and stirred for 10 min. Warmed the reaction mixture to rt and stirred for 3 h. The volatiles were evaporated in vacuo to give 1.2 g of a crude compound. This residue was purified by combi-flash (R$_f$200, Teledyne/Isco) instrument onto a redisep® R$_f$ column with gradient elution (0 to 30%) of ethyl acetate in petroleum ether to afford the title compound (0.9 g, 82%) as a colourless oil. LCMS m/z=515.57 (M+).

tert-butyl (tert-butoxycarbonyl)(1-((3aS,4R,6aR)-2,2-dimethyl-6-vinyl-3a,6a-dihydro-4H-cyclopenta[d][1,3]dioxol-4-yl)-6-methyl-1H-pyrazolo[3,4-d]pyrimidin-4-yl)carbamate

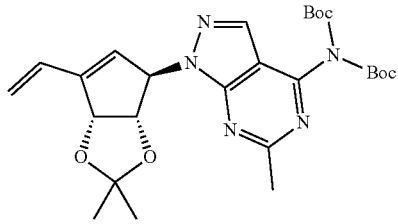 [SMILES: C=CC1=C[C@@H](n2ncc3c(N(C(=O)OC(C)(C)C)C(=O)OC(C)(C)C)nc(C)nc32)[C@@H]2OC(C)(C)O[C@H]12]

To a stirred solution of methyltriphenylphosphonium bromide (1.039 g, 2.91 mmol) in THF (3 ml) was added KHMDS (2.91 ml, 2.91 mmol) slowly at 0° C. and stirred for 3 min. A solution of tert-butyl (tert-butoxycarbonyl)(1-((3aS,4R,6aR)-6-formyl-2,2-dimethyl-3a,6a-dihydro-4H-cyclopenta[d][1,3]dioxol-4-yl)-6-methyl-1H-pyrazolo[3,4-d]pyrimidin-4-yl)carbamate (0.75 g) in THF (3 ml) was added slowly at 0° C. Stirred the reaction mixture for 5 min. The reaction mixture was quenched with water (20 ml) and extracted with ethyl acetate (20 ml×2). Layers were separated, organic layer was washed with brine (20 ml) and dried over anhydrous Na$_2$SO$_4$. The organic layer was filtered and concentrated in vacuo to give 0.6 g of a crude compound. This residue was purified by combiflash (R$_f$200, Teledyne/Isco) instrument onto a redisep® R$_f$ column with gradient elution (0 to 10%) of ethyl acetate in petroleum ether to afford the title compound (0.47 g, 62.9%) as a colourless oil. LCMS m/z=514.30 (M+1).

((3aS,4R,6aR)-4-(6-Chloro-9H-purin-9-yl)-2,2-dimethyl-3a,6a-dihydro-4H-cyclopenta [d][1,3]dioxol-6-yl)methanol

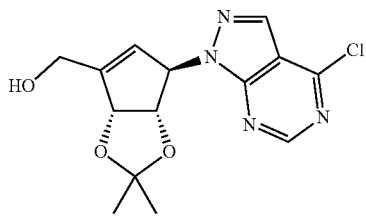 [SMILES: CC1(C)O[C@@H]2[C@H](O1)C(CO)=C[C@H]2n1ncc2c(Cl)ncnc21]

The title compound was prepared by following the same reaction protocol as was described in Journal of Medicinal Chemistry, 1992, vol. 35, #2, p. 324-331.

(3aS,4R,6aR)-4-(6-Chloro-9H-purin-9-yl)-2,2-dimethyl-3a,6a-dihydro-4H-cyclopenta [d][1,3]dioxole-6-carbaldehyde

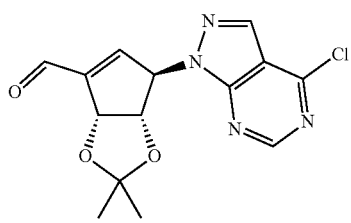 [SMILES: CC1(C)O[C@@H]2[C@H](O1)C(C=O)=C[C@H]2n1ncc2c(Cl)ncnc21]

To a stirred solution of ((3aS,4R,6aR)-4-(6-chloro-9H-purin-9-yl)-2,2-dimethyl-3a,6a-dihydro-4H-cyclopenta[d][1,3]dioxol-6-yl)methanol (2.1 g, 6.51 mmol) in CH$_2$Cl$_2$ (5 ml) at 0° C., was added Dess-Martin Periodinane (3.31 g, 7.81 mmol) portion-wise and stirred for 16 h. The reaction mixture was diluted with dichloromethane (50 mL), water (50 mL) and filtered through celite. The organic layer was separated, dried over MgSO$_4$, filtered and concentrated in vacuo to give 1.93 g of a crude compound. This residue was purified by combiflash with gradient elution (0-70%) of ethyl acetate in petroleum ether to afford the title compound (1.79 g, 86%) as a colorless oil. $^1$H NMR (400 MHz, Chloroform-d) δ 10.00 (s, 1H), 8.76 (s, 1H), 8.11 (s, 1H), 6.83-6.52 (m, 1H), 5.84-5.82 (m, 2H), 5.13-4.86 (m, 1H), 1.54 (s, 3H), 1.42 (s, 3H); LCMS m/z=320.47 (M+, 100%).

6-Chloro-9-((3aS,4R,6aR)-2,2-dimethyl-6-vinyl-3a,6a-dihydro-4H-cyclopenta [d][1,3] dioxol-4-yl)-9H-purine

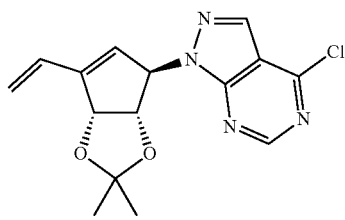 [SMILES: C=CC1=C[C@@H](n2ncc3c(Cl)ncnc32)[C@@H]2OC(C)(C)O[C@H]12]

To a stirred suspension of methyltriphenylphosphonium bromide (0.278 g, 0.779 mmol) in THF (3 mL) at 0° C., was added 1M KHMDS (0.779 ml, 0.779 mmol) dropwise and stirred the reaction mixture at 25° C. for 20 mins. Cooled the reaction mixture to −10° C. to −15° C. and slowly added a solution of (3aS,4R,6aR)-4-(6-chloro-9H-purin-9-yl)-2,2-dimethyl-3a,6a-dihydro-4H-cyclopenta[d][1,3]dioxole-6-carbaldehyde (0.1 g, 0.312 mmol) in THF (3 ml). Stirred the reaction mixture at −10° C. for 10 mins. The reaction mixture was quenched with sat. aqueous NH$_4$Cl (10 ml) and extracted with ethyl acetate (10 ml). The organic layer was separated, dried over Na2SO4, filtered and concentrated in vacuo to give 0.31 g of crude compound. This residue was purified by combiflash with gradient elution (0-15%) of ethyl acetate in petroleum ether to afford the title compound (0.021 g, 21.13%) as an off-white solid. $^1$H NMR (400 MHz, Chloroform-d) δ 8.81 (s, 1H), 8.03 (s, 1H), 6.62 (dd, J=17.6, 10.8 Hz, 1H), 5.82 (dd, J=17.5, 1.1 Hz, 1H), 5.78 (d, J=2.7 Hz, 1H), 5.75 (s, 1H), 5.65-5.62 (m, 1H), 5.54 (d, J=10.9 Hz, 1H), 4.78 (dd, J=5.9, 1.1 Hz, 1H), 1.52 (s, 3H), 1.42 (s, 3H); LCMS m/z=319.4 (M+1, 20%)

3-Benzoyl-1-((3aS,4R,6aR)-6-(((tert-butyldiphenylsilyl)oxy)methyl)-2,2-dimethyl-3a,6a-dihydro-4H-cyclopenta[d][1,3]dioxol-4-yl)pyrimidine-2,4 (1H,3H)-dione

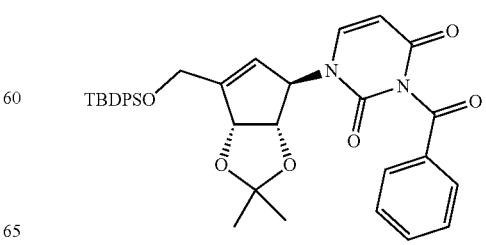

To a stirred suspension of (3aS,4S,6aR)-6-(((tert-butyldiphenylsilyl)oxy)methyl)-2,2-dimethyl-3a,6a-dihydro-4H-cyclopenta[d][1,3]dioxol-4-ol (1 g, 2.355 mmol), triphenylphosphine (1.544 g, 5.89 mmol) and 3-benzoylpyrimidine-2,4 (1H,3H)-dione (1.018 g, 4.71 mmol) in dry THF (20 ml), was added a solution of DEAD (0.932 ml, 5.89 mmol) in dry THF (5 ml) at 0° C. under nitrogen atmosphere. The resulting mixture was stirred at 25° C. for 16 h and then the solvent was removed under vacuum. This residue was purified by combiflash (R$_f$200, Teledyne/Isco) instrument onto a redisep® R$_f$ column with gradient elution (0-40%) of ethyl acetate in petroleum ether to afford the title compound (0.6 g, 40.9%) as an off-white solid. $^1$H NMR (400 MHz, DMSO-d6) δ 8.05 (dd, J=8.4, 1.3 Hz, 2H), 7.84-7.77 (m, 1H), 7.73-7.57 (m, 6H), 7.56-7.38 (m, 7H), 5.88 (d, J=8.0 Hz, 1H), 5.83-5.73 (m, 1H), 5.30 (d, J=2.6 Hz, 1H), 5.18 (d, J=5.8 Hz, 1H), 4.81-4.72 (m, 1H), 4.49-4.43 (m, 1H), 4.34-4.29 (m, 1H), 1.27 (s, 3H), 1.23 (s, 3H), 1.04 (s, 9H). LCMS m/z=623.09 (M+1; 50%).

3-Benzoyl-1-((3aS,4R,6aR)-6-(hydroxymethyl)-2,2-dimethyl-3a,6a-dihydro-4H-cyclopenta[d][1,3]dioxol-4-yl)pyrimidine-2,4 (1H,3H)-dione

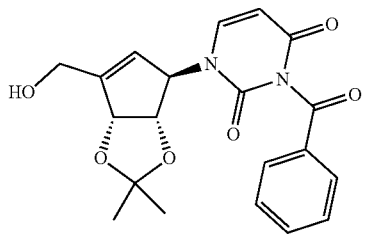 [SMILES: CC1(C)O[C@@H]2[C@H](O1)C(CO)=C[C@H]2n1ccc(=O)n(C(=O)c2ccccc2)c1=O]

To a stirred solution of 3-benzoyl-1-((3aS,4R,6aR)-6-(((tert-butyldiphenylsilyl)oxy)methyl)-2,2-dimethyl-3a,6a-dihydro-4H-cyclopenta[d][1,3]dioxol-4-yl)pyrimidine-2,4 (1H,3H)-dione (0.250 g, 0.401 mmol) in Methanol (3 ml), was added ammonium fluoride (0.074 g, 2.007 mmol). The resulting mixture was stirred at rt for 16 h. After completion of reaction, methanol was evaporated under reduced pressure. The residue was diluted with ethyl acetate (100 ml) and washed with water (50 ml). The organic layer was separated, dried over Na$_2$SO$_4$, filtered and concentrated in vacuo to give crude compound. This residue was purified by combiflash (R$_f$200, Teledyne/Isco) instrument onto a redisep® R$_f$ column with gradient elution (0-2%) of methanol in DCM to afford the title compound (0.13 g, 84%) as a pale yellow oil. $^1$H NMR (400 MHz, DMSO-d6) δ 8.08-8.00 (m, 2H), 7.85-7.76 (m, 1H), 7.70-7.58 (m, 2H), 7.53 (t, J=7.8 Hz, 1H), 5.86 (d, J=8.1 Hz, 1H), 5.63-5.56 (m, 1H), 5.26 (d, J=2.9 Hz, 1H), 5.20 (d, J=5.8 Hz, 1H), 5.11 (t, J=5.5 Hz, 1H), 4.73 (d, J=5.8 Hz, 1H), 4.13 (dd, J=5.1, 2.5 Hz, 2H), 1.33 (s, 3H), 1.27 (s, 3H). LCMS m/z=385.2 (M+1; 70%).

3-((3aS,4R,6aR)-6-(((tert-butyldiphenylsilyl)oxy)methyl)-2,2-dimethyl-3a,6a-dihydro-4H-cyclopenta[d][1,3]dioxol-4-yl)-6-chloropyrimidin-4 (3H)-one

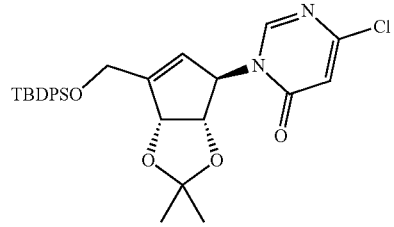

To a stirred suspension of (3aS,4S,6aR)-6-(((tert-butyldiphenylsilyl)oxy)methyl)-2,2-dimethyl-3a,6a-dihydro-4H-cyclopenta[d][1,3]dioxol-4-ol (5.0 g, 11.78 mmol), triphenylphosphine (9.27 g, 35.3 mmol) and 6-chloropyrimidin-4 (3H)-one (2.61 g, 20.02 mmol) in dry THF (180 ml), was added DIAD (6.87 ml, 35.3 mmol at 0° C. under nitrogen atmosphere. The resulting mixture was stirred at rt for 4 h and then the solvent was removed under vacuum. This residue was purified by combiflash (R$_f$200, Teledyne/Isco) instrument onto a redisep® R$_f$ column with gradient elution (0 to 20%) of ethyl acetate in petroleum ether to afford (5.22 g, 83%) of the title compound LCMS m/z=539.20 (M+2).

6-chloro-3-((3aS,4R,6aR)-6-(hydroxymethyl)-2,2-dimethyl-3a,6a-dihydro-4H-cyclopenta[d][1,3]dioxol-4-yl)pyrimidin-4 (3H)-one

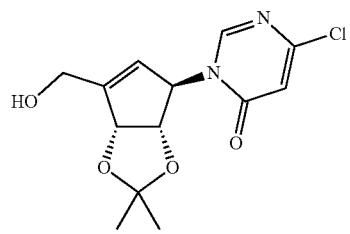 [SMILES: CC1(C)O[C@@H]2[C@H](O1)C(CO)=C[C@H]2n1cnc(Cl)cc1=O]

To a solution of 3-((3aS,4R,6aR)-6-(((tert-butyldiphenylsilyl)oxy)methyl)-2,2-dimethyl-3a,6a-dihydro-4H-cyclopenta[d][1,3]dioxol-4-yl)-6-chloropyrimidin-4 (3H)-one (5.2 g, 9.68 mmol) in THF (50 ml), was added TBAF (13.55 ml, 13.55 mmol) slowly at 0° C. and stirred at room temperature for 30 min. After evaporation of the solvent, the crude product was purified by combiflash (R$_f$200, Teledyne/Isco) instrument onto a redisep® R$_f$ column with gradient elution (0 to 55%) of ethyl acetate in petroleum ether to afford (2.3 g, 80%) of the title compound. LCMS m/z=299.27 (M+1).

3-((3aS,4R,6aR)-6-(((tert-butyldiphenylsilyl)oxy)methyl)-2,2-dimethyl-3a,6a-dihydro-4H-cyclopenta[d][1,3]dioxol-4-yl)-6-methylpyrimidin-4 (3H)-one

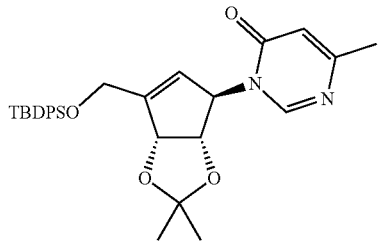

To a stirred solution of (3aS,4S,6aR)-6-(((tert-butyldiphenylsilyl)oxy)methyl)-2,2-dimethyl-3a,6a-dihydro-4H-cyclopenta[d][1,3]dioxol-4-ol (2.00 g, 4.71 mmol) in toluene (50 ml) was added 6-methylpyrimidin-4 (3H)-one (0.545 g, 4.95 mmol), triphenylphosphine (3.09 g, 11.78 mmol) and slow addition of DEAD (1.864 ml, 11.78 mmol) at 0° C. and stirred for 15 min. Warmed the reaction to room temperature and stirred for 4 h. Volatiles were removed in vacuo and the crude residue was purified by combiflash ($R_f$200, Teledyne/Isco) instrument onto a redisep® $R_f$ column with gradient elution (0 to 30%) of ethyl acetate in petroleum ether to afford the title compound (1.48 g, 60.8%). LCMS 517.2 (M+)

3-((3aS,4R,6aR)-6-(hydroxymethyl)-2,2-dimethyl-3a,6a-dihydro-4H-cyclopenta[d][1,3]dioxol-4-yl)-6-methylpyrimidin-4 (3H)-one

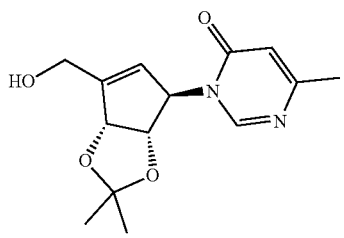 [SMILES: Cc1cc(=O)n([C@@H]2C=C(CO)[C@H]3OC(C)(C)O[C@H]32)cn1]

To a stirred solution of 3-((3aS,4R,6aR)-6-(((tert-butyldiphenylsilyl)oxy)methyl)-2,2-dimethyl-3a,6a-dihydro-4H-cyclopenta[d][1,3]dioxol-4-yl)-6-methylpyrimidin-4 (3H)-one (1.42 g, 2.75 mmol) in THF (15 ml) was added TBAF (4.40 ml, 4.40 mmol) slowly and stirred at rt for 3 h. The volatiles were removed in vacuo to give 0.82 g of a crude compound. This residue was purified by combi-flash ($R_f$200, Teledyne/Isco) instrument onto a redisep® $R_f$ column with gradient elution (0 to 15%) of ethyl acetate in petroleum ether to afford of the title compound (0.61 g, 80%) as an off-white solid. LCMS m/z=279.27 M+1.

3-((3aS,4R,6aR)-6-(((tert-butyldiphenylsilyl)oxy)methyl)-2,2-dimethyl-3a,6a-dihydro-4H-cyclopenta[d][1,3]dioxol-4-yl)-6-chloro-5-fluoropyrimidin-4 (3H)-one

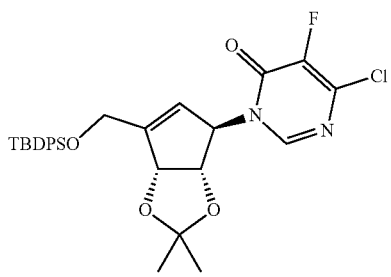

To a stirred solution of (3aS,4S,6aR)-6-(((tert-butyldiphenylsilyl)oxy)methyl)-2,2-dimethyl-3a,6a-dihydro-4H-cyclopenta[d][1,3]dioxol-4-ol (2.00 g, 4.71 mmol) in toluene (50 ml) at 0° C. was added 6-chloro-5-fluoropyrimidin-4 (3H)-one (0.735 g, 4.95 mmol), triphenylphosphine (3.09 g, 11.78 mmol) followed by slow addition of DEAD (1.864 ml, 11.78 mmol) and stirred for 30 min. The resulting mixture was warmed to rt and stirred for 2.5 h. The volatiles were removed in vacuo to give 2.5 g of a crude compound. This residue was purified by combi-flash ($R_f$200, Teledyne/Isco) instrument onto a redisep® $R_f$ column with gradient elution (0 to 15%) of ethyl acetate in petroleum ether to afford (2.1 g, 80%) of the title compound. $^1$H NMR (400 MHz, Chloroform-d) δ 8.43 (s, 1H), 7.72-7.66 (m, 4H), 7.44-7.36 (m, 6H), 6.04-5.97 (m, 2H), 5.16 (dd, J=5.8, 1.4 Hz, 1H), 4.80-4.73 (m, 1H), 4.48-4.35 (m, 2H), 1.37 (d, J=15.4 Hz, 6H), 1.10 (s, 9H).

6-chloro-5-fluoro-3-((3aS,4R,6aR)-6-(hydroxymethyl)-2,2-dimethyl-3a,6a-dihydro-4H-cyclopenta[d][1,3]dioxol-4-yl)pyrimidin-4 (3H)-one

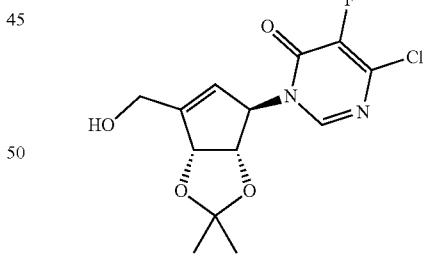

To a stirred solution of 3-((3aS,4R,6aR)-6-(((tert-butyldiphenylsilyl)oxy)methyl)-2,2-dimethyl-3a,6a-dihydro-4H-cyclopenta[d][1,3]dioxol-4-yl)-6-chloro-5-fluoropyrimidin-4 (3H)-one (2.10 g, 3.78 mmol) in THF (15 ml) was added TBAF (6.05 ml, 6.05 mmol) slowly and the reaction mixture stirred at rt for 3 h. The volatiles were removed in vacuo to give 1.2 g of a crude compound. This residue was purified by combi-flash ($R_f$200, Teledyne/Isco) instrument onto a redisep® $R_f$ column with gradient elution (0 to 15%) of ethyl acetate in petroleum ether to afford (1 g, 83%) of the title compound. $^1$H NMR (400 MHz, Chloroform-d) δ 8.42 (s, 1H), 6.00 (dd, J=2.5, 1.3 Hz, 1H), 5.97-5.93 (m, 1H), 5.32-5.29 (m, 1H), 4.83-4.80 (m, 1H), 4.49-4.36 (m, 3H), 1.48 (s, 3H), 1.41-1.40 (m, 3H).

((3aR,3bR,4aS,5R,5aS)-5-(4-Chloro-7H-pyrrolo[2,3-d]pyrimidin-7-yl)-2,2-dimethyl hexa hydrocyclopropa[3,4]cyclopenta[1,2-d][1,3]dioxol-3b-yl)methanol

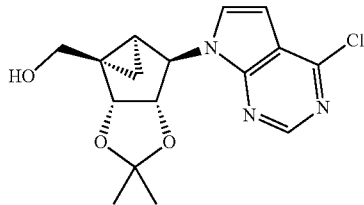 [SMILES: CC1(C)O[C@H]2[C@H](n3ccc4c(Cl)ncnc43)[C@H]3C[C@]3(CO)[C@H]2O1]

The title compound was prepared by an analogous reaction protocol as described in WO2006/091905 A1.

(3aR,3bS,4aS,5R,5aS)-5-(4-Chloro-7H-pyrrolo[2,3-d]pyrimidin-7-yl)-2,2-dimethylhexahydrocyclopropa [3,4]cyclopenta[1,2-d][1,3]dioxole-3b-carbaldehyde

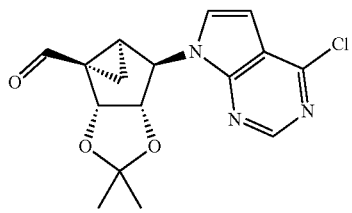 [SMILES: CC1(C)O[C@H]2[C@H](n3ccc4c(Cl)ncnc43)[C@H]3C[C@]3(C=O)[C@H]2O1]

The title compound was synthesized by following an analogous reaction protocol as was described in the preparation of (3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxole-6-carbaldehyde. ¹H NMR (400 MHz, Chloroform-d) δ 9.34 (s, 1H), 8.63 (s, 1H), 7.18 (d, J=3.6 Hz, 1H), 6.66 (d, J=3.6 Hz, 1H), 5.91 (dd, J=7.1, 1.2 Hz, 1H), 5.11 (s, 1H), 4.82 (dd, J=7.1, 1.6 Hz, 1H), 2.34 (ddd, J=9.4, 6.1, 1.6 Hz, 1H), 1.89-1.77 (m, 2H), 1.58 (s, 3H), 1.30 (s, 3H); LCMS m/z=333.9 (M+, 100%).

4-Chloro-7-((3aR,3bS,4aS,5R,5aS)-2,2-dimethyl-3b-vinylhexahydro cyclopropa [3,4] cyclo penta[1,2-d][1,3]dioxol-5-yl)-7H-pyrrolo[2,3-d]pyrimidine

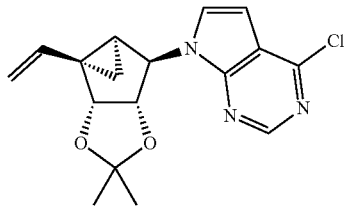 [SMILES: C=C[C@]12C[C@@H]1[C@@H](n1ccc3c(Cl)ncnc31)[C@@H]1OC(C)(C)O[C@@H]12]

To a stirred suspension of methyltriphenylphosphonium bromide (24.62 g, 68.9 mmol) in THF (200 ml), was added 1M KHMDS in THF (68.9 ml, 68.9 mmol) at 25° C. and stirred for 10 min. The resulting yellow suspension was cooled to 0° C. and a solution of (3aR,3bS,4aS, 5R,5aS)-5-(4-Chloro-7H-pyrrolo[2,3-d]pyrimidin-7-yl)-2,2-dimethylhexahydrocyclopropa [3,4]cyclopenta[1,2-d][1,3]dioxole-3b-carbaldehyde (9.2 g, 27.6 mmol) in THF (80 ml) was added slowly. The reaction mixture was stirred at the same temperature for 1 h. The reaction mixture was quenched with a saturated aq.NH₄Cl (200 ml) and extracted with ethyl acetate (200 ml). Layers were separated, organic layer was washed with brine (250 ml) and dried over anhydrous Na₂SO₄. The organic layer was filtered and concentrated in vacuo to give 11 g of crude compound. This residue was purified by combiflash (R$_f$200, Teledyne/Isco) instrument onto a redisep® R$_f$ column with gradient elution (0 to 20%) of ethyl acetate in petroleum ether to afford the title compound (7 g, 77%) as a white solid. ¹H NMR (400 MHz, Chloroform-d) δ 8.68 (s, 1H), 7.23 (d, J=3.7 Hz, 1H), 6.67 (d, J=3.6 Hz, 1H), 5.86 (dd, J=17.3, 10.6 Hz, 1H), 5.39-5.32 (m, 2H), 5.29 (s, 1H), 5.18 (dd, J=10.6, 0.9 Hz, 1H), 4.59 (dd, J=7.1, 1.6 Hz, 1H), 1.77 (ddd, J=9.3, 4.9, 1.6 Hz, 1H), 1.63 (s, 3H), 1.49 (t, J=5.3 Hz, 1H), 1.27 (s, 3H), 1.18 (ddd, J=9.3, 5.6, 1.6 Hz, 1H); LCMS m/z=332.28 (M+, 50%).

7-((3aR,3bS,4aS,5R,5aS)-2,2-Dimethyl-3b-vinylhexahydrocyclopropa [3,4]cyclopenta [1,2-d][1,3] dioxol-5-yl)-7H-pyrrolo[2,3-d]pyrimidin-4-amine

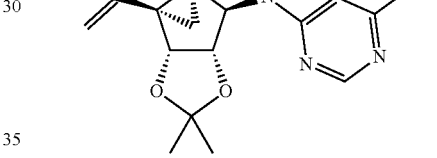

A mixture of 4-chloro-7-((3aR,3bS,4aS,5R,5aS)-2,2-dimethyl-3b-vinylhexahydro cyclopropa [3,4] cyclo penta[1,2-d][1,3]dioxol-5-yl)-7H-pyrrolo[2,3-d]pyrimidine (3 g, 9.04 mmol) and aq. ammonia (19.57 ml, 904 mmol) in dioxane (6 ml) stirred at 130° C. in a steel bomb for 16 h. The reaction mixture was diluted with ethyl acetate (20 ml) and washed with water (20 ml). Layers were separated, organic layer was washed with brine (20 ml) and dried over anhydrous Na₂SO₄. The organic layer was filtered and concentrated in vacuo to give 4.1 g of crude compound. This residue was purified by combiflash (R$_f$200, Teledyne/Isco) instrument onto a redisep® R$_f$ column with gradient elution (0 to 3%) of methanol in dichloromethane to afford the title compound (2.45 g, 87%) as a white solid. ¹H NMR (400 MHz, DMSO-d₆) δ 8.07 (s, 1H), 7.02 (s, 2H), 6.96 (d, J=3.5 Hz, 1H), 6.62 (d, J=3.5 Hz, 1H), 5.86 (dd, J=17.4, 10.7 Hz, 1H), 5.33 (dd, J=7.2, 1.3 Hz, 1H), 5.23 (dd, J=17.4, 1.3 Hz, 1H), 5.10-5.01 (m, 2H), 4.50 (dd, J=7.1, 1.6 Hz, 1H), 1.70 (ddd, J=9.3, 4.8, 1.6 Hz, 1H), 1.46 (s, 3H), 1.29-1.22 (m, 1H), 1.19 (s, 3H), 1.10 (ddd, J=9.1, 5.1, 1.5 Hz, 1H); LCMS m/z=313 (M+1, 100%).

3-Chloro-7-(2-((3aS,4R,6aR)-4-(6-chloro-9H-purin-9-yl)-2,2-dimethyl-3a,6a-dihydro-4H-cyclopenta[d][1,3]dioxol-6-yl)ethyl)-5-fluoroquinolin-2-amine

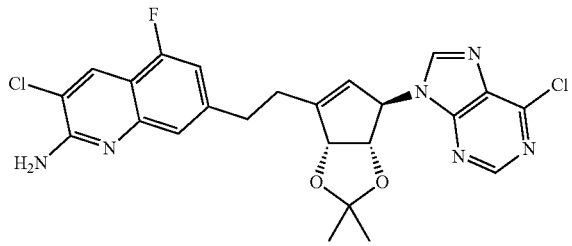 [SMILES: CC1(C)O[C@@H]2[C@H](O1)C(CCc1cc(F)c3cc(Cl)c(N)nc3c1)=C[C@H]2n1cnc2c(Cl)ncnc21]

6-Chloro-9-((3aS,4R,6aR)-2,2-dimethyl-6-vinyl-3a,6a-dihydro-4H-cyclopenta[d][1,3]dioxol-4-yl)-9H-purine (0.11 g, 0.345 mmol) in 9-BBN (0.5 molar, 3.45 ml, 1.725 mmol) was heated at 60° C. for 2 h under N2 atmosphere. The reaction mixture was cooled to 25° C., then potassium phosphate tribasic (0.366 g, 1.725 mmol) in water (0.5 ml) was added and stirred for 20 mins. A solution of 7-bromo-3-chloro-5-fluoroquinolin-2-amine (0.086 g, 0.311 mmol) in THF (1 ml) was added, followed by $PdCl_2$(dppf) (0.025 g, 0.035 mmol). The resulting mixture was stirred at 55° C. for 2 h. The reaction mixture was diluted with ethyl acetate (10 ml) and washed with water (10 ml). Layers were separated, organic layer was washed with brine (10 ml) and dried over anhydrous $Na_2SO_4$. The organic layer was filtered and concentrated in vacuo to give 0.15 g of crude compound. This residue was purified by combiflash ($R_f$200, Teledyne/Isco) instrument onto a redisep® $R_f$ column with gradient elution (0 to 2.7%) of methanol in dichloromethane to afford the title compound (0.077 g) as a colourless semisolid. LCMS m/z=514.8 (M+, 100%).

Intermediates in table-1 were synthesized by an analogous reaction protocol as was used for the preparation of 3-chloro-7-(2-((3aS,4R,6aR)-4-(6-chloro-9H-purin-9-yl)-2,2-dimethyl-3a,6a-dihydro-4H-cyclopenta[d][1,3]dioxol-6-yl)ethyl)-5-fluoroquinolin-2-amine using appropriate starting materials and at suitable temperature.

TABLE 1

| Structure & IUPAC name | Intermediates used | $^1$H NMR/LCMS data |
|---|---|---|
| tert-Butyl (1-((3aS,4R,6aR)-6-(2-(2-amino-3-chloro-5-fluoroquinolin-7-yl)ethyl)-2,2-dimethyl-3a,6a-dihydro-4H-cyclopenta[d][1,3] dioxol-4-yl)-1H-pyrazolo[3,4-d]pyrimidin-4-yl)(tert-butoxy carbonyl)carbamate | tert-Butyl (tert-butoxycarbonyl)(1-((3aS,4R,6aR)-2,2-dimethyl-6-vinyl-3a,6a-dihydro-4H-cyclopenta[d][1,3] dioxol-4-yl)-1H-pyrazolo[3,4-d]pyrimidin-4-yl)carbamate and 7-Bromo-3-chloro-5-fluoroquinolin-2-amine | $^1$H NMR (400 MHz, Chloroform-d) δ 8.75 (s, 1H), 8.36 (s, 1H), 8.14 (s, 1H), 7.51 (s, 1H), 7.09 (d, J = 10.4 Hz, 1H), 6.01 (s, 1H), 5.52 (s, 1H), 5.41 (d, J = 5.8 Hz, 1H), 4.84 (d, J = 5.8 Hz, 1H), 3.09 (t, J = 7.8 Hz, 2H), 2.70 (t, J = 7.9 Hz, 2H), 1.58 (s, 18H) 1.52 (s, 3H), 1.40 (s, 3H); LCMS m/z = 696.73 (M+, 100%). |
| 3-Chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-1,5-naphthyridin-2-amine | 4-chloro-7-((3aS,4R,6aR)-2,2-dimethyl-6-vinyl-3a6a-dihydro-4H-cyclopenta[d][1,3] dioxol-4-yl)-7H-pyrrolo[2,3-d]pyrimidine and 7-Bromo-3-chloro-1,5-naphthyridin-2-amine | $^1$H NMR (400 MHz, DMSO-d6) δ 8.64 (s, 1H), 8.55 (d, J = 2.0 Hz, 1H), 8.19 (d, J = 0.8 Hz, 1H), 7.80-7.76 (m, 1H), 7.16 (d, J = 3.7 Hz, 1H), 7.00 (s, 2H), 6.53 (d, J = 3.7 Hz, 1H), 5.68 (s, 1H), 5.57 (s, 1H), 5.37 (d, J = 5.7 Hz, 1H), 4.55 (d, J = 5.7 Hz, 1H), 3.08 (q, J = 7.7 Hz, 2H), 2.68 (q, J = 6.7 Hz, 2H), 1.37 (s, 3H), 1.29 (s, 3100%).H); LCMS m/z = 497.2 (M+, |
| tert-butyl (1-((3aS,4R,6aR)-6-(2-(2-amino-3-chloro-5-fluoroquinolin-7-yl)ethyl)-2,2-dimethyl-3a,6a-dihydro-4H-cyclopenta[d][1,3]dioxol-4-yl)-6-methyl-1H-pyrazolo[3,4-d]pyrimidin-4-yl)(tert-butoxycarbonyl)carbamate | tert-butyl (tert-butoxycarbonyl)(1-((3aS,4R,6aR)-2,2-dimethyl-6-vinyl-3a,6a-dihydro-4H-cyclopenta[d][1,3] dioxol-4-yl)-6-methyl-1H-pyrazolo[3,4-d]pyrimidin-4-yl)carbamate and 7-bromo-3-chloro-5-fluoroquinolin-2-amine | 1H NMR (400 MHz, DMSO-d6) δ 8.15 (s, 1H), 8.07 (s, 1H), 7.22 (s, 1H), 7.01 (d, J = 11.3 Hz, 2H), 6.93 (s, 2H), 5.79 (s, 1H), 5.59 (s, 1H), 5.34 (d, J = 5.7 Hz, 2H), 4.70 (d, J = 5.8 Hz, 1H), 3.00-2.93 (m, 2H), 2.64 (s, 3H), 1.50 (s, 18H), 1.39 (s, 3H), 1.30 (s, 3H); LCMS m/z = 710.40 (M+) |

TABLE 1-continued

| Structure & IUPAC name | Intermediates used | ¹H NMR/LCMS data |
|---|---|---|
| Tert-butyl 8-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-6-(difluoromethyl)-5-fluoro-3,4-dihydroisoquinoline-2(1H)-carboxylate | 4-chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine and tert-butyl 8-bromo-6-(difluoromethyl)-5-fluoro-3,4-dihydroisoquinoline-2(1H)-carboxylate | ¹H NMR (400 MHz, Chloroform-d) δ 8.70 (s, 1H), 7.35-7.31 (m, 1H), 6.99 (d, J = 3.6 Hz, 1H), 6.90 (s, 1H), 6.62-6.59 (m, 1H), 5.83 (d, J = 2.4 Hz, 1H), 5.55 (s, 1H), 5.32 (d, J = 5.7 Hz, 1H), 4.62 (d, J = 6.6 Hz, 2H), 3.68 (t, J = 5.9 Hz, 2H), 2.88 (dd, J = 17.4, 6.9 Hz, 3H), 2.70 (t, J = 8.7 Hz, 1H), 1.51 (s, 9H), 1.44 (s, 3H), 1.39 (s, 3H), 1.32 (s, 3H); LCMS m/z = 618.96 (M+, 10%). |
| 8-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-6-(difluoromethyl)-5-fluoro-4-methylisoquinoline | 4-chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine and 8-bromo-6-(difluoromethyl)-5-fluoro-4-methylisoquinoline | 1H NMR (400 MHz, DMSO-d6) δ 9.53 (d, J = 2.5 Hz, 1H), 8.67 (s, 1H), 8.56-8.49 (m, 1H), 7.75 (d, J = 6.1 Hz, 1H), 7.61-7.28 (m, 3H), 6.68 (d, J = 3.6 Hz, 1H), 5.71 (d, J = 18.2 Hz, 2H), 5.44 (d, J = 5.8 Hz, 1H), 4.59 (d, J = 5.7 Hz, 1H), 3.54 (m, 2H), 2.81-2.66 (m, 5H), 1.41 (s, 3H), 1.30 (s, 3H); LCMS m/z = 529.44 (M+, 100%). |
| 8-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-6-methylisoquinoline | 4-chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine and 8-bromo-6-methylisoquinoline | LCMS m/z = 461.2 (M+, 100%). |
| 8-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-5-fluoroisoquinoline | 4-chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine and 8-bromo-5-fluoroisoquinoline | LCMS m/z = 465.1 (M+, 100%). |

TABLE 1-continued

| Structure & IUPAC name | Intermediates used | ¹H NMR/LCMS data |
|---|---|---|
| 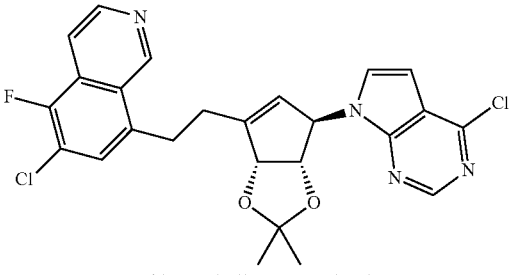 [SMILES: CC1(C)O[C@@H]2[C@H](O1)C(CCc1cc(Cl)c(F)c3ccncc13)=C[C@H]2n1ccc2c(Cl)ncnc21]<br>8-chloro-8-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-5-fluoroisoquinoline | 4-chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine and 8-bromo-6-chloro-5-fluoroisoquinoline | ¹H NMR (400 MHz, Chloroform-d) δ 9.76 (s, 1H), 8.80 (s, 1H), 8.73 (d, J = 6.0 Hz, 1H), 8.28 (d, J = 6.2 Hz, 1H), 7.74 (d, J = 6.6 Hz, 1H), 7.13 (d, J = 3.6 Hz, 1H), 6.64 (d, J = 3.6 Hz, 1H), 5.81 (s, 1H), 5.61 (s, 1H), 5.43 (d, J = 5.7 Hz, 1H), 4.72 (d, J = 5.7 Hz, 1H), 3.54 (t, J = 7.9 Hz, 2H), 2.84 (t, J = 7.7 Hz, 2H), 1.41 (s, 3H), 1.28 (d, J = 2.1 Hz, 3H); LCMS m/z = 499.31 (M+, 100%). |
| 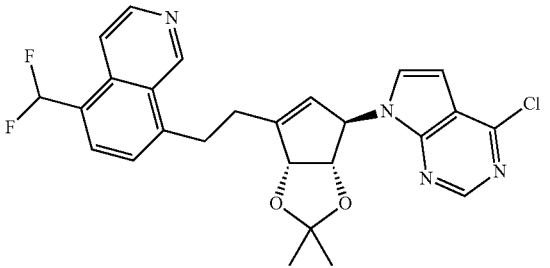 [SMILES: CC1(C)O[C@@H]2[C@H](O1)C(CCc1ccc(C(F)F)c3ccncc13)=C[C@H]2n1ccc2c(Cl)ncnc21]<br>8-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-5-(difluoromethyl)isoquinoline | 4-chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine and 8-bromo-5-(difluoromethyl)isoquinoline | LCMS m/z = 497.24 (M+, 10%). |
| 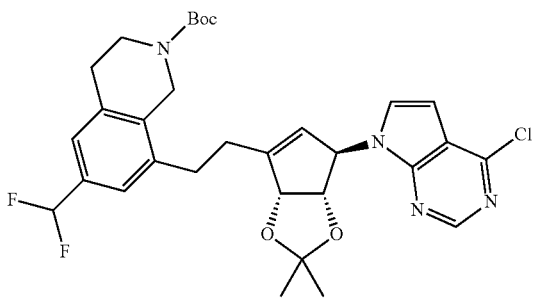 [SMILES: CC(C)(C)OC(=O)N1CCc2cc(C(F)F)cc(CCC3=C[C@@H](n4ccc5c(Cl)ncnc54)[C@@H]4OC(C)(C)O[C@H]34)c2C1]<br>tert-butyl 8-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-6-(difluoromethyl)-3,4-dihydroisoquinoline-2(1H)-carboxylate | 4-chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine and tert-butyl 8-bromo-6-(difluoromethyl)-3,4-dihydroisoquinoline-2(1H)-carboxylate | 1H NMR (400 MHz, DMSO-d6) δ 8.67 (s, 1H), 7.35 (s, 1H), 7.26 (s, 1H), 6.96 (s, 1H), 6.65 (d, J = 3.6 Hz, 1H), 5.73 (s, 1H), 5.64 (s, 1H), 5.40 (d, J = 5.7 Hz, 1H), 4.59-4.56 (m, 2H), 3.33 (s, 6H), 2.85 (t, J = 6.1 Hz, 2H), 2.58 (d, J = 9.4 Hz, 2H), 1.41 (d, J = 3.1 Hz, 12H), 1.30 (s, 3H); LCMS m/z = 601.40 (M+). |
| 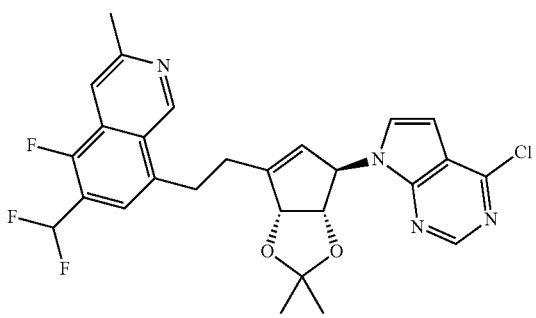 [SMILES: Cc1cc2c(F)c(C(F)F)cc(CCC3=C[C@@H](n4ccc5c(Cl)ncnc54)[C@@H]4OC(C)(C)O[C@H]34)c2cn1]<br>8-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-6-(difluoromethyl)-5-1 fluoro-3-methylisoquinoline | 1 | LCMS m/z = 529.32 (M + 1, 100%). |

TABLE 1-continued

| Structure & IUPAC name | Intermediates used | ¹H NMR/LCMS data |
|---|---|---|
| 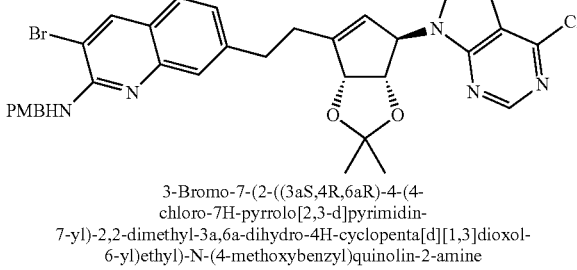<br>3-Bromo-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-N-(4-methoxybenzyl)quinolin-2-amine | 4-Chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine and 3-Bromo-7-iodo-N-(4-methoxybenzyl)quinolin-2-amine | ¹H NMR (400 MHz, DMSO-d6) δ 8.65 (s, 1H), 8.37 (s, 1H), 7.65-7.57 (m, 1H), 7.45 (d, J = 1.6 Hz, 1H), 7.36-7.30 (m, 2H), 7.26-7.14 (m, 2H), 6.99 (d, J = 3.6 Hz, 1H), 6.84-6.76 (m, 2H), 6.36 (d, J = 3.6 Hz, 1H), 5.66 (s, 1H), 5.55-5.48 (m, 1H), 5.35 (d, J = 5.7 Hz, 1H), 4.63 (d, J = 6.0 Hz, 2H), 4.49 (d, J = 5.7 Hz, 1H), 3.66 (s, 3H), 3.12-2.94 (m, 2H), 2.67 (tt, J = 14.8, 7.6 Hz, 2H), 1.39 (s, 3H), 1.29 (s, 3H); LCMS m/z = 661.5 (M+, 100%). |
| 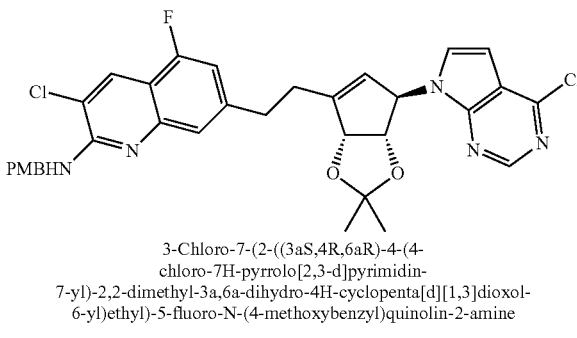<br>3-Chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-5-fluoro-N-(4-methoxybenzyl)quinolin-2-amine | 4-Chloro-7-((3aS,4R,6aR)-2,2-dimethyl-6-vinyl-3a,6a-dihydro-4H-cyclopenta [d][1,3]dioxol-4-yl)-7H-pyrrolo[2,3-d]pyrimidine and 7-Bromo-3-chloro-5-fluoro-N-(4-methoxybenzyl)quinolin-2-amine | ¹H NMR (400 MHz, DMSO-d6) δ 8.64 (t, J = 2.1 Hz, 1H), 8.18 (d, J = 2.6 Hz, 1H), 7.71 (s, 1H), 7.32 (d, J = 6.3 Hz, 3H), 7.12-6.99 (m, 2H), 6.82 (d, J = 7.6 Hz, 2H), 6.39 (s, 1H), 5.66 (s, 1H), 5.54 (s, 1H), 5.35 (d, J = 5.6 Hz, 1H), 4.63 (d, J = 6.0 Hz, 2H), 4.52 (t, J = 4.2 Hz, 1H), 3.67 (d, J = 3.1 Hz, 3H), 3.03 (s, 2H), 2.63 (d, J = 8.1 Hz, 2H), 1.38 (s, 3H), 1.28 (s, 3H); LCMS m/z = 634.47 (M+, 100%). |
| 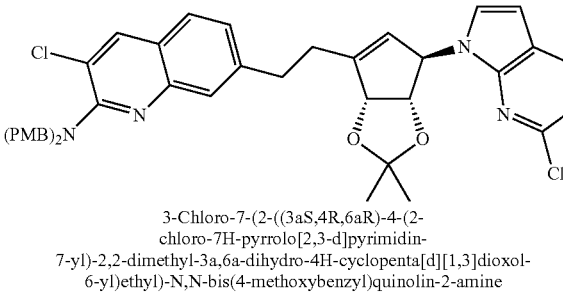<br>3-Chloro-7-(2-((3aS,4R,6aR)-4-(2-chloro-7H-pyrrolo[2,3-d]pyrimidin-7-yl)-2,2-dimethyl-3a,6a-dihydro-4H-cyclopenta[d][1,3]dioxol-6-yl)ethyl)-N,N-bis(4-methoxybenzyl)quinolin-2-amine | 2-Chloro-7-((3aS,4R,6aR)-2,2-dimethyl-6-vinyl-4,6a-dihydro-3aH-cyclopenta[d][1,3]dioxol-4-yl)-7H-pyrrolo[2,3-d]pyrimidine and 7-Bromo-3-chloro-N,N-bis(4-methoxybenzyl)quinolin-2-amine | ¹H NMR (400 MHz, DMSO-d₆) δ 8.90 (s, 1H), 8.40 (s, 1H), 7.75 (d, J = 8.3 Hz, 1H), 7.63 (s, 1H), 7.40 (dd, J = 8.3, 1.7 Hz, 1H), 7.31-7.23 (m, 4H), 6.87-6.78 (m, 4H), 6.76 (d, J = 3.6 Hz, 1H), 6.33 (d, J = 3.6 Hz, 1H), 5.58 (s, 1H), 5.51 (s, 1H), 5.34 (d, J = 5.7 Hz, 1H), 4.51 (s, 4H), 4.46 (d, J = 5.6 Hz, 1H), 3.66 (s, 6H), 3.15-3.01 (m, 2H), 2.80-2.56 (m, 2H), 1.38 (s, 3H), 1.30 (s, 3H); LCMS m/z = 737.2 (M+, 100%). |
| 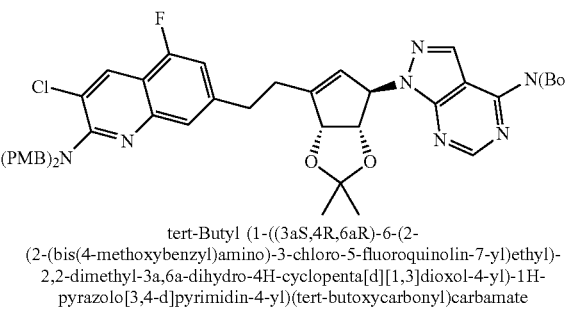<br>tert-Butyl (1-((3aS,4R,6aR)-6-(2-(2-(bis(4-methoxybenzyl)amino)-3-chloro-5-fluoroquinolin-7-yl)ethyl)-2,2-dimethyl-3a,6a-dihydro-4H-cyclopenta[d][1,3]dioxol-4-yl)-1H-pyrazolo[3,4-d]pyrimidin-4-yl)(tert-butoxycarbonyl)carbamate | tert-Butyl (tert-butoxycarbonyl)(1-((3aS,4R,6aR)-2,2-dimethyl-6-vinyl-3a,6a-dihydro-4H-cyclopenta[d][1,3]dioxol-4-yl)-1H-pyrazolo[3,4-d]pyrimidin-4-yl)carbamate and 7-Bromo-3-chloro-5-fluoro-N,N-bis(4-methoxybenzyl)quinolin-2-amine | ¹H NMR (400 MHz, DMSO-d₆) δ 8.81 (s, 1H), 8.34 (d, J = 0.8 Hz, 1H), 8.13 (s, 1H), 7.46 (s, 1H), 7.32-7.21 (m, 5H), 6.90-6.81 (m, 4H), 5.82 (s, 1H), 5.62 (s, 1H), 5.41-5.31 (m, 1H), 4.73 (d, J = 5.8 Hz, 1H), 4.54 (s, 4H), 3.70 (s, 6H), 3.02 (t, J= 7.6 Hz, 2H), 2.72-2.60 (m, 2H), 1.50 (s, 18H), 1.39 (s, 3H), 1.30 (s, 3H); LCMS m/z = 936.12 (M+, 100%). |

3-Chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-5-fluoroquinolin-2-amine

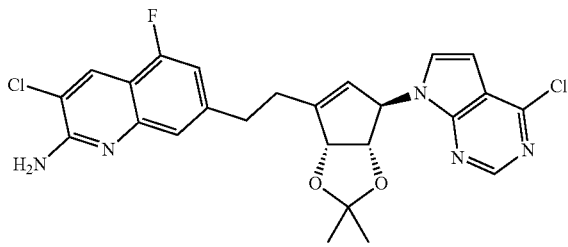 [SMILES: CC1(C)O[C@@H]2[C@H](O1)C(CCc1cc(F)c3cc(Cl)c(N)nc3c1)=C[C@H]2n1ccc2c(Cl)ncnc21]

4-Chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine (0.242 g, 0.762 mmol) in 9-BBN (0.5 molar, 4.36 ml, 2.178 mmol) was heated at 50° C. for 1 h under N2 atmosphere. The reaction mixture was cooled to 25° C., then potassium phosphate tribasic (0.578 g, 2.72 mmol) in water (0.5 ml) was added and stirred for 20 mins. A solution of 7-bromo-3-chloro-5-fluoroquinolin-2-amine (0.150 g, 0.544 mmol) in THF (0.5 ml) was added, followed by dichloro[1,1'-bis(di-t-butylphosphino)ferrocene]palladium(II) (0.035 g, 0.054 mmol). The resulting mixture was stirred at 50° C. for 6 h. The reaction mixture was diluted with water (10 ml) and extracted with ethyl acetate (10 ml). Layers were separated, organic layer was washed with brine (10 ml) and dried over anhydrous $Na_2SO_4$. The organic layer was filtered and concentrated in vacuo to give 0.345 g of crude compound. This residue was purified by combiflash ($R_f$200, Teledyne/Isco) instrument onto a redisep® $R_f$ column with gradient elution (0 to 35%) of ethyl acetate in petroleum ether to afford the title compound (0.16 g, 57.5%) as an off-white solid. $^1$H NMR (400 MHz, DMSO-d6) δ 8.64 (s, 1H), 8.18 (s, 1H), 7.25 (s, 1H), 7.09-6.96 (m, 4H), 6.44 (d, J=3.6 Hz, 1H), 5.67 (s, 1H), 5.56-5.51 (m, 1H), 5.35 (d, J=5.7 Hz, 1H), 4.52 (d, J=5.7 Hz, 1H), 3.05-2.98 (m, 2H), 2.74-2.56 (m, 2H), 1.38 (s, 3H), 1.28 (s, 3H); LCMS m/z=514.2 (M+, 100%).

Intermediates in table-2 were synthesized by an analogous reaction protocol as was used for the preparation of 3-chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-5-fluoroquinolin-2-amine using appropriate starting materials and at suitable temperature.

TABLE-2

| Structure & IUPAC name | Intermediates used | $^1$H NMR/LCMS data |
|---|---|---|
| 7-(2-((3aS,4R,6aR)-4-(4-Chloro-7H-pyrrolo[2,3-d]pyrimidin-7-yl)-2,2-dimethyl-3a,6a-dihydro-4H-cyclopenta[d][1,3]dioxol-6-yl)ethyl)quinoxalin-2-amine | 4-chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine and 7-Bromoquinoxalin-2-amine | $^1$H NMR (400 MHz, DMSO-d6) δ 8.65 (s, 1H), 8.25 (s, 1H), 7.69 (d, J = 8.3 Hz, 1H), 7.40 (d, J = 1.9 Hz, 1H), 7.29 (dd, J = 8.3, 2.0 Hz, 1H), 7.00 (d, J = 3.7 Hz, 1H), 6.93 (s, 2H), 6.42 (d, J = 3.6 Hz, 1H), 5.67 (s, 1H), 5.57-5.50 (m, 1H), 5.35 (d, J = 5.7 Hz, 1H), 4.51 (d, J = 5.7 Hz, 1H), 3.11-2.96 (m, 2H), 2.73-2.58 (m, 2H), 1.39 (s, 3H), 1.29 (s, 3H); LCMS m/z = 463.17 (M+, 10%). |
| 7-(2-((3aR,3bR,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)rthyl)quinoxalin-2-amine | 7-((3aR,3bS,4aS,5R,5aS)-2,2-Dimethyl-3b-vinylhexahydrocyclopropa[3,4]cyclopenta[1,2-d][1,3]dioxol-5-yl)-7H-pyrrolo[2,3-d]pyrimidin-4-amine and 7-Bromoquinoxalin-2-amine | $^1$H NMR (400 MHz, DMSO-d$_6$) δ 8.22 (s, 1H), 8.08 (s, 1H), 7.66 (d, J = 8.3 Hz, 1H), 7.36 (d, J = 1.8 Hz, 1H), 7.26 (dd, J = 8.4, 1.9 Hz, 1H), 7.12 (d, J = 3.5 Hz, 1H), 7.01 (s, 2H), 6.89 (s, 2H), 6.60 (d, J = 3.5 Hz, 1H), 5.22 (dd, J = 7.1, 1.3 Hz, 1H), 5.02 (s, 1H), 4.52 (dd, J = 7.4, 1.4 Hz, 1H), 2.92-2.79 (m, 2H), 2.35-2.23 (m, 1H), 1.72-1.60 (m, 1H), 1.53-1.42 (m, 4H), 1.20 (s, 3H), 0.94 (t, J = 4.7 Hz, 1H), 0.77-0.70 (m, 1H). LCMS m/z = 458.23 (M+, 10%). |
| 7-(2-((3aR,3bR,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-3-chloro-1,5-naphthyridin-2-amine | 7-((3aR,3bS,4aS,5R,5aS)-2,2-Dimethyl-3b-vinylhexahydrocyclopropa[3,4]cyclopenta[1,2-d][1,3]dioxol-5-yl)-7H-pyrrolo[2,3-d]pyrimidin-4-amine and 7-Bromo-3-chloro-1,5-naphthyridin-2-amine | LCMS m/z = 492.24 (M+, 10%). |

TABLE-2-continued

| Structure & IUPAC name | Intermediates used | ¹H NMR/LCMS data |
|---|---|---|
| Tert-butyl 6-(difluoromethyl)-8-(2-((3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxol-6-yl)ethyl)-3,4-dihydroisoquinoline-2(1H)-carboxylate | 7-((3aS,4R,6aR)-2,2-dimethyl-6-vinyl-3a,6a-dihydro-4H-cyclopenta[d][1,3]dioxol-4-yl)-4-methyl-7H-pyrrolo[2,3-d]pyrimidine and tert-butyl 8-bromo-6-(difluoromethyl)-3,4-dihydroisoquinoline-2(1H)-carboxylate | ¹H NMR (400 MHz, Chloroform-d) δ 8.88 (s, 1H), 7.27 (d, J = 1.6 Hz, 1H), 7.20 (s, 1H), 7.03 (s, 1H), 6.74 (d, J = 10.2 Hz, 1H), 6.68 (s, 1H), 6.62 (d, J = 4.0 Hz, 1H), 5.88 (s, 1H), 5.55 (s, 1H), 4.64 (s, 2H), 3.67 (s, 2H), 2.95-2.93 (m, 9H) , 2.84-2.66 (m, 1H), 1.50 (d, J = 1.6 Hz, 12H), 1.39 (s, 3H); LCMS m/z = 580.70 (M+, 20%). |
| Tert-butyl 6-(difluoromethyl)-8-(2-((3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxol-6-yl)ethyl)-5-fluoro-3,4-dihydroisoquinoline-2(1H)-carboxylate | 7-((3aS,4R,6aR)-2,2-dimethyl-6-vinyl-3a,6a-dihydro-4H-cyclopenta[d][1,3]dioxol-4-yl)-4-methyl-7H-pyrrolo[2,3-d]pyrimidine and tert-butyl 8-bromo-6-(difluoromethyl)-5-fluoro-3,4-dihydroisoquinoline-2(1H)-carboxylate | ¹H NMR (400 MHz, Chloroform-d) δ 8.97 (s, 1H), 7.33 (t, J = 7.4 Hz, 2H), 6.89 (d, J = 16.4 Hz, 1H), 5.91 (d, J = 15.7 Hz, 1H), 5.53 (d, J = 11.1 Hz, 1H), 4.63 (s, 2H), 3.68 (t, J = 5.9 Hz, 2H), 3.16 (s, 2H), 2.91-2.84 (m, 4H), 1.56-1.48 (m, 12H), 1.48-1.36 (m, 6H), 1.28 (s, 3H); LCMS m/z = 598.96 (M+, 20%). |
| 8-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-5,6-difluoroisoquinoline | 4-chloro-7-((3aS,4R,6aR)-2,2-dimethyl-6-vinyl-3a,6a-dihydro-4H-cyclopenta[d][1,3]dioxol-4-yl)-7H-pyrrolo[2,3-d]pyrimidine and 8-bromo-5,6-difluoroisoquinoline | ¹H NMR (400 MHz, DMSO-d6) δ 9.64 (s, 1H), 8.66 (s, 1H), 7.98 (d, J = 5.8 Hz, 1H), 7.74 (dd, J = 11.9, 7.6 Hz, 1H), 7.48 (d, J = 3.7 Hz, 1H), 6.68 (d, J = 3.6 Hz, 1H), 5.74-5.69 (m, 2H), 5.45 (d, J = 5.6 Hz, 1H), 4.61 (d, J = 5.7 Hz, 1H), 3.59 (dt, J = 15.0, 7.6 Hz, 1H), 3.46 (dt, J = = 15.2, 7.9 Hz, 1H), 2.71 (t, J = 7.7 Hz, 2H), 2.41-2.30 (m, 2H), 1.39 (s, 3H), 1.30 (s, 3H); LCMS m/z = 482.61 (M+, 90%). |
| 8-(2-((3aS,4R,6aR)-4-(4-chloro-5-methyl-7H-pyrrolo[2,3-d]pyrimidin-7-yl)-2,2-dimethyl-3a,6a-dihydro-4H-cyclopenta[d][1,3]dioxol-6-yl)ethyl)-6-(difluoromethyl)-5-fluoroisoquinoline | 4-chloro-7-((3aS,4R,6aR)-2,2-dimethyl-6-vinyl-3a,6a-dihydro-4H-cyclopenta[d][1,3]dioxol-4-yl)-5-methyl-7H-pyrrolo[2,3-d]pyrimidine and 8-bromo-6-(difluoromethyl)-5-fluoroisoquinoline | ¹H NMR (400 MHz, DMSO-d6) δ 9.73 (s, 1H), 8.76 (d, J = 5.7 Hz, 1H), 8.58 (s, 1H), 8.05 (d, J = 5.8 Hz, 1H), 7.75 (d, J = 6.5 Hz, 1H), 7.48 (t, J = 54.0 Hz, 1H), 7.16 (d, J = 1.3 Hz, 1H), 5.73-5.65 (m, 2H), 5.41 (d, J = 5.6 Hz, 1H), 4.53 (d, J = 5.7 Hz, 1H), 3.63-3.50 (m, 2H), 2.72 (t, J = 7.9 Hz, 2H), 2.40 (d, J = 1.1 Hz, 3H), 1.39 (d, J = 3.0 Hz, 3H), 1.29 (s, 3H); LCMS m/z = 529.32 (M+, 100%). |

3-benzoyl-1-(6-(((2-(bis(4-methoxybenzyl)amino)-3-chloroquinolin-7-yl)oxy)methyl)-2,2-dimethyl-3a,6a-dihydro-4H-cyclopenta[d][1,3]dioxol-4-yl)pyrimidine-2,4 (1H,3H)-dione

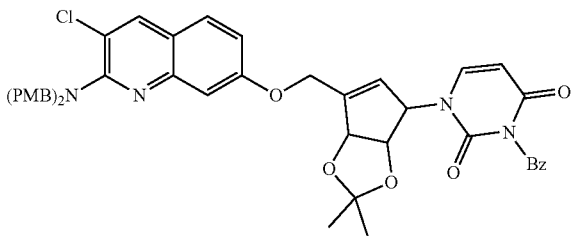

To a stirred solution of 3-benzoyl-1-((3aS,4R,6aR)-6-(hydroxymethyl)-2,2-dimethyl-3a,6a-dihydro-4H-cyclopenta[d][1,3]dioxol-4-yl)pyrimidine-2,4 (1H,3H)-dione (0.080 g, 0.208 mmol), 2-(bis(4-methoxybenzyl)amino)-3-chloro-5-fluoroquinolin-7-ol (0.151 g, 0.333 mmol) and triphenylphosphine (0.164 g, 0.624 mmol) in THF (2.5 ml) was added DIAD (0.121 ml, 0.624 mmol) dropwise at 0° C. The resulting mixture was stirred at rt for 14 h. The solvent was evaporated under reduced pressure to provide 0.21 g of a crude compound. This residue was purified by combi-flash ($R_f$200, Teledyne/Isco) instrument onto a redisep® $R_f$ column with gradient elution (0 to 1%) of methanol in dichloromethane to afford (0.14 g, 82%) of the title compound. LCMS m/z=819.05 (M+; 100%).

Intermediates in Table-4 were synthesized by an analogous reaction protocol as was used for the preparation of 3-benzoyl-1-(6-(((2-(bis(4-methoxybenzyl)amino)-3-chloroquinolin-7-yl)oxy)methyl)-2,2-dimethyl-3a,6a-dihydro-4H-cyclopenta[d][1,3]dioxol-4-yl)pyrimidine-2,4 (1H,3H)-dione using the appropriate starting materials. In some examples instead of DIAD, DEAD can also be used.

TABLE 4

| Structure & IUPAC name | Intermediates used | ¹H NMR & LCMS data |
|---|---|---|
| 3-((3aS,4R,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)-6-methylpyrimidin-4(3H)-one | 3-((3aS,4R,6aR)-6-(hydroxymethyl)-2,2-dimethyl-3a,6a-dihydro-4H-cyclopenta[d][1,3]dioxol-4-yl)-6-methylpyrimidin-4(3H)-one and 2-(bis(4-methoxybenzyl)amino)-3-chloro-5-fluoroquinolin-7-ol | ¹H NMR (400 MHz, Chloroform-d) δ 8.74 (d, J = 1.2 Hz, 1H), 8.18 (d, J = 0.7 Hz, 1H), 7.27 (d, J = 2.1 Hz, 4H), 7.00 (d, J = 2.2 Hz, 1H), 6.88-6.83 (m, 4H), 6.58 (t, J = 0.9 Hz, 1H), 6.07 (d, J = 2.3 Hz, 1H), 5.99-5.96 (m, 1H), 5.35 (d, J = 5.6 Hz, 1H), 4.94-4.75 (m, 3H), 4.60 (s, 4H), 4.16-4.12 (m, 1H), 3.81 (s, 6H), 2.46 (s, 3H), 1.51 (s, 3H), 1.42 (s, 3H). LCMS m/z = 713.11 (M+, 50%) |
| 3-((3aS,4R,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)-6-chloropyrimidin-4(3H)-one | 6-chloro-3-((3aS,4R,6aR)-6-(hydroxymethyl)-2,2-dimethyl-3a,6a-dihydro-4H-cyclopenta[d][1,3]dioxol-4-yl)pyrimidin-4(3H)-one and 2-(bis(4-methoxybenzyl)amino)-3-chloro-5-fluoroquinolin-7-ol | LCMS m/z = 733.28 (M+, 70%) |
| 3-((3aS,4R,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)-6-chloro-5-fluoropyrimidin-4(3H)-one | 6-chloro-5-fluoro-3-((3aS,4R,6aR)-6-(hydroxymethyl)-2,2-dimethyl-3a,6a-dihydro-4H-cyclopenta[d][1,3]dioxol-4-yl)pyrimidin-4(3H)-one and 2-(bis(4-methoxybenzyl)amino)-3-chloro-5-fluoroquinolin-7-ol | ¹H NMR (400 MHz, Chloroform-d) δ 8.42 (s, 1H), 8.18 (d, J = 0.7 Hz, 1H), 7.27 (d, J = 2.1 Hz, 2H), 6.99 (d, J = 2.3 Hz, 1H), 6.88-6.84 (m, 4H), 6.76 (dd, J = 11.0, 2.3 Hz, 1H), 6.06 (d, J = 18.8 Hz, 2H), 5.38 (d, J = 5.7 Hz, 1H), 4.90-4.81 (m, 3H), 4.61 (s, 4H), 3.81 (s, 6H), 1.51 (s, 3H), 1.43 (s, 3H); LCMS m/z = 751.3 (M+, 100%) |

TABLE 4-continued

| Structure & IUPAC name | Intermediates used | ¹H NMR & LCMS data |
|---|---|---|
| tert-butyl 8-(((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)methoxy)-6-(difluoromethyl)-5-fluoro-3,4-dihydroisoquinoline-2(1H)-carboxylate | ((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)methanol and tert-butyl 6-(difluoromethyl)-5-fluoro-8-hydroxy-3,4-dihydroisoquinoline-2(1H)-carboxylate | LCMS m/z = 620.84 (M+, 100%) | tert-butyl 8-(((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)methoxy)-6-(difluoromethyl)-3,4-dihydroisoquinoline-2 (1H)-carboxylate To a stirred solution of tert-butyl 6-(difluoromethyl)-8-hydroxy-3,4-dihydroisoquinoline-2 (1H)-carboxylate (250 mg, 0.834 mmol) in DMF (Volume: 5 ml) was added $Cs_2CO_3$ (306 mg, 0.938 mmol) and stirred at rt for 30 min. The reaction mixture was then cooled to 0° C. and 4-chloro-7-((3aS,4R,6aR)-6-(iodomethyl)-2,2-dimethyl-3a,6a-dihydro-4H-cyclopenta[d][1,3]dioxol-4-yl)-7H-pyrrolo[2,3-d]pyrimidine (450 mg, 1.042 mmol) in DMF (1 ml) was added and stirred for 3 h. The reaction mixture was diluted with ethyl acetate (20 ml) and washed with water (20 ml). Layers were separated, organic layer was washed with brine (20 ml) and dried over anhydrous $Na_2SO_4$. The organic layer was filtered and concentrated in vacuo to give 0.52 g of a crude compound. This residue was purified by combiflash ($R_f$200, Teledyne/Isco) instrument onto a redisep® $R_f$ column with gradient elution (0 to 20%) of ethyl acetate in petroleum ether to afford the title compound (0.4 g, 63.6%) as an off white solid. LCMS m/z=603.4 (M+).

7-(2-((3aS,4R,6aR)-4-(6-Amino-9H-purin-9-yl)-2,2-dimethyl-3a,6a-dihydro-4H-cyclopenta[d][1,3]dioxol-6-yl)ethyl)-3-chloro-5-fluoroquinolin-2-amine A mixture of 3-Chloro-7-(2-((3aS,4R,6aR)-4-(6-chloro-9H-purin-9-yl)-2,2-dimethyl-3a,6a-dihydro-4H-cyclopenta[d][1,3]dioxol-6-yl)ethyl)-5-fluoroquinolin-2-amine (0.300 g, 0.473 mmol), aq. 25% ammonia (4.09 ml, 47.3 mmol) and Dioxane (4 ml) was heated at 120° C. for 18 h in a steel bomb. The solvents was evaporated in vacuo and the residue was purified by combiflash ($R_f$200, Teledyne/Isco) instrument onto a redisep® $R_f$ column with gradient elution (0 to 5%) of methanol in dichloromethane to afford the title compound (0.24 g, 83%) as an off-white solid. LCMS m/z=496.42 (M+, 20%).

Intermediates in table-5 were synthesized by an analogous reaction protocol as was used for the preparation of 7-(2-((3aS, 4R,6aR)-4-(6-Amino-9H-purin-9-yl)-2,2-dimethyl-3a,6a-dihydro-4H-cyclopenta[d][1,3]dioxol-6-yl)ethyl)-3-chloro-5-fluoroquinolin-2-amine using appropriate starting materials. In some examples, reactions were carried out at 80° C. or 100° C.

TABLE-5

| Structure & IUPAC name | Intermediate used | ¹H NMR/LCMS data |
|---|---|---|
| 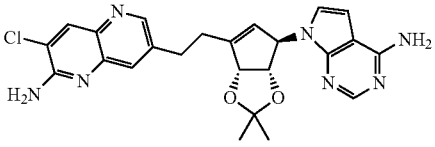 [SMILES: CC1(C)O[C@@H]2[C@H](O1)C(CCc1cnc3cc(Cl)c(N)nc3c1)=C[C@H]2n1ccc2c(N)ncnc21]<br>7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethyl)-3-chloro-1,5-naphthyridin-2-amine | 3-chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-1,5-naphthyridin-2-amine | LCMS m/z = 478.1 (M + 1; 50%). |
| 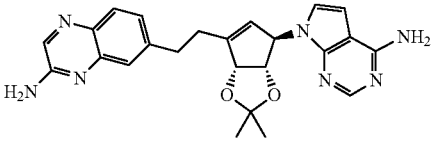 [SMILES: CC1(C)O[C@@H]2[C@H](O1)C(CCc1ccc3ncc(N)nc3c1)=C[C@H]2n1ccc2c(N)ncnc21]<br>7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethyl)quinoxalin-2-amine | 7-(2-((3aS,4R,6aR)-4-(4-Chloro-7H-pyrrolo[2,3-d]pyrimidin-7-yl)-2,2-dimethyl-3a,6a-dihydro-4H-cyclopenta[d][1,3] dioxol-6-yl)ethyl) quinoxalin-2-amine | ¹H NMR (400 MHz, DMSO-d6) δ 8.25 (s, 1H), 8.05 (s, 1H), 7.69 (d, J = 8.3 Hz, 1H), 7.40 (d, J = 1.8 Hz, 1H), 7.29 (dd, J = 8.4, 1.9 Hz, 1H), 6.97 (s, 2H), 6.91 (s, 2H), 6.37-6.31 (m, 2H), 5.52 (d, J = 15.8 Hz, 2H), 5.30 (d, J = 5.6 Hz, 1H), 4.36 (d, J = 5.6 Hz, 1H), 3.09-2.97 (m, 2H), 2.69-2.61 (m, 2H), 1.37 (s, 3H), 1.28 (s, 3H); LCMS m/z = 444.29 (M+, 30%). |
| 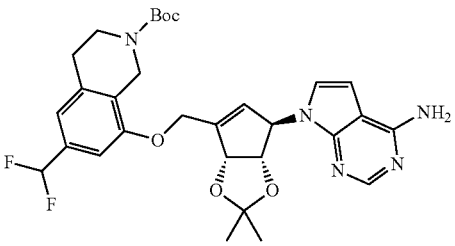 [SMILES: CC(C)(C)OC(=O)N1CCc2cc(C(F)F)cc(OCC3=C[C@@H](n4ccc5c(N)ncnc54)[C@@H]4OC(C)(C)O[C@H]34)c2C1]<br>Tert-butyl 8-(((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)methoxy)-6-(difluoromethyl)-3,4-dihydroisoquinoline-2(1H)-carboxylate | tert-butyl 8-(((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)methoxy)-6-(difluoromethyl)-3,4-dihydroisoquinoline-2(1H)-carboxylate | LCMS m/z = 583.95 (M+). |
| 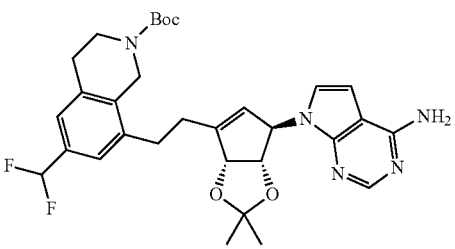 [SMILES: CC(C)(C)OC(=O)N1CCc2cc(C(F)F)cc(CCC3=C[C@@H](n4ccc5c(N)ncnc54)[C@@H]4OC(C)(C)O[C@H]34)c2C1]<br>tert-butyl 8-(2-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)ethyl)-6-(difluoromethyl)-3,4-dihydroisoquinoline-2(1H)-carboxylate | tert-butyl 8-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-6-(difluoromethyl)-3,4-dihydroisoquinoline-2(1H)-carboxylate | LCMS m/z = 582.26 (M+1). |

TABLE-5-continued

| Structure & IUPAC name | Intermediate used | ¹H NMR/LCMS data |
|---|---|---|
| 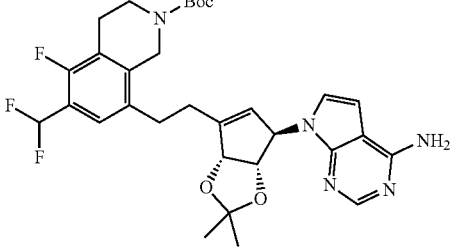<br>tert-butyl 8-(((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)methoxy)-6-(difluoromethyl)-5-fluoro-3,4-dihydroisoquinoline-2(1H)-carboxylate | tert-butyl 8-(((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)methoxy)-6-(difluoromethyl)-5-fluoro-3,4-dihydroisoquinoline-2(1H)-carboxylate | ¹H NMR (400 MHz, DMSO-d₆) δ 8.06 (s, 1H), 7.23-7.08 (m, 2H), 7.02 (d, J = 7.1 Hz, 2H), 6.80 (d, J = 3.6 Hz, 1H), 6.54 (d, J = 3.5 Hz, 1H), 5.93-5.76 (m, 1H), 5.72-5.61 (m, 1H), 5.43 (d, J = 5.7 Hz, 1H), 4.93 (s, 2H), 4.57 (d, J = 5.7 Hz, 1H), 4.49 (s, 2H), 3.62-3.54 (m, 2H), 2.74 (d, J = 5.8 Hz, 2H), 1.39 (s, 9H), 1.30, (s, 3H), 1.24 (s 3H); LCMS m/z = 602.30 (M + 1). |
| 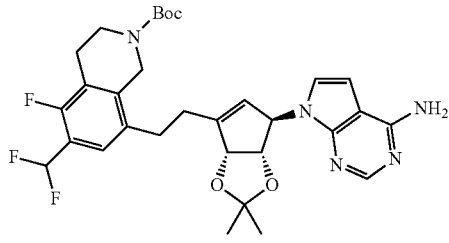 [SMILES: CC(C)(C)OC(=O)N1CCc2c(F)c(C(F)F)cc(CCC3=C[C@@H](n4ccc5c(N)ncnc54)[C@@H]4OC(C)(C)O[C@H]34)c2C1]<br>Tert-butyl 8-(2-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)ethyl)-6-(difluoromethyl)-5-fluoro-3,4-dihydroisoquinoline-2(1H)-carboxylate | tert-butyl 8-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-6-(difluoromethyl)-5-fluoro-3,4-dihydroisoquinoline-2(1H)-carboxylate (56 mg, 0.090 mmol) | LCMS m/z = 500.31 (M − 100, 2%). |
| 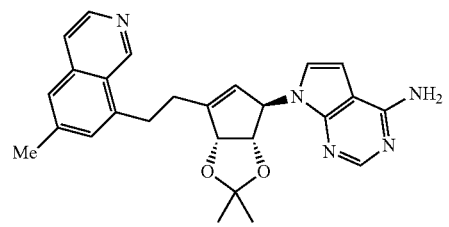 [SMILES: Cc1cc(CCC2=C[C@@H](n3ccc4c(N)ncnc43)[C@@H]3OC(C)(C)O[C@H]23)c2cnccc2c1]<br>7-((3aS,4R,6aR)-2,2-dimethyl-6-(2-(6-methylisoquinolin-8-yl)ethyl)-3a,6a-dihydro-4H-cyclopenta[d][1,3]dioxol-4-yl)-7H-pyrrolo[2,3-d]pyrimidin-4-amine | 8-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-6-methylisoquinoline | LCMS m/z = 442.3 (M+, 80%). |
| 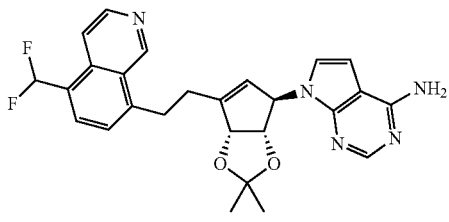 [SMILES: CC1(C)O[C@@H]2[C@H](O1)C(CCc1ccc(C(F)F)c3ccncc13)=C[C@H]2n1ccc2c(N)ncnc21]<br>7-((3aS,4R,6aR)-6-(2-(5-(difluoromethyl)isoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | 8-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-5-(difluoromethyl)isoquinoline | LCMS m/z = 478.1 (M+, 10%). |

TABLE-5-continued

| Structure & IUPAC name | Intermediate used | ¹H NMR/LCMS data |
|---|---|---|
| 7-((3aS,4R,6aR)-6-(2-(5-fluoroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | 8-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-5-fluoroisoquinoline | LCMS m/z = 446.2 (M+, 80%). |
| 7-((3aS,4R,6aR)-6-(2-(6-(difluoromethyl)-5-fluoroisoquinolin-8-yl)ethyl)-2,2-dimethyl-3a,6a-dihydro-4H-cyclopenta[d][1,3]dioxol-4-yl)-5-methyl-7H-pyrrolo[2,3-d]pyrimidin-4-amine | 8-(2-((3aS,4R,6aR)-4-(4-chloro-5-methyl-7H-pyrrolo[2,3-d]pyrimidin-7-yl)-2,2-dimethyl-3a,6a-dihydro-4H-cyclopenta[d][1,3]dioxol-6-yl)ethyl)-6-(difluoromethyl)-5-fluoroisoquinoline | LCMS: m/z = 510.44 (M + 1, 100%) |
| 7-((3aS,4R,6aR)-6-(2-(6-chloro-5-fluoroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | 6-chloro-8-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-5-fluoroisoquinoline | ¹H NMR (400 MHz, DMSO-d₆) δ 9.66 (s, 1H), 8.71 (d, J = 5.8 Hz, 1H), 8.07 (d, J = 2.5 Hz, 1H), 7.95 (d, J = 5.8 Hz, 1H), 7.76 (d, J = 7.1 Hz, 1H), 6.99 (s, 2H), 6.72 (d, J = 3.6 Hz, 1H), 6.54 (d, J = 3.6 Hz, 1H), 5.57 (d, J = 8.3 Hz, 2H), 5.42 (d, J = 5.8 Hz, 1H), 4.44 (d, J = 5.7 Hz, 1H), 3.59-3.50 (m, 2H), 2.71 (d, J = 7.5 Hz, 2H), 1.38 (d, J = 3.0 Hz, 3H), 1.29 (s, 3H); LCMS: m/z = 479.92 (M+, 100%). |
| 7-((3aS,4R,6aR)-6-(2-(5,6-difluoroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | 8-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-5,6-difluoroisoquinoline | ¹H NMR (400 MHz, DMSO-d₆) δ 9.65 (d, J = 1.5 Hz, 1H), 8.67 (d, J = 5.8 Hz, 1H), 8.07 (s, 1H), 7.98 (dd, J = 5.8, 0.9 Hz, 1H), 7.76 (dd, J = 11.8, 7.6 Hz, 1H), 6.99 (s, 2H), 6.73 (d, J = 3.5 Hz, 1H), 6.53 (d, J = 3.6 Hz, 1H), 5.59 (s, 2H), 5.41 (d, J = 5.5 Hz, 1H), 4.45 (d, J = 5.7 Hz, 1H), 3.70-3.51 (m, 2H), 3.49-3.36 (m, 2H), 1.38 (s, 3H), 1.29 (s, 3H); LCMS: m/z = 464.36 (M + 1, 20%) |

TABLE-5-continued

| Structure & IUPAC name | Intermediate used | $^1$H NMR/LCMS data |
|---|---|---|
| 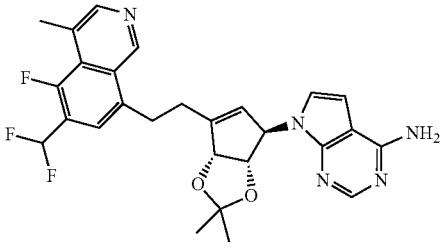 [SMILES: Cc1cncc2c(CCC3=C[C@@H](n4ccc5c(N)ncnc54)[C@@H]4OC(C)(C)O[C@H]34)cc(C(F)F)c(F)c12]<br>7-((3aS,4R,6aR)-6-(2-(6-(difluoromethyl)-5-fluoro-4-methylisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | 8-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-6-(difluoromethyl)-5-fluoro-4-methylisoquinoline | LCMS: m/z = 510.30 (M+, 100%). |
| 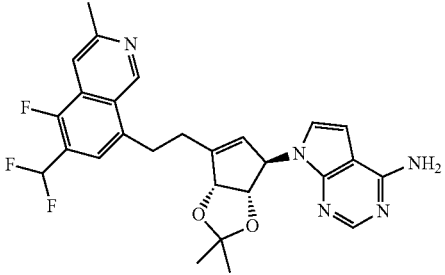 [SMILES: Cc1cc2c(F)c(C(F)F)cc(CCC3=C[C@@H](n4ccc5c(N)ncnc54)[C@@H]4OC(C)(C)O[C@H]34)c2cn1]<br>7-((3aS,4R,6aR)-6-(2-(6-(difluoromethyl)-5-fluoro-3-methylisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | 8-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-6-(difluoromethyl)-5-fluoro-3-methylisoquinoline | LCMS: m/z = 510.31 (M + 1, 20%) |
| 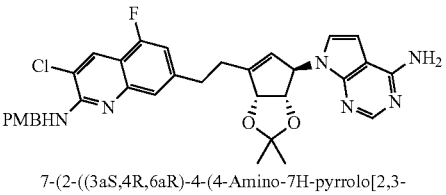<br>7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethyl)-3-chloro-5-fluoro-N-(4-methoxybenzyl) quinolin-2-amine | 3-chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-5-fluoro-N-(4-methoxy benzyl)quinolin-2-amine | $^1$H NMR (400 MHz, DMSO-$d_6$) δ 8.18 (s, 1H), 8.05 (s, 1H), 7.69 (t, J = 6.1 Hz, 1H), 7.34 (d, J = 2.1 Hz, 1H), 7.31 (d, J = 1.9 Hz, 2H), 7.05 (dd, J = 11.0, 1.4 Hz, 1H), 6.99 (s, 2H), 6.87-6.81 (m, 2H), 6.49 (d, J = 3.6 Hz, 1H), 6.38 (d, J = 3.5 Hz, 1H), 5.55 (s, 1H), 5.51 (s, 1H), 5.30 (d, J = 5.7 Hz, 1H), 4.64 (dd, J = 6.1, 3.4 Hz, 2H), 4.38 (d, J = 5.7 Hz, 1H), 3.69 (s, 3H), 3.00 (hept, J = 7.4 Hz, 2H), 2.62 (dt, J = 16.2, 7.7 Hz, 2H), 1.37 (s, 3H), 1.27 (s, 3H); LCMS m/z = 615.3 (M+; 100%). |
| 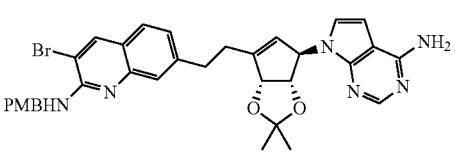<br>7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethyl)-3-bromo-N-(4-methoxybenzyl)quinolin-2-amine | 3-Bromo-7-(2-(3aS,4R,6aR)-4-(4-chloro-7H-pyrrolo[2,3-d]pyrimidin-7-yl)-2,2-dimethyl-3a,6a-dihydro-4H-cyclopenta[d][1,3] dioxol-6-yl)ethyl)-N-(4-quinolin-2-aminemethoxybenzyl) | $^1$H NMR (400 MHz, DMSO-$d_6$) δ 8.35 (s, 1H), 8.07 (d, J = 1.3 Hz, 1H), 7.64-7.58 (m, 1H), 7.45 (s, 1H), 7.39-7.29 (m, 2H), 7.18 (dd, J = 7.3, 2.7 Hz, 2H), 7.01 (s, 2H), 6.89-6.81 (m, 2H), 6.52 (d, J = 3.5 Hz, 1H), 6.40 (d, J = 3.6 Hz, 1H), 5.54 (d, J = 17.8 Hz, 2H), 5.30 (d, J = 5.7 Hz, 1H), 4.63 (dd, J = 6.2, 3.4 Hz, 2H), 4.38 (d, J = 5.7 Hz, 1H), 3.71 (s, 3H), 3.01 (q, J = 7.9 Hz, 2H), 2.63 (dd, J = 16.7, 8.1 Hz, 2H), 1.38 (s, 3H), 1.27 (s, 3H); LCMS m/z = 642.72 (M+, 20%). |

TABLE-5-continued

| Structure & IUPAC name | Intermediate used | ¹H NMR/LCMS data |
|---|---|---|
| 7-(2-((3aS,4R,6aR)-4-(2-Amino-7H-pyrrolo[2,3-d]pyrimidin-7-yl)-2,2-dimethyl-3a,6a-dihydro-4H-cyclopenta[d][1,3]dioxol-6-yl)ethyl)-3-chloro-N,N-bis(4-methoxybenzyl)quinolin-2-amine | 3-Chloro-7-(2-((3aS,4R,6aR)-4-(2-chloro-7H-pyrrolo[2,3-d]pyrimidin-7-yl)-2,2-dimethyl-3a,6a-dihydro-4H-cyclopenta[d][1,3]dioxol-6-yl)ethyl)-N,N-bis(4-methoxybenzyl)quinolin-2-amine | ¹H NMR (400 MHz, DMSO-d₆) δ 8.42 (d, J = 1.9 Hz, 1H), 8.40 (s, 1H), 7.75 (d, J = 8.3 Hz, 1H), 7.61 (s, 1H), 7.39 (dd, J = 8.3, 1.7 Hz, 1H), 7.30-7.22 (m, 4H), 6.86-6.78 (m, 4H), 6.26 (s, 2H), 6.23 (d, J = 3.7 Hz, 1H), 5.99 (d, J = 3.7 Hz, 1H), 5.46 (d, J = 8.5 Hz, 2H), 5.33 (d, J = 5.6 Hz, 1H), 4.51 (s, 4H), 4.37 (d, J = 5.6 Hz, 1H), 3.68 (s, 6H), 3.11-2.97 (m, 2H), 2.71-2.56 (m, 2H), 1.36 (s, 3H), 1.28 (s, 3H); LCMS m/z = 717.84 (M+, 50%). |
| 7-(2-((3aS,4R,6aR)-4-(4-Amino-1H-pyrazolo[3,4-d]pyrimidin-1-yl)-2,2-dimethyl-3a,6a-dihydro-4H-cyclopenta[d][1,3]dioxol-6-yl)ethyl)-3-chloro-5-fluoro-N,N-bis(4-methoxybenzyl)quinolin-2-amine | | LCMS m/z = 736.34 (M+, 50%). |
| 6-amino-3-((3aS,4R,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)pyrimidin-4(3H)-one | 3-((3aS,4R,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)-6-chloropyrimidin-4(3H)-one | ¹H NMR (400 MHz, DMSO-d₆) δ 8.29 (s, 1H), 8.12 (d, J = 0.9 Hz, 1H), 7.28-7.23 (m, 4H), 7.07-7.02 (m, 2H), 6.89-6.85 (m, 4H), 6.70 (s, 2H), 5.93 (s, 1H), 5.71 (d, J = 2.1 Hz, 1H), 5.68 (d, J = 0.9 Hz, 1H), 5.30 (d, J = 5.8 Hz, 1H), 4.90-4.79 (m, 2H), 4.65 (d, J = 5.8 Hz, 1H), 4.55 (s, 4H), 3.71 (s, 6H), 1.38 (s, 3H), 1.31 (s, 3H). |
| 6-amino-3-((3aS,4R,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)-5-fluoropyrimidin-4(3H)-one | 3-((3aS,4R,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)-6-chloro-5-fluoropyrimidin-4(3H)-one | LCMS: m/z = 732.11 (M+) |

1-((3aS,4R,6aR)-6-(((2-(Bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)pyrimidine-2,4 (1H,3H)-dione

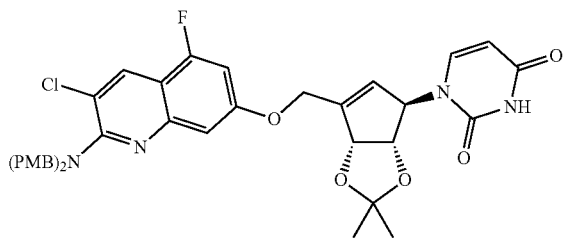

3-Benzoyl-1-((3aS,4R,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)pyrimidine-2,4 (1H,3H)-dione (1 g, 1.221 mmol) was dissolved in 7N methanolic ammonia (52.3 ml, 366 mmol). The resulting mixture was stirred at 25° C. for 3 h. The solvent was evaporated under vacuum to give 0.85 g of a crude compound. This residue was purified by combiflash (R$_f$200, Teledyne/Isco) instrument onto a redisep® R$_f$ column with gradient elution (0-12%) of methanol in DCM to afford the title compound (0.5 g, 57.3%) as an off-white solid. $^1$H NMR (400 MHz, DMSO-d6) δ 11.34 (d, J=2.3 Hz, 1H), 8.29 (s, 1H), 7.65 (d, J=1.3 Hz, 2H), 7.28-7.23 (m, 4H), 7.07-7.05 (m, 1H), 6.89-6.83 (m, 4H), 5.71 (s, 1H), 5.45 (dd, J=8.0, 2.3 Hz, 1H), 5.34-5.25 (m, 2H), 4.99-4.83 (m, 2H), 4.65 (d, J=5.8 Hz, 1H), 4.55 (s, 4H), 3.71 (s, 6H), 1.38 (s, 3H), 1.30 (s, 3H). LCMS m/z=715.21 (M+; 100%).

4-Amino-1-((3aS,4R,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)pyrimidin-2 (1H)-one

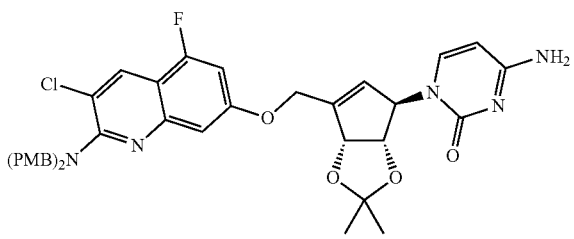

A mixture of 1-((3aS,4R,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)pyrimidine-2,4 (1H,3H)-dione (0.500 g, 0.699 mmol), DMAP (0.171 g, 1.398 mmol), triethylamine (0.195 ml, 1.398 mmol) and 2,4,6-triisopropylbenzenesulfonyl chloride (0.423 g, 1.398 mmol) in dry acetonitrile (50 ml) was stirred at 25° C. for 20 h and then at 80° C. for 2 h. After addition of 30% aq.ammonia (12.10 ml, 559 mmol), the mixture was further stirred for 5 h. Dichloromethane (200 mL) and water (100 mL) were added and the precipitated solid was filtered out and dried under vacuum to get title compound (0.25 g, 50.1%) as a pale yellow solid. $^1$H NMR (400 MHz, DMSO-d6) δ 8.29 (s, 1H), 7.38-7.18 (m, 5H), 7.19-6.97 (m, 4H), 6.86 (d, J=8.5 Hz, 4H), 5.68 (s, 1H), 5.60 (d, J=7.3 Hz, 1H), 5.31 (d, J=4.4 Hz, 2H), 5.01-4.81 (m, 2H), 4.55 (s, 5H), 3.71 (s, 6H), 1.38 (s, 3H), 1.29 (s, 3H). LCMS m/z=714.2 (M+; 100%).

7-((3aS,4R,6aR)-6-(2-(6-(difluoromethyl)-5-fluoro-1,2,3,4-tetrahydroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine

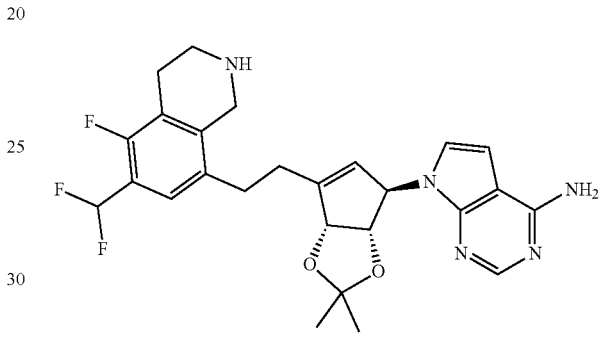

To a stirred solution of 7-((3aS,4R,6aR)-6-(2-(6-(difluoromethyl)-5-fluoroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine (1.33 g, 2.68 mmol) in acetic acid (28 ml) was added NaBH$_4$ (0.355 g, 9.39 mmol) in portions at rt and stirred for 1.5 h. The solvent was evaporated in vacuo at 40° C. This residue was diluted with DCM (30 ml) and basified with cold solution of sat. aq. NaHCO$_3$ (50 ml). Layers were separated. Organic layer washed with brine, dried over sodium sulfate and concentrated to give 1.23 g of crude compound, which was carried to next step without further purification. $^1$H NMR (400 MHz, DMSO-d$_6$) δ 8.07 (s, 1H), 7.35-7.26 (m, 1H), 7.14 (d, J=3.7 Hz, 1H), 7.03-6.95 (m, 2H), 6.73 (d, J=3.5 Hz, 1H), 6.53 (d, J=3.5 Hz, 1H), 5.58 (d, J=11.6 Hz, 2H), 5.33 (t, J=6.3 Hz, 1H), 4.42 (d, J=5.7 Hz, 1H), 3.89 (s, 2H), 2.93 (t, J=5.9 Hz, 2H), 2.89-2.74 (m, 3H), 2.65 (d, J=5.4 Hz, 2H), 1.39 (s, 3H), 1.29 (s, 4H); LCMS: m/z=499.54 (M+).

Intermediates in table-6 were synthesized by an analogous reaction protocol as was used for the preparation of 7-((3aS,4R,6aR)-6-(2-(6-(difluoromethyl)-5-fluoro-1,2,3,4-tetrahydroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine using appropriate starting materials.

TABLE 6

| Structure & IUPAC name | Intermediate used | ¹H NMR/LCMS data |
|---|---|---|
| 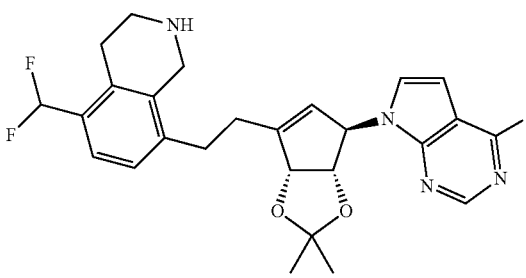<br>7-((3aS,4R,6aR)-6-(2-(5-(difluoromethyl)-1,2,3,4-tetrahydroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | 7-((3aS,4R,6aR)-6-(2-(5-(difluoromethyl)isoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | ¹H NMR (400 MHz, DMSO-d₆) δ 8.07 (s, 1H), 7.33 (d, J = 7.9 Hz, 1H), 7.24-7.10 (m, 2H), 6.99 (s, 2H), 6.72 (d, J = 3.6 Hz, 1H), 6.52 (d, J = 3.5 Hz, 1H), 5.58 (d, J = 6.9 Hz, 2H), 5.33 (d, J = 5.7 Hz, 1H), 4.43 (d, J = 5.7 Hz, 1H), 4.30-4.24 (m, 1H), 3.92 (s, 2H), 3.60-3.52 (m, 2H), 2.94 (t, J = 5.9 Hz, 2H), 2.86-2.77 (m, 4H), 1.39 (s, 3H), 1.29 (s, 3H); LCMS m/z = 482.24 (M+, 20%). |
| 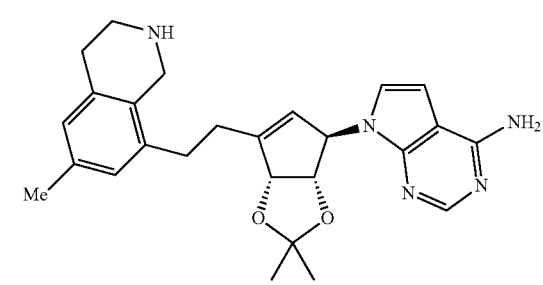<br>7-((3aS,4R,6aR)-2,2-dimethyl-6-(2-(6-methyl-1,2,3,4-tetrahydroisoquinolin-8-yl)ethyl)-3a,6a-dihydro-4H-cyclopenta[d][1,3]dioxol-4-yl)-7H-pyrrolo[2,3-d]pyrimidin-4-amine | 7-((3aS,4R,6aR)-2,2-dimethyl-6-(2-(6-methylisoquinolin-8-yl)ethyl)-3a,6a-dihydro-4H-cyclopenta[d][1,3]dioxol-4-yl)-7H-pyrrolo[2,3-d]pyrimidin-4-amine | LCMS m/z = 446.3 (M + 1, 50%) |
| 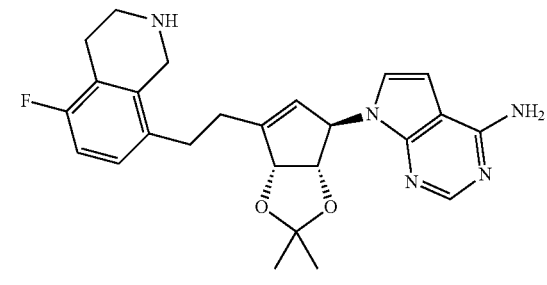<br>7-((3aS,4R,6aR)-6-(2-(5-fluoro-1,2,3,4-tetrahydroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | 7-((3aS,4R,6aR)-6-(2-(5-fluoroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | LCMS m/z = 450.2 (M+, 50%). |
| 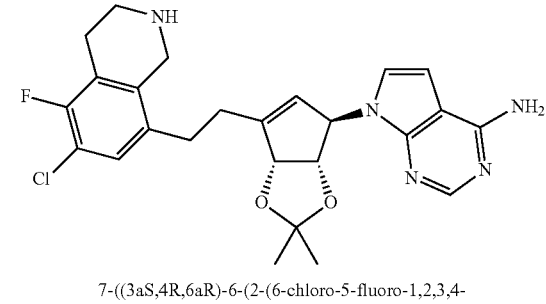<br>7-((3aS,4R,6aR)-6-(2-(6-chloro-5-fluoro-1,2,3,4-tetrahydroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | 7-((3aS,4R,6aR)-6-(2-(6-chloro-5-fluoroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | ¹H NMR (400 MHz, DMSO-d₆) δ 8.07 (s, 1H), 7.26 (d, J = 7.5 Hz, 1H), 6.99 (s, 2H), 6.71 (d, J = 3.5 Hz, 1H), 6.55-6.52 (m, 1H), 5.58 (s, 1H), 5.53 (s, 1H), 5.33 (d, J = 5.8 Hz, 1H), 4.43 (d, J = 5.6 Hz, 1H), 3.85 (s, 1H), 2.92 (d, J = 6.0 Hz, 2H), 2.84-2.70 (m, 2H), 2.66 (d, J = 6.5 Hz, 2H), 2.59-2.54 (m, 2H), 2.48-2.41 (m, 2H), 1.39 (s, 3H), 1.29 (s, 3H); LCMS m/z = 484.04 (M+, 100%). |

TABLE 6-continued

| Structure & IUPAC name | Intermediate used | ¹H NMR/LCMS data |
|---|---|---|
| 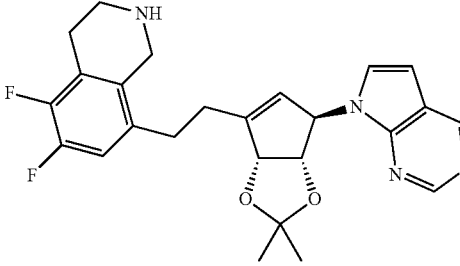<br>7-((3aS,4R,6aR)-6-(2-(5,6-difluoro-1,2,3,4-tetrahydroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | 7-((3aS,4R,6aR)-6-(2-(5,6-difluoroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | ¹H NMR (400 MHz, DMSO-d₆) δ 8.07 (s, 1H), 7.14 (dd, J = 11.8, 8.2 Hz, 1H), 6.99 (s, 2H), 6.71 (d, J = 3.7 Hz, 1H), 6.53 (d, J = 3.5 Hz, 1H), 5.58 (s, 1H), 5.54 (s, 1H), 5.33 (d, J = 5.9 Hz, 1H), 4.44 (d, J = 5.6 Hz, 1H), 3.82 (s, 2H), 2.91 (t, J = 6.0 Hz, 2H), 2.82-2.72 (m, 2H), 2.66 (t, J = 6.2 Hz, 2H), 2.58-2.53 (m, 2H), 1.39 (s, 3H), 1.29 (s, 3H).<br>LCMS: m/z = 468.36 (M + 1) |
| 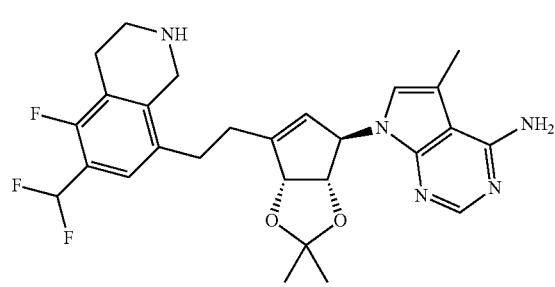<br>7-((3aS,4R,6aR)-6-(2-(6-(difluoromethyl)-5-fluoro-1,2,3,4-tetrahydroisoquinolin-8-yl)ethyl)-2,2-dimethyl-3a,6a-dihydro-4H-cyclopenta[d][1,3]dioxol-4-yl)-5-methyl-7H-pyrrolo[2,3-d]pyrimidin-4-amine | 7-((3aS,4R,6aR)-6-(2-(6-(difluoromethyl)-5-fluoroisoquinolin-8-yl)ethyl)-2,2-dimethyl-3a,6a-dihydro-4H-cyclopenta[d][1,3]dioxol-4-yl)-5-methyl-7H-pyrrolo[2,3-d]pyrimidin-4-amine | ¹H NMR (400 MHz, DMSO-d₆) δ 8.03 (s, 1H), 7.30 (d, J = 7.0 Hz, 1H), 7.14 (t, J = 54 Hz, 1H), 6.55 (s, 2H), 6.46 (d, J = 1.4 Hz, 1H), 5.56 (s, 1H), 5.54 (s, 1H), 5.30 (d, J = 5.7 Hz, 1H), 4.39 (d, J = 5.8 Hz, 1H), 3.90 (s, 2H), 2.93 (t, J = 6.0 Hz, 2H), 2.82 (q, J = 7.9 Hz, 2H), 2.71-2.63 (m, 3H), 2.34-2.31 (m, 2H), 2.30 (d, J = 1.2 Hz, 3H), 1.38 (s, 3H), 1.28 (s, 3H).<br>LCMS: m/z = 513.55 (M+, 25%) |
| 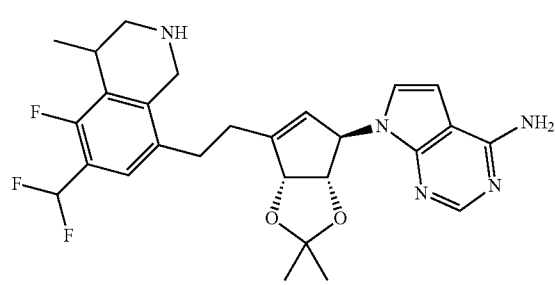<br>7-((3aS,4R,6aR)-6-(2-(6-(Difluoromethyl)-5-fluoro-4-methyl-1,2,3,4-tetrahydroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | 7-((3aS,4R,6aR)-6-(2-(6-(difluoromethyl)-5-fluoro-4-methylisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | Isomeric mixture was separated by chiral preparative HPLC. Chiral pak IG, 30 × 250 mm, 5μ column; Flow: 40 ml/min, Pump A: 0.1% Diethylamine in hexane, Pump B: IPA: DCM (1:1); A: B = 60:40 @ 225 nm.<br>Isomer-1: (Peak-1, Rt = 9 min)<br>LCMS: m/z = 513.07 (M+, 100%)<br>Isomer-2: (Peak-2, Rt = 10.3 min)<br>LCMS: m/z = 513.07 (M+, 100%) |
| 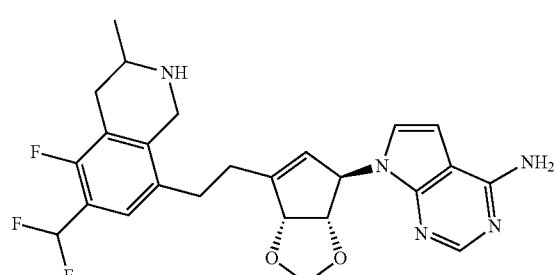<br>7-((3aS,4R,6aR)-6-(2-(6-(Difluoromethyl)-5-fluoro-3-methyl-1,2,3,4-tetrahydroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | 7-((3aS,4R,6aR)-6-(2-(6-(difluoromethyl)-7-fluoro-3-methylisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | Isomeric mixture was separated by chiral preparative HPLC. Chiral pak ID, 30 × 250 mm, 5μ column; Flow: 40 ml/min, Pump A: 0.1% diethylamine in acetonitrile, Pump B: 0.1% diethylamine in methanol; A:B = 95:5 @ 225 nm<br>Isomer-1: (Peak-1 Rt = 4.7 min)<br>LCMS m/z = 514.36 (M + 1; 20%)<br>Isomer-2: (Peak-2, Rt = 5.3 min)<br>LCMS: m/z = 514.36 (M + 1; 20%) |

7-(2-((3aS,4R,6aR)-4-(7H-Imidazo[1,2-c]pyrrolo[3,2-e]pyrimidin-7-yl)-2,2-dimethyl-3a,6a-dihydro-4H-cyclopenta[d][1,3]dioxol-6-yl)ethyl)-3-bromo-N-(4-methoxybenzyl) quinolin-2-amine

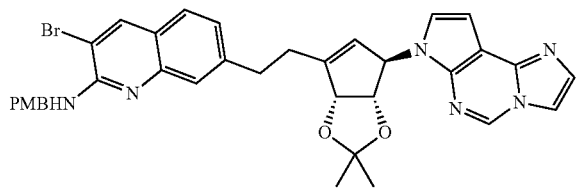

A mixture of 7-(2-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)ethyl)-3-bromo-N-(4-methoxybenzyl)quinolin-2-amine (0.050 g, 0.078 mmol), 2-chloroacetaldehyde (0.033 ml, 0.234 mmol), EtOH (0.5 ml, Ratio: 1.000) and Water (0.500 ml, Ratio: 1.000)) was heated at 60° C. for 6 h. Water and aq. NaHCO₃ was added to the reaction mixture and extracted with EtOAc (50 ml×2). The combined organic extract was dried over Na₂SO₄, filtered and concentrated under reduced pressure to get 0.065 g of crude compound. The obtained residue was purified by combiflash (R$_f$200, Teledyne/Isco) instrument onto a redisep® R$_f$ column with gradient elution (0 to 3%) of methanol in dicholomethane to afford the title compound (0.038 g, 73.3%) as an off-white solid. $^1$H NMR (400 MHz, DMSO-d$_6$) δ 9.10 (s, 1H), 8.37 (s, 1H), 7.95 (d, J=1.6 Hz, 1H), 7.61 (d, J=8.2 Hz, 1H), 7.46 (dd, J=5.5, 1.5 Hz, 2H), 7.35-7.31 (m, 2H), 7.23-7.17 (m, 2H), 6.86-6.77 (m, 2H), 6.60 (d, J=3.4 Hz, 1H), 6.45 (d, J=3.3 Hz, 1H), 5.67 (s, 1H), 5.54 (s, 1H), 5.34 (d, J=5.6 Hz, 1H), 4.64 (d, J=6.0 Hz, 2H), 4.43 (d, J=5.6 Hz, 1H), 3.66 (s, 3H), 3.03 (tq, J=14.3, 7.4 Hz, 2H), 2.77-2.59 (m, 2H), 1.40 (s, 3H), 1.29 (s, 3H); LCMS m/z=665.3 (M+; 60%).

Intermediates in table-7 were synthesized by an analogous reaction protocol as was used for the preparation of 7-(2-((3aS,4R,6aR)-4-(7H-imidazo[1,2-c]pyrrolo[3,2-e]pyrimidin-7-yl)-2,2-dimethyl-3a,6a-dihydro-4H-cyclopenta[d][1,3]dioxol-6-yl)ethyl)-3-bromo-N-(4-methoxybenzyl) quinolin-2-amine using the appropriate starting materials.

TABLE 7

| Structure & IUPAC name | Intermediate used | $^1$H NMR/LCMS data |
|---|---|---|
| 7-(2-((3aS,4R,6aR)-4-(7H-Imidazo[1,2-c]pyrrolo[3,2-e]pyrimidin-7-yl)-2,2-dimethyl-3a,6a-dihydro-4H-cyclopenta[d][1,3]dioxol-6-yl)ethyl)-3-chloro-5-fluoro-N-(4-methoxybenzyl)quinolin-2-amine | 7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethyl)-3-chloro-5-fluoro-N-(4-methoxybenzyl)quinolin-2-amine | $^1$H NMR (400 MHz, DMSO-d$_6$) δ 9.10 (s, 1H), 8.20 (s, 1H), 7.96 (d, J = 1.5 Hz, 1H), 7.70 (t, J = 6.1 Hz, 1H), 7.45 (d, J = 1.5 Hz, 1H), 7.36-7.30 (m, 3H), 7.06 (dd, J = 11.0, 1.4 Hz, 1H), 6.86-6.76 (m, 2H), 6.64 (d, J = 3.4 Hz, 1H), 6.45 (d, J = 3.3 Hz, 1H), 5.67 (s, 1H), 5.55 (s, 1H), 5.35 (d, J = 5.6 Hz, 1H), 4.64 (d, J = 6.6 Hz, 2H), 4.45 (d, J = 5.7 Hz, 1H), 3.66 (s, 3H), 3.09-2.95 (m, 2H), 2.75-2.60 (m, 2H), 1.39 (s, 3H), 1.29 (s, 3H); LCMS m/z = 639.84 (M+; 100%). |
| a) 7-(2-((3aS,4R,6aR)-4-(8H-Imidazo[1,2-a]pyrrolo[2,3-d]pyrimidin-8-yl)-2,2-dimethyl-3a,6a-dihydro-4H-cyclopenta[d][1,3]dioxol-6-yl)ethyl)-3-chloro-N,N-bis(4-methoxybenzyl)quinolin-2-amine<br><br>b) 7-(2-((3aS,4R,6aR)-4-(1H-Imidazo[1,2-a]pyrrolo[3,2-e]pyrimidin-1-yl)-2,2-dimethyl-3a,6a-dihydro-4H-cyclopenta[d][1,3]dioxol-6-yl)ethyl)-3-chloro-N,N-bis(4-methoxybenzyl)quinolin-2-amine | 7-(2-((3aS,4R,6aR)-4-(2-Amino-7H-pyrrolo[2,3-d]pyrimidin-7-yl)-2,2-dimethyl-3a,6a-dihydro-4H-cyclopenta[d][1,3]dioxol-6-yl)ethyl)-3-chloro-N,N-bis(4-methoxybenzyl)quinolin-2-amine | a) LCMS m/z = 741.59 (M+; 50%)<br>b) LCMS m/z = 741.78 (M+, 100%) |

TABLE 7-continued

| Structure & IUPAC name | Intermediate used | ¹H NMR/LCMS data |
|---|---|---|
| 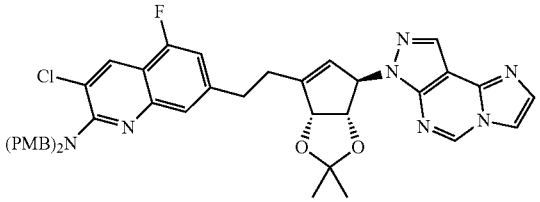<br>7-(2-((3aS,4R,6aR)-4-(7H-Imidazo[1,2-c]pyrazolo[4,3-e]pyrimidin-7-yl)-2,2-dimethyl-3a,6a-dihydro-4H-cyclopenta[d][1,3]dioxol-6-yl)ethyl)-3-chloro-5-fluoro-N,N-bis(4-methoxybenzyl)quinolin-2-amine | 7-(2-((3aS,4R,6aR)-4-(4-Amino-1H-pyrazolo[3,4-d]pyrimidin-1-yl)-2,2-dimethyl-3a,6a-dihydro-4H-cyclopenta[d][1,3]dioxol-6-yl)ethyl)-3-chloro-5-fluoro-N,N-bis(4-methoxybenzyl)quinolin-2-amine | LCMS m/z = 760.2 (M+, 100%) |

EXAMPLES

Example-1: (1S,2R,5R)-3-(2-(2-Amino-3-chloro-5-fluoroquinolin-7-yl)ethyl)-5-(6-amino-9H-purin-9-yl)cyclopent-3-ene-1,2-diol (Compound 1)

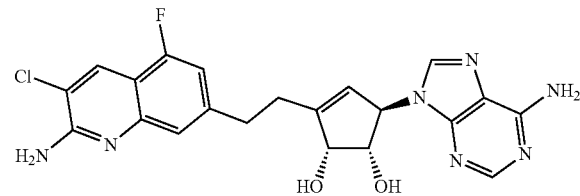 [SMILES: Nc1nc2cc(CCC3=C[C@@H](n4cnc5c(N)ncnc54)[C@H](O)[C@@H]3O)cc(F)c2cc1Cl]

The mixture of 7-(2-((3aS,4R,6aR)-4-(6-amino-9H-purin-9-yl)-2,2-dimethyl-3a,6a-dihydro-4H-cyclopenta[d][1,3]dioxol-6-yl)ethyl)-3-chloro-5-fluoroquinolin-2-amine (0.05 g, 0.101 mmol) in TFA (1.5 ml) was stirred at 0° C. for 2 h under N2 atmosphere. The reaction mixture was basified with ice cold solution of aq. sat.NaHCO₃ (20 ml) and extracted with ethyl acetate (20 ml). Layers were separated, organic layer was washed with brine (20 ml) and dried over anhydrous Na₂SO₄. The organic layer was filtered and concentrated in vacuo to give 0.12 g of crude compound. This residue was purified by combiflash (R$_f$200, Teledyne/Isco) instrument onto a redisep® R$_f$ column with gradient elution (0 to 15%) of methanol in dichloromethane to afford the title compound (19 mg, 41.3%) as a yellow solid. ¹H NMR (400 MHz, DMSO-d6) δ 8.17 (d, J=7.8 Hz, 2H), 7.91 (s, 1H), 7.47 (s, 2H), 7.23 (s, 1H), 7.09-6.92 (m, 3H), 5.62-5.58 (m, 3H), 5.36-5.31 (m, 1H), 4.47 (d, J=5.6 Hz, 1H), 4.24 (t, J=5.3 Hz, 1H), 3.04-2.85 (m, 2H), 2.64-2.53 (m, 2H); LCMS m/z=456.23 (M+, 50%).

Examples in table-8 were synthesized by following an analogous reaction protocol as was used for the preparation of (1S,2R,5R)-3-(2-(2-amino-3-chloro-5-fluoroquinolin-7-yl)ethyl)-5-(6-amino-9H-purin-9-yl)cyclopent-3-ene-1,2-diol using the appropriate starting materials. (Instead of TFA; TFA/50° C., HCl/MeOH, aq.TFA or FeCl₃.DCM could also be used at appropriate temperature). Some of the below mentioned compounds were directly purified by reverse phase preparative HPLC after basifying the reaction mixture with 7N methanolic ammonia. Out of the compounds purified by reverse phase preparative HPLC, only example 21 was purified in acidic condition whereas other compounds were purified in basic condition. The details of conditions for reverse phase preparative HPLC are as follows:

Acidic condition: YMC ODS-A, 50×250 mm, 10p; Flow: 117 ml/min, Gradient: Linear gradient from aqueous to organic; Aqueous: 0.1% formic acid in water CH₃CN (95:5), Organic: 0.1% formic acid in water:CH3CN (5:95) @ 220 nm, Basic condition: YMC Triart, 50×250 mm, 10p; Flow: 117 ml/min, Gradient: Linear gradient from aqueous to organic; Aqueous: 0.1% ammonia in water:CH3CN (95:5), Organic: 0.1% ammonia in water:CH3CN (5:95) @ 220 nm.

TABLE 8

| Structure & IUPAC name | Intermediate used | ¹H NMR/LCMS data |
|---|---|---|
| Example 2:<br><br>(1S,2R,5R)-3-(2-(6-Amino-7-chloro-1,5-naphthyridin-3-yl)ethyl)-5-(4-amino-7H-pyrrolo[2,3-d]pyrimidin-7-yl)cyclopent-3-ene-1,2-diol (Compound 2) | 7-(2-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)ethyl)-3-chloro-1,5-naphthyridin-2-amine | ¹H NMR (400 MHz, DMSO-d6) δ 8.52 (d, J = 2.1 Hz, 1H), 8.18 (s, 1H), 8.12 (s, 1H), 7.75 (d, J = 2.0 Hz, 1H), 7.40 (s, 1H), 7.27 (s, 1H), 7.14 (s, 1H), 6.99 (s, 2H), 6.76 (d, J = 3.6 Hz, 1H), 6.57 (d, J = 3.6 Hz, 1H), 5.55-5.50 (m, 1H), 5.48-5.42 (m, 1H), 5.04 (d, J = 5.6 Hz, 2H), 4.46 (t, J = 5.5 Hz, 1H), 4.00 (s, 1H), 3.11-2.92 (m, 2H), 2.65-2.54 (m, 1H); LCMS m/z = 438.17 (M+; 100%). |
| Example 3:<br><br>(1S,2R,5R)-3-(2-(3-aminoquinoxalin-6-yl)ethyl)-5-(4-amino-7H-pyrrolo[2,3-d]pyrimidin-7-yl)cyclopent-3-ene-1,2-diol (Compound 3) | 7-(2-((3aS,4R,6aR)-4-(4-Amino-7H-pyrrolo[2,3-d]pyrimidin-7-yl)-2,2-dimethyl-3a,6a-dihydro-4H-cyclopenta[d][1,3]dioxol-6-yl)ethyl)quinoxalin-2-amine | ¹H NMR (400 MHz, DMSO-d6) δ 8.25 (s, 1H), 8.03 (s, 1H), 7.69 (d, J = 8.3 Hz, 1H), 7.36 (d, J = 1.8 Hz, 1H), 7.26 (dd, J = 8.4, 1.9 Hz, 1H), 6.92 (d, J = 4.1 Hz, 4H), 6.58 (d, J = 3.5 Hz, 1H), 6.40 (d, J = 3.5 Hz, 1H), 5.52-5.47 (m, 1H), 5.46-5.42 (m, 1H), 5.02-4.94 (m, 2H), 4.46 (t, J = 5.9 Hz, 1H), 4.00-3.92 (m, 1H), 3.05-2.89 (m, 2H), 2.60-2.53 (m, 2H); LCMS m/z = 404.2 (M+; 20%). |
| Example 4:<br><br>(1R,2R,3S,4R,5S)-1-(2-(3-aminoquinoxalin-6-yl)ethyl)-4-(4-Amino-7H-pyrrolo[2,3-d]pyrimidin-7-yl)bicyclo[3.1.0]hexane-2,3-diol (Compound 4) | 7-(2-((3aR,3bR,4aS,5R,5aS)-5-(4-Amino-7H-pyrrolo[2,3-d]pyrimidin-7-yl)-2,2-dimethyltetrahydro-cyclopropa[3,4]cyclo-penta[1,2-d][1,3]dioxol-3b(3aH)-yl)ethyl)quinoxalin-2-amine | ¹H NMR (400 MHz, DMSO-d6) δ 8.23 (s, 1H), 8.10 (s, 1H), 7.66 (d, J = 8.3 Hz, 1H), 7.35 (d, J = 1.8 Hz, 1H), 7.25 (dd, J = 8.4, 1.9 Hz, 1H), 7.19 (s, 2H), 7.06 (d, J = 3.6 Hz, 1H), 6.90 (s, 2H), 6.63 (d, J = 3.5 Hz, 1H), 5.12 (d, J = 4.5 Hz, 1H), 4.90 (d, J = 1.3 Hz, 1H), 4.54 (d, J = 4.5 Hz, 2H), 3.73 (s, 1H), 2.98-2.81 (m, 2H), 2.16-2.08 (m, 1H), 1.97-1.80 (m, 1H), 1.28-1.24 (m, 2H), 0.70-0.54 (m, 1H); LCMS m/z = 417.16 (M+; 100%). |

TABLE 8-continued

| Structure & IUPAC name | Intermediate used | ¹H NMR/LCMS data |
|---|---|---|
| Example 5: (1S,2R,5R)-5-(4-Amino-1H-pyrazolo[3,4-d]pyrimidin-1-yl)-3-(2-(2-amino-3-chloro-5-fluoroquinolin-7-yl)ethyl)cyclopent-3-ene-1,2-diol (Compound 5) | | ¹H NMR (400 MHz, DMSO-d₆) δ 8.16 (d, J = 2.1 Hz, 2H), 8.09 (s, 1H), 7.67 (s, 2H), 7.21 (s, 1H), 7.00 (dd, J = 11.0, 1.4 Hz, 1H), 6.93 (s, 2H), 5.66-5.57 (m, 1H), 5.51-5.45 (m, 1H), 4.95 (dd, J = 11.4, 6.6 Hz, 2H), 4.46 (t, J = 6.0 Hz, 1H), 4.35-4.31 (m, 1H), 2.93-2.89 (m, 2H), 2.48-2.43 (m, 2H); LCMS m/z = 456.29 (M+; 50%). |
| Example 6: (1S,2R,5R)-3-(2-(2-amino-3-chloro-5-fluoroquinolin-7-yl)ethyl)-5-(4-amino-6-methyl-1H-pyrazolo[3,4-d]pyrimidin-1-yl)cyclopent-3-ene-1,2-diol (Compound 6) | | ¹H NMR (400 MHz, DMSO-d6) δ 8.16 (s, 1H), 8.02 (d, J = 2.2 Hz, 1H), 7.59 (s, 2H), 7.21 (s, 1H), 7.05-6.87 (m, 3H), 5.60 (s, 1H), 5.46 (q, J = 1.7 Hz, 1H), 4.99-4.88 (m, 2H), 4.44 (t, J = 5.8 Hz, 1H), 4.30 (q, J = 5.7 Hz, 1H), 2.98-2.81 (m, 2H), 2.39 (s, 3H). LCMS m/z = 470.17 (M+; 20%). |
| Example 7: (1S,2R,5R)-5-(4-amino-7H-pyrrolo[2,3-d]pyrimidin-7-yl)-3-(((6-(difluoromethyl)-1,2,3,4-tetrahydroisoquinolin-8-yl)oxy)methyl)cyclopent-3-ene-1,2-diol (Compound 7) | tert-butyl 8-(((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)methoxy)-6-(difluoromethyl)-3,4-dihydroisoquinoline-2(1H)-carboxylate | ¹H NMR (400 MHz, DMSO-d6) δ 8.05 (s, 1H), 7.02-6.88 (m, 6H), 6.55 (d, J = 3.6 Hz, 1H), 5.77-5.75 (m, 1H), 5.61-5.57 (m, 1H), 5.14 (s, 2H), 4.78 (bs, 2H), 4.56 (d, J = 5.6 Hz, 1H), 4.13 (m, 1H), 3.79 (s, 2H), 2.88 (t, J = 5.7 Hz, 2H), 2.71-2.66 (m, 2H). LCMS m/z = 444.23 (M + 1; 40%). |

TABLE 8-continued

| Structure & IUPAC name | Intermediate used | ¹H NMR/LCMS data |
|---|---|---|
| Example 8: <br><br> (1S,2R,5R)-5-(4-amino-7H-pyrrolo[2,3-d]pyrimidin-7-yl)-3-(2-(6-methyl-1,2,3,4-tetrahydroisoquinolin-8-yl)ethyl)cyclopent-3-ene-1,2-diol (Compound 8) | 7-((3aS,4R,6aR)-2,2-dimethyl-6-(2-(6-methyl-1,2,3,4-tetrahydroisoquinolin-8-yl)ethyl)-3a,6a-dihydro-4H-cyclopenta[d][1,3]dioxol-4-yl)-7H-pyrrolo[2,3-d]pyrimidin-4-amine | ¹H NMR (400 MHz, DMSO-d₆) δ 8.05 (s, 1H), 6.93 (s, 2H), 6.84 (d, J = 3.6 Hz, 1H), 6.82 (s, 1H), 6.73 (s, 1H), 6.53 (d, J = 3.5 Hz, 1H), 5.51 (d, J = 4.2 Hz, 1H), 5.48 (d, J = 2.0 Hz, 1H), 4.95 (dd, J = 8.6, 6.5 Hz, 2H), 4.45 (t, J = 5.9 Hz, 1H), 4.00 (q, J = 5.5 Hz, 1H), 3.83 (s, 2H), 2.90 (t, J = 5.8 Hz, 2H), 2.70-2.63 (m, 4H), 2.42-2.35 (m, 2H), 2.22 (s, 3H); LCMS m/z = 406.23 (M+, 30%). |
| Example 9: <br><br> (1S,2R,5R)-5-(4-amino-7H-pyrrolo[2,3-d]pyrimidin-7-yl)-3-(2-(5-fluoro-1,2,3,4-tetrahydroisoquinolin-8-yl)ethyl)cyclopent-3-ene-1,2-diol (Compound 9) | 7-((3aS,4R,6aR)-6-(2-(5-fluoro-1,2,3,4-tetrahydroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | ¹H NMR (400 MHz, DMSO-d₆) δ 8.05 (s, 1H), 7.05 (dd, J = 8.4, 5.9 Hz, 1H), 6.94 (s, 2H), 6.90 (d, J = 8.8 Hz, 1H), 6.84 (d, J = 3.5 Hz, 1H), 6.53 (d, J = 3.5 Hz, 1H), 5.54-5.50 (m, 1H), 5.48 (d, J = 1.8 Hz, 1H), 4.96 (t, J = 6.9 Hz, 2H), 4.44 (t, J = 5.6 Hz, 1H), 4.02 (q, J = 5.3 Hz, 1H), 3.86 (s, 2H), 2.92 (t, J = 6.0 Hz, 2H), 2.77-2.65 (m, 2H), 2.62 (t, J = 6.0 Hz, 2H), 2.43-2.36 (m, 2H); LCMS m/z = 410.3 (M+, 10%). |
| Example 10: <br><br> (1S,2R,5R)-5-(4-amino-7H-pyrrolo[2,3-d]pyrimidin-7-yl)-3-(2-(6-(difluoromethyl)-1,2,3,4-tetrahydroisoquinolin-8-yl)ethyl)cyclopent-3-ene-1,2-diol (Compound 10) | tert-butyl 8-(2-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)ethyl)-6-(difluoromethyl)-3,4-dihydroisoquinoline-2(1H)-carboxylate | ¹H NMR (400 MHz, DMSO-d₆) δ 8.05 (s, 1H), 7.21 (s, 1H), 7.13 (s, 1H), 7.09-6.77 (m, 4H), 6.53 (d, J = 3.5 Hz, 1H), 5.56-5.48 (m, 2H), 4.98 (d, J = 6.3 Hz, 2H), 4.46 (t, J = 5.7 Hz, 1H), 4.01 (q, J = 5.4 Hz, 1H), 3.90 (s, 2H), 2.91 (t, J = 5.8 Hz, 2H), 2.84-2.70 (m, 4H), 2.45 (t, J = 7.0 Hz, 2H). LCMS m/z = 442.3 (M + 1; 10%). |

TABLE 8-continued

| Structure & IUPAC name | Intermediate used | ¹H NMR/LCMS data |
|---|---|---|
| Example 11:<br>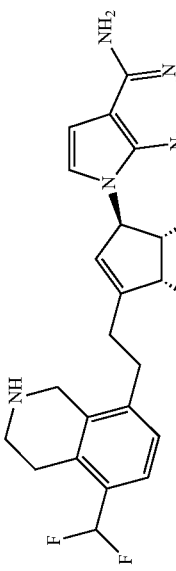<br>(1S,2R,5R)-5-(4-amino-7H-pyrrolo[2,3-d]pyrimidin-7-yl)-3-(2-(5-(difluoromethyl)-1,2,3,4-tetrahydroisoquinolin-8-yl)ethyl)cyclopent-3-ene-1,2-diol (Compound 11) | 7-((3aS,4R,6aR)-6-(2-(5-(difluoromethyl)-1,2,3,4-tetrahydroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | ¹H NMR (400 MHz, DMSO-$d_6$) δ 8.05 (s, 1H), 7.33 (d, J = 7.8 Hz, 1H), 7.23-7.09 (m, 2H), 6.93 (s, 2H), 6.85 (d, J = 3.6 Hz, 1H), 6.53 (d, J = 3.5 Hz, 2H), 5.51 (dd, J = 7.7, 3.3 Hz, 2H), 4.97 (t, J = 5.7 Hz, 2H), 4.46 (t, J = 5.9 Hz, 1H), 4.03 (q, J = 5.5 Hz, 1H), 3.92 (s, 2H), 2.94 (t, J = 5.9 Hz, 2H), 2.84-2.74 (m, 4H), 2.47-2.41 (m, 2H); LCMS m/z = 442.29 (M+, 50%). |
| Example 12:<br>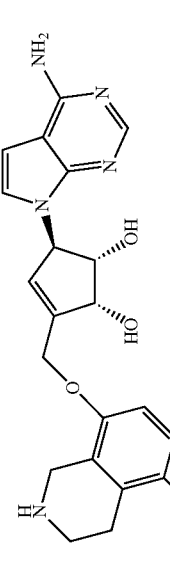<br>(1S,2R,5R)-5-(4-amino-7H-pyrrolo[2,3-d]pyrimidin-7-yl)-3-(((6-(difluoromethyl)-5-fluoro-1,2,3,4-tetrahydroisoquinolin-8-yl)oxy)methyl)cyclopent-3-ene-1,2-diol (Compound 12) | tert-butyl 8-(((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)methoxy)-6-(difluoromethyl)-5-fluoro-3,4-dihydroisoquinoline-2(1H)-carboxylate | ¹H NMR (400 MHz, DMSO-$d_6$) δ 8.05 (s, 1H), 7.32-6.92 (m, 5H), 6.55 (d, J = 3.6 Hz, 1H), 5.79-5.76 (m, 2H), 5.59 (s, 1H), 5.13 (s, 2H), 4.80 (s, 2H), 4.58-4.53 (m, 1H), 4.19-4.08 (m, 1H), 3.93-3.86 (m, 2H), 3.05-2.97 (m, 2H), 2.71-2.65 (m, 2H). LCMS m/z = 462.11 (M + 1; 40%). |

TABLE 8-continued

| Structure & IUPAC name | Intermediate used | ¹H NMR/LCMS data |
|---|---|---|
| Example 13:<br><br>(1S,2R,5R)-5-(4-amino-7H-pyrrolo[2,3-d]pyrimidin-7-yl)-3-(2-(6-(difluoromethyl)-5-fluoro-1,2,3,4-tetrahydroisoquinolin-8-yl)ethyl)cyclopent-3-ene-1,2-diol (Compound 13) | tert-butyl 8-(2-((3aS,4R,6aR)-4-(4-amino-7H-pyrrolo[2,3-d]pyrimidin-7-yl)-2,2-dimethyl-3a,6a-dihydro-4H-cyclopenta[d][1,3]dioxol-6-yl)ethyl)-6-(difluoromethyl)-5-fluoro-3,4-dihydroisoquinoline-2(1H)-carboxylate | ¹H NMR (400 MHz, DMSO-d6) δ 8.05 (s, 1H), 7.27 (s, 1H), 7.14 (s, 1H), 6.94 (s, 2H), 6.84 (d, J = 3.5 Hz, 1H), 6.53 (d, J = 3.5 Hz, 1H), 5.54-5.48 (m, 2H), 5.03 (bs, 2H), 4.45 (d, J = 5.6 Hz, 1H), 4.01 (t, J = 5.1 Hz, 1H), 3.89 (s, 2H), 2.96-2.90 (m, 2H), 2.81-2.72 (m, 2H), 2.68-2.61 (s, 2H), 2.43 (s, 2H); LCMS m/z = 460.05 (M + 1, 100%). |
| Example 14:<br><br>(1S,2R,5R)-3-(2-(6-(difluoromethyl)-1,2,3,4-tetrahydroisoquinolin-8-yl)ethyl)-5-(4-methyl-7H-pyrrolo[2,3-d]pyrimidin-7-yl)cyclopent-3-ene-1,2-diol (Compound 14) | tert-butyl 6-(difluoromethyl)-8-(2-((3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxol-6-yl)ethyl)-3,4-dihydroisoquinoline-2(1H)-carboxylate | ¹H NMR (400 MHz, DMSO-d₆) δ 8.64 (s, 1H), 7.26 (d, J = 3.6 Hz, 1H), 7.21 (bs, 1H), 7.13 (s, 1H), 6.93 (s, 1H), 6.68 (d, J = 3.6 Hz, 1H), 5.69-5.63 (m, 1H), 5.55-5.52 (m, 1H), 5.03 (s, 2H), 4.48 (d, J = 5.6 Hz, 1H), 4.07 (t, J = 5.2 Hz, 1H), 3.90 (s, 2H), 2.95-2.89 (m, 2H), 2.83-2.71 (m, 4H), 2.65 (s, 3H), 2.48-2.42 (m, 2H); LCMS m/z = 441.17 (M + 1, 30%). |

TABLE 8-continued

| Structure & IUPAC name | Intermediate used | ¹H NMR/LCMS data |
|---|---|---|
| Example 15:<br><br>(1S,2R,5R)-3-(2-(6-(difluoromethyl)-5-fluoro-1,2,3,4-tetrahydroisoquinolin-8-yl)ethyl)-5-(4-methyl-7H-pyrrolo[2,3-d]pyrimidin-7-yl)cyclopent-3-ene-1,2-diol (Compound 15) | tert-butyl 6-(difluoromethyl)-8-(2-((3aS,4R,6aR)-2,2-dimethyl-4-(4-methyl-7H-pyrrolo[2,3-d]pyrimidin-7-yl)-3a,6a-dihydro-4H-cyclopenta[d][1,3]dioxol-6-yl)ethyl)-5-fluoro-3,4-dihydroisoquinoline-2(1H)-carboxylate | ¹H NMR (400 MHz, DMSO-d6) δ 8.64 (s, 1H), 7.30-7.25 (m, 2H), 7.16-7.13 (m, 1H), 6.68 (d, J = 3.6 Hz, 1H), 5.69-5.64 (m, 1H), 5.55-5.52 (m, 1H), 5.03 (t, J = 6.3 Hz, 2H), 4.47 (t, J = 6.0 Hz, 1H), 4.08 (q, J = 5.6 Hz, 1H), 3.89 (s, 2H), 2.96-2.88 (m, 2H), 2.83-2.71 (m, 2H), 2.69-2.62 (m, 5H), 2.47-2.40 (m, 2H); LCMS m/z = 458.93 (M+, 100%) |
| Example 16:<br><br>4-Amino-1-((1R,4R,5S)-3-(((2-amino-3-chloro-5-fluoroquinolin-7-yl)oxy)methyl)-4,5-dihydroxycyclopent-2-en-1-yl)pyrimidin-2(1H)-one (Compound 16) | 4-Amino-1-((3aS,4R,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)pyrimidin-2(1H)-one | ¹H NMR (400 MHz, DMSO-d6) δ 8.10 (s, 1H), 7.28 (d, J = 7.3 Hz, 1H), 7.06-7.01 (m, 2H), 6.94 (s, 2H), 6.84-6.80 (m, 2H), 5.72 (q, J = 1.7 Hz, 1H), 5.64 (dd, J = 7.4, 1.8 Hz, 1H), 5.39-5.33 (m, 1H), 5.07 (dd, J = 6.4, 4.1 Hz, 2H), 4.87-4.70 (m, 2H), 4.47 (t, J = 5.6 Hz, 1H), 3.94 (dt, J = 6.7, 5.5 Hz, 1H). LCMS m/z = 434.2 (M + 1; 40%). |
| Example 17:<br><br>6-amino-3-((1R,4R,5S)-3-(((2-amino-3-chloro-5-fluoroquinolin-7-yl)oxy)methyl)-4,5-dihydroxycyclopent-2-en-1-yl)pyrimidin-4(3H)-one (Compound 17) | 6-amino-3-((3aS,4R,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)pyrimidin-4(3H)-one | ¹H NMR (400 MHz, DMSO-d₆) δ 6.83-6.79 (m, 2H), 6.65 (s, 2H), 5.88 (d, J = 1.7 Hz, 1H), 5.69 (d, J = 1.0 Hz, 1H), 5.61 (s, 1H), 5.15-5.05 (m, 2H), 4.78 (s, 2H), 4.49 (t, J = 6.0 Hz, 1H), 4.02-3.98 (m, 1H); LCMS m/z = 434.2 (M+; 40%). |

TABLE 8-continued

| Structure & IUPAC name | Intermediate used | 1H NMR/LCMS data |
|---|---|---|
| Example 18: [structure] 3-((1R,4R,5S)-3-(((2-amino-3-chloro-5-fluoroquinolin-7-yl)oxy)methyl)-4,5-dihydroxycyclopent-2-en-1-yl)-6-methylpyrimidin-4(3H)-one (Compound 18) | 3-((3aS,4R,6aR)-6-((((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)-6-methylpyrimidin-4(3H)-one | 1H NMR (400 MHz, DMSO-d6) δ 8.63 (d, J = 1.1 Hz, 1H), 8.09 (s, 1H), 6.94 (s, 2H), 6.84-6.77 (m, 3H), 5.91 (d, J = 1.8 Hz, 1H), 5.79-5.77 (m, 1H), 5.23-5.11 (m, 2H), 4.82-4.77 (m, 2H), 4.52 (d, J = 5.8 Hz, 1H), 4.07 (t, J = 5.1 Hz, 1H), 2.37 (s, 3H). LCMS m/z = 433.1 (M+, 35%) |
| Example 19: [structure] 6-amino-3-((1R,4R,5S)-3-(((2-amino-3-chloro-5-fluoroquinolin-7-yl)oxy)methyl)-4,5-dihydroxycyclopent-2-en-1-yl)-5-fluoropyrimidin-4(3H)-one (Compound 19) | 6-amino-3-((3aS,4R,6aR)-6-(((2-(bis(4-methoxybenzyl)amino)-3-chloro-5-fluoroquinolin-7-yl)oxy)methyl)-2,2-dimethyl-3a,6a-dihydro-4H-cyclopenta[d][1,3]dioxol-4-yl)-5-fluoropyrimidin-4(3H)-one | 1H NMR (400 MHz, DMSO-d6) δ 8.09 (s, 1H), 7.90 (s, 1H), 6.99 (s, 2H), 6.94 (s, 2H), 6.83-6.79 (m, 2H), 5.92-5.89 (m, 1H), 5.76-5.72 (m, 1H), 4.82-4.77 (m, 2H), 4.52-4.50 (m, 1H), 4.10-4.07 (m, 1H), 2.55 (s, 2H). LCMS m/z = 451.67 (M+, 15%) |
| Example 20: [structure] (1S,2R,5R)-5-(4-amino-7H-pyrrolo[2,3-d]pyrimidin-7-yl)-3-(2-(6-chloro-5-fluoro-1,2,3,4-tetrahydroisoquinolin-8-yl)ethyl)cyclopent-3-ene-1,2-diol (Compound 20) | 7-((3aS,4R,6aR)-6-(2-(6-chloro-5-fluoro-1,2,3,4-tetrahydroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | 1H NMR (400 MHz, DMSO-d6) δ 8.05 (s, 1H), 7.23 (d, J = 7.5 Hz, 1H), 6.94 (s, 2H), 6.84 (d, J = 3.6 Hz, 1H), 6.54 (d, J = 3.5 Hz, 1H), 5.49 (d, J = 15.0 Hz, 2H), 4.97 (t, J = 5.6 Hz, 2H), 4.45 (t, J = 5.7 Hz, 1H), 4.01 (q, J = 5.4 Hz, 1H), 3.83 (s, 2H), 2.91 (t, J = 5.9 Hz, 2H), 2.83-2.61 (m, 5H), 2.46-2.36 (m, 2H). LCMS m/z = 444.29 (M+, 10%) |

TABLE 8-continued

| Structure & IUPAC name | Intermediate used | ¹H NMR/LCMS data |
|---|---|---|
| Example 21:<br><br>(1S,2R,5R)-5-(4-amino-7H-pyrrolo[2,3-d]pyrimidin-7-yl)-3-(2-(5,6-difluoro-1,2,3,4-tetrahydroisoquinolin-8-yl)ethyl)cyclopent-3-ene-1,2-diol (Compound 21) | 7-((3aS,4R,6aR)-6-(2-(5,6-difluoro-1,2,3,4-tetrahydroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine | ¹H NMR (400 MHz, DMSO-d₆) δ 8.05 (s, 1H), 7.11 (dd, J = 11.9, 8.1 Hz, 1H), 6.94 (s, 2H), 6.85 (d, J = 3.5 Hz, 1H), 6.54 (d, J = 3.5 Hz, 1H), 5.47-5.30 (m, 1H), 5.47-5.45 (m, 1H), 5.01-4.94 (m, 2H), 4.45 (t, J = 5.8 Hz, 1H), 4.03 (q, J = 5.5 Hz, 1H), 3.81 (s, 2H), 3.18 (d, J = 4.2 Hz, 1H), 2.91 (t, J = 5.9 Hz, 2H), 2.73-2.62 (m, 4H), 2.43 (d, J = 10.2 Hz, 2H). LCMS m/z = 428.29 (M + 1, 50%) |
| Example 22A:<br>(Isomer-1)<br><br>(1S,2R,5R)-5-(4-amino-7H-pyrrolo[2,3-d]pyrimidin-7-yl)-3-(2-(6-(difluoromethyl)-5-fluoro-4-methyl-1,2,3,4-tetrahydroisoquinolin-8-yl)ethyl)cyclopent-3-ene-1,2-diol (Compound 22A) | 7-((3aS,4R,6aR)-6-(2-(6-(Difluoromethyl)-5-fluoro-4-methyl-1,2,3,4-tetrahydroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine<br>(Isomer-1, Peak-1, Rt = 9 min) | Isomer-1: ¹H NMR (400 MHz, DMSO-d₆) δ 8.05 (s, 1H), 7.27 (d, J = 6.5 Hz, 1H), 7.00 (s, 1H), 6.94 (s, 2H), 6.83 (d, J = 3.6 Hz, 1H), 6.53 (d, J = 3.5 Hz, 1H), 5.52 (d, J = 5.0 Hz, 2H), 4.97 (dd, J = 6.6, 3.6 Hz, 2H), 4.43 (t, J = 6.1 Hz, 1H), 4.06-3.92 (m, 2H), 3.78 (d, J = 17.0 Hz, 1H), 2.95 (s, 1H), 2.90-2.80 (m, 2H), 2.80-2.64 (m, 3H), 2.45-2.40 (m, 2H), 1.34-1.19 (m, 3H); LCMS m/z = 474.36 (M + 1, 10%) |

TABLE 8-continued

| Structure & IUPAC name | Intermediate used | 1H NMR/LCMS data |
|---|---|---|
| Example 22B: (Isomer-2) 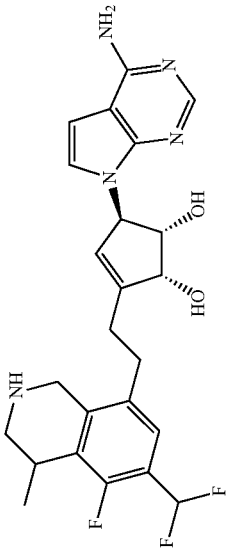 (1S,2R,5R)-5-(4-amino-7H-pyrrolo[2,3-d]pyrimidin-7-yl)-3-(2-(6-(difluoromethyl)-5-fluoro-4-methyl-1,2,3,4-tetrahydroisoquinolin-8-yl)ethyl)cyclopent-3-ene-1,2-diol (Compound 22B) | 7-((3aS,4R,6aR)-6-(2-(6-(Difluoromethyl)-5-fluoro-4-methyl-1,2,3,4-tetrahydroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine (Isomer-2, Peak-2, Rt = 10.3 min) | Isomer-2: 1H NMR (400 MHz, DMSO-$d_6$) δ 8.05 (s, 1H), 7.27 (d, J = 6.7 Hz, 1H), 7.14 (s, 1H), 6.94 (s, 2H), 6.82 (d, J = 3.5 Hz, 1H), 6.53 (d, J = 3.5 Hz, 1H), 5.52 (d, J = 4.5 Hz, 1H), 5.50-5.47 (m, 1H), 4.98 (d, J = 6.3 Hz, 2H), 4.47 (t, J = 6.0 Hz, 1H), 4.04-3.93 (m, 2H), 3.79 (d, J = 17.1 Hz, 1H), 2.95 (s, 1H), 2.83 (t, J = 3.2 Hz, 2H), 2.75 (q, J = 6.9 Hz, 3H), 2.47-2.39 (m, 2H), 1.27 (d, J = 6.8 Hz, 3H); LCMS m/z = 474.36 (M+1, 10%) |
| Example 23 A: (Isomer-1) 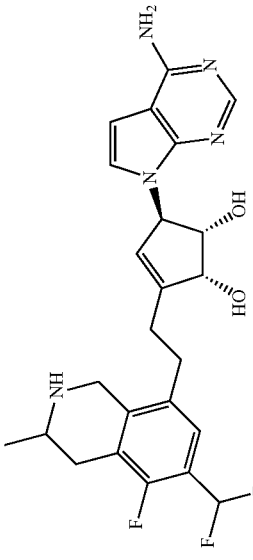 (1S,2R,5R)-5-(4-amino-7H-pyrrolo[2,3-d]pyrimidin-7-yl)-3-(2-(6-(difluoromethyl)-5-fluoro-3-methyl-1,2,3,4-tetrahydroisoquinolin-8-yl)ethyl)cyclopent-3-ene-1,2-diol (Compound 23A) | 7-((3aS,4R,6aR)-6-(2-(6-(Difluoromethyl)-5-fluoro-3-methyl-1,2,3,4-tetrahydroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine (Isomer-1, Peak-1, Rt = 4.7 min) | Isomer-1: 1H NMR (400 MHz, DMSO-d6) δ 8.05 (s, 1H), 7.27 (s, 1H), 7.14 (s, 1H), 6.94 (s, 2H), 6.85 (d, J = 3.6 Hz, 1H), 6.53 (d, J = 3.5 Hz, 1H), 5.52 (d, J = 6.5 Hz, 2H), 5.01-4.94 (m, 2H), 4.44 (t, J = 5.5 Hz, 1H), 4.07-4.00 (m, 2H), 3.85 (d, J = 17.3 Hz, 1H), 2.83-2.72 (m, 4H), 2.57-2.55 (m, 1H), 2.43 (dd, J = 16.4, 9.1 Hz, 2H), 2.28-2.18 (m, 1H), 1.17 (d, J = 6.1 Hz, 3H); LCMS m/z = 474.36 (M + 1, 20%) |

TABLE 8-continued

| Structure & IUPAC name | Intermediate used | ¹H NMR/LCMS data |
|---|---|---|
| Example 23 B: (Isomer-2) 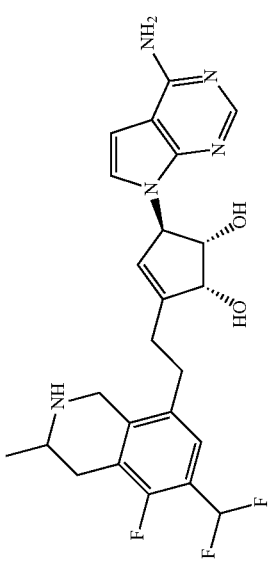 (1S,2R,5R)-5-(4-amino-7H-pyrrolo[2,3-d]pyrimidin-7-yl)-3-(2-(6-(difluoromethyl)-5-fluoro-3-methyl-1,2,3,4-tetrahydroisoquinolin-8-yl)ethyl)cyclopent-3-ene-1,2-diol (Compound 23B) | 7-((3aS,4R,6aR)-6-(2-(6-(Difluoromethyl)-5-fluoro-3-methyl-1,2,3,4-tetrahydroisoquinolin-8-yl)ethyl)-2,2-dimethyl-3a,6a-dihydro-4H-cyclopenta[d][1,3]dioxol-4-yl)-7H-pyrrolo[2,3-d]pyrimidin-4-amine (Isomer-2, Peak-2, Rt = 5.3 min) | Isomer-2: ¹H NMR (400 MHz, DMSO-d6) δ 8.05 (s, 1H), 7.28 (s, 1H), 7.14 (s, 1H), 6.93 (s, 2H), 6.81 (d, J = 3.5 Hz, 1H), 6.52 (d, J = 3.5 Hz, 1H), 5.52 (d, J = 4.5 Hz, 1H), 5.47 (d, J = 1.9 Hz, 1H), 4.97 (d, J = 5.3 Hz, 2H), 4.46 (s, 1H), 4.03-3.97 (m, 2H), 3.88 (s, 1H), 2.77 (d, J = 9.8 Hz, 4H), 2.57-2.55 (m, 1H), 2.46-2.42 (m, 2H), 2.25 (d, J = 11.1 Hz, 1H), 1.17 (d, J = 6.0 Hz, 3H); LCMS m/z = 474.42 (M + 1, 20%). |
| Example 24: 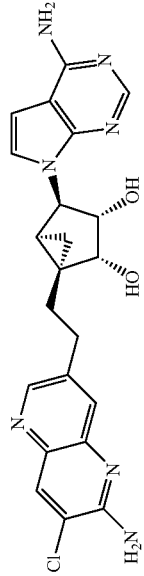 (1R,2R,3S,4R,5S)-1-(2-(6-Amino-7-chloro-1,5-naphthyridin-3-yl)ethyl)-4-(4-amino-7H-pyrrolo[2,3-d]pyrimidin-7-yl)bicyclo[3.1.0]hexane-2,3-diol (Compound 24) | 7-(2-((3aR,3bR,4aS,5R,5aS)-5-(4-Amino-7H-pyrrolo[2,3-d]pyrimidin-7-yl)-2,2-dimethyltetrahydrocyclopropa[3,4]cyclopenta[1,2-d][1,3]dioxol-3b(3aH)-yl)ethyl)-3-chloro-1,5-naphthyridin-2-amine | ¹H NMR (400 MHz, DMSO-d6) δ 8.53 (d, J = 2.1 Hz, 1H), 8.17 (s, 1H), 8.09 (s, 1H), 7.74 (d, J = 2.0 Hz, 1H), 7.12 (s, 2H), 7.09 (d, J = 3.6 Hz, 1H), 6.97 (s, 2H), 6.62 (d, J = 3.5 Hz, 1H), 5.13 (d, J = 4.5 Hz, 1H), 4.90 (d, J = 1.3 Hz, 1H), 4.55 (d, J = 3.0 Hz, 2H), 3.73 (s, 1H), 3.09 (dd, J = 7.3, 4.4 Hz, 3H), 2.98-2.90 (m, 2H), 2.22-2.14 (m, 1H), 1.88-1.81 (m, 1H); LCMS m/z = 451.86 (M+; 100%). |

TABLE 8-continued

| Structure & IUPAC name | Intermediate used | $^1$H NMR/LCMS data |
|---|---|---|
| Example 25:<br><br>(1S,2R,5R)-5-(4-amino-5-methyl-7H-pyrrolo[2,3-d]pyrimidin-7-yl)-3-(2-(6-(difluoromethyl)-5-fluoro-1,2,3,4-tetrahydroisoquinolin-8-yl)ethyl)cyclopent-3-ene-1,2-diol (Compound 25) | 7-((3aS,4R,6aR)-6-(2-(6-(difluoromethyl)-5-fluoro-1,2,3,4-tetrahydroisoquinolin-8-yl)ethyl)-2,2-dimethyl-3a,6a-dihydro-4H-cyclopenta[d][1,3]dioxol-4-yl)-5-methyl-7H-pyrrolo[2,3-d]pyrimidin-4-amine | $^1$H NMR (400 MHz, DMSO-$d_6$) δ 8.00 (s, 1H), 7.29-7.00 (m, 3H), 6.56 (d, J = 1.3 Hz, 1H), 6.49 (s, 2H), 5.49 (d, J = 4.5 Hz, 1H), 5.45 (d, J = 2.0 Hz, 1H), 4.95 (s, 2H), 4.43 (d, J = 5.6 Hz, 1H), 4.00-3.92 (m, 1H), 3.89 (s, 2H), 2.93 (t, J = 6.0 Hz, 2H), 2.84-2.71 (m, 2H), 2.65 (d, J = 6.0 Hz, 2H), 2.42 (d, J = 6.5 Hz, 2H), 2.32 (d, J = 1.2 Hz, 3H); LCMS m/z = 474.42 (M + 1, 10%). |
| Example 26:<br><br>(1S,2R,5R)-3-(2-(2-Amino-3-bromoquinolin-7-yl)ethyl)-5-(7H-imidazo[1,2-c]pyrrolo[3,2-e]pyrimidin-7-yl)cyclopent-3-ene-1,2-diol (Compound 26) | 7-(2-((3aS,4R,6aR)-4-(7H-Imidazo[1,2-c]pyrrolo[3,2-e]pyrimidin-7-yl)-2,2-dimethyl-3a,6a-dihydro-4H-cyclopenta[d][1,3]dioxol-6-yl)ethyl)-3-bromo-N-(4-methoxybenzyl)quinolin-2-amine | $^1$H NMR (400 MHz, DMSO-d6) δ 9.08 (s, 1H), 8.37 (s, 1H), 7.94 (d, J = 1.5 Hz, 1H), 7.62 (d, J = 8.2 Hz, 1H), 7.44 (d, J = 1.5 Hz, 1H), 7.37 (s, 1H), 7.18 (d, J = 8.4 Hz, 1H), 6.76 (d, J = 3.4 Hz, 1H), 6.61 (s, 2H), 6.52 (d, J = 3.3 Hz, 1H), 5.62 (s, 1H), 5.46 (s, 1H), 5.03 (d, J = 6.5 Hz, 1H), 4.98 (d, J = 6.4 Hz, 1H), 4.49 (t, J = 6.2 Hz, 1H), 3.99 (q, J = 5.6 Hz, 1H), 3.03-2.90 (m, 2H), 2.59 (t, J = 8.0 Hz, 2H); LCMS m/z = 505.31 (M+; 100%). |
| Example 27:<br><br>(1S,2R,5R)-3-(2-(2-Amino-3-chloro-5-fluoroquinolin-7-yl)ethyl)-5-(7H-imidazo[1,2-c]pyrrolo[3,2-e]pyrimidin-7-yl)cyclopent-3-ene-1,2-diol (Compound 27) | 7-(2-((3aS,4R,6aR)-4-(7H-Imidazo[1,2-c]pyrrolo[3,2-e]pyrimidin-7-yl)-2,2-dimethyl-3a,6a-dihydro-4H-cyclopenta[d][1,3]dioxol-6-yl)ethyl)-3-chloro-5-fluoro-N-(4-methoxybenzyl)quinolin-2-amine | $^1$H NMR (400 MHz, DMSO-d6) δ 9.08 (s, 1H), 8.19 (s, 1H), 7.94 (d, J = 1.5 Hz, 1H), 7.44 (d, J = 1.5 Hz, 1H), 7.23 (s, 1H), 7.02 (dd, J = 11.1, 1.4 Hz, 1H), 6.97 (s, 2H), 6.81 (d, J = 3.3 Hz, 1H), 6.54 (d, J = 3.3 Hz, 1H), 5.62 (d, J = 4.2 Hz, 1H), 5.47 (d, J = 2.0 Hz, 1H), 5.04 (d, J = 6.5 Hz, 1H), 4.99 (d, J = 6.4 Hz, 1H), 4.49 (t, J = 6.1 Hz, 1H), 4.05-4.00 (m, 1H), 3.05-2.89 (m, 2H), 2.58 (q, J = 5.9, 3.5 Hz, 2H); LCMS m/z = 479.1 (M+; 100%). |

TABLE 8-continued

| Structure & IUPAC name | Intermediate used | ¹H NMR/LCMS data |
|---|---|---|
| Example 28:<br>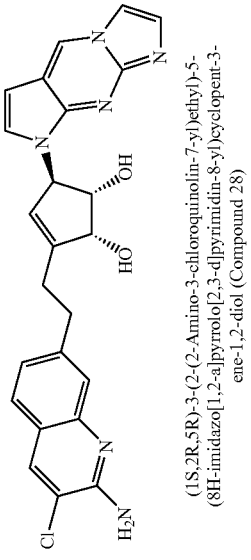<br>(1S,2R,5R)-3-(2-(2-Amino-3-chloroquinolin-7-yl)ethyl)-5-(8H-imidazo[1,2-a]pyrrolo[2,3-d]pyrimidin-8-yl)cyclopent-3-ene-1,2-diol (Compound 28) | 7-(2-((3aS,4R,6aR)-4-(1H-Imidazo[1,2-a]pyrrolo[3,2-e]pyrimidin-1-yl)-2,2-dimethyl-3a,6a-dihydro-4H-cyclopenta[d][1,3]dioxol-6-yl)ethyl)-3-chloro-N,N-bis(4-methoxybenzyl)quinolin-2-amine and 7-(2-((3aS,4R,6aR)-4-(8H-imidazo[1,2-a]pyrrolo[2,3-d]pyrimidin-8-yl)-2,2-dimethyl-3a,6a-dihydro-4H-cyclopenta[d][1,3]dioxol-6-yl)ethyl)-3-chloro-N,N-bis(4-methoxybenzyl)quinolin-2-amine | ¹H NMR (400 MHz, DMSO-d6) δ 9.23 (d, J = 3.0 Hz, 1H), 8.18 (s, 1H), 7.83 (s, 1H), 7.61 (d, J = 8.3 Hz, 1H), 7.56 (s, 1H), 7.38 (s, 1H), 7.18 (d, J = 8.3 Hz, 1H), 6.92 (d, J = 4.3 Hz, 1H), 6.70 (s, 2H), 6.29 (s, 1H), 5.56 (s, 1H), 5.46 (s, 1H), 5.03 (s, 2H), 4.48 (s, 1H), 4.01 (d, J = 6.5 Hz, 1H), 3.07-2.90 (m, 2H), 2.63-2.55 (m, 2H); LCMS m/z = 461.30 (M+; 100%). |
| Example 29:<br>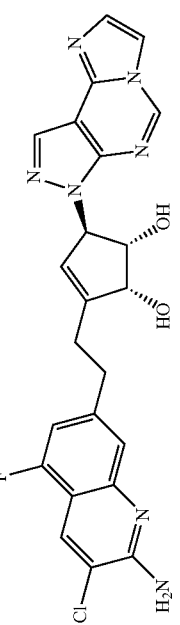<br>(1S,2R,5R)-3-(2-(2-Amino-3-chloro-5-fluoroquinolin-7-yl)ethyl)-5-(7H-imidazo[1,2-c]pyrazolo[4,3-e]pyrimidin-7-yl)cyclopent-3-ene-1,2-diol | 7-(2-((3aS,4R,6aR)-4-(7H-Imidazo[1,2-c]pyrazolo[4,3-e]pyrimidin-7-yl)-2,2-dimethyl-3a,6a-dihydro-4H-cyclopenta[d][1,3]dioxol-6-yl)ethyl)-3-chloro-5-fluoro-N,N-bis(4-methoxybenzyl)quinolin-2-amine | ¹H NMR (400 MHz, DMSO-d6) δ 9.28 (s, 1H), 8.30 (s, 1H), 8.16 (s, 1H), 8.04 (d, J = 1.6 Hz, 1H), 7.51 (d, J = 1.6 Hz, 1H), 7.22 (s, 1H), 7.00 (dd, J = 11.1, 1.4 Hz, 2H), 6.95 (s, 2H), 5.78 (t, J = 3.3 Hz, 1H), 5.55 (d, J = 1.8 Hz, 1H), 5.05 (dd, J = 6.6, 1.7 Hz, 2H), 4.49 (d, J = 6.0 Hz, 1H), 4.39-4.35 (m, 1H), 2.93 (d, J = 8.0 Hz, 2H), 2.47-2.45 (m, 1H); LCMS m/z = 480.18 (M+; 50%). |

Example 30: (1S,2R,5R)-3-(2-(2-Amino-3-chloro-5-fluoroquinolin-7-yl)ethyl)-5-(4-(methoxyamino)-7H-pyrrolo[2,3-d]pyrimidin-7-yl)cyclopent-3-ene-1,2-diol

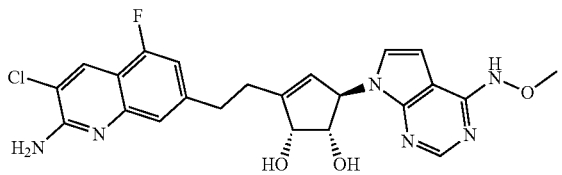 [SMILES: CONc1ncnc2c1ccn2[C@@H]1C=C(CCc2cc(F)c3cc(Cl)c(N)nc3c2)[C@@H](O)[C@H]1O]

A mixture of 3-chloro-7-(2-((3aS,4R,6aR)-4-(4-chloro-7H-pyrrolo[2,3-d]pyrimidin-7-yl)-2,2-dimethyl-3a,6a-dihydro-4H-cyclopenta[d][1,3]dioxol-6-yl)ethyl)-5-fluoroquinolin-2-amine (100 mg, 0.194 mmol) and N-Methylhydroxylamine hydrochloride (130 mg, 1.555 mmol) in t-Butanol (4 ml) was heated at 50° C. in a sealed tube for 12 h. The volatiles were evaporated in vacuo to give 135 mg of crude compound. This residue was purified by combiflash ($R_f$200, Teledyne/Isco) instrument onto a redisep® $R_f$ column with gradient elution (0 to 20%) of methanol in dichloromethane to afford the title compound (35 mg, 37.1%) as an off white solid. $^1$H NMR (400 MHz, DMSO-d6) δ 8.55 (s, 1H), 8.31 (s, 1H), 7.39 (s, 1H), 7.27 (d, J=10.7 Hz, 1H), 7.15 (d, J=3.6 Hz, 1H), 6.78 (d, J=3.5 Hz, 1H), 5.58 (d, J=4.6 Hz, 1H), 5.48 (d, J=1.8 Hz, 1H), 4.46 (d, J=5.6 Hz, 1H), 4.06 (t, J=5.3 Hz, 1H), 3.87 (s, 3H), 3.12-2.93 (m, 2H), 2.57 (d, J=6.7 Hz, 2H); LCMS m/z=485.05 (M+, 50%).

BIOLOGICAL EXAMPLES

Biochemical Assay Protocol 1

Inhibitory effect of compounds on PRMT5 was assessed using HTRF detection technology in biochemical assay. Biotinylated H4R3 (residues 1-21) was used as a substrate. Compounds were pre-incubated with 15-25 ng PRMT5:MEP50 per well of a 384-well plate for 30 min at room temperature in the assay buffer containing 20 mM Bicine, pH 7.6, 25 mM NaCl, 2 mM DTT, 0.01% Chicken albumin and 0.01% Tween-20. Reaction was initiated by adding 1 μM of SAM and 50 nM biotinylated H4R3. Total assay volume was 15 μL. Reaction was continued for 120 min at room temperature. Then detection solution containing Streptavidin-Eu cryptate, anti-rabbit IgG-XL-665, Histone H4R3 Dimethyl Symmetric (H4R3me2s) Polyclonal Antibody, all prepared in HTRF detection buffer was added and further incubated for 30 min at room temperature. HTRF signal was recorded in PHERAStar microplate reader. Ratio of signal obtained at 665 nm and 620 nm was used to compute the percent inhibition of compound as follows % Inhibition=100−((Test Ratio−Negative control Ratio)/(Positive control Ratio−Negative control Ratio)*100) where Positive control=PRMT5+SAM+H4R3

Negative control=PRMT5+H4R3

Biochemical Assay Protocol 2

Inhibitory effect of compounds on PRMT5 was assessed using HTRF detection technology in biochemical assay. Biotinylated H4R3 (residues 1-21) was used as a substrate. Compounds were pre-incubated with 2.5 ng PRMT5:MEP50 per well of a 384-well plate for 30 min at room temperature in the assay buffer containing 20 mM Bicine, pH 7.6, 25 mM NaCl, 2 mM DTT, 0.01% Chicken albumin and 0.01% Tween-20. Reaction was initiated by adding 1 μM of SAM and 50 nM biotinylated H4R3. Total assay volume was 15 μL. Reaction was continued for 4 h at room temperature. Then detection solution containing Streptavidin-Eu cryptate, anti-rabbit IgG-XL-665, Histone H4R3 Dimethyl Symmetric (H4R3me2s) Polyclonal Antibody, all prepared in HTRF detection buffer was added and further incubated for 30 min at room temperature. HTRF signal was recorded in PHERAStar microplate reader. Ratio of signal obtained at 665 nm and 620 nm was used to compute the percent inhibition of compound as follows % Inhibition=100−((Test Ratio−Negative control Ratio)/(Positive control Ratio−Negative control Ratio)*100) where Positive control=PRMT5+SAM+H4R3

Negative control=PRMT5+H4R3

| Activity range | Compound nos. |
|---|---|
| IC$_{50}$ 250 pM to 950 pM | 1, 2, 3, 4, 5, 6,7, 8, 9, 10, 11, 12, 13, 14, 15, 16, 17, 20, 21, 22A, 22B, 23A, 23B, 24, 25, 30. |
| IC$_{50}$ > 950 pM | 18, 19, 26, 27, 28, 29. |

SDMA Inhibition Assay

Protocol

Z-138 cells (ATCC, CRL-3001™) were seeded at a density of 1 million cells/well in transparent, flat bottomed tissue culture grade 48-well plates. Cells were treated with various concentration of test compounds for a period of 48 h. Cell lysate was prepared using 1× CST Lysis buffer (Cell Signaling Technology, USA) and 500 ng/well/50 μL of lysate in pH 9.6 carbonate buffer was coated on 96-well Maxisorb plate and incubated overnight at 4° C. The plate was washed twice in 1×PBS containing 0.05% Tween 20 and blocked in 1% BSA for 1 h at ambient temperature. Further, the plate was incubated first with primary antibody (anti-SDMA antibody; CST #13222s) at ambient temperature for 2 h and then with HRP-conjugated secondary antibody at ambient temperature for 1 h with 2 intermittent washing steps in between.

For luminiscence based detection, HRP substrates (substrate A+substrate B in a 1:1 proportion) were added followed by luminiscence reading after 30 min in Synergy™ 2 reader (Biotek, USA).

For absorbance based detection, TMB substrate was added followed by addition of STOP solution (2N $H_2SO_4$) post colour development and absorbance (excitation 450 nm and emission 540 nm) was measured in Synergy™ 2 reader (Biotek, USA).

% inhibition of SDMA was calculated relative to the vehicle control samples containing media with 0.1% DMSO alone as per the formula below.

(Avg. of Untreated Control−Avg. of Test)×100

Avg. Of Untreated Control

The IC$_{50}$ values of individual compounds were calculated with Non Linear Regression Analysis using Graph Pad Prism (Graph Pad software, Inc, USA).

| Activity range | Compound nos. |
|---|---|
| $IC_{50}$ 100 pM to 1 nM | 1, 5, 10, 15, 19, 22B, 23A, 30 |
| $IC_{50}$ 1.1 nM to 50 nM | 2, 3, 4, 6, 7, 8, 9, 11, 12, 13, 14, 17, 18, 20, 21, 22A, 23B, 24, 25, 26 |

Anticancer Activity Assay

Z-138 cells were seeded at a density of 2000-3000 cells per well in culture media (IMDM+10% FBS). PANC-1 (ATCC, CRL-1469™) and MIA PaCa-2 (ATCC, CRL-1420™) cells were seeded at a density of 200-300 cells per well in culture media (DMEM+10% FBS). Cells were seeded in opaque, flat bottomed tissue culture grade 96-well plates and Z-138 cells (suspension) were seeded and treated on the same day with various concentrations of test compounds. PANC-1 and MIA PaCa-2 cells, being adherent, were kept for overnight settlement at standard cell culture conditions (37° C., 5% $CO_2$). On the following day, cells were treated with various concentrations of test compounds. Cells were treated with test compounds for a period of 96 h, 7 days and 10 days, for Z-138 cells, PANC-1 cells and MIA PaCa-2 cells, respectively. Cell viability was assessed using CellTiterGlo™ (Promega, USA) as per manufacturer's instructions. Relative Light Units (RLU) were read in Synergy™ 2 reader (Biotek, USA). The assay measures cellular ATP as an indicator of cell viability. RLU is proportional to the number of viable cells in the respective well. % inhibition of cell viability was calculated relative to the vehicle control samples containing media with 0.1% DMSO alone as per the formula below.

(Avg. of Untreated Control−Avg. of Test)×100

Avg. Of Untreated Control

The $IC_{50}$ values of individual compounds were calculated with Non Linear Regression Analysis using Graph Pad Prism (Graph Pad software, Inc, USA).

Anti-Cancer Assay (Z-138)

| Activity range | Compound nos |
|---|---|
| $IC_{50}$ 0.1 pM-100 pM | 1, 22B, 23A, 30 |
| $IC_{50}$ 101 pM-1 nM | 5, 6, 10, 13, 14, 15, 21 |
| $IC_{50}$ > 1 nM | 2, 3, 4, 7, 8, 9, 11, 12, 17, 18, 19, 20, 22A, 23B, 24, 25, 26, 27, 28. |

Anti-Cancer Assay (MiaPaCa-2)

| Activity Range | Compound nos |
|---|---|
| $IC_{50}$ 1 pM to 40 nM | 1, 2, 5, 6, 13, 22B, 23A, 27, 30 |

In Vivo Efficacy Experiments

Tumor xenograft for mantle cell lymphoma was established by injection of cells into the right flank of female NOD.CB17-Prkdc<scid>/J mice with an age between 7-11 weeks purchased from The Jackson Laboratory, USA. All animal study proposals were reviewed and approved by the Institutional Animal Ethics Committee (IAEC) prior to initiation of experimentation.

Z-138 Xenograft

For Z-138 xenograft mouse model, Z-138 cells (ATCC® CRL-3001™) were grown in IMDM medium supplemented with 10% FBS. Cells were incubated under standard conditions at 37° C. and 5% $CO_2$. For generating tumors, Z-138 cells in IMDM medium were mixed with Matrigel (Corning® Matrigel® Basement Membrane Matrix) in a ratio of 1:1. $10 \times 10^6$ cells) in a volume of 200 µL were injected subcutaneously in each mouse to establish tumors. Mice were randomized into treatment groups of 8-10 mice, once tumors reached an average volume between 100 to 120 $mm^3$. Treatment was initiated on day of randomization and continued until end of the study. The Vehicle and test compound treatment groups were administered respective treatments orally, using gavage tubing, at an application volume of 10 mL/kg per mouse twice a day.

Mice were housed in individually ventilated cages (IVC) at room temperature of 22+3° C., humidity 50+20% and 12/12 h light/dark cycle. All the experimental activities were carried-out inside the biosafety cabinets to ensure sterility.

Tumor size was measured with Digimatic Vernier caliper (Mitutoyo, Japan) when the tumors became palpable. Tumor volume (T. V.) is calculated by using the formula:

Tumor volume (mm3)=(L×W2)/2

Where, L: Length of tumor, W: Width of tumor in millimeter

Percent tumor growth inhibition (% TGI) is calculated using the formula:

% TGI=[1−(Tf−Ti)/(Cf−Ci)]×100

Where, Tf and Ti, are the final and initial tumor volumes (test compound), and Cf and Ci are the final and initial mean tumor volumes (vehicle group), respectively.

Percent tumor regression is calculated as:

% TR:(Ti−Tf)/(Ti)×100

Where, Tf and Ti, are the final and initial tumor volumes, respectively.

In Vivo Efficacy Experiments

Tumor fragment xenograft for pancreatic cancer was established by implantation of tumor fragments 30-45 mm3 subcutaneously into the right flank of female athymic nude FOXn1<nu>/J/*Mus musculus* mice with an age between 10-11 weeks purchased from the Jackson Laboratory, USA. All animal study proposals were reviewed and approved by the Institutional Animal Ethics Committee (IAEC) prior to initiation of experimentation.

We claim:

1. A compound of general formula (I), its stereoisomer, or its pharmaceutically acceptable salt,

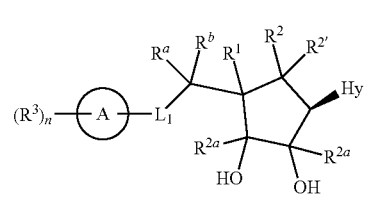

wherein, $L_1$ is selected from bond, —$CR^aR^b$ and O;
$R^a$ and $R^b$ are hydrogen;
ring A is selected from formula (i), (ii), (iii) and (iv), wherein the substituent $R^3$ on ring A may be substituted on any of the ring carbon atoms,

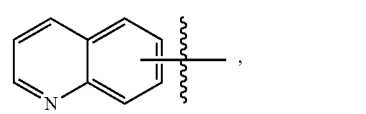

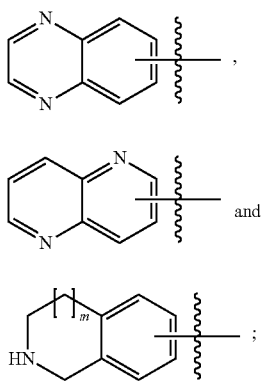

Hy is selected from formula (a-1) to (h-1), provided that when Hy is (h-1) then ring A cannot be formula (i),

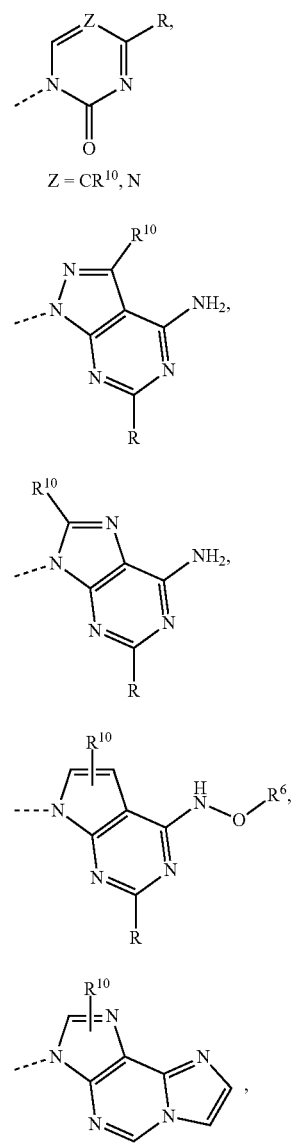

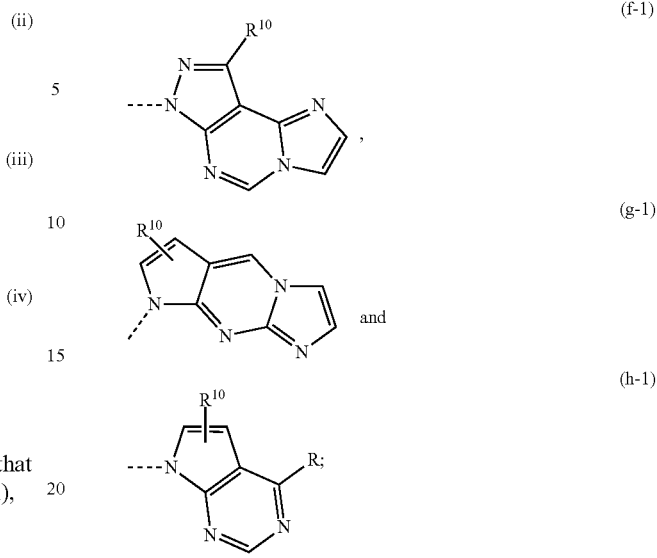

R is selected from —NR$^4$R$^5$, and hydrogen Z is selected from CR$^{10}$ and N;

R$^1$ and R$^2$ together with the carbon atoms to which they are attached form a bond in order to form a —C=C—; or R$^1$ and R$^2$ together with the carbon atoms to which they are attached form a cyclopropane ring;

R$^{2'}$ and R$^{2a}$ are hydrogen;

R$^3$ is independently selected at each occurrence from halogen, substituted or unsubstituted alkyl, and —NR$^7$R$^8$ R$^4$ and R$^5$ are hydrogen;

R$^6$ is selected from hydrogen, unsubstituted alkyl, and unsubstituted cycloalkyl;

R$^7$ and R$^8$ are hydrogen;

R$^{10}$ is selected from hydrogen, halogen, and substituted or unsubstituted alkyl;

'n' is an integer ranging from 0 to 4, both inclusive;

'm' is an integer ranging from 0 to 1, both inclusive;

when an alkyl group is substituted, it is substituted with 1 to 4 substituents independently selected from oxo (=O), halogen, cyano, cycloalkyl, aryl, heteroaryl, heterocyclyl, —OR$^{7a}$, —C(=O)OH, —C(=O)O(alkyl), —NR$^{8a}$R$^{8b}$, —NR$^{8a}$C(=O)R$^{9a}$, and —C(=O)NR$^{8a}$R$^{8b}$;

when the heteroaryl group is substituted, it is substituted with 1 to 4 substituents independently selected from halogen, cyano, alkyl, haloalkyl, cycloalkyl, heterocyclyl, —OR$^{7a}$, —NR$^{8a}$R$^{8b}$, —NR$^{7a}$C(=O)R$^{9a}$, and —C(=O)NR$^{8a}$R$^{8b}$;

when the heterocylyl group is substituted, it is substituted with 1 to 4 substituents independently selected from halogen, cyano, alkyl, haloalkyl, cycloalkyl, heterocyclyl, —OR$^{7a}$, —NR$^{8a}$R$^{8b}$, —NR$^{7a}$C(=O)R$^{9a}$, and —C(=O)NR$^{8a}$R$^{8b}$;

when the aryl group is substituted, it is substituted with 1 to 4 substituents independently selected from halogen, cyano, alkyl, haloalkyl, cycloalkyl, heterocyclyl, —OR$^{7a}$, —NR$^{8a}$R$^{8b}$, —NR$^{7a}$C(=O)R$^{9a}$, and —C(=O)NR$^{8a}$R$^{8b}$;

when the cycloalkyl group is substituted, it is substituted with 1 to 4 substituents independently selected from halogen, cyano, alkyl, haloalkyl, —OR$^{7a}$, —NR$^{8a}$R$^{8b}$, —NR$^{7a}$C(=O)R$^{9a}$, and —C(=O)NR$^{8a}$R$^{8b}$;

$R^{7a}$ is selected from hydrogen, alkyl, haloalkyl, and cycloalkyl;

$R^{8a}$ and $R^{8b}$ are each independently selected from hydrogen, alkyl, and cycloalkyl; and $R^{9a}$ is selected from alkyl and cycloalkyl.

2. The compound of formula (I), its stereoisomer, or its pharmaceutically acceptable salt, as claimed in claim 1, wherein the compound is selected from:

(1S,2R,5R)-3-(2-(2-Amino-3-chloro-5-fluoroquinolin-7-yl)ethyl)-5-(6-amino-9H-purin-9-yl)cyclopent-3-ene-1 2-diol (Compound 1);

(1S,2R,5R)-3-(2-(6-Amino-7-chloro-1,5-naphthyridin-3-yl)ethyl)-5-(4-amino-7H-pyrrolo [2,3-d]pyrimidin-7-yl)cyclopent-3-ene-1,2-diol(Compound 2);

(1S,2R,5R)-5-(4-Amino-7H-pyrrolo[2,3-d]pyrimidin-7-yl)-3-(2-(3-aminoquinoxalin-6-yl)ethyl)cyclopent-3-ene-1 2-diol (Compound 3);

(1R,2R,3S,4R,5S)-4-(4-Amino-7H-pyrrolo[2,3-d]pyrimidin-7-yl)-1-(2-(3-aminoquinoxalin-6-yl)ethyl)bicyclo [3.1.0]hexane-2,3-diol (Compound 4);

(1S,2R,5R)-5-(4-Amino-1H-pyrazolo[3,4-d]pyrimidin-1-yl)-3-(2-(2-amino-3-chloro-5-fluoroquinolin-7-yl) ethyl)cyclopent-3-ene-1 2-diol (Compound 5);

(1S,2R,5R)-3-(2-(2-amino-3-chloro-5-fluoroquinolin-7-yl)ethyl)-5-(4-amino-6-methyl-1H-pyrazolo[3,4-d]pyrimidin-1-yl)cyclopent-3-ene-1 2-diol (Compound 6);

(1S,2R,5R)-5-(4-amino-7H-pyrrolo[2,3-d]pyrimidin-7-yl)-3-(((6-(difluoromethyl)-1,2,3,4-tetrahydroisoquinolin-8-yl)oxy)methyl)cyclopent-3-ene-1 2-diol (Compound 7);

(1S,2R,5R)-5-(4-amino-7H-pyrrolo[2,3-d]pyrimidin-7-yl)-3-(2-(6-methyl-1,2,3,4-tetrahydroisoquinolin-8-yl)ethyl)cyclopent-3-ene-1,2-diol(Compound 8);

(1S,2R,5R)-5-(4-amino-7H-pyrrolo[2,3-d]pyrimidin-7-yl)-3-(2-(5-fluoro-1,2,3,4-tetrahydroisoquinolin-8-yl)ethyl)cyclopent-3-ene-1,2-diol(Compound 9);

(1S,2R,5R)-5-(4-amino-7H-pyrrolo[2,3-d]pyrimidin-7-yl)-3-(2-(6-(difluoromethyl)-1,2,3,4-tetrahydroisoquinolin-8-yl)ethyl)cyclopent-3-ene-1,2-diol(Compound 10);

(1S,2R,5R)-5-(4-amino-7H-pyrrolo[2,3-d]pyrimidin-7-yl)-3-(2-(5-(difluoromethyl)-1,2,3,4-tetrahydroisoquinolin-8-yl)ethyl)cyclopent-3-ene-1,2-diol(Compound 11);

(1S,2R,5R)-5-(4-amino-7H-pyrrolo[2,3-d]pyrimidin-7-yl)-3-(((6-(difluoromethyl)-5-fluoro-1,2,3,4-tetrahydroisoquinolin-8-yl)oxy)methyl)cyclopent-3-ene-1,2-diol (Compound 12);

(1S,2R,5R)-5-(4-amino-7H-pyrrolo[2,3-d]pyrimidin-7-yl)-3-(2-(6-(difluoromethyl)-5-fluoro-1,2,3,4-tetrahydroisoquinolin-8-yl)ethyl)cyclopent-3-ene-1,2-diol (Compound 13);

(1S,2R,5R)-3-(2-(6-(difluoromethyl)-1,2,3,4-tetrahydroisoquinolin-8-yl)ethyl)-5-(4-methyl-7H-pyrrolo[2,3-d]pyrimidin-7-yl)cyclopent-3-ene-1,2-diol(Compound 14);

(1S,2R,5R)-3-(2-(6-(difluoromethyl)-5-fluoro-1,2,3,4-tetrahydroisoquinolin-8-yl)ethyl)-5-(4-methyl-7H-pyrrolo[2,3-d]pyrimidin-7-yl)cyclopent-3-ene-1,2-diol (Compound 15);

4-Amino-1-((1R,4R,5S)-3-(((2-amino-3-chloro-5-fluoroquinolin-7-yl)oxy) methyl)-4,5-dihydroxycyclopent-2-en-1-yl)pyrimidin-2(1H)-one(Compound 16);

6-amino-3-((1R,4R,5S)-3-(((2-amino-3-chloro-5-fluoroquinolin-7-yl)oxy)methyl)-4,5-dihydroxycyclopent-2-en-1-yl)pyrimidin-4(3H)-one (Compound 17);

3-((1R,4R,5S)-3-(((2-amino-3-chloro-5-fluoroquinolin-7-yl)oxy)methyl)-4,5-dihydroxycyclopent-2-en-1-yl)-6-methylpyrimidin-4(3H)-one(Compound 18);

6-amino-3-((1R,4R,5S)-3-(((2-amino-3-chloro-5-fluoroquinolin-7-yl)oxy)methyl)-4,5-dihydroxycyclopent-2-en-1-yl)-5-fluoropyrimidin-4(3H)-one(Compound 19);

(1S,2R,5R)-5-(4-amino-7H-pyrrolo[2,3-d]pyrimidin-7-yl)-3-(2-(6-chloro-5-fluoro-1,2,3,4-tetrahydroisoquinolin-8-yl)ethyl)cyclopent-3-ene-1 2-diol (Compound 20);

(1S,2R,5R)-5-(4-amino-7H-pyrrolo[2,3-d]pyrimidin-7-yl)-3-(2-(5,6-difluoro-1,2,3,4-tetrahydroisoquinolin-8-yl)ethyl)cyclopent-3-ene-1,2-diol(Compound 21);

(1S,2R,5R)-5-(4-amino-7H-pyrrolo[2,3-d]pyrimidin-7-yl)-3-(2-(6-(difluoromethyl)-5-fluoro-4-methyl-1,2,3,4-tetrahydroisoquinolin-8-yl)ethyl)cyclopent-3-ene-1,2-diol((Compound 22A and B);

(1S,2R,5R)-5-(4-amino-7H-pyrrolo[2,3-d]pyrimidin-7-yl)-3-(2-(6-(difluoromethyl)-5-fluoro-3-methyl-1,2,3,4-tetrahydroisoquinolin-8-yl)ethyl)cyclopent-3-ene-1,2-diol(Compound 23A and B);

(1R,2R,3S,4R,5S)-1-(2-(6-Amino-7-chloro-1,5-naphthyridin-3-yl)ethyl)-4-(4-amino-7H-pyrrolo[2,3-d]pyrimidin-7-yl)bicyclo[3.1.0]hexane-2,3-diol(Compound 24);

(1S,2R,5R)-5-(4-amino-5-methyl-7H-pyrrolo[2,3-d]pyrimidin-7-yl)-3-(2-(6-(difluoromethyl)-5-fluoro-1,2,3,4-tetrahydroisoquinolin-8-yl)ethyl)cyclopent-3-ene-1 2-diol(Compound 25);

(1S,2R,5R)-3-(2-(2-Amino-3-bromoquinolin-7-yl)ethyl)-5-(7H-imidazo[1,2-c]pyrrolo[3,2-e]pyrimidin-7-yl)cyclopent-3-ene-1,2-diol(Compound 26);

(1S,2R,5R)-3-(2-(2-Amino-3-chloro-5-fluoroquinolin-7-yl)ethyl)-5-(7H-imidazo[1,2-c]pyrrolo[3,2-e]pyrimidin-7-yl)cyclopent-3-ene-1,2-diol (Compound 27);

(1S,2R,5R)-3-(2-(2-Amino-3-chloroquinolin-7-yl)ethyl)-5-(8H-imidazo[1,2-a]pyrrolo[2,3-d]pyrimidin-8-yl)cyclopent-3-ene-1,2-diol (Compound 28);

(1S,2R,5R)-3-(2-(2-Amino-3-chloro-5-fluoroquinolin-7-yl)ethyl)-5-(7H-imidazo[1 2-c]pyrazolo[4,3-e]pyrimidin-7-yl)cyclopent-3-ene-1,2-diol(Compound 29); and (1S,2R,5R)-3-(2-(2-Amino-3-chloro-5-fluoroquinolin-7-yl)ethyl)-5-(4-(methoxyamino)-7H-pyrrolo[2,3-d]pyrimidin-7-yl)cyclopent-3-ene-1,2-diol (Compound 30).

3. The compound of formula (I), its stereoisomer, or its pharmaceutically acceptable salt, as claimed in claim 1, wherein the compound is selected from:

(1S,2R,5R)-3-(2-(2-Amino-3-chloro-5-fluoroquinolin-7-yl)ethyl)-5-(6-amino-9H-purin-9-yl)cyclopent-3-ene-1,2-diol(Compound 1);

(1S,2R,5R)-5-(4-Amino-1H-pyrazolo[3,4-d]pyrimidin-1-yl)-3-(2-(2-amino-3-chloro-5-fluoroquinolin-7-yl) ethyl)cyclopent-3-ene-1 2-diol (Compound 5);

(1S,2R,5R)-3-(2-(2-amino-3-chloro-5-fluoroquinolin-7-yl)ethyl)-5-(4-amino-6-methyl-1H-pyrazolo[3,4-d]pyrimidin-1-yl)cyclopent-3-ene-1,2-diol(Compound 6);

(1S,2R,5R)-5-(4-amino-7H-pyrrolo[2,3-d]pyrimidin-7-yl)-3-(2-(6-(difluoromethyl)-1,2,3,4-tetrahydroisoquinolin-8-yl)ethyl)cyclopent-3-ene-1 2-diol (Compound 10);

(1S,2R,5R)-5-(4-amino-7H-pyrrolo[2,3-d]pyrimidin-7-yl)-3-(2-(6-(difluoromethyl)-5-fluoro-1,2,3,4-tetrahydroisoquinolin-8-yl)ethyl)cyclopent-3-ene-1,2-diol (Compound 13);

(1S,2R,5R)-3-(2-(6-(difluoromethyl)-1,2,3,4-tetrahydroisoquinolin-8-yl)ethyl)-5-(4-methyl-7H-pyrrolo[2,3-d]pyrimidin-7-yl)cyclopent-3-ene-1,2-diol(Compound 14);

(1S,2R,5R)-3-(2-(6-(difluoromethyl)-5-fluoro-1,2,3,4-tetrahydroisoquinolin-8-yl)ethyl)-5-(4-methyl-7H-pyrrolo[2,3-d]pyrimidin-7-yl)cyclopent-3-ene-1,2-diol (Compound 15);

(1S,2R,5R)-5-(4-amino-7H-pyrrolo[2,3-d]pyrimidin-7-yl)-3-(2-(6-(difluoromethyl)-5-fluoro-4-methyl-1,2,3,4-tetrahydroisoquinolin-8-yl)ethyl)cyclopent-3-ene-1,2-diol(Compound 22A and B); and (1S,2R,5R)-5-(4-amino-7H-pyrrolo[2,3-d]pyrimidin-7-yl)-3-(2-(6-(difluoromethyl)-5-fluoro-3-methyl-1,2,3,4-tetrahydroisoquinolin-8-yl)ethyl)cyclopent-3-ene-1,2-diol(Compound 23A and B).

4. A pharmaceutical composition comprising at least one compound of claim 1, its stereoisomer, or its pharmaceutically acceptable salt, and a pharmaceutically acceptable carrier.

5. A method for treating a disease, disorder, syndrome or condition associated with PRMT5 enzyme, comprising administering to a subject in need thereof an effective amount of compound as claimed in claim 1.

6. A method as claimed in claim 5, wherein the said disease, disorder, syndrome or condition associated with PRMT5 enzyme is glioblastoma multiforme, prostate cancer, pancreatic cancer, mantle cell lymphoma, non-Hodgkin's lymphomas and diffuse large B-cell lymphoma, acute myeloid leukemia, acute lymphoblastic leukemia, multiple myeloma, non-small cell lung cancer, small cell lung cancer, breast cancer, triple negative breast cancer, gastric cancer, colorectal cancer, ovarian cancer, bladder cancer, hepatocellular cancer, melanoma, sarcoma, oropharyngeal squamous cell carcinoma, chronic myelogenous leukemia, epidermal squamous cell carcinoma, nasopharyngeal carcinoma, neuroblastoma, endometrial carcinoma, and cervical cancer.

7. A method as claimed in claim 5, wherein the said disease, disorder, syndrome or condition associated with PRMT5 enzyme is cancer.

8. A pharmaceutical composition comprising at least one compound of claim 2, its stereoisomer, or its pharmaceutically acceptable salt, and a pharmaceutically acceptable carrier.

9. A pharmaceutical composition comprising at least one compound of claim 3, its stereoisomer, or its pharmaceutically acceptable salt, and a pharmaceutically acceptable carrier.

10. A method for treating a disease, disorder, syndrome or condition associated with PRMT5 enzyme, comprising administering to a subject in need thereof an effective amount of compound as claimed in claim 2.

11. A method for treating a disease, disorder, syndrome or condition associated with PRMT5 enzyme, comprising administering to a subject in need thereof an effective amount of compound as claimed in claim 3.

* * * * *